(12) United States Patent
Akama et al.

(10) Patent No.: US 9,617,285 B2
(45) Date of Patent: Apr. 11, 2017

(54) 1-HYDROXY-BENZOOXABOROLES AS ANTIPARASITIC AGENTS

(71) Applicants: Eli Lilly and Company, Indianapolis, IN (US); Anacor Pharmaceuticals, Inc., Palo Alto, CA (US)

(72) Inventors: Tsutomu Akama, Sunnyvale, CA (US); Kurt Jarnagin, San Mateo, CA (US); Jacob J. Plattner, Orinda, CA (US); Shon Roland Pulley, Noblesville, IN (US); William Hunter White, Greenfield, IN (US); Yong-Kang Zhang, San Jose, CA (US); Yasheen Zhou, Moraga, CA (US)

(73) Assignees: ELI LILLY AND COMPANY, Indianapolis, IN (US); ANACOR PHARMACEUTICALS, INC., Palo Alto, CA (US)

( * ) Notice: Subject to any disclaimer, the term of this patent is extended or adjusted under 35 U.S.C. 154(b) by 0 days.

(21) Appl. No.: 14/760,208

(22) PCT Filed: Mar. 6, 2014

(86) PCT No.: PCT/US2014/020966
§ 371 (c)(1),
(2) Date: Jul. 10, 2015

(87) PCT Pub. No.: WO2014/149793
PCT Pub. Date: Sep. 25, 2014

(65) Prior Publication Data
US 2015/0353581 A1    Dec. 10, 2015

Related U.S. Application Data

(60) Provisional application No. 61/786,839, filed on Mar. 15, 2013.

(51) Int. Cl.
*C07F 5/02* (2006.01)
*A01N 55/08* (2006.01)

(52) U.S. Cl.
CPC ............ *C07F 5/025* (2013.01); *A01N 55/08* (2013.01)

(58) Field of Classification Search
None
See application file for complete search history.

(56) References Cited

U.S. PATENT DOCUMENTS

2008/0200540 A1    8/2008    Gibson et al.

FOREIGN PATENT DOCUMENTS

| | | | |
|---|---|---|---|
| EP | 953565 | A2 | 11/1999 |
| EP | 1445251 | A1 | 8/2004 |
| EP | 2314292 | A1 | 4/2011 |
| WO | 02/49641 | A2 | 6/2002 |
| WO | 02/060257 | A1 | 8/2002 |
| WO | 02/102155 | A1 | 12/2002 |
| WO | 03/059868 | A1 | 7/2003 |
| WO | 03/080577 | A2 | 10/2003 |
| WO | 03/097036 | A1 | 11/2003 |
| WO | 03/097585 | A2 | 11/2003 |
| WO | 03/104187 | A1 | 12/2003 |
| WO | 2004/000793 | A2 | 12/2003 |
| WO | 2005/044784 | A1 | 5/2005 |
| WO | 2005/058802 | A1 | 6/2005 |
| WO | 2005/121075 | A1 | 12/2005 |
| WO | 2006089067 | A2 | 8/2006 |
| WO | 2007/017088 | A1 | 2/2007 |
| WO | 2007078340 | A2 | 7/2007 |
| WO | 2010/048191 | A1 | 4/2010 |
| WO | 2011/017125 | A1 | 2/2011 |
| WO | 2011/019612 | A1 | 2/2011 |
| WO | 2011/061326 | A1 | 5/2011 |
| WO | 2015021396 | * | 2/2015 ............ A61K 31/96 |

OTHER PUBLICATIONS

Zhengyan Fu et al., "A Convenient and Efficient Synthesis of Dipeptidyl Benzoxaboroles and Their Peptidomimetics," Synthesis, 2013-10, pp. 2843-2852, 45(20).

Ducray et al., "Discovery of Amino-Acetonitrile Derivatives, A New Class of Synthetic Anthelmintic Compounds," Bioorganic & Medicinal Chemistry Letters, 2008, pp. 2935-2938, 18(9).

Kaminsky et al., "A New Class of Anthelmintics Effective Against Drug-Resistant Nematodes," Nature, 2008, pp. 176-180, 452(7184), London, United Kingdom.

\* cited by examiner

*Primary Examiner* — Noble Jarrell
(74) *Attorney, Agent, or Firm* — McAndrews, Held & Malloy, Ltd.

(57) ABSTRACT

Provided are compounds useful for controlling endoparasites both in animals and agriculture. Further provided are methods for controlling endoparasite infestations of an animal by administering an effective amount of a compound as described above, or a pharmaceutically acceptable salt thereof, to an animal, as well as formulations for controlling endoparasite infestations using the compounds described above or an acceptable salt thereof, and an acceptable carrier. The claimed compounds are described by the following Markush formula: A typical example for a compound according to above formula is: A typical example for a compound according to above formula is:

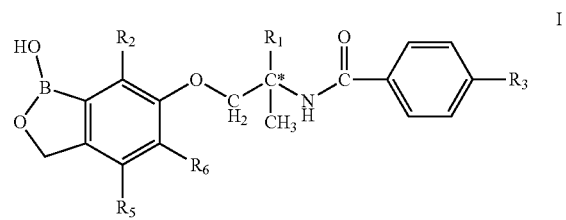

17 Claims, No Drawings

1-HYDROXY-BENZOOXABOROLES AS ANTIPARASITIC AGENTS

Globally, parasitic infections in animals, including humans, are responsible for significant suffering and economic loss. Specifically, endoparasitic infections and in particular helminthiases caused by nematodes (roundworms including filarial worms) and flatworms (cestodes, or tapeworms and trematodes, or flukes), can inflict significant disease through infection of, and damage to various organ systems, for example, the gastrointestinal tract, the lymphatic system, various tissues, the liver, lungs, heart and the brain with sequelae that include neurological and metabolic dysfunction, nutritional deficiencies, delayed growth, loss of productivity and death. In agriculture and horticulture, some nematodes are considered beneficial; however, predatory nematodes such cutworms and root-knot nematodes attack and damage various plant parts including leaves, stems and roots, inflicting significant economic losses to this industry as well.

Numerous classes of drugs are used to treat endoparasitic infections and more specifically, antihelminthic drugs are used to treat nematode infections in animals. While there are a large number of drugs approved for treatment of human and veterinary helminth infections, the most widely used drugs tend to fall within a limited number of older chemical classes, for example macrocyclic lactones (e.g., avermectins, milbemycins); benzimidazoles (e.g., fenbendazole, thiabendazole, flubendazole); imidathiazoles (e.g., tetramisole and levamisole); tetrahydropyrimidines (e.g., morantel, pyrantel), salicylanilides (e.g., closantel, niclosamide); pyrazinaisoquinolines (e.g., praziquantel); various heterocyclic compounds (e.g., piperazine, diethylcarbamazine, phenothiazine) and arsenicals (e.g., melorsamine) as well as various natural or plant-derived remedies (e.g., bromelain from pineapple and papaya). Many compounds within these older chemical classes suffer from a variety of shortcomings such as questionable safety, poor drug-ability and/or efficacy profiles, limited spectrum, or growing resistance issues due to inappropriate use patterns (e.g., overuse of macrocyclic lactones without integrated pest management strategies involving chemical class rotation by growers and producers). A very limited number of newer antihelminthic agents have been developed recently that appear to address some of these shortcomings, and include the aminoacetonitrile derivatives (e.g., monepantel); spiroindoles (e.g., derquantel); and cyclooctadepsipeptides (e.g., emodepside). However, there is still a pressing need for additional antihelminthic agents with superior and/or varying attributes in terms of spectrum and activity, physical-chemical properties and drug-ability profile, mammalian safety and more diverse and convenient treatment options to ensure long-term viability.

The present invention encompasses endoparasiticidal compounds, methods, and formulations for use in and on animals and plants, which provide alternative options for combating endoparasitic infestations, particularly helminth infestations. Further, certain aspects of the invention overcome at least some limitations in the use of current therapies, particularly in providing effective, safe control of endoparasites.

Provided are compounds of the formula I:

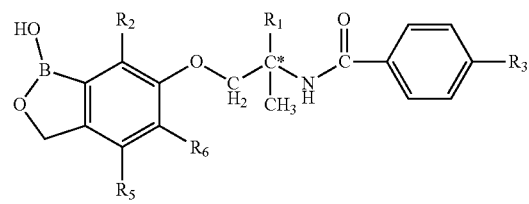

wherein C* is a carbon atom which is a stereocenter having a configuration which is (R) or (S);

$R_1$ is cyano or carbamoyl;

$R_2$ is hydrogen, halo, $C_1$-$C_3$ alkyl, $C_1$-$C_3$ alkyl substituted 1-3 times with halo, $C_1$-$C_3$ alkoxy, $C_1$-$C_3$ alkoxy substituted 1-3 times with halo, cyclopropyl, cyclopropoxy, phenoxy, phenyl, thienyl, furyl, amino, aminomethyl, dimethylamino, cyano, acetylamino, methoxycarbonyl, —$CH_2$—NH—C(O)—O—C($CH_3$)$_3$, or —O($CH_2$)$_2$—$R_4$, wherein $R_4$ is methoxy, amino, or —NH—C(O)—O—C($CH_3$)$_3$;

$R_3$ is cyano, trifluoromethoxy, trifluoromethylthio, trifluoromethylsulfonyl, trifluoromethylsulfinyl, or pentafluorosulfanyl;

$R_5$ is hydrogen, halo, $C_1$-$C_3$ alkyl, $C_1$-$C_3$ alkoxy, or aminomethyl; and $R_6$ is hydrogen, halo, $C_1$-$C_3$ alkyl, or trifluoromethyl;

or a salt thereof. In an embodiment, $R_1$, $R_2$, $R_3$, $R_5$, and $R_6$ are as described herein, and C* is a stereocenter with a (R) configuration. In an embodiment, $R_1$, $R_2$, $R_3$, $R_5$, and $R_6$ are as described herein, and C* is a stereocenter with a (S) configuration.

Provided are compounds of the formula Ia:

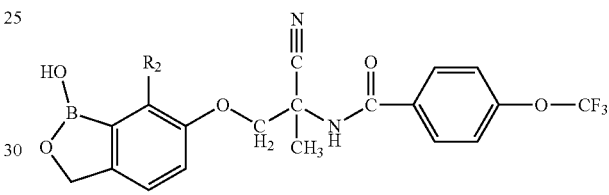

wherein $R_2$ is as described herein, or a salt thereof. In an embodiment, $R_2$ is selected from the group of bromo, chloro, methyl, ethyl, propyl, isopropyl, cyclopropyl, phenyl, trifluoromethoxy, methoxy, ethoxy, propoxy, isopropoxy, or a salt thereof.

Provided are compounds of the formula Ib:

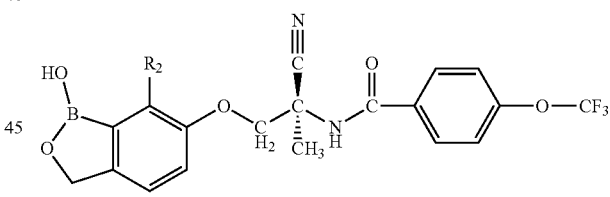

wherein $R_2$ is as described herein, or a salt thereof. In an embodiment, $R_2$ is selected from the group of bromo, chloro, methyl, ethyl, propyl, isopropyl, cyclopropyl, phenyl, trifluoromethoxy, methoxy, ethoxy, propoxy, isopropoxy, or a salt thereof.

In an embodiment, the compounds are of the formula II:

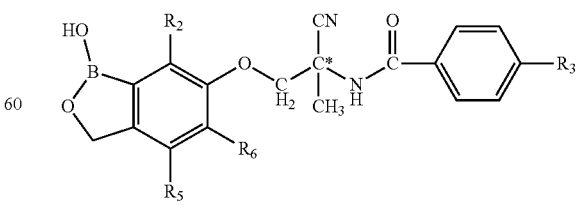

wherein $R_2$, $R_3$, $R_5$, and $R_6$ are as described herein, or a salt thereof. In an embodiment, $R_2$, $R_3$, $R_5$, and $R_6$ are as described herein, and C* is a stereocenter with a (R)

configuration. In an embodiment, $R_2$, $R_3$, $R_5$, and $R_6$ are as described herein, and C* is a stereocenter with a (S) configuration.

In an embodiment, the compounds are of the formula III:

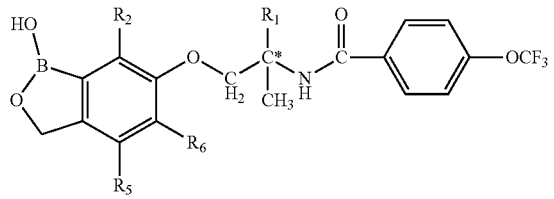

III wherein $R_1$, $R_2$, $R_5$, and $R_6$ are as described herein, or a salt thereof. In an embodiment, $R_1$, $R_2$, $R_5$, and $R_6$ are as described herein, and C* is a stereocenter with a (R) configuration. In an embodiment, $R_1$, $R_2$, $R_5$, and $R_6$ are as described herein, and C* is a stereocenter with a (S) configuration.

In an embodiment, the compounds are of the formula IV:

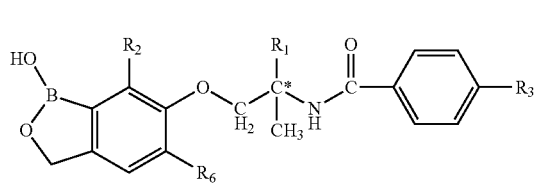

IV wherein $R_1$, $R_2$, $R_3$, and $R_6$ are as described herein, or a salt thereof. In an embodiment, $R_1$, $R_2$, $R_3$, and $R_6$ are as described herein, and C* is a stereocenter with a (R) configuration. In an embodiment, $R_1$, $R_2$, $R_3$, and $R_6$ are as described herein, and C* is a stereocenter with a (S) configuration.

In an embodiment, the compounds are of the formula V:

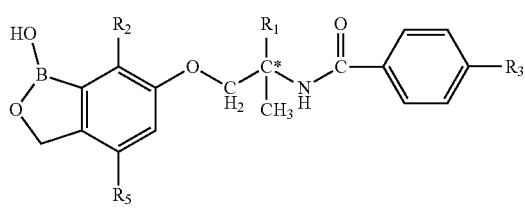

V wherein $R_1$, $R_2$, $R_3$, and $R_5$ are as described herein, or a salt thereof. In an embodiment, $R_1$, $R_2$, $R_3$, and $R_5$ are as described herein, and C* is a stereocenter with a (R) configuration. In an embodiment, $R_1$, $R_2$, $R_3$, and $R_5$ are as described herein, and C* is a stereocenter with a (S) configuration.

In an embodiment, the compounds are of the formula VI:

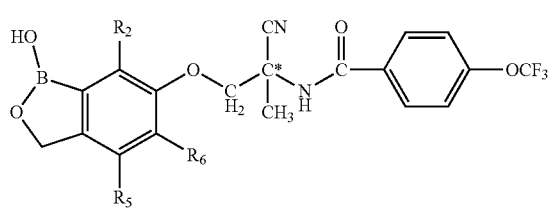

VI wherein $R_2$, $R_5$, and $R_6$ are as described herein, or a salt thereof. In an embodiment, $R_2$, $R_5$, and $R_6$ are as described herein, and C* is a stereocenter with a (R) configuration. In an embodiment, $R_2$, $R_5$, and $R_6$ are as described herein, and C* is a stereocenter with a (S) configuration.

In an embodiment, the compounds are of the formula VII:

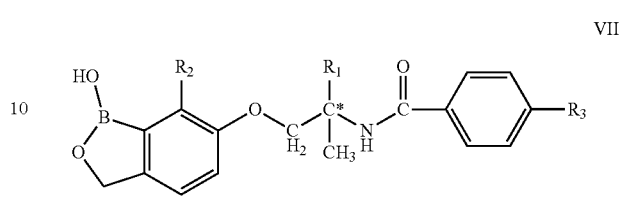

VII wherein $R_1$, $R_2$, and $R_3$ are as described herein, or a salt thereof. In an embodiment, $R_1$, $R_2$, and $R_3$ are as described herein, and C* is a stereocenter with a (R) configuration. In an embodiment, $R_1$, $R_2$, and $R_3$ are as described herein, and C* is a stereocenter with a (S) configuration.

In an embodiment, the compounds are of the formula VIII:

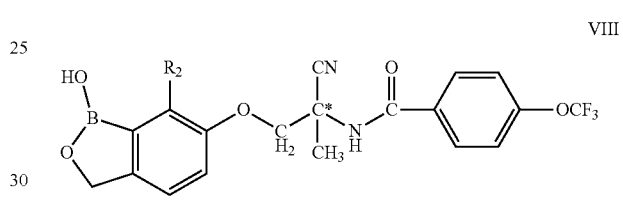

VIII wherein $R_2$ is as described herein, or a salt thereof. In an embodiment, $R_2$ is halogen. In an embodiment, $R_2$ is halogen and C* is a stereocenter with a (R) configuration. In an embodiment, $R_2$ is halogen and C* is a stereocenter with a (S) configuration. In an embodiment, $R_2$ is Cl. In an embodiment, $R_2$ is Cl and C* is a stereocenter with a (R) configuration. In an embodiment, $R_2$ is Cl and C* is a stereocenter with a (S) configuration. In an embodiment, $R_2$ is Br. In an embodiment, $R_2$ is Br and C* is a stereocenter with a (R) configuration. In an embodiment, $R_2$ is Br and C* is a stereocenter with a (S) configuration. In an embodiment, $R_2$ is $C_1$ or $C_2$ or $C_3$ alkyl. In an embodiment, $R_2$ is $C_1$ or $C_2$ or $C_3$ alkyl and C* is a stereocenter with a (R) configuration. In an embodiment, $R_2$ is $C_1$ or $C_2$ or $C_3$ alkyl and C* is a stereocenter with a (S) configuration. In an embodiment, $R_2$ is $C_1$ or $C_2$ or $C_3$ alkyl. In an embodiment, $R_2$ is $C_1$ or $C_2$ or $C_3$ alkyl and C* is a stereocenter with a (R) configuration. In an embodiment, $R_2$ is $C_1$ or $C_2$ or $C_3$ alkyl and C* is a stereocenter with a (S) configuration. In an embodiment, $R_2$ is methyl. In an embodiment, $R_2$ is methyl and C* is a stereocenter with a (R) configuration. In an embodiment, $R_2$ is methyl and C* is a stereocenter with a (S) configuration. In an embodiment, $R_2$ is ethyl. In an embodiment, $R_2$ is ethyl and C* is a stereocenter with a (R) configuration. In an embodiment, $R_2$ is ethyl and C* is a stereocenter with a (S) configuration. In an embodiment, $R_2$ is propyl. In an embodiment, $R_2$ is propyl and C* is a stereocenter with a (R) configuration. In an embodiment, $R_2$ is propyl and C* is a stereocenter with a (S) configuration. In an embodiment, $R_2$ is isopropyl. In an embodiment, $R_2$ is isopropyl and C* is a stereocenter with a (R) configuration. In an embodiment, $R_2$ is isopropyl and C* is a stereocenter with a (S) configuration. In an embodiment, $R_2$ is $C_1$ or $C_2$ or $C_3$ alkyloxy. In an embodiment, $R_2$ is $C_1$ or $C_2$ or $C_3$ alkyloxy and C* is a stereocenter with a (R) configuration. In an embodiment, $R_2$ is $C_1$ or $C_2$ or $C_3$ alkyloxy and C* is a stereocenter with a (S) configuration. In an embodiment, $R_2$ is methoxy. In an embodiment, $R_2$ is methoxy and C* is a stereocenter with a (R) configuration. In an embodiment, $R_2$ is methoxy and C* is a stereocenter with a (S) configuration. In an embodiment, $R_2$ is ethoxy. In an embodiment, $R_2$ is ethoxy and C* is a stereocenter with a (R) configuration. In an embodiment, $R_2$ is ethoxy and C* is a stereocenter with a (S) configuration. In an embodiment, $R_2$ is propoxy. In an embodiment, $R_2$ is propoxy and C* is a stereocenter with a (R) configuration. In an embodiment, $R_2$ is propoxy and C* is a stereocenter with a (S) configuration. In an embodiment, $R_2$ is isopropoxy. In an embodiment, $R_2$ is isopropoxy and C* is a stereocenter with a (R) configuration. In an embodiment, $R_2$ is isopropoxy and C* is a stereocenter with a (S) configuration. In an embodiment, $R_2$ is $C_1$ or $C_2$ or $C_3$ alkyloxy, substituted with one, two, or three times with halo. In an embodiment, $R_2$ is $C_1$ or $C_2$ or $C_3$ alkyloxy, substituted with one, two, or three times with halo and C* is a stereocenter with a (R) configuration. In an embodiment, $R_2$ is $C_1$ or $C_2$ or $C_3$ alkyloxy, substituted with one, two, or three times with halo and C* is a stereocenter with a (S) configuration. In an embodiment, $R_2$ is $C_1$ or $C_2$ or $C_3$ alkyloxy, substituted with one, two, or three fluorines. In an embodiment, $R_2$ is $C_1$ or $C_2$ or $C_3$ alkyloxy, substituted with one, two, or three fluorines and C* is a stereocenter with a (R) configuration. In an embodiment, $R_2$ is $C_1$ or $C_2$ or $C_3$ alkyloxy, substituted with one, two, or three fluorines and C* is a stereocenter with a (S) configuration. In an embodiment, $R_2$ is $C_1$ or $C_2$ or $C_3$ alkyloxy, substituted with one fluorine. In an embodiment, $R_2$ is $C_1$ or $C_2$ or $C_3$ alkyloxy, substituted with one fluorine and C* is a stereocenter with a (R) configuration. In an embodiment, $R_2$ is $C_1$ or $C_2$ or $C_3$ alkyloxy, substituted with one fluorine and C* is a stereocenter with a (S) configuration. In an embodiment, $R_2$ is $C_1$ or $C_2$ or $C_3$ alkyloxy, substituted with two fluorines. In an embodiment, $R_2$ is $C_1$ or $C_2$ or $C_3$ alkyloxy, substituted with two fluorines and C* is a stereocenter with a (R) configuration. In an embodiment, $R_2$ is $C_1$ or $C_2$ or $C_3$ alkyloxy, substituted with two fluorines and C* is a stereocenter with a (S) configuration. In an embodiment, $R_2$ is trifluoromethoxy. In an embodiment, $R_2$ is trifluoromethoxy and C* is a stereocenter with a (R) configuration. In an embodiment, $R_2$ is trifluoromethoxy and C* is a stereocenter with a (S) configuration. In an embodiment, $R_2$ is $C_3$ cycloalkyl. In an embodiment, $R_2$ is cyclopropyl. In an embodiment, $R_2$ is cyclopropyl and C* is a stereocenter with a (R) configuration. In an embodiment, $R_2$ is cyclopropyl and C* is a stereocenter with a (S) configuration.

In an embodiment, the compounds are of the formula IX:

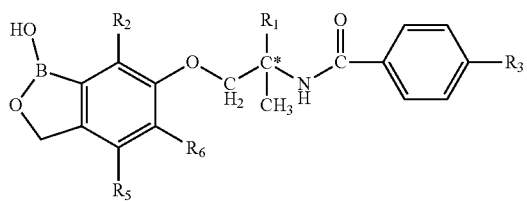

IX wherein $R_1$, $R_3$, $R_5$, and $R_6$ are as described herein, and $R_2$ is halogen, or a salt thereof. In an embodiment, $R_1$, $R_3$, $R_5$, and $R_6$ are as described herein, and $R_2$ is halogen, and C* is a stereocenter with a (R) configuration. In an embodiment, $R_1$, $R_3$, $R_5$, and $R_6$ are as described herein, and $R_2$ is halogen, and C* is a stereocenter with a (S) configuration.

In an embodiment, the compounds are of the formula X:

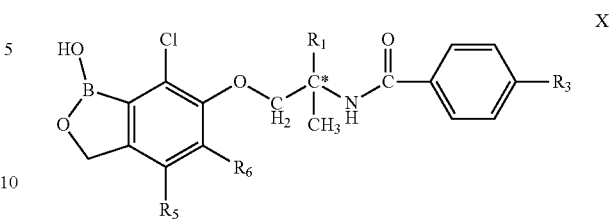

X wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XI:

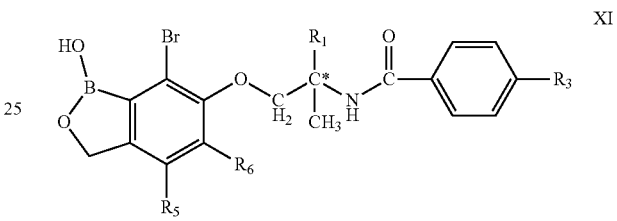

XI wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XII:

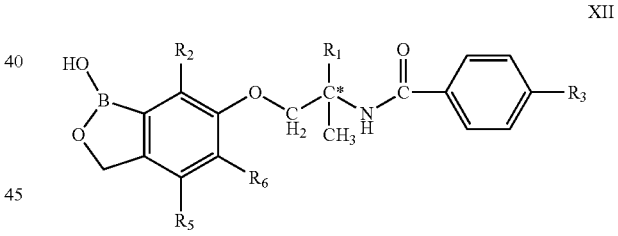

XII wherein $R_1$, $R_3$, $R_5$, and $R_6$ are as described herein, and $R_2$ is $C_1$ or $C_2$ or $C_3$ alkyl, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XIII:

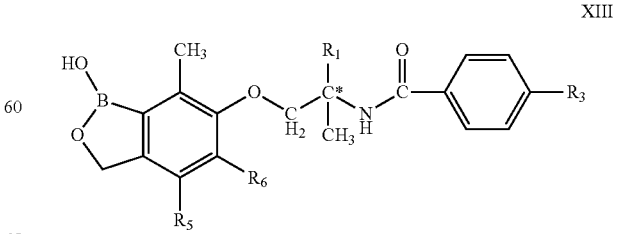

XIII wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XIV:

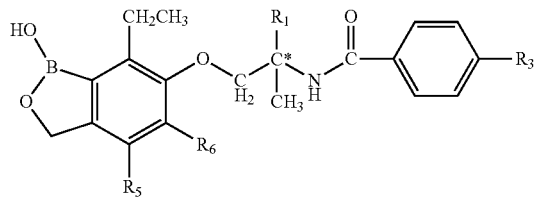

XIV wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XV:

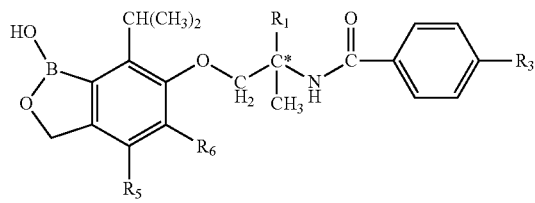

XV wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XVI:

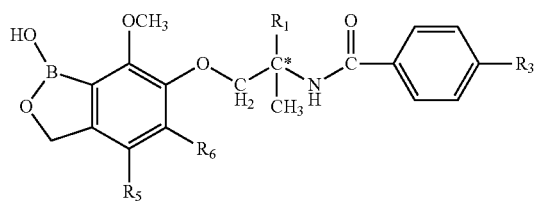

XVI wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XVII:

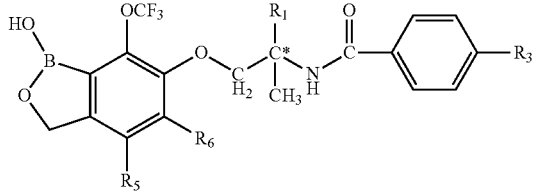

XVII wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XVIII:

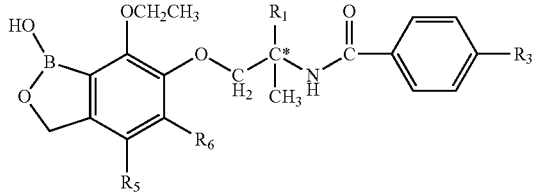

XVIII wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XIX:

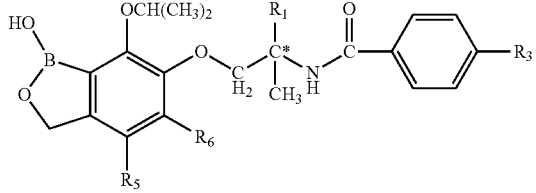

XIX wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

In an embodiment, the compounds are of the formula XX:

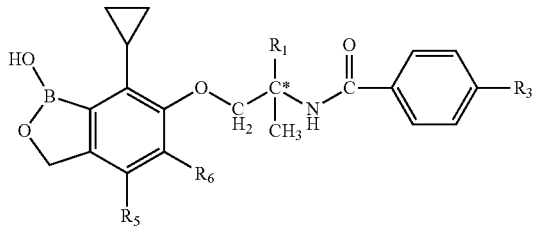

XX wherein $R_1$, $R_3$, $R_5$, and $R_6$ are as described herein, or a salt thereof. In an embodiment, $R_1$, $R_3$, $R_5$, and $R_6$ are as described herein and C* is a stereocenter with a (R) configuration. In an embodiment, $R_1$, $R_3$, $R_5$, and $R_6$ are as described herein and C* is a stereocenter with a (S) configuration.

The invention provides compounds of the formula XXI and XXII, and salts thereof:

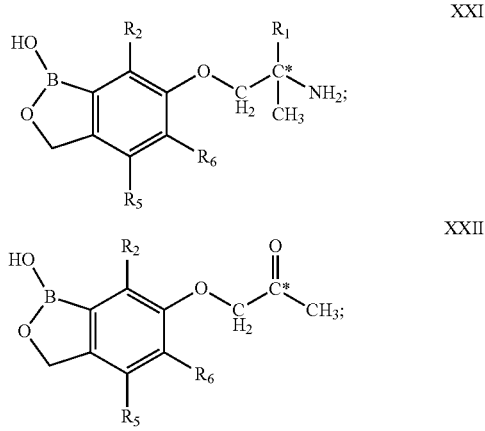

wherein $R_2$, $R_5$, and $R_6$ are as described herein.

The invention provides formulations, including pharmaceutical formulations and agricultural formulations, comprising a compound or salt of a formula described herein and one or more acceptable carriers. The formulation may further comprise at least one additional active ingredient. A pharmaceutical formulation of the invention may be a human pharmaceutical formulation or a veterinary pharmaceutical formulation.

The invention provides a method of controlling endoparasite infestations of an animal in need thereof comprising administering an effective amount of a compound or salt of a formula described herein to said animal. The method may further provide administering at least one other active ingredient to said animal.

The present invention provides a method for preventing and treating diseases transmitted through endoparasites comprising administering at least one compound, or salt thereof, described herein to an animal in need thereof.

The invention provides a method for controlling endoparasites, characterized in that a compound or salt of a formula described herein is allowed to act on the pests and/or their habitat. The invention provides the use of a compound or salt thereof of a formula described herein for controlling such pests.

The invention provides a compound, or salt thereof, described herein for use in therapy. The invention further provides a compound, or salt thereof, described herein for use in controlling endoparasite infestations. The invention also provides use of a compound, or salt thereof, described herein for the manufacture of a formulation or medicament for controlling endoparasite infestations.

The host animal may be a mammal or non-mammal, such as a bird (turkeys, chickens) or fish. Where the host animal is a mammal, it may be a human or non-human mammal. Non-human mammals include domestic animals, such as livestock animals and companion animals. Livestock animals include, but are not limited to, cattle, camellids, pigs, sheep, goats, and horses. Companion animals include, but are not limited to, dogs, rabbits, cats, and other pets owned and maintained in close association with humans as part of the human-animal bond.

Endoparasites include helminth pests which commonly infect animals, and include the egg, larval, and adult stages thereof. Such pests include nematodes, cestodes, and trematodes, particularly ruminant (blood-feeding) and/or pathogenic nematodes, as well as hookworms, tapeworms, and heartworms, and are commercially important because these pests cause serious diseases in animals, e.g. in sheep, pigs, goats, cattle, horses, donkeys, camels, dogs, cats, rabbits, guinea-pigs, hamsters, chicken, turkeys, guinea fowls and other farmed birds, as well as exotic birds. Typical nematode Genera include are *Haemonchus, Trichostrongylus, Fasciola, Ostertagia, Nematodirus, Cooperia, Ascaris, Bunostonum, Oesophagostomum, Charbertia, Trichuris, Strongylus, Trichonema, Dictyocaulus, Capillaria, Heterakis, Toxocara, Ascaridia, Oxyuris, Ancylostoma, Uncinaria, Toxascaris*, and *Parascaris*. The trematodes include, in particular, the family of Fasciolideae, especially *Fasciola hepatica*. Of particular note are those nematodes which infect the gastrointestinal tracts of animals, such as *Ostertagia, Trichostrongylus, Haemonchus*, and *Cooperia*.

In an embodiment, the worm is a parasitic worm. In an embodiment, the worm is a helminth. In an embodiment, the worm is a roundworm (Nematode). In an embodiment, the worm is a segmented flatworm (Cestode). In an embodiment, the worm is a non-segmented flatworms (Trematode). Killing or inhibiting the growth of these worms is commercially and medically important because they cause serious diseases in a broad spectrum of animals, such as those animals described herein. In an embodiment, the worm is a member of *Haemonchus* spp. or *Trichostrongylus* spp. or *Teladorsagia (Ostertagia)* spp. or *Nematodirus leporis* or *Cooperia oncophora* or *Cooperia punctata* or *Ascaris* spp. or *Oesophagostomum* spp. or *Bunostomum* spp. or *Charbertia* spp. or *Trichuris* spp. or *Strongylus* spp. or *Trichonema* spp. or *Triodontophorus* spp. or *Dictyocaulus* spp. or *Heterakis* spp. or *Toxocara* spp. or *Ascaridia* spp. or *Enterobius* (formerly Oxyuris) spp. or *Ancylostoma* spp. or *Uncinaria* spp. or *Necator* spp. or *Toxascaris leonina* or *Parascaris equorum, Taenia* spp. or *Hymenolepsis* spp. or *Eichonicoccus* spp. or *Pseudophyllid* cestodes or liver flukes or lung flukes or blood flukes or the family of Fasciolideae, especially *Fasciola hepatica*, or *Schistosoma* spp. or Filarioidea including *Dirofilaria* spp. or *Litomosoides* spp. or *Onchocerca* spp. or *Brugia* spp. or *Wuchereria* spp. In an embodiment, the worm is an ascarid or filarid or hookworm or pinworm or whipworm. In an embodiment, the worm is *Litomosoides sigmodontis* or *Haemonchus contortus* or *Trichostrongylus colubriformis* or *Dirofilaria immitis*. In an embodiment, the worm is *Wuchereria bancrofti* or *Brugia malayi* or *Brugia timori* or *Schistosoma mansoni*.

In another aspect, the invention provides a method of treating a disease. The method includes administering to the animal a therapeutically effective amount of a compound, or salt thereof, described herein, sufficient to treat the disease. In another aspect, the invention provides a method of preventing a disease. The method includes administering to the animal a prophylactally effective amount of a compound, or salt thereof, described herein, sufficient to prevent the disease. In an embodiment, a compound, or salt thereof, described herein, can be used in human medical therapy, particularly in the treatment of worm-associated disease. In an embodiment, a compound, or salt of a formula described herein can be used in human medical therapy, particularly in the treatment of worm-associated disease. In an embodiment, the compound or salt of a formula described herein can be used in human medical therapy, particularly in the prophylaxis of worm-associated disease. In an embodiment, the compound or salt of a formula described herein can be used in veterinary medical therapy, particularly in the treatment of worm-associated disease. In an embodiment, the compound or salt of a formula described herein can be used in veterinary medical therapy, particularly in the prophylaxis of worm-associated disease. In an embodiment, the compound or salt of a formula described herein can be used in human medical therapy, particularly in the treatment of helminth-associated disease. In an embodiment, the compound or salt of a formula described herein can be used in human medical therapy, particularly in the prophylaxis of helminth-associated disease. In an embodiment, the compound or salt of a formula described herein can be used in veterinary medical therapy, particularly in the treatment of helminth-associated disease. In an embodiment, the compound or salt of a formula described herein can be used in veterinary medical therapy, particularly in the prophylaxis of helminth-associated disease. In an embodiment, the animal being administered the compound is not otherwise in need of treatment with a compound or salt of a formula described herein.

In an embodiment, the disease is associated with a worm. In an embodiment, the disease is caused by a worm. In an embodiment, the disease is associated with a worm described herein. In an embodiment, the disease is associated with a nematode. In an embodiment, the disease is associated with a nematode described herein. In an embodiment, the disease is associated with a worm which is *Litomosoides sigmodontis* or *Haemonchus contortus* or *Trichostrongylus colubriformis* or *Dirofilaria immitis*. In an embodiment, the disease is associated with a worm which is *Wuchereria bancrofti* or *Brugia malayi* or *Brugia timori* or *Schistosoma mansoni*. In an embodiment, the disease is associated with a trematode. In an embodiment, the disease is associated with a trematode described herein. In an embodiment, the disease is associated with *Schistosoma*. In an embodiment, the disease is a member selected from enterobiasis, oxyuriasis, ascariasis, dracunculiasis, filariasis, onchocerciasis, schistosomiasis, and trichuriasis. In an embodiment, the disease is schistosomiasis. In an embodiment, the disease is urinary schistosomiasis. In an embodiment, the disease is intestinal schistosomiasis. In an embodiment, the disease is Asian intestinal schistosomiasis. In an embodiment, the disease is visceral schistosomiasis. In an embodiment, the disease is acute schistosomiasis. In an embodiment, the disease is lymphatic filariasis. In an embodiment, the disease is bancroftian filariasis. In an embodiment, the disease is lymphadenitis. In an embodiment, the disease is lymphangitis. In an embodiment, the disease is lymphedema. In an embodiment, the disease is subcutaneous filariasis. In an embodiment, the disease is serious cavity filariasis. In an embodiment, the disease is elephantiasis. In an embodiment, the disease is elephantiasis tropica. In an embodiment, the disease is onchocerciasis.

Controlling refers to either ameliorating or eliminating a current infestation, or preventing an infestation, in or on an animal host or a plant.

Effective amount refers to the amount of a compound, or a salt thereof, as described herein sufficient to control an endoparasite infestation, and includes causing a measurable reduction in the endoparasite infestation population, and as such will depend upon several factors. For use on or in animals, ranges for a compound, or a salt thereof, as described herein in the methods include from 0.01 to 1000 mg/kg and more desirably, 0.1 to 100 mg/kg of the animal's body weight. The frequency of the administration will also be dependent upon several factors, and can be a single dose administered once a day, once a week, or once a month, for a duration determined by the attending doctor or veterinarian. Additional active ingredients may be administered with a compound, or a salt thereof, as described herein.

Pharmaceutically acceptable as used in this application, for example with reference to salts and formulation components such as carriers, includes "veterinarily acceptable", and thus includes both human and animal applications independently.

Salts of the compounds of the invention, including pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol. 66, No. 1, January 1977.

A compound, or a salt thereof, as described herein may be formulated as pharmaceutical compositions for administration. Such pharmaceutical compositions and processes for making the same are known in the art for both humans and non-human animals. See, e.g., REMINGTON: THE SCIENCE AND PRACTICE OF PHARMACY, (A. Gennaro, et al., eds., 19$^{th}$ ed., Mack Publishing Co., 1995). Formulations can be administered through various means, including oral administration such as oral drench, intraruminal device, and in-feed additives or the like; parenteral administration such as injection (intramuscular, subcutaneous, intravenous, intraperitoneal) or the like; topical application with or without transdermal penetration such as dipping, spray, bathing, washing, pouring-on and spotting-on, and dusting, or the like; and transdermal and transdermal depot, and the like. Additional active ingredients may be included in the formulation containing a compound of the invention or a salt thereof and may be, for example a compound with different parasiticidal activity that complements a compound of the invention in terms of conveying improved parasite spectrum, or duration of activity. Such active ingredients include, but are not limited to, endoparasiticides belonging to the macrocyclic lactone (e.g., ivermectin, milbemycin), benzimidazole (e.g., flubendazole), imidathioazole (e.g., levamisole), spiroindole (e.g., derquantel), piperazine, tribendimidine, salicylanilide (e.g., niclosamide), tetrahydropyrimidine (e.g., pyrantel), benzamide (e.g., closantel), cyclooctadepsipeptide (e.g., emodepside) or aminoacetonitrile derivative (e.g., monepantel) class as well as antiprotozoal agents such as pentamidine, pyramethamine, suramin, nitazoxanide, and melarsoprol. An additional active ingredient may also be an ectoparasicidal or endectoparasiticidal compound including, but not limited to, a macrocyclic lactone (e.g., ivermectin, milbemycin), spinosyn (e.g., spinosad, spinetoram), pyrazole or phenylpyrazole (e.g., fipronil, tebufenpyrad), formamidine (e.g., amitraz), neonicotinoid (e.g., imidacloprid, thiamethoxam), cyclodiene organochlorine (e.g., dieldrin, DDT), nodulasporamide, pthalamide (e.g., tetramethrin), pyrethroid (e.g., permethrin), diamide (e.g., chlorantraniliprole), oxadiazine (e.g., indoxicarb), organophosphate (e.g., diazinon), dinitrophenol (e.g., DNOC), carbamate (e.g., carbaryl), semicarbazone (e.g., metaflumizone), isoxazoline (e.g., fluralaner), pyrimidinamine (e.g., pyrimidifen), pyrrole (e.g., chlorfenapyr), tetramic acid (e.g., spirotetramet), and thiazole (e.g., clothianidin), as well as various unclassified parasiticides such as acequinocyl, pyridalyl and insect growth regulators (e.g., juvenile hormone mimics, chitinase inhibitors).

Carrier is used herein to describe any ingredient other than the active component(s) in a formulation. The choice of carrier will to a large extent depend on factors such as the particular mode of administration or application, the effect of the carrier on solubility and stability, and the nature of the dosage form.

Halogen or halo refers to fluorine, bromine, chlorine, and iodine.

$C_1$-$C_3$ alkyl substituted 1-3 times halo and $C_1$-$C_3$ alkoxy substituted 1-3 times with halo refer to a $C_1$-$C_3$ alkyl (methyl, ethyl, propyl, or isopropyl) or a $C_1$-$C_3$ alkoxy (methoxy, ethoxy, propoxy, or isopropoxy) mono, di, or tri substituted with halogen. Examples of such include fluoromethyl, fluoroethyl, fluoropropyl, fluoroisopropyl, chloromethyl, chloroethyl, chloropropyl, chloroisopropyl, bromomethyl, bromoethyl, bromopropyl, bromoisopropyl, iodomethyl, iodoethyl, iodopropyl, iodoisopropyl, difluoromethyl, difluoroethyl, difluoropropyl, difluoroisopropyl, dichloromethyl, dichloroethyl, dichloropropyl, dichloroisopropyl, dibromomethyl, dibromoethyl, dibromopropyl, dibromoisopropyl, diiodomethyl, diiodoethyl, diiodopropyl, diiodoisopropyl, trifluoromethyl, trifluoroethyl, trifluoropropyl, trifluoroisopropyl, trichloromethyl, trichloroethyl, trichloropropyl, trichloroisopropyl, tribromomethyl, tribromoethyl, tribromopropyl, tribromoisopropyl, triiodomethyl, triiodoethyl, triiodopropyl, triiodoisopropyl, fluoromethoxy, fluoroethoxy, fluoropropoxy, fluoroisopropoxy, chloromethoxy, chloroethoxy, chloropropoxy, chloroisopropoxy, bromomethoxy, bromoethoxy, bromopropoxy, bromoisopropoxy, iodomethoxy, iodoethoxy, iodopropoxy, iodoisopropoxy, difluoromethoxy, difluoroethoxy, difluoropropoxy, difluoroisopropoxy, dichloromethoxy, dichloroethoxy, dichloropropoxy, dichloroisopropoxy, dibromomethoxy, dibromoethoxy, dibromopropoxy, dibromoisopropoxy, diiodomethoxy, diiodoethoxy, diiodopropoxy, diiodoisopropoxy, trifluoromethoxy, trifluoroethoxy, trifluoropropoxy, trifluoroisopropoxy, trichloromethoxy, trichloroethoxy, trichloropropoxy, trichloroisopropoxy, tribromomethoxy, tribromoethoxy, tribromopropoxy, tribromoisopropoxy, triiodomethoxy, triiodoethoxy, triiodopropoxy, and triiodoisopropoxy.

Given their activity, certain of the compounds, or a salt thereof, as described herein are suitable as soil insecticides against pests in the soil, as well as insecticides for plants, such as cereals, cotton, rice, maize, soya, potatoes, vegetables, fruit, tobacco, hops, citrus, and avocados. Certain compounds, or a salt thereof, as described herein are suitable for protecting plants and plant organs, for increasing the harvest yields, and for improving the quality of the harvested material which are encountered in agriculture, in horticulture, in forests, in gardens, and leisure facilities, and in the protection of stored products and of materials. They may be employed as plant protection agents.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with a compound, or a salt thereof, as described herein is carried out by conventional and known means, including directly acting on, or by allowing the compounds to act on, the surroundings, habitat or storage space by the customary treatment methods, for example by immersion, spraying, evaporation, fogging, scattering, painting on, injection and, in the case of propagation material, in particular in the case of seeds, also by applying one or more coats.

The compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

Killing or inhibiting the growth of worms with a compound, or a salt thereof, as described herein is commercially and agriculturally important because they cause serious diseases in a broad spectrum of plants, such as a plant described herein. In an embodiment, the worm is contacted with the compound of the invention inside a plant. In an embodiment, the worm is contacted with the compound of the invention outside of a plant. In an embodiment, the worm is a nematode which compromises or negatively impacts the integrity, growth and health of edible or non-edible crop and/or non-crop plants (i.e., legumes, tubers, fruit and/or nut-bearing plants, shrubs, bushes and trees, grain crops, and vines) such as corn, potato, soybean, tomato, wheat, barley, rice, beets, tobacco, carrots, apples, citrus crops, bananas, deciduous and coniferous trees. In an embodiment, the worm is a sting nematode. In an embodiment, the worm is of the *Belonolaimus* genus. In an embodiment, the worm is a needle nematode. In an embodiment, the worm is of the *Longidorus* genus. In an embodiment, the worm is a ring nematode. In an embodiment, the worm is of the *Criconemoides* genus. In an embodiment, the worm is a root-knot nematode. In an embodiment, the worm is of the *Meloidognue* genus. In an embodiment, the worm is a false root-knot nematode. In an embodiment, the worm is of the *Naccobus* genus. In an embodiment, the worm is a spiral nematode. In an embodiment, the worm is of the *Helicotylenchus* genus. In an embodiment, the worm is a lesion nematode. In an embodiment, the worm is of the *Pratylenchus* genus. In an embodiment, the worm is a corn cyst nematode. In an embodiment, the worm is of the *Heterodera* genus. In an embodiment, the worm is a stubby-root nematode. In an embodiment, the worm is of the *Trichodorus* genus. In an embodiment, the worm is of the *Paratrichodorus* genus. In an embodiment, the worm is a lance nematode. In an embodiment, the worm is of the *Hoplolaimus* genus. In an embodiment, the worm is a stunt nematode. In an embodiment, the worm is of the *Tylenchorhynchus* genus. In an embodiment, the worm is a pinewood nematode. In an embodiment, the worm is of the *Bursaphelenchus* genus. In an embodiment, the worm is a burrowing nematode. In an embodiment, the worm is a banana-root nematode. In an embodiment, the worm is of the *Radopholus* genus. In an embodiment, the worm is of the *Aphelenchoides* genus.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are extenders, solvents, and carriers.

The invention encompasses the following clauses.

Clause 1. A compound of the formula I:

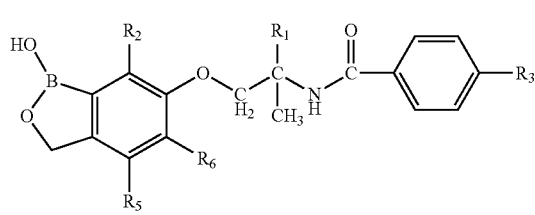

wherein $R_1$ is cyano or carbamoyl;

$R_2$ is hydrogen, halo, $C_1$-$C_3$ alkyl, $C_1$-$C_3$ alkyl substituted 1-3 times with halo, $C_1$-$C_3$ alkoxy, $C_1$-$C_3$ alkoxy substituted 1-3 times with halo, cyclopropyl, cyclopropoxy, phenoxy, phenyl, thienyl, furyl, amino, aminomethyl, dimethylamino, cyano, acetylamino, methoxycarbonyl, —$CH_2$—NH—C(O)—O—$C(CH_3)_3$, or —$O(CH_2)_2$—$R_4$, wherein $R_4$ is methoxy, amino, or —NH—C(O)—O—$C(CH_3)_3$;

$R_3$ is cyano, trifluoromethoxy, trifluoromethylthio, trifluoromethylsulfonyl, trifluoromethylsulfinyl, or pentafluorosulfanyl;

$R_5$ is hydrogen, halo, $C_1$-$C_3$ alkyl, $C_1$-$C_3$ alkoxy, or aminomethyl; and $R_6$ is hydrogen, halo, $C_1$-$C_3$ alkyl, or trifluoromethyl;

or a salt thereof.

Clause 2. The compound of clause 1, or a salt thereof, of the formula Ia:

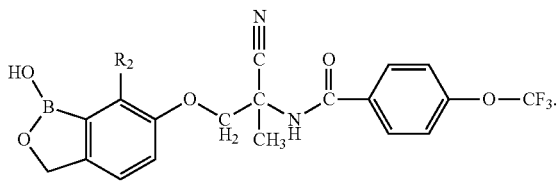

Clause 3. The compound of clause 1 or 2, or a salt thereof, of the formula Ib:

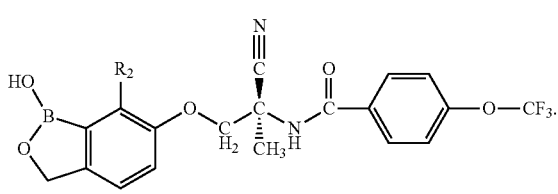

Clause 4. The compound of any of clauses 1-3, or a salt thereof, wherein $R_2$ is selected from the group of bromo, chloro, methyl, ethyl, propyl, isopropyl, cyclopropyl, phenyl, trifluoromethoxy, methoxy, ethoxy, propoxy, and isopropoxy.

Clause 5. The compound of any of clauses 1-4, or a salt thereof, being

N-(2-cyano-1-(1-hydroxy-1,3-dihydrobenzo[c][1,2]oxaborol-6-yloxy)propan-2-yl)-4-(trifluoromethoxy)benzamide;

N-(2-cyano-1-(1-hydroxy-5-(trifluoromethyl)-1,3-dihydrobenzo[c][1,2]oxaborol-6-yloxy)propan-2-yl)-4-(trifluoromethoxy)benzamide;

N-(2-cyano-1-(5-fluoro-1-hydroxy-1,3-dihydrobenzo[c][1,2]oxaborol-6-yloxy)propan-2-yl)-4-(trifluoromethoxy)benzamide;

N-(1-(7-chloro-5-fluoro-1-hydroxy-1,3-dihydrobenzo[c][1,2]oxaborol-6-yloxy)-2-cyanopropan-2-yl)-4-(trifluoromethoxy)benzamide;

N-(2-cyano-1-(5,7-dichloro-1-hydroxy-1,3-dihydrobenzo[c][1,2]oxaborol-6-yloxy)propan-2-yl)-4-(trifluoromethoxy)benzamide;

N-(1-(5-chloro-1-hydroxy-1,3-dihydrobenzo[c][1,2]oxaborol-6-yloxy)-2-cyanopropan-2-yl)-4-(trifluoromethoxy)benzamide;

N-(1-(7-chloro-1-hydroxy-1,3-dihydrobenzo[c][1,2]oxaborol-6-yloxy)-2-cyanopropan-2-yl)-4-(trifluoromethylthio)benzamide;

N-(1-(4-chloro-1-hydroxy-1,3-dihydrobenzo[c][1,2]oxaborol-6-yloxy)-2-cyanopropan-2-yl)-4-(trifluoromethoxy)benzamide;

N-(1-(7-chloro-4,5-difluoro-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-(trifluoromethyl)-1,3-dihydrobenzo[c][1,2]oxaborol-6-yloxy)propan-2-yl)-4-(trifluoromethoxy)benzamide;

N-(2-cyano-1-(4,7-dichloro-1-hydroxy-1,3-dihydrobenzo[c][1,2]oxaborol-6-yloxy) propan-2-yl)-4-(trifluoromethoxy)benzamide;

N-(2-cyano-1-(7-fluoro-1-hydroxy-1,3-dihydrobenzo[c][1,2]oxaborol-6-yloxy)propan-2-yl)-4-(trifluoromethoxy)benzamide;

N-(1-(7-chloro-4-fluoro-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-(2,2,2-trifluoroethyl)-1,3-dihydrobenzo[c][1,2]oxaborol-6-yloxy)propan-2-yl)-4-(trifluoromethoxy)benzamide;

N-(2-cyano-1-(1-hydroxy-7-(2-methoxyethoxy)-1,3-dihydrobenzo[c][1,2]oxaborol-6-yloxy)propan-2-yl)-4-(trifluoromethoxy)benzamide;

tert-butyl 2-(6-(2-cyano-2-(4-(trifluoromethoxy)benzamido)propoxy)-1-hydroxy-1,3-dihydro benzo[c][1,2]oxaborol-7-yloxy)ethylcarbamate;

N-(1-(7-(2-aminoethoxy)-1-hydroxy-1,3-dihydrobenzo[c][1,2]oxaborol-6-yloxy)-2-cyanopropan-2-yl)-4-(trifluoromethoxy)benzamide;

N-(1-amino-3-(7-(2-aminoethoxy)-1-hydroxy-1,3-dihydrobenzo[c][1,2]oxaborol-6-yloxy)-2-methyl-1-oxopropan-2-yl)-4-(trifluoromethoxy)benzamide;

N-(2-cyano-1-(7-cyano-1-hydroxy-1,3-dihydrobenzo[c][1,2]oxaborol-6-yloxy)propan-2-yl)-4-(trifluoromethoxy)benzamide;

N-(2-cyano-1-(1-hydroxy-7-phenoxy-1,3-dihydrobenzo[c][1,2]oxaborol-6-yloxy)propan-2-yl)-4-(trifluoromethoxy)benzamide;

N-(1-(4-(aminomethyl)-1-hydroxy-1,3-dihydrobenzo[c][1,2]oxaborol-6-yloxy)-2-cyanopropan-2-yl)-4-(trifluoromethoxy)benzamide;

N-(1-amino-3-(4-(aminomethyl)-1-hydroxy-1,3-dihydrobenzo[c][1,2]oxaborol-6-yloxy)-2-methyl-1-oxopropan-2-yl)-4-(trifluoromethoxy)benzamide;

N-(2-cyano-1-(1-hydroxy-7-propyl-1,3-dihydrobenzo[c][1,2]oxaborol-6-yloxy)propan-2-yl)-4-(trifluoromethoxy)benzamide;

N-(2-cyano-1-(1-hydroxy-4-methyl-1,3-dihydrobenzo[c][1,2]oxaborol-6-yloxy)propan-2-yl)-4-(trifluoromethoxy)benzamide;

N-(1-(4-(aminomethyl)-7-chloro-1-hydroxy-1,3-dihydrobenzo[c][1,2]oxaborol-6-yloxy)-2-cyanopropan-2-yl)-4-(trifluoromethoxy)benzamide;

N-(1-amino-3-(4-(aminomethyl)-7-chloro-1-hydroxy-1,3-dihydrobenzo[c][1,2]oxaborol-6-yloxy)-2-methyl-1-oxopropan-2-yl)-4-(trifluoromethoxy)benzamide;

N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide;

N-(2-cyano-1-(7-(furan-2-yl)-1-hydroxy-1,3-dihydrobenzo[c][1,2]oxaborol-6-yloxy)propan-2-yl)-4-(trifluoromethoxy)benzamide;

N-(1-(7-acetamido-1-hydroxy-1,3-dihydrobenzo[c][1,2]oxaborol-6-yloxy)-2-cyanopropan-2-yl)-4-(trifluoromethoxy)benzamide;

N-(2-cyano-1-(7-(dimethylamino)-1-hydroxy-1,3-dihydrobenzo[c][1,2]oxaborol-6-yloxy)propan-2-yl)-4-(trifluoromethoxy)benzamide;

tert-butyl (6-(2-cyano-2-(4-(trifluoromethoxy)benzamido)propoxy)-1-hydroxy-1,3-dihydrobenzo[c][1,2]oxaborol-7-yl)methylcarbamate;

N-(1-(7-(aminomethyl)-1-hydroxy-1,3-dihydrobenzo[c][1,2]oxaborol-6-yloxy)-2-cyanopropan-2-yl)-4-(trifluoromethoxy)benzamide;

N-(1-amino-3-(7-(aminomethyl)-1-hydroxy-1,3-dihydrobenzo[c][1,2]oxaborol-6-yloxy)-2-methyl-1-oxopropan-2-yl)-4-(trifluoromethoxy)benzamide;

N-(1-(7-amino-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-iodo-1,3-dihydrobenzo[c][1,2]oxaborol-6-yloxy)propan-2-yl)-4-(trifluoromethoxy)benzamide;

Methyl 6-(2-cyano-2-(4-(trifluoromethoxy)benzamido)propoxy)-1-hydroxy-1,3-dihydrobenzo[c][1,2]oxaborole-7-carboxylate;

N-(2-cyano-1-(1-hydroxy-7-(thiophen-2-yl)-1,3-dihydrobenzo[c][1,2]oxaborol-6-yloxy)propan-2-yl)-4-(trifluoromethoxy)benzamide;

N-(2-cyano-1-(7-cyclopropoxy-1-hydroxy-1,3-dihydrobenzo[c][1,2]oxaborol-6-yl oxy)propan-2-yl)-4-(trifluoromethoxy)benzamide;

N-(1-(7-chloro-1-hydroxy-5-methyl-1,3-dihydrobenzo[c][1,2]oxaborol-6-yloxy)-2-cyanopropan-2-yl)-4-(trifluoromethoxy)benzamide;

N-(2-Cyano-1-(1-hydroxy-4,7-dimethyl-1,3-dihydrobenzo[c][1,2]oxaborol-6-yloxy)-propan-2-yl)-4-(trifluoromethoxy)benzamide;

N-(1-(7-chloro-1-hydroxy-4-methoxy-1,3-dihydrobenzo[c][1,2]oxaborol-6-yloxy)-2-cyanopropan-2-yl)-4-(trifluoromethoxy)benzamide;

N-(1-(7-chloro-1-hydroxy-1,3-dihydrobenzo[c][1,2]oxaborol-6-yloxy)-2-cyanopropan-2-yl)-4-(trifluoromethoxy)benzamide;

N-(1-(7-bromo-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-methyl-1,3-dihydrobenzo[c][1,2]-oxaborol-6-yloxy)propan-2-yl)-4-(trifluoromethoxy)benzamide;

N-(2-cyano-1-(7-ethyl-1-hydroxy-1,3-dihydrobenzo[c][1,2]-oxaborole-6-yloxy)propan-2-yl)-4-(trifluoromethoxy)benzamide;

N-(2-cyano-1-(1-hydroxy-7-methoxy-1,3-dihydrobenzo[c][1,2]oxaborol-6-yloxy)propan-2-yl)-4-(trifluoromethoxy)benzamide;

N-(2-cyano-1-(1-hydroxy-7-isopropyl-1,3-dihydrobenzo[c][1,2]oxaborol-6-yloxy)propan-2-yl)-4-(trifluoromethoxy)benzamide;

N-(1-((7-chloro-1-hydroxy-1,3-dihydrobenzo[c][1,2]oxaborol-6-yl)oxy)-2-cyanopropan-2-yl)-4-((trifluoromethyl)sulfonyl)benzamide;

N-(1-(7-chloro-1-hydroxy-1,3-dihydrobenzo[c][1,2]oxaborol-6-yloxy)-2-cyanopropan-2-yl)-4-(pentafluorothio)benzamide;

N-(1-(7-chloro-1-hydroxy-1,3-dihydrobenzo[c][1,2]oxaborol-6-yloxy)-2-cyanopropan-2-yl)-4-cyanobenzamide;

N-(2-cyano-1-(1-hydroxy-7-phenyl-1,3-dihydrobenzo[c][1,2]oxaborol-6-yloxy)propan-2-yl)-4-(trifluoromethoxy)benzamide; or N-(2-cyano-1-(1-hydroxy-7-propyl-1,3-dihydrobenzo[c][1,2]oxaborol-6-yloxy)propan-2-yl)-4-(trifluoromethoxy)benzamide Clause 6. The compound of any of clauses 1-4, or a salt thereof, being (S)—N-(1-(7-chloro-1-hydroxy-1,3-dihydrobenzo[c][1,2]oxaborol-6-yloxy)-2-cyanopropan-2-yl)-4-(trifluoromethylsulfonyl)benzamide;

(S)—N-(1-((7-chloro-1-hydroxy-1,3-dihydrobenzo[c][1,2]oxaborol-6-yl)oxy)-2-cyanopropan-2-yl)-4-((trifluoromethyl)thio)benzamide;

(S)—N-(1-(7-chloro-1-hydroxy-1,3-dihydrobenzo[c][1,2]oxaborol-6-yloxy)-2-cyanopropan-2-yl)-4-(pentafluorothio)benzamide;

(S)—N-(1-(7-chloro-1-hydroxy-1,3-dihydrobenzo[c][1,2]oxaborol-6-yloxy)-2-cyanopropan-2-yl)-4-cyanobenzamide;

(S)—N-(2-cyano-1-(1-hydroxy-7-phenyl-1,3-dihydrobenzo[c][1,2]oxaborol-6-yloxy) propan-2-yl)-4-(trifluoromethoxy)benzamide; or (S)—N-(2-cyano-1-(1-hydroxy-7-(trifluoromethoxy)-1,3-dihydrobenzo[c][1,2]oxaborol-6-yloxy)propan-2-yl)-4-(trifluoromethoxy)benzamide.

Clause 7. (S)—N-(1-(7-chloro-1-hydroxy-1,3-dihydrobenzo[c][1,2]oxaborol-6-yloxy)-2-cyanopropan-2-yl)-4-(trifluoromethoxy)benzamide, or a salt thereof.

Clause 8. (S)—N-(1-(7-bromo-1-hydroxy-1,3-dihydrobenzo[c][1,2]oxaborol-6-yloxy)-2-cyanopropan-2-yl)-4-(trifluoromethoxy)benzamide, or a salt thereof.

Clause 9. (S)—N-(2-cyano-1-(1-hydroxy-7-methyl-1,3-dihydrobenzo[c][1,2]oxaborol-6-yloxy)propan-2-yl)-4-(trifluoromethoxy)benzamide, or a salt thereof.

Clause 10. (S)—N-(2-cyano-1-(7-ethyl-1-hydroxy-1,3-dihydrobenzo[c][1,2]oxaborol-6-yloxy)propan-2-yl)-4-(trifluoromethoxy)benzamide, or a salt thereof.

Clause 11. (S)—N-(2-cyano-1-(1-hydroxy-7-methoxy-1,3-dihydrobenzo[c][1,2]oxaborol-6-yloxy)propan-2-yl)-4-(trifluoromethoxy)benzamide, or a salt thereof.

Clause 12. (S)—N-(2-cyano-1-(1-hydroxy-7-isopropyl-1,3-dihydrobenzo[c][1,2]oxaborol-6-yloxy)propan-2-yl)-4-(trifluoromethoxy)benzamide, or a salt thereof.

Clause 13. (S)—N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide, or a salt thereof.

Clause 14. N-(2-cyano-1-(7-cyclopropyl-1-hydroxy-1,3-dihydrobenzo[c][1,2]oxaborol-6-yloxy)propan-2-yl)-4-(trifluoromethoxy)benzamide, or a salt thereof.

Clause 15. N-[1-cyano-2-(7-ethoxy-1-hydroxy-1,3-dihydrobenzo[c][1,2]oxaborol-6-yloxy)-1-methyl-ethyl]-4-trifluoromethoxy-benzamide, or a salt thereof.

Clause 16. N-(2-cyano-1-(1-hydroxy-7-isopropoxy-1,3-dihydrobenzo[c][1,2]oxaborol-6-yloxy)propan-2-yl)-4-(trifluoromethoxy)benzamide, or a salt thereof.

Clause 17. N-(2-cyano-1-(1-hydroxy-7-(trifluoromethoxy)-1,3-dihydrobenzo[c][1,2]oxaborol-6-yloxy)propan-2-yl)-4-(trifluoromethoxy)benzamide, or a salt thereof.

Clause 18. N-(1-(7-chloro-1-hydroxy-1,3-dihydrobenzo[c][1,2]oxaborol-6-yloxy)-2-cyanopropan-2-yl)-4-(trifluoromethoxy)benzamide, or a salt thereof.

Clause 19. N-(1-(7-bromo-1-hydroxy-1,3-dihydrobenzo[c][1,2]oxaborol-6-yloxy)-2-cyanopropan-2-yl)-4-(trifluoromethoxy)benzamide, or a salt thereof.

Clause 20. N-(2-cyano-1-(7-ethyl-1-hydroxy-1,3-dihydrobenzo[c][1,2]-oxaborole-6-yloxy)propan-2-yl)-4-(trifluoromethoxy)benzamide, or a salt thereof.

Clause 21. N-(2-cyano-1-(1-hydroxy-7-methoxy-1,3-dihydrobenzo[c][1,2]oxaborol-6-yloxy)propan-2-yl)-4-(trifluoromethoxy)benzamide, or a salt thereof.

Clause 22. N-(2-cyano-1-(1-hydroxy-7-isopropyl-1,3-dihydrobenzo[c][1,2]oxaborol-6-yloxy)propan-2-yl)-4-(trifluoromethoxy)benzamide, or a salt thereof.

Clause 23. N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide, or a salt thereof.

Clause 24. The compound of any of clauses 1-23, or salt thereof, wherein it is a pharmaceutically acceptable salt thereof.

Clause 25 A formulation comprising the compound, or salt thereof, of any of clauses 1-24, and at least one acceptable carrier.

Clause 26. The formulation of clause 25 wherein said formulation further comprises at least one additional active ingredient.

Clause 27. The formulation of clause 25 or 26, wherein said formulation is a human pharmaceutical formulation.

Clause 28. The formulation of clause 25 or 26, wherein said formulation is a veterinary pharmaceutical formulation.

Clause 29. A method of controlling an endoparasite infestation in or on an animal in need thereof comprising administering an effective amount of the compound, or salt thereof, of any of clauses 1-24 to said animal.

Clause 30. The method of clause 29, wherein at least one other active ingredient is administered to said animal.

Clause 31. The method of clause 29 or 30, wherein said animal is a human.

Clause 32. The method of clause 29 or 30, wherein said animal is a companion animal.

Clause 33. The method of clause 32, wherein said companion animal is a dog, cat, or horse.

Clause 34. The method of clause 29 or 30, wherein said animal is a livestock animal.

Clause 35. The method of clause 34, wherein said livestock animal is a cow or a sheep.

Clause 36. The method of any of clauses 29-35, wherein said endoparasite is a helminth.

Clause 37. A method for preventing or treating diseases transmitted through endoparasites, comprising administering an effective amount of a compound, or salt thereof, of any of clauses 1-24 to an animal in need thereof.

Clause 38. The method of clause 37, wherein at least one additional active ingredient is administered to said animal.

Clause 39. The method of clause 37 or 38, wherein said animal is a human.

Clause 40. The method of clause 37 or 38, wherein said animal is a companion animal.

Clause 41. The method of clause 40, wherein said companion animal is a dog, cat, or horse.

Clause 42. The method of clause 37 or 38, wherein said animal is a livestock animal.

Clause 43. The method of clause 42, wherein said livestock animal is a cow or a sheep.

Clause 44. The method of any of clauses 37-43, wherein said endoparasite is a helminth.

Clause 45. A method for controlling endoparasite pests, characterized in that the compound, or salt thereof, of any of clauses 1-24 is allowed to act on the pests or their habitat, or both.

Clause 46. The method of clause 45 wherein the compound, or salt thereof, is placed on a plant or an animal.

Clause 47. Use of the compound, or salt thereof, of any of clauses 1-24, for controlling endoparasites.

Clause 48. The compound, or salt thereof, of any of clauses 1-24, for use in therapy.

Clause 49. The compound, or salt thereof, of any of clauses 1-24, for use in controlling an endoparasite infestation.

Clause 50. A compound of the formula XXI:

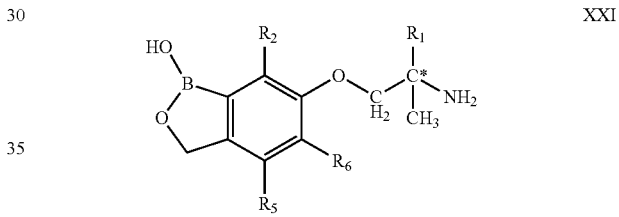

XXI wherein C* is a carbon atom which is a stereocenter having a configuration which is (R) or (S);

$R_2$ is hydrogen, halo, $C_1$-$C_3$ alkyl, $C_1$-$C_3$ alkyl substituted 1-3 times with halo, $C_1$-$C_3$ alkoxy, $C_1$-$C_3$ alkoxy substituted 1-3 times with halo, cyclopropyl, cyclopropoxy, phenoxy, phenyl, thienyl, furyl, amino, aminomethyl, dimethylamino, cyano, acetylamino, methoxycarbonyl, —$CH_2$—NH—C(O)—O—C($CH_3$)$_3$, or —O($CH_2$)$_2$—$R_4$, wherein $R_4$ is methoxy, amino, or —NH—C(O)—O—C($CH_3$)$_3$;

$R_5$ is hydrogen, halo, $C_1$-$C_3$ alkyl, $C_1$-$C_3$ alkoxy, or aminomethyl; and $R_6$ is hydrogen, halo, $C_1$-$C_3$ alkyl, or trifluoromethyl; or a salt thereof.

Clause 51. A compound of the formula XXII:

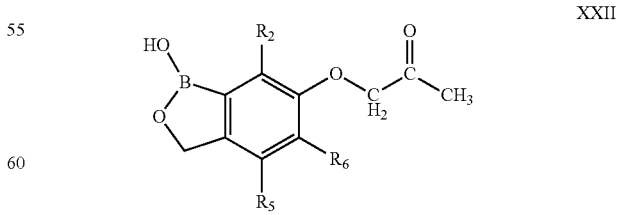

XXII wherein $R_2$ is hydrogen, halo, $C_1$-$C_3$ alkyl, $C_1$-$C_3$ alkyl substituted 1-3 times with halo, $C_1$-$C_3$ alkoxy, $C_1$-$C_3$ alkoxy substituted 1-3 times with halo, cyclopropyl, cyclopropoxy, phenoxy, phenyl, thienyl, furyl, amino, aminomethyl, dimethylamino, cyano, acetylamino, methoxycarbonyl, —CH$_2$—NH—C(O)—O—C(CH$_3$)$_3$, or —O(CH$_2$)$_2$—R$_4$, wherein R$_4$ is methoxy, amino, or —NH—C(O)—O—C(CH$_3$)$_3$;

R$_5$ is hydrogen, halo, C$_1$-C$_3$ alkyl, C$_1$-C$_3$ alkoxy, or aminomethyl; and R$_6$ is hydrogen, halo, C$_1$-C$_3$ alkyl, or trifluoromethyl; or a salt thereof.

Clause 52. The compound, or salt thereof, of clause 50 or 51, wherein R$_2$ is selected from the group of bromo, chloro, methyl, ethyl, propyl, isopropyl, cyclopropyl, phenyl, trifluoromethoxy, methoxy, ethoxy, propoxy, and isopropoxy.

Clause 53. The compound, or salt thereof, of any of clauses 50-52, wherein R$_5$ and R$_6$ are each hydrogen.

Clause 54. The compound of clause 53, or a salt thereof, which is 2-amino-3-(7-bromo-1-hydroxy-1,3-dihydrobenzo[c][1,2]oxaborol-6-yloxy)-2-methylpropanenitrile;
2-amino-3-(7-chloro-1-hydroxy-1,3-dihydrobenzo[c][1,2]oxaborol-6-yloxy)-2-methylpropanenitrile;
2-amino-3-(7-methyl-1-hydroxy-1,3-dihydrobenzo[c][1,2]oxaborol-6-yloxy)-2-methylpropanenitrile;
2-amino-3-(7-ethyl-1-hydroxy-1,3-dihydrobenzo[c][1,2]oxaborol-6-yloxy)-2-methylpropanenitrile;
2-amino-3-(7-propyl-1-hydroxy-1,3-dihydrobenzo[c][1,2]oxaborol-6-yloxy)-2-methylpropanenitrile;
2-amino-3-(7-isopropyl-1-hydroxy-1,3-dihydrobenzo[c][1,2]oxaborol-6-yloxy)-2-methylpropanenitrile;
2-amino-3-(7-cyclopropyl-1-hydroxy-1,3-dihydrobenzo[c][1,2]oxaborol-6-yloxy)-2-methylpropanenitrile;
2-amino-3-(7-phenyl-1-hydroxy-1,3-dihydrobenzo[c][1,2]oxaborol-6-yloxy)-2-methylpropanenitrile;
2-amino-3-(7-trifluoromethoxy-1-hydroxy-1,3-dihydrobenzo[c][1,2]oxaborol-6-yloxy)-2-methylpropanenitrile;
2-amino-3-(7-methoxy-1-hydroxy-1,3-dihydrobenzo[c][1,2]oxaborol-6-yloxy)-2-methylpropanenitrile
2-amino-3-(7-ethoxy-1-hydroxy-1,3-dihydrobenzo[c][1,2]oxaborol-6-yloxy)-2-methylpropanenitrile; or
2-amino-3-(7-propoxy-1-hydroxy-1,3-dihydrobenzo[c][1,2]oxaborol-6-yloxy)-2-methylpropanenitrile.

Clause 55. The compound, or salt thereof, of clause 53, which is 1-((7-bromo-1-hydroxy-1,3-dihydrobenzo[c][1,2]oxaborol-6-yl)oxy)propan-2-one;
1-((7-chloro-1-hydroxy-1,3-dihydrobenzo[c][1,2]oxaborol-6-yl)oxy)propan-2-one;
1-((7-methyl-1-hydroxy-1,3-dihydrobenzo[c][1,2]oxaborol-6-yl)oxy)propan-2-one;
1-((7-ethyl-1-hydroxy-1,3-dihydrobenzo[c][1,2]oxaborol-6-yl)oxy)propan-2-one;
1-((7-propyl-1-hydroxy-1,3-dihydrobenzo[c][1,2]oxaborol-6-yl)oxy)propan-2-one;
1-((7-isopropyl-1-hydroxy-1,3-dihydrobenzo[c][1,2]oxaborol-6-yl)oxy)propan-2-one;
1-((7-cyclopropyl-1-hydroxy-1,3-dihydrobenzo[c][1,2]oxaborol-6-yl)oxy)propan-2-one;
1-((7-phenyl-1-hydroxy-1,3-dihydrobenzo[c][1,2]oxaborol-6-yl)oxy)propan-2-one;
1-((7-trifluoromethoxy-1-hydroxy-1,3-dihydrobenzo[c][1,2]oxaborol-6-yl)oxy)propan-2-one;
1-((7-methoxy-1-hydroxy-1,3-dihydrobenzo[c][1,2]oxaborol-6-yl)oxy)propan-2-one;
1-((7-ethoxy-1-hydroxy-1,3-dihydrobenzo[c][1,2]oxaborol-6-yl)oxy)propan-2-one; or
1-((7-propoxy-1-hydroxy-1,3-dihydrobenzo[c][1,2]oxaborol-6-yl)oxy)propan-2-one.

The following abbreviations have been used: AcOH is acetic acid; aq. is aqueous; Ar is argon; BnBr is benzyl bromide; Boc is tert-butoxy carbonyl; Boc$_2$O is di-tert-butyl dicarbonate; Cs$_2$CO$_3$ is cesium carbonate; DCM is dichloromethane or methylene chloride; DHP is dihydropyran; DIEA or DIPEA is N,N-diisopropylethylamine; DMAP is 4-(dimethylamino)pyridine; DMF is N,N-dimethylformamide; DMSO is dimethylsulfoxide; EtOAc is ethyl acetate; EA is ethyle amine; EtOH is ethanol; Et$_2$O is diethyl ether; equiv or eq is equivalent; h is hours; HATU is O-(7-azabenzotriazol-1-yl)-N,N,N',N'-tetramethyluronium hexafluorophosphate; HCl is hydrochloric acid; HPLC is high pressure liquid chromatography; KOAc or AcOK is potassium acetate; K$_2$CO$_3$ is potassium carbonate; LiAlH$_4$ or LAH is lithium aluminum hydride; LDA is lithium diisopropylamide; MeCN or ACN is methyl cyanide or cyanomethane or ethanenitrile or acetonitrile which are all names for the same compound; MeOH is methanol; METB is methyl tertiary butyl ether; MgSO$_4$ is magnesium sulfate; mins or min is minutes; NMP is N-Methyl-2-pyrrolidone; NaOH is sodium hydroxide; Na$_2$SO$_4$ is sodium sulfate; NBS is N-bromosuccinimide; NH$_4$Cl is ammonium chloride; NIS is N-iodosuccinimide; N$_2$ is nitrogen; n-BuLi is n-butyllithium; overnight is O/N; PdCl$_2$(pddf) is 1,1'-Bis(diphenylphosphino)ferrocene]dichloropalladium(II); Pd/C is the catalyst known as palladium on carbon; POCl$_3$ is phosphorus chloride oxide; RT or rt or r.t. is rt; sat. is saturated; SFC is supercritical fluid chromatography; TEA or Et$_3$N is triethylamine; TFA is trifluoroacetic acid; Tf$_2$O is trifluoromethanesulfonic anhydride; and THF is tetrahydrofuran.

EXAMPLE 1

(S)—N-(1-(7-chloro-1-hydroxy-1,3-dihydrobenzo[c][1,2]oxaborol-6-yloxy)-2-cyanopropan-2-yl)-4-(trifluoromethoxy)benzamide

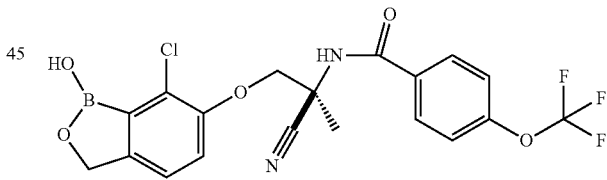

To a solution of 2-bromo-4-fluorobenzaldehyde (250 g, 1.23 mol) in methanol (MeOH) (1000 mL) is added NaBH$_4$ (93 g, 2.46 mol) at 0° C. in portions and the resulting solution is slowly warmed to rt with a stirring overnight. MeOH is evaporated and the residue is dissolved in EtOAc, washed with water, dried over MgSO$_4$ to provide the desired alcohol (240 g, 1.17 mol, yield 95%) as white solid. $^1$H NMR (400 MHz, CDCl$_3$): δ7.49 (m, 1H), 7.33 (m, 1H), 7.09 (m, 1H), 4.73 (s, 2H), 2.14 (s, 1H) ppm.

A mixture of (2-bromo-4-fluorophenyl)methanol (250 g, 1.22 mol) and 3,4-dihydro-2H-pyran (205 g, 2.44 mol) is dissolved in DCM (2000 mL). To this solution is added pyridinium p-toluenesulfonate (15 g, 0.06 mol). The resulting solution is stirred overnight at rt and then treated with saturated NaHCO$_3$. After extraction with EtOAc, the organic layer is washed with water and brine, dried, concentrated and purified by column chromatography over silica gel to provide the product of this step (281 g, yield 80%) as colorless oil.

To a solution of benzyl alcohol (73 g, 0.675 mol) in DMF (300 ml) is added NaH (36 g, 0.9 mol) at rt in portions and the resulting solution is stirred for 1 h. Then 2-((2-bromo-4-fluorobenzyl)oxy)tetrahydro-2H-pyran (130 g, 0.45 mol) in DMF (500 mL) is added to the mixture at rt and stirred for another 1 h. The reaction mixture is heated at 60-80° C. for 30 min then treated with cold water. The mixture is extracted with MTBE, washed with water, dried over MgSO$_4$ and purified by column chromatography over silica gel eluted with petroleum ether to provide the product of this step (140 g, 83%) as colorless oil.

To the solution of 2-((4-(benzyloxy)-2-bromobenzyl)oxy) tetrahydro-2H-pyran (117 g, 0.31 mol) in dry THF (2000 mL) at −78° C. under nitrogen is added 2.5M n-BuLi (160 mL, 0.357 mol) dropwise. The mixture is stirred for 60 min at −78° C. and followed by addition of B(iPrO)$_3$ (76 g, 0.403 mol) dropwise at −78° C. The mixture is allowed to warm to rt gradually and stirred overnight at rt. After 6N HCl is added to the solution adjusting pH=3, the mixture is stirred for 2 h, evaporated, extracted with EtOAc and dried over Na$_2$SO$_4$. The residue after rotary evaporation is purified by recrystallization to give the desired compound.

To the solution of 6-(benzyloxy)benzo[c][1,2]oxaborol-1 (3H)-ol (50 g, 208 mmol) in EtOAc (800 mL) under nitrogen is added Pd(OH)$_2$ (5 g). The reaction mixture is vacuumed and back-filled with hydrogen for three times, and then hydrogenated at 60° C. and 50 psi overnight. After filtration and rotary evaporation, the residue is purified by recrystallization to give the desired compound.

To benzo[c][1,2]oxaborole-1,6(3H)-diol (2.5 g, 16.7 mmol) in DCM (100 mL) and DMF (10 mL) is added NCS (2.4 g, 18.3 mmol). The reaction mixture is stirred overnight, concentrated and purified by column chromatography to give the desired product as white solid (2.1 g; yield 84%).

To a suspension of 7-chlorobenzo[c][1,2]oxaborole-1,6 (3H)-diol (10 g, 54.3 mmol), K$_2$CO$_3$ (19 g, 136 mmol) in acetone (200 mL) is added 1-chloropropan-2-one (15 g, 143 mmol). The reaction mixture is refluxed for 4 h, cooled to rt, partitioned between
EtOAc and H$_2$O, extracted with EtOAc (3×200 mL). The combined organic layer is washed with brine, dried over Na$_2$SO$_4$, concentrated under reduced pressure to give the residue, which is recrystallized to give the desired product as off-white solid (9.4 g, yield 72%).

To a mixed solution of 1-((7-chloro-1-hydroxy-1,3-dihydrobenzo[c][1,2]oxaborol-6-yl)oxy)propan-2-one (10 g, 41.7 mmol), NH$_4$Cl (4.4 g, 83.4 mmol) and ammonia in methanol (100 mL) is added NaCN (3.1 g, 62.5 mmol), and the mixture is stirred at rt overnight. The reaction is partitioned between EtOAc and H$_2$O, extracted with EtOAc (200 mL×3), washed with brine, dried over Na$_2$SO$_4$ and concentrated under reduced pressure to give the desired compound as a pale yellow solid (5.3 g, yield 48%).

A mixture of 2-amino-3-(7-chloro-1-hydroxy-1,3-dihydrobenzo[c][1,2]oxaborol-6-yloxy)-2-methylpropanenitrile (4.0 g, 15 mmol), 4-(trifluoromethoxy)benzoic acid (3.4 g, 16 mmol), HATU (6.8 g, 18 mmol) and DIPEA (5.8 g, 45 mmol) in DMF (20 mL) is stirred overnight at rt. The reaction is partitioned between EtOAc and H$_2$O, extracted with EtOAc (100 mL×3), washed with brine (100 mL×2), dried by Na$_2$SO$_4$, concentrated under reduced pressure and purified by column chromatography to give the desired product N-(1-(7-chloro-1-hydroxy-1,3-dihydrobenzo[c][1,2]oxaborol-6-yloxy)-2-cyanopropan-2-yl)-4-(trifluoromethoxy)benzamide (designated as Example 1a) as white solid (4.1 g, yield 60%). $^1$H NMR (DMSO-d$_6$, 400 MHz): δ 9.15 (s, 1H), 9.09 (s, 1H), 7.99 (d, J=8.0 Hz, 2H), 7.51 (d, J=8.0 Hz, 2H), 7.33 (m, 2H), 4.93 (s, 2H), 4.59 (d, J=9.2 Hz, 1H), 4.39 (d, J=9.2 Hz, 1H), 1.87 (s, 3H) ppm. HPLC purity: 98.5% at 220 nm and 97.1% at 254 nm MS: m/z=455 (M+1).

The chiral enantiomer, (S)—N-(1-(7-chloro-1-hydroxy-1,3-dihydrobenzo[c][1,2]oxaborole-6-yloxy)-2-cyanopropan-2-yl)-4-(trifluoromethoxy)benzamide, is obtained from its racemic mixture N-(1-(7-chloro-1-hydroxy-1,3-dihydrobenzo[c][1,2]oxaborol-6-yloxy)-2-cyanopropan-2-yl)-4-(trifluoromethoxy)benzamide (4.8 g) by using chiral supercritical fluid chromatography (SFC, column: Chiralpak AD-H, 250×30 mm i.d; 35% methanol/CO$_2$; flow rate: 62 g/min; injection amount: 50 mg/injection). The solvent of the desired chiral chromatography peak 1 fractions is removed and then freeze-dried to give the desired enantiomer (1.92 g, yield 80%) as white solid. $^1$H NMR (DMSO-d$_6$, 400 MHz): δ 9.17 (s, 1H), 9.10 (s, 1H), 7.99 (d, J=8.4 Hz, 2H), 7.51 (d, J=8.4 Hz, 2H), 7.34 (s, 2H), 4.93 (s, 2H), 4.58 (d, J=9.2 Hz, 1H), 4.39 (d, J=9.2 Hz, 1H), 1.87 (s, 3H) ppm. MS: m/z=455 (M+1). HPLC purity: 97.37% at 220 nm and 97.85% at 254 nm Chiral HPLC purity: 99.9%. Specific rotation: [α]=+10.6° in CH$_2$Cl$_2$ at 20° C.

EXAMPLE 2

(S)—N-(1-(7-bromo-1-hydroxy-1,3-dihydrobenzo[c][1,2]oxaborol-6-yloxy)-2-cyanopropan-2-yl)-4-(trifluoromethoxy)benzamide

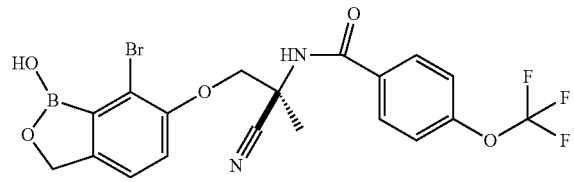 [SMILES: C[C@](C#N)(COc1ccc2c(c1Br)B(O)OC2)NC(=O)c1ccc(OC(F)(F)F)cc1]

A mixture of benzo[c][1,2]oxaborole-1,6(3H)-diol (1.9 g, 12.6 mmol) and NBS (2.2 g, 12.6 mmol) in DCM (100 mL) and DMF (20 mL) is stirred at rt overnight. The resulting mixture is concentrated by rotary evaporator. The residue is dissolved in EtOAc, washed with water and brine, dried over Na$_2$SO$_4$ and concentrated to dryness. The residue is triturated with EtOAc/DCM/Petroleum ether (20 mL×2, 1/1/10) to give the desired product as a white solid (2.0 g, yield 69.0%).

To a stirring solution of 7-bromobenzo[c][1,2]oxaborole-1,6(3H)-diol (2.4 g, 10.5 mmol) in DMF (30 mL) is slowly added NaH (840 mg, 21 mmol) at 0° C. and the mixture is stirred for 30 min. Then bromoacetone (2.9 g, 21 mmol) is added slowly. After addition, the resulting mixture is stirred at 0° C. for 2 h and at rt for 4 h. The mixture is poured into water, acidified with 1N HCl solution and extracted with EtOAc. The separated organics are dried, concentrated and the residue is purified by recrystallization from EtOAc/Petroleum ether (1/3) to give the desired product (2 g, yield 67%).

A mixture of 1-(7-bromo-1-hydroxy-1,3-dihydrobenzo[c][1,2]oxaborol-6-yloxy)propan-2-one (4.2 g, 14.7 mmol), NH$_4$Cl (1.97 g, 36.8 mmol) and NaCN (1.44 g, 29.4 mmol) in EtOH/NH$_3$.H$_2$O (80 mL/80 mL) is stirred at rt for 4 h. The reaction solution is carefully neutralized with concentrated HCl. The mixture is extracted with EtOAc. The organic layer is dried, concentrated and the residue is purified a residue by recrystallization from EtOAc/PE (1/3) to give the desired product (3.5 g, yield 78%).

To the mixture of 2-amino-3-(7-bromo-1-hydroxy-1,3-dihydrobenzo[c][1,2]oxaborol-6-yloxy)-2-methylpropanenitrile (2.5 g, 8.0 mmol) and DIPEA (2.1 g, 16 mmol) in dry THF (200 mL) is added dropwise at 0° C. a THF solution of 4-trifluoromethoxybenzoyl chloride (1.8 g, 8.0 mmol, in 20 mL THF), which is freshly prepared from its carboxylic acid and $SOCl_2$. After addition, the resulting mixture is slowly warmed to rt and stirred for 2 h before adding diluted HCl solution. The separated organics is dried and concentrated to give a residue, which is purified by silica gel chromatography (DCM: MeOH=100:1 to 30:1) and reverse phase preparative HPLC to give N-(1-(7-bromo-1-hydroxy-1,3-dihydrobenzo[c][1,2]oxaborol-6-yloxy)-2-cyanopropan-2-yl)-4-(trifluoromethoxy)benzamide (designated as Example 2a) (2.0 g, yield 50%). $^1$H NMR (400 MHz, DMSO-$d_6$): δ 9.08 (s, 1H), 9.05 (s, 1H), 7.98 (d, 2H, J=12 Hz), 7.49 (d, 2H, J=8.0 Hz), 7.35 (d, 1H, J=8.0 Hz), 7.27 (d, 1H, J=8.0 Hz), 4.92 (s, 2H), 4.58 (d, 1H, J=9.2 Hz), 4.38 (d, 1H, J=9.2 Hz), 1.88 (s, 3H) ppm. HPLC purity: 96.8% at 220 nm and 95.3% at 254 nm MS: m/z=497 and 499 [M−1]$^−$ By following the procedure described in Example 1, the racemic mixture is separated to collect peak 1 giving the chiral enantiomer (S)—N-(1-(7-bromo-1-hydroxy-1,3-dihydrobenzo[c][1,2]oxaborole-6-yloxy)-2-cyanopropan-2-yl)-4-(trifluoromethoxy)benzamide. $^1$H NMR: (DMSO-d6, 400 MHz): δ 9.10 (s, 1H), 9.07 (s, 1H), 8.00 (d, 2H, J=8.6 Hz), 7.51 (d, 2H, J=8.6 Hz), 7.34 (d, 1H, J=8.0 Hz), 7.27 (d, 1H, J=8.0 Hz), 4.92 (s, 2H), 4.58 (d, 1H, J=9.2 Hz), 4.38 (d, 1H, J=9.2 Hz), 1.88 (s, 3H) ppm. HPLC purity: 98.0% at 220 nm and 97.5% at 254 nm MS: m/z=499 and 501 [M+1]$^+$. Chiral HPLC purity: 100%.

EXAMPLE 3

(S)—N-(2-cyano-1-(1-hydroxy-7-methyl-1,3-dihydrobenzo[c][1,2]oxaborol-6-yloxy)propan-2-yl)-4-(trifluoromethoxy)benzamide

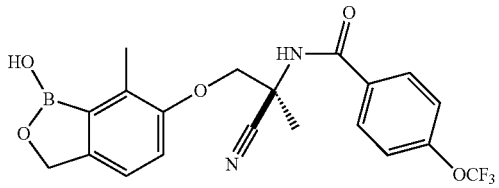 [SMILES: Cc1c(OC[C@](C)(C#N)NC(=O)c2ccc(OC(F)(F)F)cc2)ccc2c1B(O)OC2]

Phosphorous oxychloride (8.3 mL, 89 mmol) is added dropwise to DMF (25 mL) stirring at 0° C. in a round-bottom flask under $N_2$ atmosphere. The mixture is then transferred via cannula to a solution of 2-methylresorcinol (5 g, 40.3 mmol) in DMF (25 mL) stirring at 0° C. in a round-bottom flask under $N_2$ atmosphere. The mixture is stirred for 1.5 h, then slowly warming to rt. The mixture is cooled to 0° C. and quenched with 2N NaOH until pH=6. The mixture is extracted with ethyl acetate (3×150 mL) and the organic layers are dried over $Na_2SO_4$, filtered and concentrated under reduced pressure. The resulting residue is washed with DCM (2×20 mL) to give the desired product (3.7 g, yield 60%) as a yellow solid.

A mixture of 2,4-dihydroxy-3-methylbenzaldehyde (5.0 g, 19.7 mmol), $NaHCO_3$ (1.89 g, 22.46 mmol) and KI (654 mg, 3.94 mmol) in MeCN (50 mL) is slowly heated to 60° C. At this time, BnBr (2.8 mL, 23.7 mmol) is added. The mixture is stirred overnight at 80° C. The mixture is cooled to rt and the solvent is evaporated. The residue is quenched with 10% aqueous HCl to pH=6 and extracted with EA (150 mL*2). The combined organic extracts are washed with brine (50 mL*2), dried over $Na_2SO_4$, filtered and concentrated under reduced pressure. The residue is purified by column chromatography on silica gel eluted with PE-EA (10:1) to give the desired product (2.7 g, yield: 57%) as a light yellow solid.

To a solution of 4-(benzyloxy)-2-hydroxy-3-methylbenzaldehyde (1.2 g, 4.96 mmol) and $Et_3N$ (2.1 mL, 14.9 mmol) in DCM (30 mL) at 0° C. is added dropwise $(Tf)_2O$ (1.6 mL, 9.9 mmol) in DCM (10 mL). The reaction mixture is stirred at rt for 2 h. Water (50 mL) is added and the mixture is extracted with DCM (50 mL*2). The combined organic extracts are washed with brine, dried over $Na_2SO_4$, filtered and concentrated under reduced pressure. The residue is purified by column chromatography on silica gel eluted with PE-EA (10:1) to give the desired product (1.25 g, yield 67%) as a yellow solid.

To a solution of 3-(benzyloxy)-6-formyl-2-methylphenyl-trifluoromethanesulfonate (1.8 g, 4.8 mmol), $Pin_2B_2$ (3.7 g, 14.4 mmol) and KOAc (941 mg, 9.6 mmol) in 1,4-dioxane (180 mL) is added $PdCl_2(dppf)_2$ (351 mg, 0.48 mmol). The reaction mixture is stirred at 80° C. under argon atmosphere overnight. The solvent is removed and the residue is purified by column chromatography on silica gel eluted with PE-EA (10:1) to give the desired product (900 mg, yield 53%) as a yellow solid.

To a solution of 4-(benzyloxy)-3-methyl-2-(4,4,5,5-tetramethyl-1,3,2-dioxaborolan-2-yl)benzaldehyde (588 mg, 1.67 mmol) in THF (30 mL) is added $NaBH_4$ (63 mg, 1.67 mmol). The reaction mixture is stirred at rt for 2 h, then it is slowly added 3N HCl to pH=1. The reaction mixture is stirred at rt overnight. The solvent is evaporated, and the residue is purified by column chromatography on silica gel eluted with PE-EA (5:1) to give the desired product (350 mg, yield 83%) as a white solid.

The solution of 6-(benzyloxy)-7-methylbenzo[c][1,2]oxaborol-1(3H)-ol (350 mg, 1.38 mmol) in MeOH (15 mL) is hydrogenated using 10% Pd/C (88 mg, 0.083 mmol) as catalyst under atmospheric pressure overnight. The catalyst is removed by filtration on Celite and the solvent is evaporated under reduced pressure. The residue is purified by column chromatography on silica gel eluted with PE-EA (2:1) to give the desired product (200 mg, yield 88%) as a white solid.

To a mixture of 7-methylbenzo[c][1,2]oxaborole-1,6(3H)-diol (100 mg, 0.61 mmol) and $K_2CO_3$ (252 mg, 1.83 mmol) in acetone (20 mL) is added bromoacetone (125 mg, 0.91 mmol). The reaction mixture is refluxed for 3 h. The solvent is evaporated under reduced pressure. The residue is purified by column chromatography on silica gel eluted with PE-EA (3:1) to give the desired product (100 mg, yield 78%) as a white solid.

A mixture of 1-(1-hydroxy-7-methyl-1,3-dihydrobenzo[c][1,2]oxaborol-6-yloxy)propan-2-one (100 mg, 0.45 mmol), $NH_4Cl$ (36 mg, 0.675 mmol) and ammonia (7N in methanol, 3 mL) in MeOH (3 mL) is stirred at rt for 20 min before addition of NaCN (46 mg, 0.91 mmol). The reaction mixture is stirred at rt for 5 h. DCM (50 mL) is added and the solvent is removed under reduced pressure. The residue is extracted with THF, and THF is evaporated to give the desired product (crude) as a white solid (140 mg). It is used to next step without further purification.

A solution of 4-(trifluoromethoxy)benzoic acid (94 mg, 0.45 mmol), HATU (346 mg, 0.91 mmol) and DIPEA (175 mg, 1.36 mmol) in DMF (3 mL) is stirred at rt for 30 min. Then 2-amino-3-(1-hydroxy-7-methyl-1,3-dihydrobenzo[c][1,2]oxaborol-6-yloxy)-2-methylpropanenitrile (140 mg, crude, 0.45 mmol) is added. The reaction mixture is stirred at rt overnight. It is purified by prep-HPLC to give N-(2-cyano-1-(1-hydroxy-7-methyl-1,3-dihydrobenzo[c][1,2]oxaborol-6-yloxy)propan-2-yl)-4-(trifluoromethoxy)benzamide (designated as Example 3a) (69 mg, yield 35% over two steps) as a white solid. $^1$H NMR (500 MHz, DMSO-d$_6$): δ 9.07 (s, 1H), 8.97 (s, 1H), 8.00 (d, J=8.0 Hz, 2H), 7.52 (d, J=8.0 Hz, 2H), 7.17 (d, J=8.0 Hz, 1H), 7.10 (d, J=8.0 Hz, 1H), 4.89 (s, 2H), 4.48 (d, J=9.5 Hz, 1H), 4.26 (d, J=9.0 Hz, 1H), 2.35 (s, 3H), 1.85 (s, 3H) ppm; HPLC purity: 98.56% at 214 nm and 100% at 254 nm; MS: m/z=435.0 (M+1, ESI+).

By following the procedure described in Example 1, the racemic mixture is separated to collect peak 1 giving the chiral enantiomer (S)—N-(2-cyano-1-(1-hydroxy-7-methyl-1,3-dihydrobenzo[c][1,2]oxaborol-6-yloxy)propan-2-yl)-4-(trifluoromethoxy)benzamide. $^1$H NMR (400 MHz, DMSO-d$_6$): δ 9.08 (s, 1H), 8.97 (s, 1H), 8.00 (d, J=8.0 Hz, 2H), 7.52 (d, J=8.0 Hz, 2H), 7.17 (d, J=8.0 Hz, 1H), 7.10 (d, J=8.0 Hz, 1H), 4.90 (s, 2H), 4.48 (d, J=9.5 Hz, 1H), 4.26 (d, J=9.0 Hz, 1H), 2.35 (s, 3H), 1.85 (s, 3H) ppm; HPLC purity: 100% at 214 nm and 100% at 254 nm; Chiral HPLC purity: 100%; MS: m/z=435.1 (M+1, ESI+).

EXAMPLE 4

(S)—N-(2-cyano-1-(7-ethyl-1-hydroxy-1,3-dihydrobenzo[c][1,2]oxaborol-6-yloxy)propan-2-yl)-4-(trifluoromethoxy)benzamide

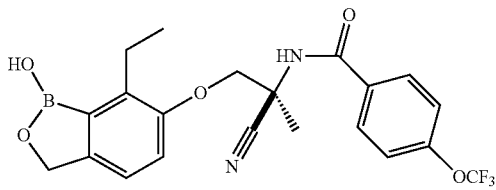 [SMILES: CCc1c(OC[C@](C)(C#N)NC(=O)c2ccc(OC(F)(F)F)cc2)ccc2c1B(O)OC2]

A. Preparation of 1-(7-ethyl-1-hydroxy-1,3-dihydrobenzo[c][1,2]oxaborol-6-yloxy)propan-2-one 1-(7-ethyl-1-hydroxy-1,3-dihydrobenzo[c][1,2]oxaborol-6-yloxy)-propan-2-one may be prepared using the one of the following procedures 1, 2a, and 2b.

Procedure 1. To a solution of 1-(2,6-dihydroxyphenyl)ethanone (10 g, 65.79 mmol) in 200 mL of CF$_3$COOH is added Et$_3$SiH (21 mL, 131.58 mmol) dropwise. The reaction mixture is stirred for 3 h and the solvent is evaporated. Water is added and extracted with EA (200 mL*2). The combined organic extracts are washed with brine (50 mL*2), dried over Na$_2$SO$_4$, filtered and concentrated under reduced pressure. The residue is purified by column chromatography on silica gel eluted with PE-EA (4:1) to give the desired product (7.0 g, yield 78%) as a white solid.

Phosphorous oxychloride (11 mL, 118.3 mmol) is added dropwise to DMF (150 mL) stirring at 0° C. in a round-bottom flask under N$_2$ atmosphere. The mixture is then transferred via cannula to a solution of 2-ethylbenzene-1,3-diol (7.0 g, 50.7 mmol) in DMF (100 mL) stirring at 0° C. in a round-bottom flask under N$_2$ atmosphere. The mixture is stirred for 1.5 hr, slowly warming to rt. The mixture is cooled to 0° C. and quenched with 2N NaOH until pH=6. The mixture is extracted with ethyl acetate (150 mL*3) and the organic layers are dried over Na$_2$SO$_4$, filtered and concentrated under reduced pressure. The resulting residue is washed with DCM (20 mL*2) to give the desired product (5.0 g, yield 63%) as a yellow solid.

To a mixture of 3-ethyl-2,4-dihydroxybenzaldehyde (5.0 g, 30 mmol), NaHCO$_3$ (3.3 g, 39 mmol) and KI (996 mg, 6 mmol) in MeCN (80 mL) is slowly warmed to 60° C. At this time, BnBr (4.3 mL, 36.14 mmol) is added. The mixture is warmed to 80° C. and stirred overnight. The mixture is then cooled to rt and the solvent is evaporated. The residue is quenched with 10% aqueous HCl to pH=6 and extracted with EA (150 mL*2). The combined organic extracts are washed with brine (50 mL*2), dried over Na$_2$SO$_4$, filtered and concentrated under reduced pressure. The residue is purified by column chromatography on silica gel eluted with PE-EA (10:1) to give 4 the desired product (5.0 g, yield 65%) as a light yellow solid.

To a solution of 4-(benzyloxy)-3-ethyl-2-hydroxybenzaldehyde (5.0 g, 19.53 mmol) and Et$_3$N (5.6 mL, 39.06 mmol) in DCM (120 mL) at 0° C. is added dropwise (Tf)$_2$O (4.9 mL, 29.3 mmol) in DCM (30 mL). The reaction mixture is stirred at rt for 2 h. Water (50 mL) is added and the mixture is extracted with DCM (50 mL*2). The combined organic extracts are washed with brine, dried over Na$_2$SO$_4$, filtered and concentrated under reduced pressure. The residue is purified by column chromatography on silica gel eluted with PE-EA (10:1) to give the desired product (2.1 g of pure product and 1 g of crude) as a yellow solid.

To a mixture of 3-(benzyloxy)-2-ethyl-6-formylphenyl trifluoromethanesulfonate (500 mg, 1.29 mmol), Pin$_2$B$_2$ (982 mg, 3.89 mmol) and KOAc (379 mg, 3.87 mmol) in 1,4-dioxane (60 mL) is added PdCl$_2$(dppf)$_2$ (94 mg, 0.129 mmol). The reaction mixture is stirred at 80° C. under argon atmosphere overnight. The solvent is removed and the residue is purified by column chromatography on silica gel eluted with PE-EA (10:1) to give the desired product (216 mg, yield 46%) as a yellow solid.

To a solution of 4-(benzyloxy)-3-ethyl-2-(4,4,5,5-tetramethyl-1,3,2-dioxaborolan-2-yl)benzaldehyde (300 mg, 0.82 mmol) in THF (30 mL) is added NaBH$_4$ (31 mg, 0.82 mmol). The reaction mixture is stirred at rt for 2 h, and then 3N HCl is slowly added to pH=1. The reaction mixture is stirred at rt overnight. The solvent is evaporated, and the residue is purified by column chromatography on silica gel eluted with PE-EA (5:1) to give the desired product (176 mg, yield 80%) as a white solid.

The solution of 6-(benzyloxy)-7-ethylbenzo[c][1,2]oxaborol-1(3H)-ol (176 mg, 0.657 mmol) in MeOH (30 mL) is hydrogenated using 10% Pd/C (42 mg, 0.039 mmol) as catalyst under atmospheric pressure overnight. The catalyst is removed by filtration on Celite and the solvent is evaporated under reduced pressure. The residue is purified by column chromatography on silica gel eluted with PE-EA (2:1) to give the desired product (100 mg, yield 85%) as a white solid.

To a mixture of 7-ethylbenzo[c][1,2]oxaborole-1,6(3H)-diol (100 mg, 0.56 mmol) and K$_2$CO$_3$ (232 mg, 1.68 mmol) in acetone (30 mL) is added bromoacetone (153 mg, 1.12 mmol). The reaction mixture is refluxed for 3 h. The solid is removed by filtration and the filtrate is evaporated to give the desired product (crude) (178 mg) as a white solid (1-(7-ethyl-1-hydroxy-1,3-dihydrobenzo[c][1,2]oxaborol-6-yloxy) propan-2-one).

Procedure 2. 2-Bromo-4-fluorobenzaldehyde (400 g, 2.0 mol) is dissolved in MeOH (4 L). To this solution is added NaBH$_4$ (149 g, 2.0 eq) portionwise. Then the resulting mixture is stirred for another 2 hrs. After evaporation, the residue is poured into ice-water (2 L) and neutralized with 6 M HCl until pH is 4~5. The mixture is extracted with ethyl acetate (3×900 mL) and the combined organic layer is washed with 5% NaHCO$_3$ and water, dried over Na$_2$SO$_4$, and concentrated to give a white solid (354 g, 90% yield).

To a solution of the compound prepared in the last paragraph (362 g, 1.77 mol) in DCM (1.7 L) is added DHP (223 g, 1.5 e.q.) and PPTS (22 g, 0.05 e.q.). The resulting solution is stirred at r.t. overnight and then quenched with water (2 L). The separated organic layer is dried over Na$_2$SO$_4$ and evaporated in vacuo to give a brown-red oil (504 g, 90% yield), which is used for next step without further purification.

n-BuLi (440 mL, 2.5M, 1.1 mol) is added dropwise to a solution of diisopropylamine (112 g, 1.10 mol) in THF (750 mL) at −30~−40° C. After addition, the resulting mixture is stirred for another 2 hrs to provide an LDA solution. To a solution of the compound prepared in the last paragraph (211 g, 0.73 mol) and EtOTf (260 g, 1.46 mol) in THF (750 mL) is added dropwise the above prepared LDA solution in THF at −30~−40° C. Upon addition, the mixture is warmed to r.t. and stirred for 2 hrs. The resulting solution is quenched with water (2 L) and extracted with ethyl acetate (3×800 mL). The combined organic layer is adjusted to pH 2~3 with 1M HCl, and washed with 5% NaHCO$_3$ and water. The organics are dried over Na$_2$SO$_4$ and concentrated to give yellow oil (218 g, 82% yield measured by HNMR.

Procedure 2a. To a solution of BnOH (106 g, 0.98 mol) in DMF (900 mL) is added 60% NaH (52 g, 1.31 mol) portionwise at 0° C. Upon addition, the mixture is warmed to r.t. and stirred for 1 hr. Then a solution of the compound prepared in Procedure 2 (207 g, 0.65 mol) in DMF (200 mL) is added and the mixture is stirred at 80~90° C. for 4 hrs. The resulting solution is quenched with water (2 L) and adjusted to pH 3~4 with 6M HCl. The mixture is extracted with ethyl acetate (3×800 mL) and the separated organic layer is washed with 5% NaHCO$_3$ and water. The organics are dried over Na$_2$SO$_4$ and concentrated in vacuo to give a brown-black oil (220 g, 75% yield measured by HNMR), which is used for next step without further purification.

To a solution of the compound prepared in the preceding paragraph (109 g, 0.27 mol) in THF (950 mL) is added dropwise n-BuLi (141 mL, 2.5 M) at −65~−70° C. and the mixture is stirred for 1 hr. Then B(OMe)$_3$ (110 g, 0.41 mol) is added dropwise slowly below −65° C. After addition, the resulting mixture is warmed to r.t. and stirred for 2 hrs. To the resulting solution is added 6M HCl (400 mL), stirred for another 6 h, extracted with ethyl acetate (3×500 mL) and the organic layer is washed with 5% NaHCO$_3$ and water. The organics are dried over Na$_2$SO$_4$ and evaporated in vacuo to give a residue, which is recrystallized to afford white solid (32 g, 44% yield).

To a solution of the compound prepared in the last paragraph (59 g, 0.22 mol) in THF (1.8 L) is added 10% Pd/C (11.9 g). The mixture is stirred under 1 atm H$_2$ at 40° C. for 12 hrs, then filtered and the filtrate is condensed under reduced pressure to give a white solid (38 g, 98% yield).

To a stirred solution of the compound prepared in the last paragraph (20.3 g, 114 mmol), K$_2$CO$_3$ (63.2 g, 456 mmol) and NaI (5.2 g, 34 mmol) in acetone (400 mL) is slowly added 1-chloro-2-propaone (21.2 g, 228 mmol) and then stirred at reflux for 3 hrs. The mixture is concentrated, then water (1 L) is added and acidified with diluted HCl to pH 3~4. The mixture is extracted with EtOAc (3×300 mL). The separated organics are dried and concentrated to give a residue, which is recrystallized with MTBE at −30° C. to afford a white solid (12.3 g, 46% yield) (1-(7-ethyl-1-hydroxy-1,3-dihydrobenzo[c][1,2]-oxaborol-6-yloxy)propan-2-one).

Procedure 2b. To a stirred solution of (2-methyl-1,3-dioxolan-2-yl)methanol (81.9 g, 2 e.q.) in DMF (345 mL) is slowly added t-BuOK (117 g, 3 e.q.) at ice-water bath. The resulting mixture is warmed to room temperature and stirred for 1 hr. Then the compound prepared from Procedure 2 (110 g, 1 e.g.) is added, and the mixture is stirred at 95~100° C. for 3 hrs. The solid is filtered and the filter cake iss washed with MTBE. The combined filtrate is poured into ice-water (1 L) and acidified with diluted HCl to pH 4~5. The mixture is extracted with EtOAc (3×600 mL). The organic layer is washed with 5% NaHCO$_3$ and water. The organics are dried over Na$_2$SO$_4$ and evaporated in vacuo to give a brown-black oil, which is purified by flash chromatography (EtOAc: PE=100:1 to 30:1) to give yellow oil (86 g, 60% yield).

To a solution of the compound prepared in the last paragraph (8.9 g, 24 mmol) in THF (100 mL) is added dropwise n-BuLi (12 mL, 2.5 M) at −65~−70° C. and stirred for 1 hr. Then B(OMe)$_3$ (5 g, 48 mmol) is added dropwise below −65° C. After addition, the resulting mixture is warmed to room temperature and stirred for 2 hrs. To the resulting solution is added 8M HCl (70 mL), stirred for another 6 hrs, extracted with ethyl acetate (3×500 mL), and the organic layer is washed with 5% NaHCO$_3$ and water. The organics are dried over Na$_2$SO$_4$ and evaporated in vacuo to give a residue, which is recrystallized with EtOAc at −30° C. to afford a white solid (2.7 g, 53% yield) (1-(7-ethyl-1-hydroxy-1,3-dihydrobenzo[c][1,2]oxaborol-6-yloxy)propan-2-one).

B. Preparation of (S)—N-(2-cyano-1-(7-ethyl-1-hydroxy-1,3-dihydrobenzo[c][1,2]oxaborol-6-yloxy) propan-2-yl)-4-(trifluoromethoxy)benzamide A mixture of 1-(7-ethyl-1-hydroxy-1,3-dihydrobenzo[c][1,2]oxaborol-6-yloxy) propan-2-one (178 mg, 0.56 mmol) from Procedure 1, Procedure 2a, or Procedure 2a, NH$_4$Cl (60 mg, 1.12 mmol) and ammonia (7N in methanol, 2 mL) in MeOH (2 mL) is stirred at rt for 20 min before addition of NaCN (70 mg, 1.43 mmol). The reaction mixture is stirred at rt for 5 h. DCM (50 mL) is added and the solvent is removed under reduced pressure. The residue is extracted with THF, and THF is rotary evaporated to give the desired product (crude) as a white solid (160 mg). It is used in the next step without further purification.

A solution of 4-(trifluoromethoxy)benzoic acid (115 mg, 0.56 mmol), HATU (426 mg, 1.12 mmol) and DIPEA (145 mg, 1.12 mmol) in DMF (5 mL) is stirred at rt for 30 min before 2-amino-3-(7-ethyl-1-hydroxy-1,3-dihydrobenzo[c][1,2]oxaborol-6-yloxy)-2-methylpropanenitrile (160 mg, crude, 0.56 mmol) is added. The reaction mixture is stirred at rt overnight. It is purified by prep-HPLC to give N-(2-cyano-1-(7-ethyl-1-hydroxy-1,3-dihydrobenzo[c][1,2]oxaborol-6-yloxy)propan-2-yl)-4-(trifluoromethoxy)benzamide (designated as Example 4a) (40 mg, yield 16% over three steps) as a white solid. $^1$H NMR (400 MHz, DMSO-d$_6$): δ 9.09 (s, 1H), 8.95 (s, 1H), 8.02 (d, J=8.0 Hz, 2H), 7.52 (d, J=8.0 Hz, 2H), 7.18 (d, J=8.0 Hz, 1H), 7.10 (d, J=8.0 Hz, 1H), 4.90 (s, 2H), 4.49 (d, J=8.8 Hz, 1H), 4.25 (d, J=9.2 Hz, 1H), 2.84 (q, J=7.6 Hz, 2H), 1.85 (s, 3H), 1.10 (t, J=7.6 Hz, 3H) ppm; HPLC purity: 100% at 214 nm and 100% at 254 nm; MS: m/z=449.1 (M+1, ESI+).

By following the procedure described in Example 1, the racemic mixture is separated to collect peak 1 giving the chiral enantiomer (S)—N-(2-cyano-1-(7-ethyl-1-hydroxy-1,3-dihydrobenzo[c][1,2]oxaborole-6-yloxy)propan-2-yl)-4-(trifluoromethoxy)benzamide. $^1$H NMR (400 MHz, DMSO-$d_6$): δ 9.09 (s, 1H), 8.94 (s, 1H), 8.01 (d, J=8.0 Hz, 2H), 7.52 (d, J=8.0 Hz, 2H), 7.18 (d, J=8.0 Hz, 1H), 7.10 (d, J=8.0 Hz, 1H), 4.90 (s, 2H), 4.49 (d, J=8.8 Hz, 1H), 4.25 (d, J=9.2 Hz, 1H), 2.84 (q, J=7.6 Hz, 2H), 1.85 (s, 3H), 1.10 (t, J=7.6 Hz, 3H) ppm; HPLC purity: 100% at 214 nm and 100% at 254 nm; Chiral HPLC purity: 99.3%; MS: m/z=449 (M+1, ESI+).

EXAMPLE 5

(S)—N-(2-cyano-1-(1-hydroxy-7-methoxy-1,3-dihydrobenzo[c][1,2]oxaborol-6-yloxy)propan-2-yl)-4-(trifluoromethoxy)benzamide

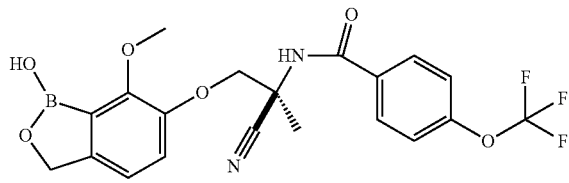 [SMILES: COc1c(OC[C@](C)(C#N)NC(=O)c2ccc(OC(F)(F)F)cc2)ccc2c1B(O)OC2]

To a solution of 4-hydroxy-3-methoxy-benzaldehyde (44.0 g, 0.29 mol) and Et$_3$N (38.0 g, 52.6 mL, 0.38 mol) in DCM (500 mL) is added CH$_3$COCl (29.6 g, 27 mL, 0.38 mol) at 0° C. After the addition is completed, the reaction mixture is stirred at 0° C. for 30 min and filtered. The filtered cake is washed with CH$_2$Cl$_2$. The combined filtrate is washed successively with water and brine and dried over Na$_2$SO$_4$. Removal of the solvent gave the desired product (56.5 g, 100%) as a yellow solid.

To fuming HNO$_3$ (600 mL) is added 4-formyl-2-methoxyphenyl acetate (10.0 g, 51.2 mmol) in portions at −10° C., and the mixture is stirred for 45 min. The acidic solution is slowly poured into ice-water (1 L) and the precipitated product is collected by filtration. The precipitate is washed several times with ice water (250 mL) and dried. The crude product is recrystallized from EA/PE (3:7) to give the desired product (8.00 g, yield 75%) as yellow needles.

Fe(OH)$_2$ solution is prepared by portion-wise addition of conc. NH$_4$OH (550 mL) solution to a vigorously stirred solution of FeSO$_4$.7H$_2$O (540 g) in water (1.0 L), and then 4-formyl-2-methoxy-3-nitrophenyl acetate (50.0 g, 0.21 mol) is added in portions. The reaction mixture is refluxed for 20 min. Following with addition of warm water (600 mL), the mixture is filtered. The residue is washed with warm water (1 L), and the combined filtrates are acidified with H$_2$SO$_4$ (3 N) and extracted with ether (3×400 mL). The combined organic extracts are concentrated to afford the desired product (26.9 g, yield 81%) as a white solid.

To a stirring solution of 2-amino-4-hydroxy-3-methoxybenzaldehyde (10.0 g, 0.06 mol) in HBr (30 mL, 48%) is added water (50 mL) and the mixture is cooled to 0° C. A cold solution of sodium nitrite (4.35 g, 0.06 mol) in water (50 mL) is added dropwise during 30 min and the mixture is stirred for additional 45 min. Freshly prepared CuBr powder (3.44 g) is added and the suspension is heated at 70° C. for 1 h when the solid product is separated out. The reaction mixture is cooled and extracted with ether (2×100 mL). The combined organic extracts are washed with brine, dried, and evaporated to dryness. The residue is recrystallized from ethanol to afford the desired product (9.50 g, yield 70%) as a white solid.

To a stirring solution of 2-bromo-4-hydroxy-3-methoxybenzaldehyde (5 g, 0.02 mol) in dry DMF (100 mL) are added benzyl bromide (7.4 g, 0.04 mol), potassium carbonate (15.2 g, 0.11 mol) and sodium iodide (1.32 g, 8.7 mmol). The mixture is refluxed overnight, cooled and filtered. DMF is removed and the crude product is purified by column chromatography over silica gel eluted with 3% ethyl acetate in petroleum ether to afford the desired product (5.00 g, yield 90%) as a white solid.

The mixture of 4-benzyloxy-2-bromo-3-methoxybenzaldehyde (2 g, 6.25 mmol), KOAc (2.63 g, 26.9 mmol), bispinacoldiboron (3.17 g, 12.5 mmol) and PdCl$_2$(dppf)$_2$ (0.53 g, 0.63 mmol) in 1,4-dioxane (100 is stirred at 70° C. under N$_2$ over a weekend. The mixture is filtered and the filtrate is concentrated under reduced pressure. The residue is purified by flash column to give the desired product (0.80 g, yield 35%).

To a stirring solution of the 4-benzyloxy-3-methoxy-2-(4,4,5,5-tetramethyl-[1,3,2]dioxa borolan-2-yl)benzaldehyde (1.40 g, 3.80 mmol) in methanol (100 mL) is added sodium borohydride (433 mg, 11.4 mmol). The reaction mixture is stirred at −30° C. for 10 min then stirred at rt for 2 h when LCMS indicated that the starting material had been consumed. To the resulting mixture is added 2N HCl (20 mL) followed by stirring at rt for 30 min Removal of the solvent gave the solid that is washed with water and petroleum ether to provide the desired product (800 mg, yield 78%).

To a solution of 6-(benzyloxy)-7-methoxybenzo[c][1,2]oxaborol-1(3H)-ol (1.60 g, 5.92 mmol) in MeOH (20 mL) is added Pd/C (160 mg, 10%) under N$_2$. The mixture is hydrogenated at rt overnight. LCMS analysis indicated that the starting material had been consumed. The mixture is filtrated and concentrated to give the desired product (700 mg, yield 70%).

The mixture of 7-methoxybenzo[c][1,2]oxaborole-1,6(3H)-diol (150 mg, 0.18 mmol), 1-bromo-propan-2-one (300 mg, 2.13 mmol) and K$_2$CO$_3$ (300 mg, 2.13 mmol) in acetone is stirred at rt over a weekend. The reaction mixture is diluted with diethyl ether and filtered through a short path of silica gel. The filtrate is evaporated under reduced pressure to give the desired product (78.6 mg, yield 40%).

To a solution of 1-(1-hydroxy-7-methoxy-1,3-dihydrobenzo[c][1,2]oxaborol-6-yloxy)-propan-2-one (200 mg, 0.85 mmol) in MeOH (10 mL) at −30° C. is bubbled with NH$_3$ for 20 min. Then KCN (110 mg, 1.69 mmol), NH$_4$Cl (149 mg, 2.80 mmol) and NH$_3$.H$_2$O (10 mL) are added. The mixture is stirred overnight at rt. By following the method described previously, normal work-up gave the desired product (170 mg, yield 76%).

The mixture of 2-amino-3-(1-hydroxy-7-methoxy-1,3-dihydrobenzo[c][1,2]oxaborol-6-yloxy)-2-methylpropanenitrile (125 mg, 0.48 mmol), 4-trifluoromethoxybenzoic acid (128 mg, 0.62 mmol), HATU (235 mg, 0.62 mmol) and DIPEA (185 mg, 1.44 mmol) in DMF (5 mL) is stirred at rt overnight. By following the method described previously, normal work-up gave the residue that is purified by pre-HPLC to afford N-(2-cyano-1-(1-hydroxy-7-methoxy-1,3-dihydrobenzo[c][1,2]oxaborol-6-yloxy)propan-2-yl)-4-(trifluoromethoxy)benzamide (designated as Example 5a) (120 mg, yield 54%). $^1$H NMR (400 MHz, DMSO-$d_6$): δ 9.09 (s, 1H), 8.98 (s, 1H), 7.98 (d, J=8.8 Hz, 2H), 7.50 (d, J=8.0 Hz, 2H), 7.22 (d, J=8.0 Hz, 1H), 6.98 (d, J=8.0 Hz, 1H), 4.90 (s, 2H), 4.46 (d, J=9.6 Hz, 1H), 4.26 (d, J=10.0 Hz, 1H), 3.94 (s, 3H), 1.84 (s, 3H) ppm. HPLC purity: 100% at both 220 nm and 254 nm MS: m/z=451.0 (M+1, ESI$^+$).

By following the procedure described in Example 1, the racemic mixture is separated to collect peak 1 giving the chiral enantiomer (S)—N-(2-cyano-1-(1-hydroxy-7-methoxy-1,3-dihydrobenzo[c][1,2]oxaborol-6-yloxy)propan-2-yl)-4-(trifluoromethoxy)benzamide. $^1$H NMR (400 MHz, DMSO-d$_6$): δ 9.09 (s, 1H), 8.98 (s, 1H), 7.98 (d, J=8.8 Hz, 2H), 7.50 (d, J=8.0 Hz, 2H), 7.22 (d, J=8.0 Hz, 1H), 6.98 (d, J=8.0 Hz, 1H), 4.90 (s, 2H), 4.46 (d, J=9.6 Hz, 1H), 4.26 (d, J=10.0 Hz, 1H), 3.95 (s, 3H), 1.84 (s, 3H) ppm. HPLC purity: 99.5% at 220 nm and 98.8% at 254 nm Chiral HPLC purity: 99.3%; MS: m/z=451.1 (M+1, ESI$^+$).

EXAMPLE 6

(S)—N-(2-cyano-1-(1-hydroxy-7-isopropyl-1,3-dihydrobenzo[c][1,2]oxaborol-6-yloxy)propan-2-yl)-4-(trifluoromethoxy)benzamide

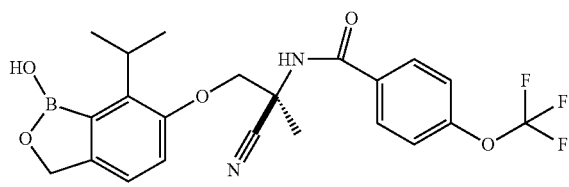 [SMILES: CC(C)c1c(OC[C@](C)(C#N)NC(=O)c2ccc(OC(F)(F)F)cc2)ccc2c1B(O)OC2]

To a solution of 1-(2,6-dihydroxyphenyl)ethanone (50.0 g, 3290 mmol) and potassium carbonate (136.2 g, 986.8 mmol) in DMF (200 mL) is added CH$_3$I (48.6 mL, 822.5 mmol) slowly at rt. The mixture is stirred for 16 h at rt, poured into ice water (1000 mL) and stirred for 30 min. The precipitate is filtered, washed with water and dried to give the desired product as a light yellow solid (50 g, yield 84%).

To a solution of 1-(2,6-dimethoxyphenyl)ethanone (50.0 g, 277.8 mmol) in THF (500 mL) is added MeMgBr (370.4 mL, 1111.2 mmol, 3.0M) dropwise at 0° C. The reaction mixture is stirred for 16 h at rt. The mixture is quenched with aqueous solution of NH$_4$Cl at 0° C. and extracted with EA (200*3 mL). The organic layers are washed with water and brine, dried over Na$_2$SO$_4$, filtered, and concentrated. The resulting oil is purified by silica gel column chromatography using PE:EA=20:1 as eluent to give the desired product (40.8 g, yield 75%) as yellow oil.

To a solution of 2-(2,6-dimethoxyphenyl)propan-2-ol (40.8 g, 208.2 mmol) in DCM (300 mL) is added TFA (46 mL, 624.6 mmol) and Et$_3$SiH (95 mL, 624.6 mmol) slowly at −30° C. Then the mixture is stirred for 6 h at rt. EA (500 mL) is added and the solution is washed with water (200 mL*3), dried over Na$_2$SO$_4$, filtered and concentrated under the reduced pressure. The residue is purified by silica gel column chromatography using PE:EA=30:1 as eluent to give the desired product (28 g, yield 75%) as light yellow oil.

To a solution of 2-isopropyl-1,3-dimethoxybenzene (28.0 g, 155.6 mmol) in DCM (200 mL) is added BBr$_3$ (130 mL, 389.0 mmol, 3.0M) slowly at −30° C. Then the mixture is stirred for 16 h at rt. The resulting solution is poured into ice water and extracted with EA. The combined organic layers are washed with brine, dried over Na$_2$SO$_4$, filtered and concentrated under the reduced pressure. The residue is purified by silica gel column chromatography using PE:EA=10:1 as eluent to give the desired product (19 g, yield 80%) as a white solid.

To DMF (20 mL) is added POCl$_3$ (34 mL, 375.0 mmol) slowly at 0° C. The reaction mixture is stirred for 20 min at 0° C., and then the solution of 2-isopropylbenzene-1,3-diol (19 g, 125 mmol) in DMF (15 mL) is added slowly at 0° C. The mixture is stirred for 3 h at rt. The resulting solution is poured into ice water and stirred for 1 h. The solution is left overnight allowing formation of precipitate. The solid is filtered, washed with water and dried to give the desired product (13.5 g, yield 65.0%) as a white solid.

A mixture of 2,4-dihydroxy-3-isopropylbenzaldehyde (13.5 g, 750 mmol), NaHCO$_3$ (18.9 g, 225.0 mmol) and KI (2.49 g, 150 mmol) in MeCN (200 mL) is slowly warmed to 60° C. Benzyl bromide (10.1 mL, 82.5 mmol) is added and the mixture is stirred at 80° C. overnight. The mixture is then cooled to rt, filtered and the solvent is concentrated by rotary evaporation. The residue is purified by silica gel column chromatography using PE:EA=10:1 as eluent to give the desired product as a yellow solid (13.8 g, yield 68.0%).

To a solution of 4-(benzyloxy)-2-hydroxy-3-isopropylbenzaldehyde (13.8 g, 51.1 mmol) and pyridine (21.0 mL, 255.6 mmol) in DCM (100 mL) is added Tf$_2$O (24.2 mL, 127.7 mmol) slowly at 0° C. The reaction mixture is stirred for 3 h at rt. The mixture is poured into water and extracted with EA (150 mL*3). The combined organic layers are washed with brine, dried over Na$_2$SO$_4$, filtered and concentrated under the reduced pressure. The residue is purified by silica gel column chromatography using PE:EA=20:1 as eluent to give the desired product (11.3 g, yield 55.0%) as a light yellow solid.

A mixture of 3-(benzyloxy)-6-formyl-2-isopropylphenyl trifluoromethanesulfonate (11.3 g, 28.1 mmol), KOAc (13.8 g, 140.5 mmol), 5,5,5',5'-tetramethyl-2,2'-bi(1,3,2-dioxaborinane) (19.0 g, 84.3 mmol) and PdCl$_2$(dppf)$_2$ (1.13 g, 1.54 mmol) in 1.4-dioxane (300 mL) is heated to 100° C. and stirred for 16 h under N$_2$. The mixture is then cooled to rt, filtered and concentrated by rotary evaporation. The residue is purified by silica gel column chromatography using PE:EA=5:1 as eluent to give the desired product as a yellow solid (7.2 g, yield 70%). It is used in next step directly.

To a solution of 4-(benzyloxy)-2-(5,5-dimethyl-1,3,2-dioxaborinan-2-yl)-3-isopropylbenzaldehyde (7.2 g, 19.7 mmol) in THF (100 mL) is added NaBH$_4$ (1.5 g, 39.4 mmol). The reaction mixture is stirred at rt for 3 h, and then to it is slowly added HCl (10.0 mL, 6N) with ice bath cooling. The mixture is continued to stir for 16 h at rt. The reaction mixture is poured into water and extracted with EA (150 mL*3). The combined organic layers are washed with brine, dried over Na$_2$SO$_4$, filtered and concentrated under the reduced pressure. The residue is purified by silica gel column chromatography using PE:EA=20:1 as eluent to give 6 the desired product (4.2 g, yield 75.0%) as a white solid.

To a solution of 6-(benzyloxy)-7-isopropylbenzo[c][1,2]oxaborol-1(3H)-ol (4.2 g, 14.9 mmol) in MeOH (50 mL) and EA (50 mL) is hydrogenated using 10% Pd/C (1.49 g, 1.49 mmol) as catalyst under atmospheric pressure overnight. The catalyst is removed by filtration on Celite and the solvent is evaporated under reduced pressure. The residue is purified by silica gel column chromatography using PE:EA=2:1 as eluent to give the desired product (2.28 g, yield 80%) as light yellow oil.

To a mixture of 7-isopropylbenzo[c][1,2]oxaborole-1,6(3H)-diol (2.28 g, 11.9 mmol) and K$_2$CO$_3$ (4.92 g, 35.6 mmol) in acetone (50 mL) is added bromoacetone (3.25 g, 23.7 mmol). The reaction mixture is refluxed for 6 h. The solvent is evaporated under reduced pressure. The residue is purified by silica gel column chromatography using PE:EA=3:1 as eluent to give the desired product (1.47 g, yield: 50.0%) as a white solid.

A mixture of 1-(1-hydroxy-7-isopropyl-1,3-dihydrobenzo[c][1,2]oxaborol-6-yloxy) propan-2-one (1.47 g, 5.93 mmol), NH$_4$Cl (0.634 g, 11.85 mmol) and ammonia (7N in methanol, 3 mL) in MeOH (10 mL) is stirred at rt for 20 min before addition of NaCN (0.581 g, 11.85 mmol). The reaction mixture is stirred at rt overnight. DCM (50 mL) is added and the solvent is removed under the reduced pressure at rt. The residue is washed with THF and filtered. The filtrate is rotary evaporated to give the desired product (crude) (1.7 g) as light yellow oil. It is used without further purified in the next step.

A solution of 4-(trifluoromethoxy)benzoic acid (1.83 g, 8.90 mmol), DIPEA (3.0 mL, 17.79 mmol) and HATU (3.38 g, 8.90 mmol) in DMF (20 mL) is stirred at rt for 10 min before crude 2-amino-3-(1-hydroxy-7-isopropyl-1,3-dihydrobenzo[c][1,2]oxaborol-6-yloxy)-2-methylpropanenitrile (1.7 g, 6.2 mmol) in DMF (10 mL) is added. The reaction mixture is stirred at rt overnight. It is purified by prep-HPLC to give N-(2-cyano-1-(1-hydroxy-7-isopropyl-1,3-dihydrobenzo[c][1,2]oxaborol-6-yloxy)propan-2-yl)-4-(trifluoromethoxy)benzamide (designated as Example 6a) (548 mg, yield 20% over two steps) as a white solid. $^1$H NMR (400 MHz, DMSO-d$_6$) δ 9.09 (s, 1H), 9.05 (s, 1H), 8.01 (d, J=8.0 Hz, 2H), 7.52 (d, J=8.0 Hz, 2H), 7.17 (d, J=8.0 Hz, 1H), 7.12 (d, J=8.0 Hz, 1H), 4.89 (s, 2H), 4.49 (d, J=8.8 Hz, 1H), 4.26 (d, J=8.8 Hz, 1H), 3.69-3.73 (m, 1H), 1.86 (s, 3H), 1.30 (d, J=5.2 Hz, 3H), 1.28 (d, J=5.2 Hz, 3H) ppm; HPLC purity: 100.0% at 214 nm and 100.0% at 254 nm; MS: m/z=463.0 (M+1, ESI+).

By following the procedure described in Example 1, the racemic mixture is separated to collect peak 1 giving the chiral enantiomer (S)—N-(2-cyano-1-(1-hydroxy-7-isopropyl-1,3-dihydrobenzo-[c][1,2]oxaborol-6-yloxy)propan-2-yl)-4-(trifluoromethoxy)benzamide. $^1$H NMR (400 MHz, DMSO-d$_6$): δ 9.09 (s, 1H), 9.05 (s, 1H), 8.02 (d, J=8.0 Hz, 2H), 7.52 (d, J=8.0 Hz, 2H), 7.18 (d, J=8.0 Hz, 1H), 7.12 (d, J=8.0 Hz, 1H), 4.89 (s, 2H), 4.49 (d, J=8.8 Hz, 1H), 4.27 (d, J=8.8 Hz, 1H), 3.69-3.73 (m, 1H), 1.86 (s, 3H), 1.30 (d, 3H), 1.28 (d, 3H) ppm; HPLC purity: 100.0% at 214 nm and 100.0% at 254 nm; Chiral HPLC purity: 100%; MS: m/z=463.1 (M+1, ESI+).

EXAMPLE 7

N-(2-cyano-1-(7-cyclopropyl-1-hydroxy-1,3-dihydrobenzo[c][1,2]oxaborol-6-yloxy)propan-2-yl)-4-(trifluoromethoxy)benzamide

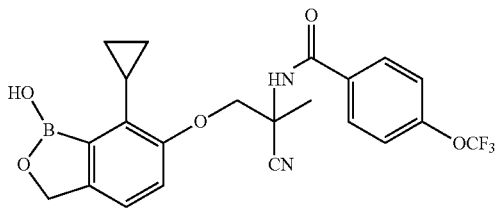 [SMILES: CC(C#N)(COc1ccc2c(c1C1CC1)B(O)OC2)NC(=O)c1ccc(OC(F)(F)F)cc1]

To a solution of resorcinol (110 g, 1 mol) and I$_2$ (254 g, 1 mmol) in H$_2$O (1 L) is slowly added NaHCO$_3$ (92.4 g, 1.1 mol) in portions at 0° C. with vigorous stirring (caution: strong release of CO$_2$). After warming to rt, the mixture is stirred for 10 min. The mixture is extracted with EtOAc (3×500 mL). The combined organic layer is dried and concentrated to give the crude product, which is purified by silica gel chromatography (PE:EA=50:1 to 25:1) to give the desired product (153 g, 65% yield) as a white solid.

POCl$_3$ (166 mL, 1.82 mol) is added dropwise to DMF (330 mL) at 0° C. The mixture is stirred at rt for 1.5 h. A solution of 2-iodobenzene-1,3-diol (43 g, 182 mmol) in DMF (170 mL) is added dropwise keeping the temperature below 30° C. The reaction is stirred at rt overnight. The mixture is poured into ice water (2 L), adjusted to pH 2-3 with NaHCO$_3$, and extracted with EtOAc (3×800 mL). The organics are dried and concentrated to give a residue, which is used for next step without purification.

To a solution of the residue, obtained from the previous step, in DCM (350 mL) is added DIPEA (70.6 g, 546 mmol) at 0° C. MOMCl (29.3 g, 364 mmol) is added dropwise at 0° C. over ten minutes. The mixture is stirred at rt for 2 h. Then H$_2$O (400 mL) is added, neutralized with 6N HCl to pH=6~7, and extracted with DCM (3×400 mL). The organics are dried and concentrated to give a residue, which is purified by silica gel chromatography (PE:EA=50:1 to 28:1) to give the desired product (15 g, 23.4% yield over two steps) as a white solid.

To a stirring solution of 3-iodo-2,4-bis(methoxymethoxy)benzaldehyde (7.0 g, 20 mmol), cyclopropylboronic acid (6.9 g, 80 mmol) and K$_3$PO$_4$ (25.4 g, 120 mmol) in toluene (120 mL) and H$_2$O (33 mL) are added Pd(OAc)$_2$ (0.90 g, 4 mmol) and tricyclohexyl phosphine (1.1 g, 4 mmol) under N$_2$. The resulting mixture is refluxed overnight. The mixture is poured into ice-water (100 mL) and extracted with EtOAc (3×200 mL). The extracts are dried over sodium sulfate and concentrated to give a residue, which is purified by silica gel chromatography (PE:EA=100:1 to 50:1) to give the desired product (4.5 g, 84.9% yield) as a light yellow oil.

To a stirring solution of 3-cyclopropyl-2,4-bis(methoxymethoxy)benzaldehyde (8.3 g, 31.2 mmol) in THF (60 mL) is added 2N HCl (50 mL) dropwise with ice-water bath cooling. The mixture is stirred at rt for 8 h. The mixture is concentrated and extracted with EtOAc (3×90 mL). The extracts are dried over sodium sulfate and concentrated to give a residue, which is purified by silica gel chromatography (PE:EA=100:1 to 50:1) to give the desired product (3.5 g, 50.7% yield) as a light yellow oil.

To a stirring solution of 3-cyclopropyl-2-hydroxy-4-(methoxymethoxy)benzaldehyde (1.2 g, 5.4 mmol) and pyridine (1.09 g, 14 mmol) in DCM (15 mL) is added Tf$_2$O (1.97 g, 7.0 mmol) dropwise at 0° C. The mixture is warmed to rt and stirred at rt for 1 h. The mixture is concentrated to give a residue, which is purified by silica gel chromatography (PE:EA=125:1 to 100:1) to give the desired product (0.97 g, 51% yield) as a light yellow oil.

To a stirring solution of 2-cyclopropyl-6-formyl-3-(methoxymethoxy)phenyl trifluoro methanesulfonate (2.3 g, 6.5 mmol), 5,5,5',5'-tetramethyl-2,2'-bi(1,3,2-dioxaborinane) (2.9 g, 13 mmol) and KOAc (1.9 g, 19.5 mmol) in dry 1,4-dioxane (40 mL) is added PdCl$_2$(dppf)$_2$ (0.53 g, 0.65 mmol) under N$_2$. The resulting mixture is stirred at 80° C. for 1 h. The mixture is concentrated and extracted with DCM to give a crude product, which is purified by silica gel chromatography (PE:EA=85:1 to 20:1) to give the desired product (1.5 g, 72% yield) as a light yellow oil.

To a solution of 3-cyclopropyl-2-(5,5-dimethyl-1,3,2-dioxaborinan-2-yl)-4-(methoxymethoxy)benzaldehyde (1.5 g, 4.7 mmol) in MeOH (45 mL) at ice-water bath is added NaBH$_4$ (1.07 g, 28.3 mmol) in portions. The mixture is stirred at rt for 1 h, and then 12N HCl (15 mL) is added dropwise at 0° C. The reaction is warmed to rt and stirred for 4 h. The mixture is concentrated, adjusted with sodium carbonate solution to pH=3-4, extracted with EtOAc (3×90 mL), dried over sodium sulfate and concentrated to give a residue, which is purified by silica gel chromatography (DCM:CH$_3$OH=250:1 to 110:1) to give the desired product (0.55 g, 61% yield) as a white solid.

To a stirring mixture of 7-cyclopropylbenzo[c][1,2]oxaborole-1,6(3H)-diol (0.55 g, 2.9 mmol) and K$_2$CO$_3$ (1.60 g, 11.6 mmol) in acetone (50 mL) is slowly added 1-bromo-2-propaone (0.60 g, 4.4 mmol), and then refluxed for 4 h. The mixture is poured into water, acidified with diluted HCl solution to pH=3-4 and extracted with EtOAc (3×80 mL). The combined organics is dried and concentrated to give a residue, which is purified by silica gel chromatography (DCM:CH$_3$OH=500:1 to 125:1) to give the desired product (0.48 g, 67% yield) as a white solid.

To a stirring solution of 1-(7-cyclopropyl-1-hydroxy-1,3-dihydrobenzo[c][1,2]oxaborole-6-yloxy)propan-2-one (394 mg, 1.6 mmol) and TMSCN (317 mg, 3.2 mmol) in NH$_3$/CH$_3$OH (7 mol/L, 20 mL) is added NH$_4$Cl (171 mg, 3.2 mmol) at 0° C. under N$_2$. The resulting mixture is stirred at rt overnight. Then the reaction is concentrated to give light yellow solid. THF (30 mL) is added and filtered. The filtrate is concentrated to give the desired product as light yellow oil (440 mg), which is used for next step without purification.

To a mixture of 2-amino-3-(7-cyclopropyl-1-hydroxy-1,3-dihydrobenzo[c][1,2]oxaborole-6-yloxy)-2-methylpropanenitrile (440 mg) and 4-(trifluoromethoxy)benzoyl chloride (395 mg, 1.76 mmol) in THF (20 mL) is added dropwise DIPEA (3.2 mL) under N$_2$. The resulting mixture is stirred at rt for 2 h. Then the mixture is concentrated and adjusted with 1N HCl to pH=2-3, extracted with EtOAc (3×90 mL) to give a crude product, which is purified with prep-HPLC (column: Agilent XDB-C18, 150 mm*20 mm Sum; mobile phase: [A-H$_2$O+0.1% TFA; B-MeCN] B %: 10%-90%, flow rate: 30 mL/min), concentrated, filtered to give N-(2-cyano-1-(7-cyclopropyl-1-hydroxy-1,3-dihydrobenzo[c][1,2]oxaborol-6-yloxy) propan-2-yl)-4-(trifluoromethoxy)benzamide (146 mg, yield 20%). $^1$H NMR (DMSO-d$_6$, 400 MHz): δ 9.05 (s, 1H), 8.96 (s, 1H), 8.01 (d, 2H, J=6.8 Hz), 7.51 (d, 2H, J=8.0 Hz), 7.05-7.10 (m, 2H), 4.88 (s, 2H), 4.43 (d, 1H, J=8.0 Hz), 4.24 (d, 1H, J=8.0 Hz), 2.34-2.40 (m, 1H), 1.83 (s, 3H), 1.22-1.32 (m, 2H), 0.73-0.77 (m, 2H) ppm. HPLC purity: 99.7% at 220 nm and 99.8% at 254 nm; MS: m/z=461.2 (M+1, ESI+).

EXAMPLE 8

N-[1-Cyano-2-(7-ethoxy-1-hydroxy-1,3-dihydrobenzo[c][1,2]oxaborol-6-yloxy)-1-methyl-ethyl]-4-trifluoromethoxy-benzamide

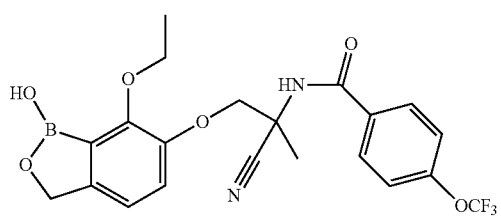 [SMILES: CCOc1c(OCC(C)(C#N)NC(=O)c2ccc(OC(F)(F)F)cc2)ccc2c1B(O)OC2]

To a solution of 3-ethoxy-4-hydroxy-benzaldehyde (50.0 g, 0.30 mol) and Et$_3$N (39.2 g, 54 mL, 0.39 mol) in DCM (500 mL) at 0° C. is added CH$_3$COCl (30.6 g, 28 mL, 0.39 mol) at 0° C. After the addition is complete, the reaction mixture is stirred at 0° C. for 30 min. Then the filter cake washed with DCM, and the combined filtrate is washed with water and brine. the organic layer is dried over Na$_2$SO$_4$ and evaporated to give the desired product (62.0 g, 100% yield) as a yellow solid.

To fuming HNO$_3$ (110 mL, d, 1.52) is added in portions 2-ethoxy-4-formylphenyl acetate (25.0 g, 98.8 mmol) at −10° C., and the mixture is stirred at this temperature for 45 min. The acidic solution is slowly poured into ice-water (1 L) and the precipitated is collected by filtration. The precipitate is washed several times with ice water (250 mL) and dried. The crude product is recrystallized from EtOAc/PE (3/7) to give the desired product (8.00 g, 75% yield) as yellow solid.

Fe(OH)$_2$ solution is prepared by portion wise addition of conc. NH$_4$OH (683 mL) solution to a vigorously stirring solution of FeSO$_4$ (668 g) in water (1.2 L). To it 2-ethoxy-4-formyl-3-nitro-phenyl acetate (64.0 g, 0.25 mol) is added in portions and the reaction mixture is refluxed for 20 min. Following addition of warm water (500 mL), the mixture is filtered. The residue is washed with warm water (750 mL), and the combined filtrates are acidified with H$_2$SO$_4$ (3 N) and extracted with ether (3×200 mL). The combined organic extracts are concentrated to afford the desired product (23.0 g, 92% yield) as a white solid.

2-Amino-3-ethoxy-4-hydroxybenzaldehyde (10.0 g, 55.2 mmol) is added to a mixed solution of HBr (28 mL, 48%) and water (50 mL). The mixture is cooled to 0° C. A cold solution of sodium nitrite (3.25 g, 58.0 mmol) in water (50 mL) is added dropwise during 30 min and the mixture is stirred for another 45 min. CuBr powder (3.16 g) is added and the suspension is heated at 70° C. for 1 h. The reaction mixture is cooled and extracted with ether (2×100 mL). The combined organic extracts are washed with brine, dried, and evaporated to dryness. The residue is recrystallized from ethanol to afford the desired product (11.0 g, 47% yield) as a white solid.

To a stirring solution of 2-bromo-3-ethoxy-4-hydroxybenzaldehyde (10.0 g, 40.8 mmol) in dry MeCN (150 mL) are added benzyl bromide (10.5 g, 61.2 mmol), potassium carbonate (14.0 g, 102 mmol), and sodium iodide (2.45 g, 16.3 mmol). The mixture is stirred at rt overnight, and then filtered. MeCN is removed and the crude product is purified by column chromatography over silica gel eluted with 1-3% EA in PE to afford the desired product (5.0 g, yield 90%) as a white solid.

The mixture of 4-benzyloxy-2-bromo-3-ethoxybenzaldehyde (1 g, 0.30 mmol), KOAc (11.3 g, 129 mmol), bispinacoldiboron (1.52 g, 0.60 mmol) and PdCl$_2$(dppf)$_2$ (244 mg, 0.03 mmol) in THF (50 mL) is stirred at 50° C. overnight. It is filtered and the filtrate is removed under reduced pressure. The residue is purified by column chromatography over silica gel eluted with 1-4% EA in PE to give the desired product (0.30 g, yield 26%).

To a stirring solution of 4-benzyloxy-3-methoxy-2-(4,4,5,5-tetramethyl-[1,3,2]dioxaborolan-2-yl)benzaldehyde (900 mg, 2.35 mmol) in methanol (100 mL) is added sodium borohydride (268 mg, 7.07 mmol). The reaction mixture is stirred at −30° C. for 10 min, then stirred at rt for another 2 h until LCMS indicated that the starting material had been consumed. 6N HCl (10 mL) is added slowly and the reaction mixture is stirred at rt for 30 min Removal of solvents gave a solid residue that is washed with water and PE to provide the desired product (500 mg, yield 75%).

To a solution of 6-(benzyloxy)-7-ethoxybenzo[c][1,2]oxaborol-1(3H)-ol (250 mg, 0.88 mmol) in MeOH (20 mL)

is added Pd/C (25 mg, 10% mol) and the reaction mixture is stirred under H$_2$ at rt for 4 h. LCMS indicated that the starting material had been consumed. It is filtrated and concentrated to give the desired product (150 mg, yield 77%).

The mixture of 7-ethoxybenzo[c][1,2]oxaborole-1,6(3H)-diol (150 mg, 0.77 mmol), 1-bromopropan-2-one (212 mg, 1.54 mmol) and K$_2$CO$_3$ (212 mg, 1.54 mmol) in acetone is stirred at rt for 2 days, The reaction mixture is diluted with diethyl ether and filtered through a short path of silica gel. The filtrate is evaporated under reduced pressure to give the desired product (100 mg, yield 52%).

Into a solution of 1-(7-ethoxy-1-hydroxy-1,3-dihydrobenzo[c][1.2]oxaborol-6-yloxy) propan-2-one (60 mg, 0.24 mmol) in MeOH (10 mL) at −30° C. is bubbled NH$_3$ for 20 min. Then KCN (32 mg, 0.48 mmol), NH$_4$Cl (42 mg, 0.79 mmol) and 28% NH$_3$.H$_2$O (4 mL) is added. The mixture is stirred at rt overnight. Solvent is evaporated and the residue is purified by prep-HPLC to give the desired product (50 mg, yield 76%).

To the mixture of 2-amino-3-(7-ethoxy-1-hydroxy-1,3-dihydrobenzo[c][1,2]oxaborol-6-yloxy)-2-methylpropanenitrile (60 mg, 0.22 mmol), 4-trifluoromethoxybenzoic acid (67 mg, 0.33 mmol) and HATU (164 mg, 0.43 mmol) in DMF (5 mL) is added DIPEA (84 mg, 0.65 mmol). The mixture is stirred at rt overnight and evaporated. The residue is purified by prep-HPLC to give the title compound N-(2-cyano-1-(7-ethoxy-1-hydroxyl-1,3-dihydrobenzo[c][1,2]oxaborol-6-yloxy)propan-2-yl)-4-(trifluoromethoxy)benzamide (33 mg, 30%) as white solid. $^1$H NMR (400 MHz, DMSO-d$_6$): δ 9.01 (s, 1H), 8.98 (s, 1H), 7.99 (d, J=8.8 Hz, 2H), 7.50 (d, J=8.4 Hz, 2H), 7.21 (d, J=8.0 Hz, 1H), 6.98 (d, J=8.4 Hz, 1H), 4.89 (s, 2H), 4.47 (d, J=9.2 Hz, 1H), 4.26-4.19 (m, 3H), 1.84 (s, 3H), 1.24 (t, J=7.2 Hz, 3H) ppm. HPLC purity: 98.6% at 220 nm; MS: m/z=465.1 (M+1, ESI+).

EXAMPLE 9

N-(2-cyano-1-(1-hydroxy-7-isopropoxy-1,3-dihydrobenzo[c][1,2]oxaborol-6-yloxy) propan-2-yl)-4-(trifluoromethoxy)benzamide

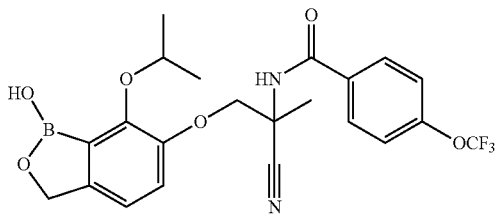 [SMILES: CC(C)Oc1c(OCC(C)(C#N)NC(=O)c2ccc(OC(F)(F)F)cc2)ccc2c1B(O)OC2]

Into a round-bottom flask equipped with a stir bar are placed 3,4-dihydroxybenzaldehyde (10.0 g, 72.5 mmol), sodium bicarbonate (7.91 g, 94.2 mmol), KI (2.07 g, 14.5 mmol) and MeCN (200 mL). The flask is fitted with a refluxing condenser and slowly heated to 60° C. At this time, benzyl bromide (8.5 mL, 72.5 mmol) is added and the mixture heated to 80° C. After refluxing overnight, the mixture is then cooled to rt and concentrated by rotary evaporation. The residue is quenched with 10% aq. HCl (50 mL) and extracted with EtOAc (3×100 mL). The combined organic extracts are washed with brine (100 mL), dried with Na$_2$SO$_4$, filtered, and concentrated. The resulting oil is purified by flash chromatography (SiO$_2$, 100% hexane until removal of benzyl bromide, then PE:EA=6:1) to afford an amorphous yellow solid (13.3 g, yield 80.6%).

To the solution of 4-(benzyloxy)-3-hydroxybenzaldehyde (13.3 g, 58.3 mmol) in 1,4-dioxane/H$_2$O (2:1, 150 mL), NBS (11.4 g, 64.2 mmol) in a solution of 1,4-dioxane/H$_2$O (2:1, 50 mL) is added dropwise at 0° C. The reaction mixture is warmed to rt for 3 h. Then EA (300 mL) is added and the organic layer is washed with water and brine, dried with Na$_2$SO$_4$, filtered, and concentrated. The resulting oil is purified by flash chromatography using PE:EA (15:1) as eluent to give the desired product (14.0 g, yield 77.8%) as a yellow solid.

The solution of 4-(benzyloxy)-2-bromo-3-hydroxybenzaldehyde (5.0 g, 16.3 mmol) and NaH (1.95 g, 48.9 mmol, 60% in mineral oil) in DMF (25 mL) is stirred at rt for 0.5 h, then 2-iodopropane (5.54 g, 32.6 mmol) is added and stirred at rt overnight. The reaction mixture is filtered and the filtrate is poured into water (120 mL), extracted with EA (150 ml*3). The combined organic layers are washed with water and brine, dried over Na$_2$SO$_4$, filtered and concentrated under reduced pressure. The residue is purified by silica gel column chromatography using PE:EA (4:1) as eluent to give the desired product (3.8 g, yield 67.0%) as a light yellow solid.

A mixture of 4-(benzyloxy)-2-bromo-3-isopropoxybenzaldehyde (3.8 g, 10.9 mmol), 5,5,5',5'-tetramethyl-2,2'-bi(1,3,2-dioxaborinane) (7.35 g, 32.7 mmol), Pd(dppf)$_2$Cl$_2$ (796 mg, 1.09 mmol) and KOAc (5.34 g, 54.45 mmol) in 1,4-dioxane (100 mL) is stirred at 100° C. overnight under argon. Water (100 mL) is added and the mixture is extracted with DCM (200 mL*2). The combined organic layers are washed with brine, dried over Na$_2$SO$_4$, filtered and concentrated under reduced pressure. The residue is purified by silica gel column chromatography using PE:EA (5:1) as eluent to give the desired product (2.7 g, yield 65.0%) as a white solid. It is used in next step directly.

To a solution of 4-(benzyloxy)-2-(5,5-dimethyl-1,3,2-dioxaborinan-2-yl)-3-isopropoxy benzaldehyde (1.0 g, 2.62 mmol) in THF (20 mL) is added NaBH$_4$ (200 mg, 5.24 mmol). The reaction mixture is stirred at rt for 2 h, then to it is slowly added HCl (3M) at ice bath to pH=2. The solvent is evaporated and the residue is purified by column chromatography on silica gel eluted with PE-EA (3:1) to give the desired product (547 mg, yield 70.0%) as a white solid.

The solution of 6-(benzyloxy)-7-isopropoxybenzo[c][1,2]oxaborol-1(3H)-ol (1.47 g, 4.93 mmol) in MeOH (20 mL) and EA (20 mL) is hydrogenated using 10% Pd/C (493 mg, 0.493 mmol) as catalyst under atmospheric pressure overnight. The catalyst is removed by filtration on Celite and the solvent is evaporated under reduced pressure. The residue is purified by column chromatography on silica gel eluted with PE-EA (2:1) to give the desired product (720 mg, yield 71.0%) as a white solid.

To a solution of 7-isopropoxybenzo[c][1,2]oxaborole-1,6(3H)-diol (400 mg, 1.92 mmol) and K$_2$CO$_3$ (796 mg, 5.77 mmol) in acetone (20 mL) is added bromoacetone (395 mg, 2.88 mmol). The reaction mixture is refluxed for 3 h. The solvent is evaporated under reduced pressure. The residue is purified by column chromatography on silica gel eluted with PE-EA (3:1) to give 1 the desired product (290 mg, yield 57.2%) as a white solid.

The mixture of 1-(1-hydroxy-7-isopropoxy-1,3-dihydrobenzo[c][1,2]oxaborol-6-yloxy) propan-2-one (190 mg, 0.72 mmol), NH$_4$Cl (77 mg, 1.44 mmol) and ammonia (7N in methanol, 1 mL) in MeOH (2 mL) is stirred at rt for 20 min before addition of NaCN (71 mg, 1.44 mmol). The reaction mixture is stirred at rt overnight. DCM (50 mL) is added and the solvent is removed under reduced pressure at rt. The residue is washed with THF and filtered. The filtrate is evaporated to give the desired product (crude) (300 mg) as colorless oil. It is used without further purification in the next step.

The solution of 4-(trifluoromethoxy)benzoic acid (223 mg, 1.08 mmol), DIPEA (0.4 mL, 2.16 mmol) and HATU (410 mg, 1.08 mmol) in DMF (3 mL) is stirred at rt for 10 min, and then crude 2-amino-3-(1-hydroxy-7-isopropoxy-1,3-dihydrobenzo[c][1,2]-oxaborol-6-yloxy)-2-methylpropanenitrile (300 mg, 0.72 mmol) in DMF (2 mL) is added. The reaction mixture is stirred at rt overnight. It is purified by prep-HPLC to give the title compound N-(2-cyano-1-(1-hydroxy-7-isopropoxy-1,3-dihydrobenzo-[c][1,2]oxaborol-6-yloxy)propan-2-yl)-4-(trifluoromethoxy)benzamide (50 mg, yield 13.7% over two steps) as a white solid. $^1$H NMR (500 MHz, DMSO-d$_6$): δ 8.98 (s, 1H), 8.91 (s, 1H), 7.99 (d, J=8.0 Hz, 2H), 7.50 (d, J=8.0 Hz, 2H), 7.21 (d, J=8.0 Hz, 1H), 7.00 (d, J=8.0 Hz, 1H), 4.89 (s, 2H), 4.67-4.70 (m, 1H), 4.47 (d, J=9.5 Hz, 1H), 4.24 (d, J=9.5 Hz, 1H), 1.84 (s, 3H), 1.20 (d, J=4.5 Hz, 3H), 1.18 (d, J=4.5 Hz, 3H) ppm; HPLC purity: 96.24% at 214 nm and 100% at 254 nm; MS: m/z=479.1 (M+1, ESI+).

EXAMPLE 10

N-(2-cyano-1-(1-hydroxy-1,3-dihydrobenzo[c][1,2]oxaborol-6-yloxy)propan-2-yl)-4-(trifluoromethoxy)benzamide

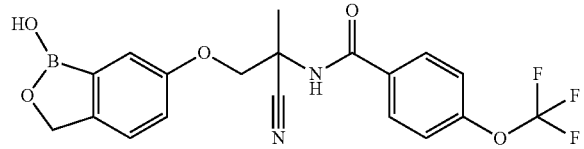 [SMILES: CC(C#N)(COc1ccc2c(c1)B(O)OC2)NC(=O)c1ccc(OC(F)(F)F)cc1]

The title compound is synthesized by following the procedures in Example 1 starting from the alkylation reaction of benzo[c][1,2]oxaborole-1,6(3H)-diol with 1-chloropropan-2-one. The title compound is obtained as white solid. $^1$H NMR (DMSO-d$_6$, 400 MHz): δ 9.14 (s, 1H), 9.06 (s, 1H), 8.01 (d, J=8.0 Hz, 2H), 7.51 (d, J=8.0 Hz, 2H), 7.36-7.33 (m, 2H), 7.15 (d, J=6.4 Hz, 1H), 4.94 (s, 2H), 4.54 (d, J=8.8 Hz, 1H), 4.29 (d, J=8.8 Hz, 1H), 1.83 (s, 3H) ppm. HPLC purity: 98.6% at 220 nm and 95.5% at 254 mm MS: m/z=421.1 (M+1, ESI+).

EXAMPLE 11

N-(2-cyano-1-(1-hydroxy-5-(trifluoromethyl)-1,3-dihydrobenzo[c][1,2]oxaborol-6-yloxy) propan-2-yl)-4-(trifluoromethoxy)benzamide

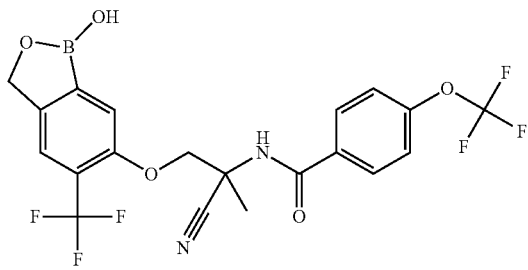 [SMILES: CC(C#N)(COc1cc2c(cc1C(F)(F)F)COB2O)NC(=O)c1ccc(OC(F)(F)F)cc1]

To a solution of 2,4-dihydroxybenzoic acid methyl ester (30.0 g, 176 mmol) in acetone (750 mL) at 0° C. is added potassium carbonate (33.9 g, 194 mmol). The mixture is stirred at rt for 1 h, and then BnBr (27.1 g, 194 mmol) is added dropwise at 0° C. The mixture is refluxed overnight, cooled to rt, filtered to remove solids and the filtrate is concentrated under reduced pressure. The residue is purified by column chromatography using silica gel (PE:EA, 100:1 to 10:1, v:v) to provide the desired product (43.2 g, yield 95%) as a white solid.

To a solution of 4-benzyloxy-2-hydroxybenzoic acid methyl ester (43.2 g, 165 mmol) in THF (1000 mL) is added a solution of potassium tert-butoxide in THF (203 mL, 203 mmol). After 30 min, iodomethane (308 g, 214 mmol) is added and the reaction is stirred overnight at 35° C. The reaction mixture is evaporated in vacuo and the residue is mixed with water and neutralized with 1 N HCl. The resulting solid is collected by filtration, washed with water and dried. The solid is dissolved in EA, washed with water, 1N aqueous NaOH, brine, dried over Na$_2$SO$_4$, filtered and concentrated under reduced pressure. The residue is purified by column chromatography using silica gel (PE:EA, 50:1 to 20:1, v:v) to provide 4 the desired product (35.7 g, yield 78%) as a white solid.

To a solution of 4-benzyloxy-2-methoxybenzoic acid methyl ester (35.7 g, 128 mmol) in acetonitrile (750 mL) at 0° C. is slowly added NIS (35.3 g, 154 mmol) followed by trifluoroacetic acid (22.2 g, 192 mmol). The reaction mixture is stirred overnight at 35° C., cooled to rt and concentrated under reduced pressure. The reaction mixture is diluted with water (500 mL), extracted with DCM (3×300 mL). The organic layer is washed with brine, dried over Na$_2$SO$_4$, filtered and concentrated under reduced pressure. The residue is purified by column chromatography using silica gel (PE:EA, 10:1 to 2:1, v:v) to give the desired product (51.3 g, 99% yield) as a white solid.

To a solution of 4-benzyloxy-5-iodo-2-methoxybenzoic acid methyl ester (51.3 g, 126 mmol) in NMP (750 mL) at rt is added CuI (123 g, 630 mmol) and potassium trifluoroacetate (96.8 g, 630 mmol). After being degassed and backfilled with N$_2$, the reaction mixture is stirred for 5 h at 150° C. under N$_2$, cooled to rt, filtered through a celite pad. The filter cake is washed with EA. The filtrate is dried over Na$_2$SO$_4$, filtered and concentrated under reduced pressure. The residue is purified by column chromatography using silica gel (PE:EA, 10:1 to 3:1, v:v) to give the desired product (36.4 g, 85% yield) as a white solid.

To a solution of 4-benzyloxy-2-methoxy-5-trifluoromethylbenzoic acid methyl ester (15.0 g, 43.2 mmol) in DCM (300 mL) is added dropwise the solution of BCl$_3$ in heptane (1.0 M, 43.2 mL) at −70° C. The reaction mixture is stirred for 5 h below −30° C., poured into ice-water and extracted with DCM (3×25 mL). The organic layer is washed with brine, dried over Na$_2$SO$_4$, filtered and concentrated under reduced pressure. The residue is purified by column chromatography using silica gel (PE-EA, 5:1 to 3:1, v:v) to give the desired product (10.7 g, 76% yield) as a white solid.

To the mixture of 4-benzyloxy-2-hydroxy-5-trifluoromethylbenzoic acid methyl ester (6.00 g, 18.0 mmol), TEA (3.67 g, 36.0 mmol) and DMAP (3.36 g, 27.0 mmol) in DCM (120 mL) is added dropwise Tf$_2$O (26.5 g, 27.0 mmol) at 0° C. The reaction mixture is stirred for 2 h at rt, poured into ice-water and extracted with DCM (3×200 mL). The organic layer is washed with brine, dried over Na$_2$SO$_4$, filtered and concentrated under reduced pressure. The residue is purified by column chromatography using silica gel (PE:EA, 100:1 to 20:1, v:v) to give the desired product (7.50 g, 91% yield) as a white solid.

To a solution of 4-benzyloxy-2-trifluoromethanesulfonyloxy-5-trifluoromethylbenzoic acid methyl ester (7.50 g; 16.0 mmol) in 1,4-dioxane (200 mL) at rt are added bis(pinacolato)diboron (8.32 g, 32.0 mmol) and KOAc (4.81 g, 48.0 mmol). After being degassed and backfilled with N$_2$, Pd(dppf)Cl$_2$ (2.37 g, 3.2 mmol) is added. The reaction mixture is stirred for 2 h at 110° C. under N$_2$, cooled to rt, filtered through a celite pad. The filter cake is washed with EA. The filtrate is dried over Na$_2$SO$_4$, filtered and concentrated under reduced pressure. The residue is purified by column chromatography using silica gel (PE:EA, 100:1 to 30:1, v:v) to give the desired product (4.28 g, 61% yield) as a white solid.

To a solution 4-benzyloxy-2-(4,4,5,5-tetramethyl-[1,3,2]dioxaborolan-2-yl)-5-trifluoromethylbenzoic acid methyl ester (4.00 g, 9.00 mmol) in EtOH (50 mL) is added NaBH$_4$ (1.05 mmol, 27.0 mmol) in portions at 0° C. The mixture is stirred for 3 h at 35° C., cooled to rt and then 2 N HCl (50 mL) is added. The mixture is stirred for 2 h at 35° C. Most of EtOH is evaporated and the resulting mixture is portioned between EA and water. The organic layer is washed with brine, dried over Na$_2$SO$_4$, filtered and concentrated under reduced pressure. The residue is purified by prep-HPLC to give the desired product (1.62 g, yield 58.4%) as a white solid.

The mixture of 6-(benzyloxy)-5-(trifluoromethyl)benzo[c][1,2]oxaborol-1(3H)-ol (1.62 g, 5.15 mmol) and Pd/C (10% wt, 100 mg) in MeOH (50 mL) is degassed with H$_2$ and stirred for 5 h at 40° C. under H$_2$ (1 atm). Then the mixture is cooled to rt, and filtered through a celite pad. The filter cake is washed with EA. The filtrate is dried over Na$_2$SO$_4$, filtered and concentrated under reduced pressure. The residue is purified by prep-HPLC to give the desired product (830 mg, 74% yield) as a white solid.

To a mixture of 5-(trifluoromethyl)benzo[c][1,2]oxaborole-1,6(3H)-diol (600 mg, 2.75 mmol) and K$_2$CO$_3$ (691 mg, 4.95 mmol) in acetonitrile (50 mL) is added dropwise 1-bromopropan-2-one (542 mg, 3.85 mmol) at 0° C. It is stirred overnight at rt under N$_2$, and filtered through a celite pad. The filter cake is washed with EA (200 mL). The filtrate is dried over Na$_2$SO$_4$, filtered and concentrated under reduced pressure. The residue is purified by prep-HPLC to afford the desired product (262 mg, 35% yield) as a white solid.

To a solution of 1-(1-hydroxy-5-trifluoromethyl-1,3-dihydro-benzo[c][1,2]oxaborol-6-yloxy)-propan-2-one (160 mg, 0.58 mmol) in MeOH (5 mL) is bubbled with NH$_3$ for 20 min at −30° C. Then KCN (75 mg, 1.13 mmol), NH$_4$Cl (107 mg, 1.97 mmol) and NH$_3$·H$_2$O (2 mL) is added. The reaction mixture is stirred overnight at rt, evaporated, and purified by prep-HPLC to give the desired product (90.0 mg, yield 51%) as a light yellow solid.

To a solution of 4-trifluoromethoxybenzoic acid (126 mg, 0.60 mmol) and DIPEA (157 mg, 1.20 mmol) in DMF (3 mL) is added HATU (233 mg, 0.60 mmol). The mixture is stirred for 2 h at 35° C. Then the solution of 2-amino-3-(1-hydroxy-5-trifluoromethyl-1,3-dihydro-benzo[c][1,2]oxaborol-6-yloxy)-2-methyl-propionitrile (90.0 mg, 0.300 mmol) in DMF (2 mL) is added dropwise at 0° C. The reaction mixture is stirred overnight at 35° C. under N$_2$, cooled to rt, diluted with water (100 mL), and extracted with EA (3×25 mL). The organic layer is washed with brine, dried over Na$_2$SO$_4$, filtered and concentrated under reduced pressure. The residue is purified by prep-HPLC to give the title compound N-[1-cyano-2-(1-hydroxy-5-trifluoromethyl-1,3-dihydro-benzo[c][1,2]oxaborol-6-yloxy)-1-methyl-ethyl]-4-trifluoromethoxybenzamide (25 mg, yield 17%) as a white solid. $^1$H NMR (400 MHz, DMSO-d$_6$): δ 9.41 (s, 1H), 9.10 (s, 1H), 7.99 (d, J=8.4 Hz, 2H), 7.75 (s, 1H), 7.55-7.51 (m, 3H), 5.00 (s, 2H), 4.70 (d, J=8.8 Hz, 1H), 4.43 (d, J=8.8 Hz, 1H), 1.84 (s, 3H) ppm; HPLC purity: 97.2% at 220 nm and 96.9% at 254 nm; MS: m/z=489 (M+1, ESI+).

EXAMPLE 12

N-(2-cyano-1-(5-fluoro-1-hydroxy-1,3-dihydrobenzo[c][1,2]oxaborol-6-yloxy)propan-2-yl)-4-(trifluoromethoxy)benzamide

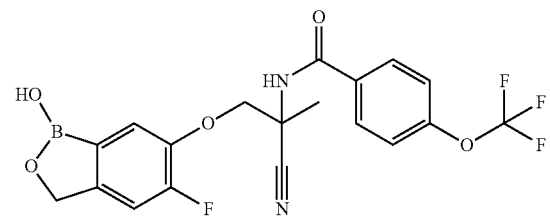 [SMILES: CC(C#N)(COc1cc2c(cc1F)COB2O)NC(=O)c1ccc(OC(F)(F)F)cc1]

The solution of 2-bromo-4,5-difluorobenzoic acid (1.00 g, 4.24 mmol) and SOCl$_2$ (2 mL) in MeOH (12 mL) is refluxed for 2 h and cooled to rt. The reaction mixture is evaporated and the residue is purified by column chromatography on silica gel to give the desired product. (0.97 g, 92% yield).

A solution of phenylmethanol (4.32 g, 0.04 mol) in dry THF (250 mL) is added NaH (1.60 g, 0.04 mol, 60% in oil). The reaction mixture is stirred at 80° C. for 2 h. Then the mixture is cooled and 2-bromo-4,5-difluorobenzoic acid methyl ester (10.0 g, 0.04 mol) is added at 0° C. The reaction mixture wad stirred at 0° C. overnight. The solution is quenched with water (50 mL) and extracted with Et$_2$O (60 mL×2). The combined organic layers are washed with saturated NaCl solution, dried over Na$_2$SO$_4$ and concentrated under vacuum. The residue is purified by column chromatography on silica gel to give the desired product (9.00 g, 66%).

The mixture of 4-benzyloxy-2-bromo-5-fluorobenzoic acid methyl ester (3.00 g, 8.85 mmol), KOAc (3.72 g, 38.0 mmol), Pin$_2$B$_2$ (3.37 g, 13.3 mmol) and PdCl$_2$(dppf)$_2$ (1.44 g, 1.77 mmol) in 1,4-dioxane (100 mL) is heated at 85° C. for 6 h until TLC indicated that the starting material had been consumed. It is filtered and the filtrate is removed under reduced pressure. The residue is purified by column to give the desired product (4.00 g, 83% yield).

To a stirring solution of 4-benzyloxy-5-fluoro-2-(4,4,5,5-tetramethyl-[1,3,2]dioxaborolan-2-yl)benzoic acid methyl ester (5 g, 12.9 mmol) in methanol (100 mL) is added sodium borohydride (2.95 g, 77.7 mmol) at 0° C. It is stirred at 0° C. for 10 min and then at rt for 2 h until LCMS indicated that the starting material had been consumed. It is added with 2N HCl (20 mL), stirred at rt for 30 min. More water is added and the solid participate is collected and washed with water and petroleum ether to provide the desired product (3.00 g, 90% yield).

To a solution of 6-(benzyloxy)-5-fluorobenzo[c][1,2]oxaborol-1(3H)-ol (3.00 g, 0.116 mmol) in MeOH (150 mL) is added Pd/C (50 mg, 10% wt) and the reaction mixture is degassed with H$_2$ and stirred at 30° C. for 3 h. LCMS indicated that the starting material had been consumed. It is filtrated and concentrated then give the desired product (1.20 g, 84.6% yield).

The solution of 5-fluorobenzo[c][1,2]oxaborole-1,6(3H)-diol (100 mg, 0.60 mmol), 1-bromo-propan-2-one (123 mg, 0.89 mmol), and K$_2$CO$_3$ (164 mg, 1.19 mmol) in MeCN is stirred at rt overnight. It is diluted with diethyl ether and filtered through a short path of silica gel. The filtrate is concentrated. The residue is dissolved in EA, washed with H$_2$O, dried and filtered. Removal of solvent gave the desired product (80.0 mg, 67% yield).

To a solution of 1-(5-fluoro-1-hydroxy-1,3-dihydro-benzo[c][1,2]oxaborol-6-yloxy)-propan-2-one (250 mg, 1.13 mmol) in MeOH (20 mL) at −30° C. is bubbled NH$_3$ for 20 min, then KCN (146 mg, 2.25 mmol), NH$_4$Cl (197 mg, 3.71 mmol) and NH$_3$.H$_2$O (5 mL) are added. The mixture is stirred overnight at rt, evaporated and extracted with THF. Removal of solvent gave the desired product (278 mg, 99% yield).

To a solution of 2-amino-3-(5-fluoro-1-hydroxy-1,3-dihydro-benzo[c][1,2]oxaborole-6-yloxy)-2-methyl-propionitrile (278 mg, 1.112 mmol), 4-trifluoromethoxybenzoic acid (345 mg, 1.668 mmol) and HATU (843 mg, 2.224 mmol) in DMF (5 mL) is added DIPEA (430 mg, 0.3336 mmol). The mixture is stirred at rt overnight and evaporated. The residue is purified by prep-HPLC to give target compound N-(2-cyano-1-(5-fluoro-1-hydroxy-1,3-dihydrobenzo[c][1,2]oxaborol-6-yloxy)propan-2-yl)-4-(trifluoromethoxy)benzamide (106 mg, 22% yield). $^1$H NMR (400 MHz, DMSO-d$_6$): δ 9.26 (s, 1H), 9.16 (s, 1H), 8.05 (d, J=8.4 Hz, 2H), 7.56 (d, J=8.0 Hz, 3H), 7.39 (d, J=10.8 Hz, 1H), 4.97 (s, 2H), 4.66 (d, J=9.2 Hz, 1H), 4.44 (d, J=9.2 Hz, 1H), 1.90 (s, 3H) ppm; HPLC purity: 99.3% at both 220 nm and 254 nm; MS: m/z=439.1 (M+1, ESI+).

EXAMPLE 13

N-(1-(7-chloro-5-fluoro-1-hydroxy-1,3-dihydrobenzo[c][1,2]oxaborol-6-yloxy)-2-cyanopropan-2-yl)-4-(trifluoromethoxy)benzamide

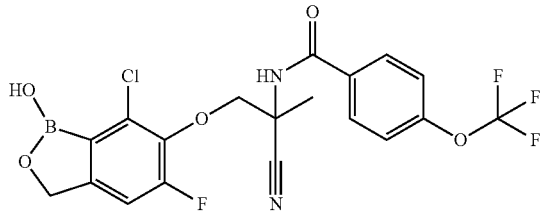 [SMILES: CC(C#N)(COc1c(F)cc2c(c1Cl)B(O)OC2)NC(=O)c1ccc(OC(F)(F)F)cc1]

To a solution of 5-fluorobenzo[c][1,2]oxaborole-1,6(3H)-diol (100 mg, 0.60 mmol) in anhydrous CH$_2$Cl$_2$ (5 mL) and DMF (1 mL) is added NCS (87.4 mg, 0.65 mmol) at 20° C. It is stirred at rt overnight. The solvent of the reaction mixture is removed under vacuo and the residue is purified by pre-HPLC give the desired product (73.6 mg, 48% yield).

The solution of 7-chloro-5-fluorobenzo[c][1,2]oxaborole-1,6(3H)-diol (50.0 mg, 0.25 mmol), 1-bromo-propan-2-one (52.0 mg, 0.375 mmol), K$_2$CO$_3$ (69 mg, 0.50 mmol) in MeCN is stirred at rt for 3 h, The reaction mixture is diluted with diethyl ether and filtered through a short path of silica gel. The filtrate is removed under reduced pressure and dissolved in EtOAc. It is washed with water, dried, filtered and evaporated to give the desired product (30 mg, 47% yield).

1-(7-chloro-5-fluoro-1-hydroxy-1,3-dihydro-benzo[c][1,2]oxaborol-6-yloxy)propan-2-one (300 mg, 1.16 mmol) in MeOH (20 mL) at −30° C. is bubbled NH$_3$ for 20 min, and then KCN (151 mg, 2.32 mmol), NH$_4$Cl (203 mg, 3.83 mmol) and NH$_3$.H$_2$O (10 mL) are added. The mixture is stirred overnight at rt, evaporated and dissolved in THF. Removal of solvent gave 2 the desired product (250 mg, 76% yield).

To a solution of 2-amino-3-(7-chloro-5-fluoro-1-hydroxy-1,3-dihydro-benzo[c][1,2]oxaborol-6-yloxy)-2-methyl-propionitrile (250 mg, 0.83 mmol), 4-trifluoromethoxybenzoic acid (257 mg, 1.25 mmol) and HATU (630 mg, 1.66 mmol) in DMF (5 mL) is added DIPEA (322 mg, 2.5 mmol). The mixture is stirred at rt overnight, evaporated and the residue is purified by pre-HPLC to give the title compound N-(1-(7-chloro-5-fluoro-1-hydroxy-1,3-dihydrobenzo[c][1,2]oxaborol-6-yloxy)-2-cyano-propan-2-yl)-4-(trifluoromethoxy)benzamide (96.0 mg, 24% yield). $^1$H NMR (400 MHz, DMSO-d$_6$): δ 9.19 (s, 1H), 8.95 (s, 1H), 7.90 (d, J=8.8 Hz, 2H), 7.42 (d, J=8.4 Hz, 2H), 7.30 (d, J=10.8 Hz, 1H), 4.84 (s, 2H), 4.50 (d, J=9.2 Hz, 1H), 4.35 (d, J=9.6 Hz, 1H), 1.84 (s, 3H) ppm; HPLC purity: 98.5% at 220 nm and 97.8% at 254 nm; MS: m/z=473.3 (M+1, ESI+).

EXAMPLE 14

N-(2-cyano-1-(5,7-dichloro-1-hydroxy-1,3-dihydrobenzo[c][1,2]oxaborol-6-yloxy)propan-2-yl)-4-(trifluoromethoxy)benzamide

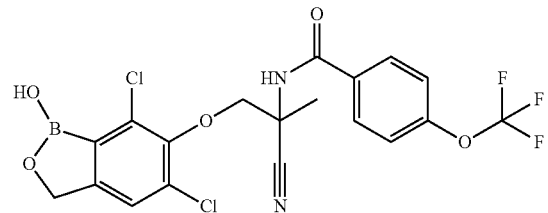 [SMILES: CC(C#N)(COc1c(Cl)cc2c(c1Cl)B(O)OC2)NC(=O)c1ccc(OC(F)(F)F)cc1]

The title compound is synthesized by following the procedures in Example 1 using 5,7-dichlorobenzo[c][1,2]oxaborole-1,6(3H)-diol for alkylation with 1-chloropropan-2-one. The starting material, 5,7-dichlorobenzo[c][1,2]oxaborole-1,6(3H)-diol, is prepared by bis-chloronation of benzo[c][1,2]oxaborole-1,6(3H)-diol with 3.5 eq NCS in THF at rt overnight (yield 28%). $^1$H NMR (400 MHz, DMSO-d$_6$): δ 9.93 (s, 1 H), 9.18 (s, 1 H), 7.43 (d, J=8.0 Hz, 1 H), 4.88 (s, 2 H) ppm. The final title compound, is obtained as white solid. $^1$H NMR (400 MHz, DMSO-d$_6$): δ 9.34 (s, 1H), 9.03 (s, 1H), 8.00 (d, J=8.0 Hz, 2H), 7.58 (s, 1H), 7.51 (d, J=8.0 Hz, 2H), 4.94 (s, 2H), 4.48 (d, J=8.0 Hz, 1H), 4.31 (d, J=8.0 Hz, 1H), 1.96 (s, 3H) ppm; HPLC purity: 98.9% at 220 nm; MS: m/z=489 [M+1]$^+$.

EXAMPLE 15

N-(1-(5-chloro-1-hydroxy-1,3-dihydrobenzo[c][1,2]oxaborol-6-yloxy)-2-cyanopropan-2-yl)-4-(trifluoromethoxy)benzamide

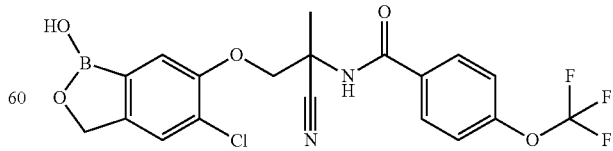

A mixture of 2,4-dihydroxybenzoic acid methyl ester (15.0 g, 89.2 mmol), potassium carbonate (13.6 g, 98.4 mmol) and benzyl bromide (16.8 g, 98.2 mmol) in acetone (375 mL) is refluxed overnight. The mixture is cooled to rt and filtered. Solvent is removed and the residue is purified by silica gel chromatography eluted with 20% of EtOAc in petroleum ether to afford the desired product (20.0 g, 87% yield) as white solid.

To a solution of 4-benzyloxy-2-hydroxybenzoic acid methyl ester (5.20 g, 20.0 mmol) in DCM (52 mL) is added a solution of sulfuryl chloride (3.00 g, 22.0 mmol) in DCM (30 ml), and it is stirred at rt for 6 h. The reaction mixture is quenched with ice water and extracted with EtOAc. Evaporation of the solvent under reduced pressure gave the crude product which is crystallized from EtOAc to give the desired product (4.50 g, 76% yield) as white solid.

To a solution of 4-benzyloxy-5-chloro-2-hydroxybenzoic acid methyl ester (4.50 g, 15.4 mmol) and pyridine (3.65 g, 46.2 mmol) in DCM (100 mL) is added dropwise Tf$_2$O (4.80 g, 17.0 mmol) at 0° C. under nitrogen atmosphere. The reaction mixture is stirred at 0° C. for 1 h. The reaction mixture is diluted with ice water and stirred for 15 min. The organic layer thus separated is washed sequentially with water and brine. The residue thus obtained is purified by column chromatography using 4% ethyl acetate in hexane as an eluent to give the desired product (crude) (6.80 g) which is used directly in next step without further purification.

A mixture of crude methyl 4-(benzyloxy)-5-chloro-2-(trifluoromethylsulfonyloxy)benzoate (6.80 g), bis(pinacolato)diboron (5.80 g, 22.8 mmol), Pd(dppf)Cl$_2$ (0.63 g, 7.71 mmol), KOAc (3.00 g, 30.6 mmol) in 1,4-dioxane (90 mL) is degassed with N$_2$ for 5 min. The reaction mixture is stirred at 70-80° C. for 16 h. TLC (EtOAc/PE=1/5) indicated complete consumption of the starting material. The reaction mixture is poured into water (400 mL) and extracted with EtOAc (100 mL×3). The combined organic phases are dried over anhydrous Na$_2$SO$_4$, and concentrated in vacuo to give crude product, which is purified by column chromatography (silica gel, EtOAc/PE=1/10) to get the desired product (6.19 g, quant. yield) as crude, which is used directly in next step without further purification.

To a mixture of crude 4-benzyloxy-5-chloro-2-(4,4,5,5-tetramethyl-[1,3,2]dioxaborolan-2-yl)benzoic acid methyl ester (6.19 g) in EtOH (125 mL) is added NaBH$_4$ (3.60 g, 38.5 mmol) in small portions at 0° C. under nitrogen atmosphere. The reaction mixture is stirred at 0° C. for 4 h. The reaction mixture is poured into 6 N HCl (125 mL) and stirred at rt overnight. The suspended solid is filtered and washed with 1N HCl to give the desired product (3.50 g, 83% yield) as yellow solid.

To a solution of 6-(benzyloxy)-5-chlorobenzo[c][1,2]oxaborol-1(3H)-ol (1.00 g, 3.64 mmol) in EtOH (50 mL) at rt under N$_2$ is added 10% Pd/C (0.10 g). The reaction mixture is stirred at rt for 3 h. The mixture is filtered and concentrated under reduced pressure. The residue is mixed with 6N HCl. The suspended solid is filtered and washed with 1N HCl to give the desired product (600 mg, 89% yield) as yellow solid.

To a solution of 5-chlorobenzo[c][1,2]oxaborole-1,6(3H)-diol (500 mg, 2.71 mmol) and K$_2$CO$_3$ (750 mg, 5.42 mmol) in MeCN (50 mL) is added dropwise 1-bromoacetone (750 mg, 5.42 mmol) at 15° C. under N$_2$. The mixture is stirred at 15° C. overnight. The reaction solution is partitioned between EtOAc (100 mL) and water (50 mL). The aqueous layer is extracted with EtOAc (50 mL×2). The combined organic layers are washed with brine and dried over Na$_2$SO$_4$. The solvent is removed under reduced pressure to afford the desired product (580 mg, 89% yield) as oil.

To a solution of 1-(5-chloro-1-hydroxy-1,3-dihydrobenzo[c][1,2]oxaborol-6-yloxy)-propan-2-one (400 mg, 1.66 mmol) in MeOH (10 mL) is bubbled NH$_3$ at −30° C. to 0° C. for 1 h. Afterwards, the solution is added to a mixture of KCN (250 mg, 3.84 mmol) and NH$_4$Cl (400 mg, 7.48 mmol) in 28% NH$_3$.H$_2$O (10 mL). The mixture is sealed and stirred at rt for 18 h. The reaction solution is partitioned between EtOAc (50 mL) and brine (25 mL). The aqueous layer is extracted with EtOAc (50 mL×2). The combined organic layers are washed with brine and dried over Na$_2$SO$_4$. The solvent is removed under reduced pressure to afford the desired product (400 mg, 90% yield) as white solid.

To a solution of 2-amino-3-(5-chloro-1-hydroxy-1,3-dihydrobenzo[c][1,2]oxaborol-6-yloxy)-2-methylpropanenitrile (250 mg, 0.94 mmol) and 4-trifluoromethoxybenzoic acid (290 mg, 1.41 mmol) in DMF (5 mL) at rt under N$_2$ are added HATU (711 mg, 1.87 mmol) and DIPEA (364 mg, 2.82 mmol) The reaction mixture is stirred at 30-35° C. overnight. The reaction mixture is purified by prep-HPLC to get a solid (235 mg, 55% yield). $^1$H NMR (400 MHz, DMSO-d$_6$): δ 9.24 (s, 1H), 9.10 (s, 1H), 8.00 (d, J=8.4 Hz, 2H), 7.56 (s, 1H), 7.51 (d, J=8.0 Hz, 2H), 7.46 (s, 1H), 4.92 (s, 2H), 4.63 (d, J=9.2 Hz, 1H), 4.39 (d, J=9.2 Hz, 1H), 1.87 (s, 3 H) ppm; HPLC purity: 98.1% at 220 nm and 98.5% at 254 nm: MS: m/z=455.1 (M+1, ESI+).

EXAMPLE 16

N-(1-(7-chloro-1-hydroxy-1,3-dihydrobenzo[c][1,2]oxaborol-6-yloxy)-2-cyanopropan-2-yl)-4-(trifluoromethylthio)benzamide

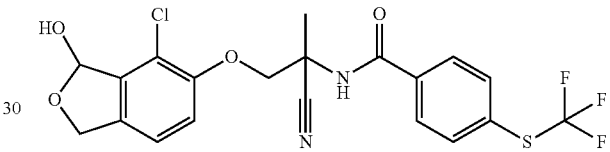

The solution of 4-((trifluoromethyl)thio)benzoic acid (277 mg, 1.25 mmol), HATU (950 mg, 2.5 mmol) and DIPEA (645 mg, 5.0 mmol) in DMF (4 mL) is stirred at rt for 30 min. Then 2-amino-3-((7-chloro-1-hydroxy-1,3-dihydrobenzo[c][1,2]oxaborol-6-yl)oxy)-2-methylpropanenitrile (400 mg, 1.5 mmol) is added. The mixture is stirred at rt overnight, added with water, extracted with EA (50 mL×3). The organic layer is washed with aq. NaHCO$_3$ (50 mL×3), brine (50 mL×3), dried over Na$_2$SO$_4$, and concentrated under reduced pressure. The residue is purified by prep-HPLC to give the title compound N-(1-((7-chloro-1-hydroxy-1,3-dihydrobenzo[c][1,2]oxaborol-6-yl)oxy)-2-cyanopropan-2-yl)-4-(trifluoromethoxy)benzamide as a solid (190 mg, yield 27%). $^1$H NMR (400 MHz, DMSO-d$_6$): δ 9.18 (m, 2H), 7.96 (d, J=8.0 Hz, 2H), 7.86 (d, J=8.0 Hz, 2H), 7.33 (m, 2H), 4.92 (s, 2H), 4.58 (d, J=8.0 Hz, 1H), 4.40 (d, J=8.0 Hz, 1H), 1.86 (s, 3H) ppm. Purity: 97.4% at 220 and 97.1% at 254 nm; MS: m/z=471.1 (M+1, ESI+).

EXAMPLE 17

(S)—N-(1-(7-chloro-1-hydroxy-1,3-dihydrobenzo[c][1,2]oxaborol-6-yloxy)-2-cyanopropan-2-yl)-4-(trifluoromethylsulfonyl)benzamide

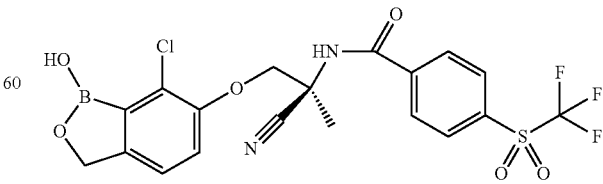

To the solution of 4-(trifluoromethylthio)benzoic acid (5 g, 22.5 mmol) is dissolved in water (50 mL) and acetic acid (150 mL) is added potassium permanganate (20 g, 126.5 mmol) at rt. The reaction is stirred for 16 h, diluted with ethyl acetate and washed with water. The organic layer is dried over MgSO$_4$ and concentrated to give 4-(trifluoromethylsulfonyl)benzoic acid (5 g, 87% yield).

4-(Trifluoromethylsulfonyl)benzoic acid (2 g, 7.87 mmol) is dissolved in DCM (20 ml) and SOCl$_2$ (20 ml). The mixture is stirred at 60° C. for 1 h. Then the solution is concentrated in vacuo to got the acyl chloride, which is added to a mixture of 2-amino-3-(7-chloro-1-hydroxy-1,3-dihydrobenzo[c][1,2]oxaborol-6-yloxy)-2-methylpropanenitrile (2.1 g, 7.87 mmol) and DIPEA (3 g, 23.6 mmol) in THF (40 ml). The mixture is stirred at rt overnight. The reaction mixture is concentrated, dissolved in EA (100 ml), and washed with brine (3×40 ml). The organic layer is dried over Na$_2$SO$_4$, concentrated under reduced pressure, and purified by prep-HPLC to give N-(1-(7-chloro-1-hydroxy-1,3-dihydrobenzo[c][1,2]oxaborole-6-yloxy)-2-cyanopropan-2-yl)-4-(trifluoromethylsulfonyl)benzamide (designated as Example 17a) (1.7 g, 43% yield) as white solid. $^1$H NMR (400 MHz, DMSO-d$_6$): δ ppm 9.46 (s, 1H), 9.17 (s, 1H), 8.31 (d, J=8.0 Hz, 2H), 8.21 (d, J=8.0 Hz, 2H), 7.34 (m, 2H), 4.92 (s, 2H), 4.58 (d, J=8.0 Hz, 1H), 4.43 (d, J=8.0 Hz, 1H), 1.88 (s, 3H) ppm; Purity: 95.8% at 220 nm; MS: m/z=503.1 [M+1]$^+$.

By following the procedure described in Example 1, the racemic mixture is separated to collect peak 1 giving the chiral enantiomer (S)—N-(1-(7-chloro-1-hydroxy-1,3-dihydrobenzo[c][1,2]oxaborol-6-yloxy)-2-cyanopropan-2-yl)-4-(trifluoromethylsulfonyl)benzamide. $^1$H NMR (400 MHz, DMSO-d$_6$): δ ppm 9.44 (s, 1H), 9.14 (s, 1H), 8.31 (d, J=8.0 Hz, 2H), 8.21 (d, J=8.0 Hz, 2H), 7.34 (m, 2H), 4.93 (s, 2H), 4.59 (d, J=8.0 Hz, 1H), 4.43 (d, J=8.0 Hz, 1H), 1.89 (s, 3H) ppm; Purity: 99.6% at 220 nm and 99.7% at 254 nm; Chiral purity: 99.6% at 220 nm; Specific rotation: [α]=+11.12° in CH$_2$Cl$_2$ at 20° C. MS: m/z=503.2 [M+1]$^+$.

EXAMPLE 18

(S)—N-(1-((7-chloro-1-hydroxy-1,3-dihydrobenzo[c][1,2]oxaborol-6-yl)oxy)-2-cyanopropan-2-yl)-4-((trifluoromethyl)thio)benzamide

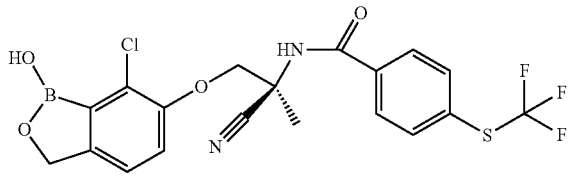 [SMILES: C[C@](C#N)(COc1ccc2c(c1Cl)B(O)OC2)NC(=O)c1ccc(SC(F)(F)F)cc1]

A mixture of 4-((trifluoromethyl)thio)benzoic acid (1.84 g, 8.27 mmol) in DCM (20 mL) and SOCl$_2$ (20 mL) is stirred at 60° C. for 1 h. The solution is concentrated in vacuo to got the acyl chloride, which is added to a mixture of 2-amino-3-(7-chloro-1-hydroxy-1,3-dihydrobenzo[c][1,2]oxaborol-6-yloxy)-2-methylpropanenitrile (2.2 g, 8.27 mmol) and DIPEA (3.2 g, 24.8 mmol) in THF (50 mL). The mixture is stirred at rt overnight and concentrated. The residue is dissolved in EA (200 mL), washed with brine (3×30 mL), dried over Na$_2$SO$_4$, concentrated under reduced pressure and purified by column chromatography to give the desired (N-(1-((7-chloro-1-hydroxy-1,3-dihydrobenzo[c][1,2]oxaborole-6-yl)oxy)-2-cyanopropan-2-yl)-4-((trifluoromethyl)thio)benzamide as pale white solid (1.8 g, yield 47%). $^1$H NMR (400 MHz, DMSO-d$_6$): δ 9.18 (m, 2H), 7.96 (d, 2H), 7.86 (d, 2H), 7.33-7.32 (m, 2H), 4.92 (s, 2H), 4.57 (d, 1H), 4.40 (d, 1H), 1.86 (s, 3H) ppm; HPLC purity: 97.4% at 220 nm and 97.1% at 254 nm MS: m/z=471.1 (M+1, ESI+).

By following the procedure described in Example 1, the racemic mixture is separated to collect peak 1 giving the chiral enantiomer (S)—N-(1-((7-chloro-1-hydroxy-1,3-dihydrobenzo[c][1,2]oxaborol-6-yl)oxy)-2-cyanopropan-2-yl)-4-((trifluoromethyl)thio)benzamide. $^1$H NMR (DMSO-d$_6$, 400 MHz): δ 9.17 (s, 1H), 9.15 (s, 1H), 7.96 (d, J=8.4 Hz, 2H), 7.86 (d, J=8.4 Hz, 2H), 7.36-7.32 (m, 2H), 4.92 (s, 2H), 4.58 (d, J=9.2 Hz, 1H), 4.40 (d, J=9.2 Hz, 1H), 1.87 (s, 3H) ppm. MS: m/z=471 (M+1, ESI+). HPLC purity: 95.9% at 220 nm and 97.9% at 254 nm Chiral HPLC purity: 98.5%. Specific rotation: [α]=+9.06° in CH$_2$Cl$_2$ at 20° C.

EXAMPLE 19

N-(1-(4-chloro-1-hydroxy-1,3-dihydrobenzo[c][1,2]oxaborol-6-yloxy)-2-cyanopropan-2-yl)-4-(trifluoromethoxy)benzamide

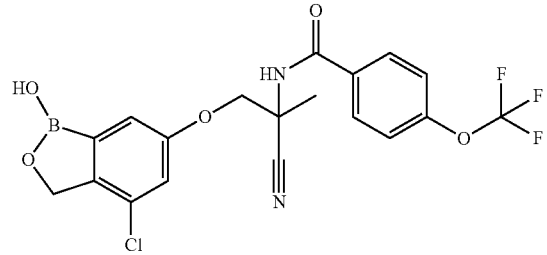 [SMILES: CC(C#N)(COc1cc(Cl)c2c(c1)B(O)OC2)NC(=O)c1ccc(OC(F)(F)F)cc1]

To a solution of 1-chloro-3,5-dimethoxybenzene (10.0 g, 58 mmol) in DMF (70.0 mL) is added POCl$_3$ (17 mL, 18.4 mmol) dropwise at 0° C. The reaction mixture is stirred at rt for 30 min and at 100° C. for additional 2 h. The resulting reaction is poured into ice water, extracted with EA, dried over Na$_2$SO$_4$, and concentrated under reduced pressure to give the desired product as a yellow solid (7.7 g, yield 66%).

To a solution of 2-chloro-4,6-dimethoxybenzaldehyde (8.0 g, 39.9 mmol) in DCM (50.0 mL) is added BBr$_3$ (170 mL, 170 mmol, 1M) dropwise at 0° C. under Ar atmosphere. The reaction mixture is stirred at rt overnight, quenched with ice water, concentrated, extracted with EA for three times, dried over Na$_2$SO$_4$, and concentrated under reduced pressure to give the desired product as a red solid (5.0 g, yield 73.5%).

To a solution of 2-chloro-4,6-dihydroxybenzaldehyde (5 g, 29 mmol) in DCM (100.0 mL) is added DHP (5 mL, 54.8 mmol) and then pyridinium p-toluenesulfonate (PPTS, 0.72 g, 2.92 mmol). The reaction mixture is stirred at rt overnight, quenched with sat NaHCO$_3$ at 0° C., extracted with DCM for three times, dried over Na$_2$SO$_4$, and concentrated under reduced pressure. The residue is purified by column chromatography to give the desired compound as colorless oil (5 g, yield 66.0%).

To a solution of 2-chloro-6-hydroxy-4-((tetrahydro-2H-pyran-2-yl)oxy)benzaldehyde (4.0 g, 15.6 mmol) and pyridine (6 mL) in DCM (60 mL) is added Tf$_2$O (4.0 mL, 24.4 mmol) at −10° C. under Ar atmosphere. The reaction mixture is stirred at 0° C. for 2 h, quenched with cold brine, extracted with DCM for three times, dried over Na$_2$SO$_4$, and concentrated under reduced pressure. The residue is purified by column chromatography (PE:EA=100:1) to give the desired compound as colorless oil (4.0 g, yield 66.2%).

The solution of 3-chloro-2-formyl-5-((tetrahydro-2H-pyran-2-yl)oxy)phenyl trifluoromethane sulfonate (4.0 g, 10.1 mmol), bis(pinacolato)diboron (8.0 g, 32.48 mmol), PdCl$_2$(dppf)$_2$ (400 mg, 0.52 mmol) and KOAc (3.09 g, 31.48 mmol) in 1,4-dioxane (80.0 mL) is stirred under N$_2$ at rt for 10 min and at 80° C. for 1.5 h. It is quenched with cold water, extracted with EA for three times, dried over Na$_2$SO$_4$ and concentrated under reduced pressure. The residue is purified by column chromatography to give the desired compound as colorless oil (4 g).

To a solution of 2-chloro-4-(tetrahydro-2H-pyran-2-yloxy)-6-(4,4,5,5-tetramethyl-1,3,2-dioxaborolan-2-yl)benzaldehyde (4 g, 10.1 mmol) in MeOH (50.0 mL) is added NaBH$_4$ (775 mg, 20.4 mmol) at 0° C. The reaction mixture is stirred at rt for 2 h, quenched with sat. NH$_4$Cl, extracted with EA for three times, dried over Na$_2$SO$_4$, and concentrated under reduced pressure. The residue is dissolved in MeOH and mixed with cold 3N HCl at 0° C. The mixture is stirred at rt for 2 h, extracted with EA, dried over Na$_2$SO$_4$ and concentrated under reduced pressure. The residue is purified by prep-HPLC to give the desired compound as white solid (470 mg, yield 25%).

To a mixture of 4-chlorobenzo[c][1,2]oxaborole-1,6(3H)-diol (200 mg, 1.08 mmol) and K$_2$CO$_3$ (450 mg, 3.26 mmol) in acetone (10 mL) is added 1-bromopropan-2-one (150 mg, 1.63 mmol). The reaction mixture is stirred at 60° C. overnight, and cooled to rt. The resulting reaction is partitioned between EA and H$_2$O, extracted with EA for three times (50 mL×3). The organic layer is washed with brine (50 mL×3), dried over Na$_2$SO$_4$, and concentrated to give the desired product as an oil, which is used directly for the next step without further purification. (160 mg, yield 65.0%).

To the stirring solution of NaCN (51.5 mg, 1.05 mmol), 25% NH$_3$.H$_2$O (1.5 mL) in MeOH (1.0 mL) is added NH$_4$Cl (64.2 mg, 1.2 mmol), followed by 1-((4-chloro-1-hydroxy-1,3-dihydrobenzo[c][1,2]oxaborol-6-yl)oxy)propan-2-one (160 mg, 0.7 mmol). The mixture is stirred at rt overnight, quenched with water, and extracted with EA (50 mL×3). The organic layer is washed with brine (50 mL×3), dried over Na$_2$SO$_4$, and concentrated under reduced pressure. The residue is purified by prep-HPLC to give the desired compound as a yellow solid (150 mg. yield 57.4%).

A solution of 4-(trifluoromethoxy)benzoic acid (138.0 mg, 0.67 mmol), HATU (513 mg, 1.35 mmol) and DIPEA (348 mg, 2.7 mmol) in DMF (1.5 mL) is stirred at rt for 30 min before 2-amino-3-((4-chloro-1-hydroxy-1,3-dihydrobenzo[c][1,2]oxaborol-6-yl)oxy)-2-methylpropanenitrile (150 mg, 0.56 mmol) is added. The mixture is stirred at rt overnight, added with water, and extracted with EA (50 mL×3). The organic layer is washed with aq. NaHCO$_3$ (50 mL×3), brine (50 mL×3), dried over Na$_2$SO$_4$, and concentrated under reduced pressure. The residue is purified by prep-HPLC to give N-(1-(4-chloro-1-hydroxy-1,3-dihydrobenzo[c][1,2]oxaborol-6-yloxy)-2-cyanopropan-2-yl)-4-(trifluoromethoxy)benzamide as a white solid (37 mg, yield 15.6%). $^1$H NMR (400 MHz, DMSO-d$_6$): δ 9.42 (s, 1H), 9.06 (s, 1H), 8.00 (d, J=8.8 Hz, 2H), 7.51 (d, J=8.0 Hz, 2H), 7.32 (d, J=2.0 Hz, 1H), 7.28 (d, J=2.0 Hz, 1H), 4.93 (s, 2H), 4.56 (d, J=9.2 Hz, 1H), 4.36 (d, J=9.2 Hz, 1H), 1.82 (s, 2H) ppm. Purity: 96.4% (220 nm); MS: 455 (M+1, ESI+).

EXAMPLE 20

N-(1-(7-chloro-4,5-difluoro-1-hydroxy-1,3-dihydrobenzo[c][1,2]oxaborol-6-yloxy)-2-cyanopropan-2-yl)-4-(trifluoromethoxy)benzamide

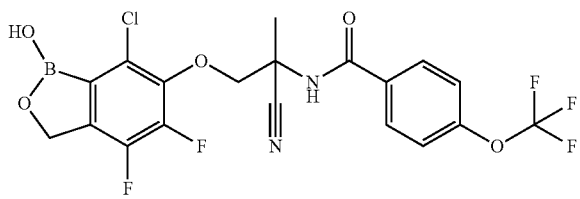 [SMILES: CC(C#N)(COc1c(F)c(F)c2c(c1Cl)B(O)OC2)NC(=O)c1ccc(OC(F)(F)F)cc1]

To a solution of 5-bromo-1,2-difluoro-3-methoxybenzene (8.9 g, 39.9 mmol) in THF (200 mL), LDA (17.6 mL, 43.9 mmol) is added dropwise at −78° C. and the mixture is stirred at the same temperature for 2 h. DMF (9.6 g, 131.7 mmol) is added at −78° C., and the mixture is stirred at −78° C. for 4 h. The reaction is quenched with saturated aq. NH$_4$Cl, extracted with EA, dried over Na$_2$SO$_4$, and recrystallized to afford the desired product as a white solid (6 g, yield 60%). $^1$H NMR (400 MHz, CDCl$_3$): δ 10.20 (s, 1H), 7.04-7.06 (m, 1H), 3.99 (s, 3H) ppm.

To a solution of 6-bromo-2,3-difluoro-4-methoxybenzaldehyde (6 g, 23.9 mmol) in MeOH (120 mL), NaBH$_4$ (1.1 g, 28.7 mmol) is added at rt. It is stirred at rt for 1 h. The solvent is evaporated under reduced pressure. The residue is dissolved in EA, washed with water, dried over Na$_2$SO$_4$ to afford the desired product as a white solid (6 g, yield 99%).

To a solution of (6-bromo-2,3-difluoro-4-methoxyphenyl)methanol (6 g, 23.9 mmol) and DHP (4.36 mL, 47.8 mmol) in DCM (120 mL), PPTS (602 mg, 2.4 mmol) is added and the mixture is refluxed for 1 h. The solvent is evaporated under reduced pressure, and the residue is purified by column chromatography to afford the desired product as colorless oil (7 g, yield 87%).

To a solution of 2-((6-bromo-2,3-difluoro-4-methoxybenzyl)oxy)tetrahydro-2H-pyran (5.3 g, 15.7 mmol) in THF (80 mL), BuLi (7.5 mL, 18.8 mmol) is added dropwise at −78° C. After being stirred at −78° C. for 2 h, (i-PrO)$_3$B (5.5 mL, 23.6 mmol) is added dropwise at the same temperature, and the mixture is stirred at rt for 1 h. The reaction is quenched with aq. NH$_4$Cl, extracted with EA, dried over Na$_2$SO$_4$, and evaporated under reduced pressure. The residue is purified by column chromatography to afford the desired product as white solid (1.3 g, yield 41%).

To a solution of 4,5-difluoro-6-methoxybenzo[c][1,2]oxaborol-1(3H)-ol (900 mg, 4.5 mmol) in DCM (25 mL), BBr$_3$ (4.1 mL, 45 mmol) is added dropwise at −78° C. The resulting mixture is stirred overnight, poured into ice water, extracted with EA, dried over Na$_2$SO$_4$, and evaporated under reduced pressure to afford the desired product as brown solid (840 mg).

To a solution of 4,5-difluorobenzo[c][1,2]oxaborole-1,6 (3H)-diol (840 mg, 4.5 mmol) in CHCl$_3$ (25 mL), SO$_2$Cl$_2$ (3.6 mL, 45 mmol) is added at rt under argon atmosphere. The reaction mixture is refluxed for 2 h, quenched with water, extracted with EA, dried over Na$_2$SO$_4$, and evaporated under reduced pressure to afford the crude desired product as brown solid. It is used directly for the next step without further purification (570 mg).

To a mixture of 7-chloro-4,5-difluorobenzo[c][1,2]oxaborole-1,6(3H)-diol (570 mg, 2.6 mmol) and K$_2$CO$_3$ (1.1 g, 7.8 mmol) in acetone (25 mL), chloroacetone (0.6 mL, 7.8 mmol) is added at rt under argon atmosphere. The mixture is heated at 60° C. overnight. It is evaporated under reduced pressure giving the residue that is diluted with water, acified with HCl to pH=4-5, extracted with EA, dried over Na$_2$SO$_4$, and evaporated under reduced pressure to afford the crude product as brown solid (380 mg, crude). Part of the crude product (200 mg) is purified by prep-HPLC to afford the desired product as a white solid (65 mg).

To a solution of NaCN (17 mg, 0.35 mmol) in NH$_3$.H$_2$O (1 mL) and MeOH (1 mL) is added NH$_4$Cl (23 mg, 0.43 mmol) at rt. It is stirred for 5 min under argon atmosphere, and 1-((7-chloro-4,5-difluoro-1-hydroxy-1,3-dihydrobenzo[c][1,2]oxaborol-6-yl)oxy)propan-2-one (65 mg, 0.24 mmol) is added and the mixture is stirred at rt overnight. The resulting mixture is acidified to pH=7 and extracted with EA (2×8 mL). The combined organic layers are washed with brine, dried over Na$_2$SO$_4$, concentrated to afford the desired product as white solid (40 mg, yield 55%).

To a solution of 4-(trifluoromethoxy)benzoic acid (27 mg, 0.13 mmol) in DMF (1 mL) are added HATU (60 mg, 0.16 mmol) and DIPEA (51 mg, 0.4 mmol). It is stirred at rt for 2 h, and 2-amino-3-((7-chloro-4,5-difluoro-1-hydroxy-1,3-dihydrobenzo[c][1,2]oxaborol-6-yl)oxy)-2-methylpropanenitrile (40 mg, 0.13 mmol) is added. The mixture is stirred at rt under argon atmosphere overnight. The resulting mixture is extracted with EA (2×4 mL). The organic phase is washed with water and brine, dried over $Na_2SO_4$, concentrated under reduced pressure and purified by pre-HPLC to afford N-(1-((7-chloro-4,5-difluoro-1-hydroxy-1,3-dihydrobenzo[c][1,2]oxaborol-6-yl)oxy)-2-cyanopropan-2-yl)-4-(trifluoromethoxy)benzamide (6.5 mg, yield 10%) as white powder. $^1$H NMR (400 MHz, DMSO-$d_6$): δ 9.48 (br s, 1H), 9.02 (s, 1H), 7.97 (d, J=8.4 Hz, 2H), 7.49 (d, J=8.0 Hz, 2H), 5.05 (s, 2H), 4.64 (d, J=9.6 Hz, 1H), 4.52 (d, J=9.2 Hz, 1H), 1.90 (s, 3H) ppm; HPLC purity: 96.3% at 220 nm; MS: m/z=491.0 (M+1, ESI+).

EXAMPLE 21

(S)—N-(1-(7-chloro-1-hydroxy-1,3-dihydrobenzo[c][1,2]oxaborol-6-yloxy)-2-cyanopropan-2-yl)-4-(pentafluorothio)benzamide

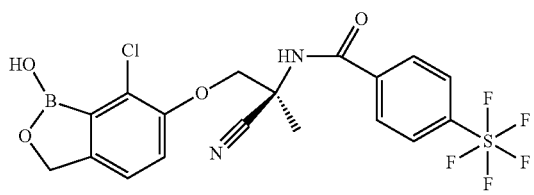 [SMILES: C[C@](C#N)(COc1ccc2c(c1Cl)B(O)OC2)NC(=O)c1ccc(S(F)(F)(F)(F)F)cc1]

A mixture of 4-(pentafluorothio)benzoic acid (4.0 g, 16.1 mmol), HATU (8.0 g, 20.96 mmol) and DIPEA (6.0 g, 48.3 mmol) in DMF (50 mL) is stirred at rt for 30 min To the mixture is added 2-amino-3-((7-chloro-1-hydroxy-1,3-dihydrobenzo[c][1,2]oxaborol-6-yl)oxy)-2-methylpropanenitrile (4.5 g, 18.8 mmol). The mixture is stirred at 35° C. overnight. The reaction is partitioned between EA and $H_2O$ and the aqueous phase is extracted with EA (100 mL×3). The combined organic layers is washed with sat $NaHCO_3$, brine (50 mL×3), and dried over $Na_2SO_4$. Concentration under reduced pressure gave the residue, which is purified by column chromatography providing the desired compound N-(1-(7-chloro-1-hydroxy-1,3-dihydrobenzo[c][1,2]oxaborol-6-yloxy)-2-cyanopropan-2-yl)-4-(pentafluorothio)benzamide (designated as Example 21a) as white solid (1.6 g, yield 21.3%). $^1$H NMR (400 MHz, DMSO-$d_6$): δ 9.24 (s, 1H), 9.13 (s, 1H), 8.08-8.06 (m, 4H), 7.36-7.32 (m, 2H), 4.92 (s, 2H), 4.58 (d, J=9.6 Hz, 1H), 4.39 (d, J=9.6 Hz, 1H), 1.88 (s, 3H) ppm; HPLC purity: 99.4% at 220 nm and 98.5% at 254 nm; ESI: MS: m/z=497.0 (M+1, ESI+).

By following the procedure described in Example 1, the racemic mixture is separated to collect peak 1 giving the chiral enantiomer (S)—N-(1-(7-chloro-1-hydroxy-1,3-dihydrobenzo[c][1,2]oxaborol-6-yloxy)-2-cyanopropan-2-yl)-4-(pentafluorothio)benzamide. $^1$H NMR (400 MHz, DMSO-$d_6$): δ 9.24 (s, 1H), 9.13 (s, 1H), 8.09-8.03 (m, 4H), 7.36-7.32 (m, 2H), 4.92 (s, 2H), 4.58 (d, J=9.6 Hz, 1H), 4.42 (d, J=9.6 Hz, 1H), 1.88 (s, 3H) ppm; HPLC purity: 99.4% at 220 nm and 98.4% at 254 nm; Chiral HPLC purity: 100% at 230 nm; ESI: MS: m/z=495.0 (M−1, ESI−).

EXAMPLE 22

(S)—N-(1-(7-chloro-1-hydroxy-1,3-dihydrobenzo[c][1,2]oxaborol-6-yloxy)-2-cyanopropan-2-yl)-4-cyanobenzamide

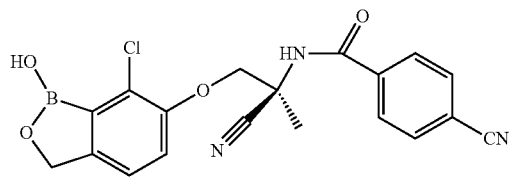 [SMILES: C[C@](C#N)(COc1ccc2c(c1Cl)B(O)OC2)NC(=O)c1ccc(C#N)cc1]

A mixture of 4-cyanobenzoic acid (2.65 g, 18.05 mmol), HATU (7.50 g, 19.6 mmol) and DIPEA (5.82 g, 45.1 mmol) in DMF (50 mL) is stirred at rt for 30 min before 2-amino-3-((7-chloro-1-hydroxy-1,3-dihydrobenzo[c][1,2]oxaborol-6-yl)oxy)-2-methylpropanenitrile (4.0 g, 15.04 mmol) is added. The mixture is stirred at 35° C. overnight. The reaction is partitioned between EA and $H_2O$, extracted with EA (100 mL×3), washed with saturated $NaHCO_3$, brine (50 mL×3), dried by $Na_2SO_4$, and concentrated under reduced pressure. The crude product is purified by column chromatography to give N-(1-(7-chloro-1-hydroxy-1,3-dihydrobenzo[c][1,2]oxaborol-6-yloxy)-2-cyanopropan-2-yl)-4-cyanobenzamide (designated as Example 22a) as white solid (1.2 g, yield 20.1%). $^1$H NMR (400 MHz, DMSO-$d_6$): δ 9.22 (s, 1H), 9.14 (s, 1H), 8.01 (s, 4H), 7.33-7.32 (m, 2H), 4.92 (s, 2H), 4.58 (d, J=9.2 Hz, 1H), 4.40 (d, J=9.6 Hz, 1H), 1.87 (s, 3H) ppm. HPLC purity: 97.7% at 220 nm and 96.8% at 254 nm; ESI: MS: m/z=394.1 (M−1, ESI−).

By following the procedure described in Example 1, the racemic mixture is separated to collect peak 1 giving the chiral enantiomer (S)—N-(1-(7-chloro-1-hydroxy-1,3-dihydrobenzo[c][1,2]oxaborol-6-yloxy)-2-cyanopropan-2-yl)-4-cyanobenzamide. $^1$H NMR (400 MHz, DMSO-$d_6$): δ 9.23 (s, 1H), 9.14 (br s, 1H), 8.01 (s, 4H), 7.33-7.32 (m, 2H), 4.92 (s, 2H), 4.58 (d, J=9.2 Hz, 1H), 4.41 (d, J=9.6 Hz, 1H), 1.87 (s, 3H) ppm. HPLC purity: 97.4% at 220 nm and 97.4% at 254 nm; Chiral HPLC purity: 98.1% at 230 nm; ESI: MS: m/z=396.2 (M+1, ESI+).

EXAMPLE 23

N-(2-cyano-1-(1-hydroxy-7-(trifluoromethyl)-1,3-dihydrobenzo[c][1,2]oxaborol-6-yloxy) propan-2-yl)-4-(trifluoromethoxy)benzamide

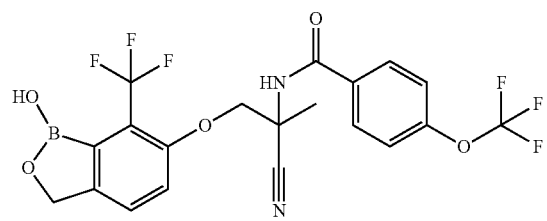 [SMILES: CC(C#N)(COc1ccc2c(c1C(F)(F)F)B(O)OC2)NC(=O)c1ccc(OC(F)(F)F)cc1]

To a solution of methyl 2,4-dihydroxybenzoate (4.2 g, 25 mmol) in $H_2O$/MeOH/THF (90 mL, 1:1:1) is added iodine (6.73 g, 26.5 mmol) and $NaHCO_3$ (2.31 g, 27.5 mmol) in one portion at 0° C. After stirring for 1 h, the precipitate is separated by filtration. The solid is washed with water several times and dried to give the desired product (3.5 g, yield 48%) as a grey solid.

BnBr (1.88 g, 11.0 mmol) is added to a solution of 2,4-dihydroxy-3-iodobenzoate (1.47 g, 5.0 mmol) and $Cs_2CO_3$ (3.59 g, 11.0 mmol) in DMF (50 mL). The mixture is stirred for 18 h, added with water (100 mL) and stirred for 1 h. It is extracted with EA, dried over $Na_2SO_4$, filtered and concentrated under reduced pressure. The residue is purified by column chromatography on silica gel eluted with PE-EA (6:1) to give the desired product (1.97 g, yield 83%) as a white solid.

$FSO_2CF_2CO_2CH_3$ (2.83 g, 14.75 mmol) is added to a mixture of methyl 2,4-bis(benzyloxy)-3-iodobenzoate (1.4 g, 2.95 mmol), HMPA (2.64 g, 14.75 mmol) and CuI (1.13 g, 5.9 mmol) in DMF (40 mL) and the mixture is stirred at 80° C. for 18 h and cooled to rt. It is added with saturated aqueous $NH_4Cl$ and extracted with EA twice. The combined organic extracts are washed with saturated $NaHCO_3$, brine, dried over $Na_2SO_4$, filtered and concentrated under reduced pressure. The residue is purified by column chromatography on silica gel eluted with PE-EA (6:1) to give the desired product (0.93 g, yield 76%) as a white solid.

The solution of methyl 2,4-bis(benzyloxy)-3-(trifluoromethyl)benzoate (0.93 g, 2.23 mmol) in MeOH (30 mL) is hydrogenated using 10% Pd/C (100 mg) as catalyst under atmospheric pressure overnight. The catalyst is removed by filtration through Celite and the solvent is evaporated under reduced pressure to give the desired product (505 mg, yield 96%) as a grey solid.

A solution of methyl 2,4-dihydroxy-3-(trifluoromethyl)benzoate (708 mg, 3.0 mmol), $NaHCO_3$ (290 mg, 3.45 mmol) and KI (100 mg, 0.6 mmol) in MeCN (40 mL) is slowly warmed to 60° C. before BnBr (616 mg, 3.6 mmol) is added. The mixture is stirred at 80° C. overnight. The mixture is cooled to rt and evaporated. The residue is quenched with 10% aq HCl to pH=6 and extracted with EA (50 mL*2). The combined organic extracts are washed with brine (50 mL*2), dried over $Na_2SO_4$, filtered and concentrated under reduced pressure. The residue is purified by column chromatography on silica gel eluted with PE-EA (5:1) to give the desired product (667 mg, yield 68%) as a white solid.

To a solution of methyl 4-(benzyloxy)-2-hydroxy-3-(trifluoromethyl)benzoate (652 mg, 2.0 mmol) and $Et_3N$ (606 mg, 6.0 mmol) in DCM (30 mL) at 0° C. is added dropwise $(Tf)_2O$ (846 mg, 3.0 mmol) in DCM (3 mL). The reaction mixture is stirred at rt for 3 h. Water (50 mL) is added and the mixture is extracted with DCM (50 mL*2). The combined organic extracts are washed with brine, dried over $Na_2SO_4$, filtered and concentrated under reduced pressure. The residue is purified by column chromatography on silica gel eluted with PE-EA (8:1) to give the desired product (834 mg, yield: 91%) as a white solid.

To a solution of methyl 4-(benzyloxy)-3-(trifluoromethyl)-2-(trifluoromethylsulfonyloxy)benzoate (378 mg, 0.83 mmol), 5,5,5',5'-tetramethyl-2,2'-bi(1,3,2-dioxaborinane) (563 mg, 2.49 mmol) and KOAc (244 mg, 2.49 mmol) in 1,4-dioxane (30 mL) is added $PdCl_2(dppf)_2$ (61 mg, 0.083 mmol). The reaction mixture is stirred at 50° C. under argon atmosphere overnight. The solvent is removed and the residue is purified by column chromatography on silica gel eluted with PE-EA (5:1) to give the desired product (295 mg, yield 84%) as a white solid.

To a solution of methyl 4-(benzyloxy)-2-(5,5-dimethyl-1,3,2-dioxaborinan-2-yl)-3-(trifluoromethyl)benzoate (211 mg, 0.5 mmol) in dry THF (10 mL) is added $LiAlH_4$ (57 mg, 1.5 mmol) at 0° C. The reaction mixture is stirred at rt for 4 h, and then added with 3N HCl to pH=2. The reaction mixture is stirred at rt overnight. The solvent is evaporated, the residue is purified by prep-HPLC to give the desired product (43 mg, yield 28%) as a white solid.

The solution of 6-(benzyloxy)-7-(trifluoromethyl)benzo[c][1,2]oxaborol-1 (3H)-ol (125 mg, 0.41 mmol) in MeOH (10 mL) is hydrogenated using 10% Pd/C (15 mg) as catalyst under atmospheric pressure overnight. The catalyst is removed by filtration through Celite and the solvent is evaporated under reduced pressure to give the desired product (84 mg, yield 95%) as a grey solid.

To a solution of 7-(trifluoromethyl)benzo[c][1,2]oxaborole-1,6(3H)-diol (146 mg, 0.67 mmol) and $K_2CO_3$ (277 mg, 2.01 mmol) in acetone (15 mL) is added bromoacetone (184 mg, 1.34 mmol). The reaction mixture is refluxed for 3 h. The solvent is evaporated under reduced pressure. The residue is purified by prep-HPLC and then prep-TLC eluted with PE-EA (3:2) to give the desired product (48 mg, yield 26%) as a white solid.

A mixture of 1-(1-hydroxy-7-(trifluoromethyl)-1,3-dihydrobenzo[c][1,2]-oxaborol-6-yloxy)propan-2-one (48 mg, 0.18 mmol), $NH_4Cl$ (19 mg, 0.36 mmol) and ammonia (7N in MeOH, 1 mL) in MeOH (3 mL) is stirred at rt for 20 min before addition of NaCN (22 mg, 0.45 mmol). The reaction mixture is stirred at rt for 5 h. DCM (50 mL) is added and the solvent is removed under reduced pressure. The residue is washed with THF. THF solution is rotary evaporated to give the desired product (crude) as a white solid (54 mg). It is used to next step without further purification.

A solution of 4-(trifluoromethoxy)benzoic acid (45 mg, 0.22 mmol), HATU (137 mg, 0.36 mmol) and DIPEA (70 mg, 0.54 mmol) in DMF (5 mL) is stirred at rt for 30 min before 2-amino-3-(1-hydroxy-7(trifluoromethyl)-1,3-dihydrobenzo-[c][1,2]oxaborol-6-yloxy)-2-methylpropanenitrile (54 mg, crude, 0.18 mmol) is added. The reaction mixture is stirred at rt overnight. It is purified by prep-HPLC to give N-(2-cyano-1-(1-hydroxy-7-(trifluoromethyl)-1,3-dihydrobenzo-[c][1,2]oxaborol-6-yloxy)propan-2-yl)-44 trifluoromethoxy)benzamide (12 mg, yield 14% over two steps) as a white solid. $^1H$ NMR (400 MHz, DMSO-$d_6$): δ 9.11 (s, 1H), 9.07 (s, 1H), 7.98 (d, J=8.8 Hz, 2H), 7.64 (d, J=8.4 Hz, 1H), 7.51 (d, J=8.4 Hz, 2H), 7.44 (d, J=8.8 Hz, 1H), 4.96 (s, 2H), 4.62 (d, J=9.2 Hz, 1H), 4.39 (d, J=9.2 Hz, 1H), 1.83 (s, 3H) ppm; HPLC purity: 100% at 214 nm and 100% at 254 nm; MS: m/z=489.0 (M+1, ESI+).

EXAMPLE 24

N-(2-cyano-1-(4,7-dichloro-1-hydroxy-1,3-dihydrobenzo[c][1,2]oxaborol-6-yloxy)propan-2-yl)-4-(trifluoromethoxy)benzamide

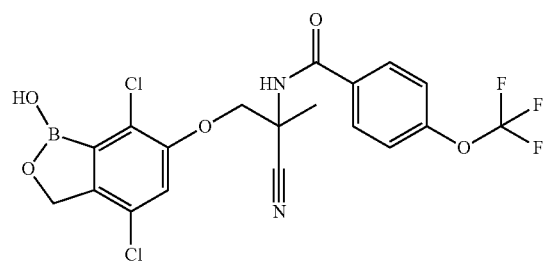 [SMILES: CC(C#N)(COc1cc(Cl)c2c(c1Cl)B(O)OC2)NC(=O)c1ccc(OC(F)(F)F)cc1]

To a solution of 3-bromo-5-chlorophenol (20.6 g, 100 mmol) and imidazole (145 g, 220 mmol) in DMF (80 mL) is added TBDMSCl (16.5 g, 110 mmol) at 0° C., and the mixture is stirred at rt overnight. Water is added at 0° C., and aqueous layer is extracted with DCM. The organic layer is washed with brine, dried over $Na_2SO_4$ and evaporated in vacuo. The residue is purified by silica gel chromatography (PE:EA=100:1) to give the desired product as a colorless oil (33 g).

To a solution of 2,2,6,6-tetramethylpiperidine (7.33 g, 52 mmol) in THF (150 mL) is slowly added n-butyllithium (20.8 mL, 52 mmol) at −78° C. It is stirred at 0° C. for 1 h. Then the mixture is re-cooled to −78° C. and a solution of (3-bromo-5-chlorophenoxy)-(tert-butyl)dimethylsilane (12.8 g, 40 mmol) in 50 mL THF is added. It is stirred at −78° C. for 2 h before DMF (5.8 g, 80 mmol) is added. The mixture is stirred −78° C. for 1 h, added with 1N HCl until pH 4, and extracted with EtOAc. The organic layer is washed with brine, and dried over $Na_2SO_4$ and concentrated to give a solid, which is rinsed with DCM to give the desired product (6 g, yield 64%).

To a solution of 2-bromo-6-chloro-4-hydroxybenzaldehyde (2.3 g, 10 mmol) in MeOH (100 mL) at 0° C. is added portionwise $NaBH_4$ (1.1 g, 30 mmol). The mixture is stirred at rt for 1 h. Aqueous $NH_4Cl$ is added and extracted with EtOAc. The organic layer is dried and concentrated to give the desired product (1.6 g, yield 69%).

At 0° C., TFA (260 mg, 2.3 mmol) is slowly added to a mixture of ethoxyethene (5.0 g, 69.6 mmol) and 3-bromo-5-chloro-4-(hydroxymethyl)phenol (5.5 g, 23.2 mmol) in DCM (200 mL). It is slowly warmed to rt and stirred overnight. The mixture is washed $H_2O$, dried, concentrated and purified by column to give the desired product (4.5 g, yield 51%).

To a solution of 1-bromo-3-chloro-5-(1-ethoxyethoxy)-2-((1-ethoxyethoxy)methyl)benzene (3.8 g, 10 mmol) and $B(O-iPr)_3$ (TIPB, 3.3 g, 12 mmol) in THF (50 mL) is added n-BuLi (2.5 N, 5.2 mL, 13 mmol) at −78° C. It is stirred for 1 h, and then slowly warmed to 0° C. 2N HCl is added until pH=6. EtOAc is added and the organics is separated, dried and concentrated to the desired product (3.1 g, crude).

To a solution of 3-chloro-5-(1-ethoxyethoxy)-2-((1-ethoxyethoxy)methyl)phenylboronic acid (3.1 g, 8.9 mmol) in acetone (20 mL) is added 4N HCl (14 mL). It is stirred at rt for 5 h. TLC monitoring showed the starting material is consumed. The resulting mixture is concentrated under reduced pressure and washed with hexane to give the desired product (1.7 g).

To a solution of 4-chlorobenzo[c][1,2]oxaborole-1,6(3H)-diol (1.75 g, 9.5 mmol) in DCM (80 mL) and DMF (15.0 mL) is added NCS (1.37 g, 10.2 mmol). The reaction mixture is stirred overnight, and the result reaction is concentrated under reduced pressure. The residue is purified by column chromatography to give the desired product as white solid (2 g, yield 95%).

To a stirred solution of 4,7-dichlorobenzo[c][1,2]oxaborole-1,6(3H)-diol (3.0 g, 13.2 mmol) in DMF (30 mL) is slowly added NaH (660 mg, 27.5 mmol) at 0° C., and stirred for 10 min before bromoacetone (3.74 g, 27.5 mmol) is added slowly at the same temperature. The resulting mixture is stirred at 0° C. for 3 h. The mixture is poured into water, acidified with diluted HCl solution to pH=5 and extracted with EtOAc. The organic layer is dried and concentrated to give a residue, which is purified by silica gel chromatography (DCM:MeOH=100:1 to 30:1) to give the desired product (1.0 g).

To a stirring solution of 1-(4,7-dichloro-1-hydroxy-1,3-dihydrobenzo[c][1,2]oxaborol-6-yloxy)propan-2-one (1.0 g, crude, 3.6 mmol) and $NH_4Cl$ (390 mg, 7.3 mmol) in 7N $NH_3$MeOH (30 mL) is added TMSCN (723 mg, 7.3 mmol) in one portion. It is stirred at rt overnight. TLC monitoring showed the ketone compound is consumed. The mixture is concentrated to give a residue, which is then dissolved with EtOAc (50 mL). After washing with water, the organic layer is dried and concentrated to give the desired product (crude, 600 mg), which is used for next step without purification.

To a stirring mixture of 2-amino-3-(4,7-dichloro-1-hydroxy-1,3-dihydrobenzo[c][1,2]oxaborol-6-yloxy)-2-methylpropanenitrile (600 mg, crude, 2.0 mmol) and DIPEA (645 mg, 5.0 mmol) in dry THF (20 mL) is added a solution of 4-(trifluoromethoxy)benzoyl chloride (449 mg, 2.0 mmol) in THF (2 mL) dropwise at 0° C. The resulting mixture is slowly warmed to rt and stirred overnight. Diluted HCl is added until pH=5 and it is extracted with EtOAc. The organic layer is dried and concentrated to give a residue, which is purified by silica gel chromatography (DCM:MeOH=50:1 to 10:1) to give a crude product. The crude product is further purified by prep-HPLC (Column: Agilent XDB-C18, 150 mm*20 mm 5 um, mobile phase A: H2O+0.1% TFA; mobile phase B: ACN, B % 40~100, flow rate: 30 mL/min) to give N-(2-cyano-1-(4,7-dichloro-1-hydroxy-1,3-dihydrobenzo[c][1,2]oxaborol-6-yloxy)propan-2-yl)-4-(trifluoromethoxy)benzamide as a white solid (80 mg). $^1$H NMR (DMSO-$d_6$, 400 MHz): δ 9.41 (s, 1H), 9.07 (s, 1H), 7.98 (d, 2H, J=8.0 Hz), 7.51 (d, 2H, J=8.0 Hz), 7.49 (s, 1H), 4.90 (dd, 2H), 4.61 (d, 1H, J=9.6 Hz), 4.45 (d, 1H, J=9.6 Hz), 1.85 (s, 3H) ppm; HPLC purity: 97.9% at 220 nm and 95.8% at 254 mm MS: m/z=489.0 (M+1, ESI+).

EXAMPLE 25

N-(2-cyano-1-(7-fluoro-1-hydroxy-1,3-dihydrobenzo[c][1,2]oxaborol-6-yloxy)propan-2-yl)-4-(trifluoromethoxy)benzamide

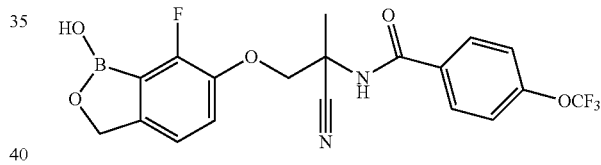

To a stirring solution of 1,2,3-trifluoro-4-nitrobenzene (80 g, 0.45 mol) in MeOH (800 mL) is slowly added MeONa (54 g, 0.99 mmol) in portions at 0° C. The resulting mixture is stirred at rt overnight. TLC showed the reaction is completed. The solvent is evaporated and the residue is washed with water, acidified with diluted HCl solution to pH=7.0 and extracted with EtOAc. The separated organics is dried and concentrated to give a residue, which is purified by silica gel chromatography (PE:EtOAc=100:1 to 30:1) to give the desired product (72 g, 80% yield).

To a mixture of 2-fluoro-1,3-dimethoxy-4-nitrobenzene (30.0 g, 0.15 mol) and $NH_4Cl$ (31.2 g, 0.6 mol) in mixed solvents of $H_2O$ (155 mL) and ethanol (620 mL) is added iron powder (67.2 g, 1.2 mol) in small portions. After completing the addition, the mixture is refluxed for 3 h under nitrogen, filtered through celite and concentrated in vacuo. The residue is extracted with $CH_2Cl_2$ (3×300 mL). The separated organics is dried and concentrated to give crude 3-fluoro-2,4-dimethoxyaniline, which is used for next step without further purification.

To a solution of 3-fluoro-2,4-dimethoxyaniline (30 g, 0.18 mol) in THF/con.HCl/$H_2O$ (v:v:v=1:1:1, 210 mL) is added $NaNO_2$ solution (18 g, 0.26 mol, 3M) dropwise below 0° C. The mixture is stirred at 0° C. for 0.5 h, and then KI solution (58 g, 0.35 mmol) is added slowly dropwise over 0.5 h. The reaction mixture is stirred at rt overnight. Then the mixture is evaporated and extracted with EtOAc (3×300 mL). The organics is dried over Na$_2$SO$_4$ and concentrated to give a residue, which is purified by silica gel chromatography (PE:EtOAc=100:1 to 40:1) to give the desired product (24.67 g, 50% yield) as a white solid.

To a stirring solution of 2-fluoro-4-iodo-1,3-dimethoxybenzene (20 g, 70.9 mmol) in THF (250 mL) is added n-BuLi (2.5M, 29.8 ml) dropwise at −78° C. The mixture is stirred at this temperature for 0.5 h. DMF (7.76 g, 106.3 mmol) is then added dropwise at −78° C. The mixture is then stirred at −78° C. for 1 h. The mixture is quenched with saturated NH$_4$Cl, extracted with EtOAc (2×200 mL). The combined extracts are washed with 1N HCl solution, dried over sodium sulfate and concentrated to give a residue, which is purified by silica gel chromatography (PE:EtOAc=90:1 to 50:1) to give the desired product (11.7 g, 90% yield) as a white solid.

To a stirring solution of 3-fluoro-2,4-dimethoxybenzaldehyde (10 g, 54.2 mmol) in DCM (200 mL) is slowly added BBr$_3$ (40.76 g, 16.3 mmol) at −78° C. The mixture is slowly warmed to rt and stirred for 6 h. TLC showed the reaction is completed. The mixture is poured into ice water, extracted with DCM. The organic layers is dried and concentrated. The crude product is purified by silica gel chromatography (PE:EtOAc=50:1 to 10:1) to give the desired product (8.0, 90% yield) as a white solid.

To a mixture of 3-fluoro-2,4-dihydroxybenzaldehyde (2 g, 12.8 mmol) and K$_2$CO$_3$ (1.7 g, 12.8 mmol) in acetone (20 mL) is added MOMCl (1.5 g, 19.2 mmol) slowly at 0° C. The resulting mixture is stirred at 0° C. for 5 h, poured into water, washed with saturated NaHCO$_3$ and extracted with EtOAc. The separated organics is dried and concentrated to give a residue, which is purified by silica gel chromatography (PE:EtOAc=100:1 to 30:1) to give the desired product (1.8 g, yield 70%) as a white solid.

To a stirring solution of 3-fluoro-2-hydroxy-4-(methoxymethoxy)benzaldehyde (3 g, 14.9 mmol) in DCM (20 mL) is added pyridine (2.35 g, 29.8 mmol) at 0° C. It is stirred for 10 min. Then Tf$_2$O (4.62 g, 16.4 mmol) is added dropwise. The resulting mixture is stirred at rt for 4 h. The mixture is poured into water, adjusted with diluted HCl solution to pH=7 and extracted with EtOAc. The organic layer is dried and concentrated to give a residue, which is purified by silica gel chromatography (petroleum ether:EtOAc=100:1 to 30:1) to give the desired product (3.1 g, yield 61%).

To a stirring solution of 2-fluoro-6-formyl-3-(methoxymethoxy)phenyl trifluoromethane sulfonate (3.0 g, 9.04 mmol), (PinB)$_2$ (4.59 g, 18.1 mmol) and KOAc (1.78 g, 18.1 mmol) in dry dioxane (40 mL) is added PdCl$_2$(dppf) (0.74 g, 0.9 mmol) under N$_2$. The resulting mixture is stirred at 70-75° C. for 1 h. and filtered. The filtrate is concentrated to give a crude product, which is purified by silica gel chromatography (petroleum ether:EtOAc=40:1 to 27:1) to give the desired product (2.43 g, 83% yield) as a white solid.

To a mixture of 3-fluoro-4-(methoxymethoxy)-2-(4,4,5,5-tetramethyl-1,3,2-dioxaborolan-2-yl)benzaldehyde (2.3 g, 7.42 mmol) in MeOH (20 mL) is added NaBH$_4$ (1.33 g, 37.1 mmol) carefully at 0° C. Then the mixture stirred at rt for 0.5 h, added with conc. HCl (6 ml) and stirred overnight. The reaction mixture is concentrated and the residue is extracted with EtOAc (2×50 mL). The organic layer is dried over Na$_2$SO$_4$ and concentrated. The crude product is purified by silica gel chromatography (DCM:MeOH=100:1 to 40:1) to give the desired product (0.7 g, 60% yield) as a white solid.

To a stirring solution of 7-fluorobenzo[c][1,2]oxaborole-1,6(3H)-diol (0.6 mg, 2.87 mmol) and K$_2$CO$_3$ (0.77 g, 55.65 mmol) in acetone (15 mL) is added 1-bromopropan-2-one (0.96 g, 7.14 mmol) under N$_2$. The resulting mixture is stirred rt overnight, filtered and concentrated to give a crude product, which is purified by silica gel chromatography (DCM:CH$_3$OH=125:1 to 70:1) to give the desired product (179 mg, 20% yield) as a white solid.

To a stirring solution of 1-(7-fluoro-1-hydroxy-1,3-dihydrobenzo[c][1,2]oxaborol-6-yloxy)propan-2-one (179 mg, 0.72 mmol) in NH$_3$ of MeOH (7N, 8 mL) is added NH$_4$Cl (189 mg, 3.58 mmol) and TMSCN (213 mg, 2.15 mmol) at 0° C. The mixture is stirred at rt overnight. The solvent is evaporated and the residue is washed with THF (50 ml) and filtered. The filtrate is evaporated and the crude product, the desired product (160 mg), is used for next step without further purification.

To a stirring mixture of 2-amino-3-(7-fluoro-1-hydroxy-1,3-dihydrobenzo[c][1,2]oxaborol-6-yloxy)-2-methylpropanenitrile (160 mg, crude, 0.64 mmol) and DIPEA (165 mg, 1.28 mmol) in dry THF (20 mL) is added a solution of 4-(trifluoromethoxy)benzoyl chloride (143 mg, 0.64 mmol) in THF (10 mL) dropwise at 0° C. The resulting mixture is slowly warmed to rt and stirred overnight. Diluted HCl is added until pH=5.0. It is extracted with EtOAc. The organic layer is dried and concentrated to give a residue, which is purified by silica gel chromatography (DCM:MeOH=100:1 to 30:1) to give the desired product as a white solid (85 mg, 30% yield over two steps).

EXAMPLE 26

N-(1-(7-chloro-4-fluoro-1-hydroxy-1,3-dihydrobenzo[c][1,2]oxaborol-6-yloxy)-2-cyanopropan-2-yl)-4-(trifluoromethoxy)benzamide

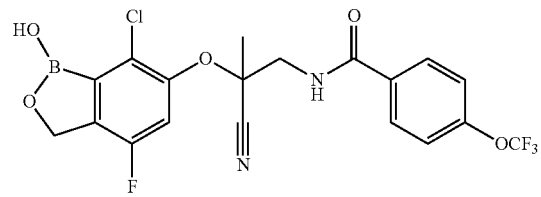 [SMILES: CC(C#N)(CNC(=O)c1ccc(OC(F)(F)F)cc1)Oc1cc(F)c2c(c1Cl)B(O)OC2]

To a solution of 3-bromo-5-fluorophenol (19 g, 100 mmol) and imidazole (15 g, 220 mmol) in DMF (80 mL) is added TBDMSCl (16.5 g, 110 mmol) at 0° C., and the mixture is stirred at rt overnight. Water is added at 0° C., and aqueous layer is extracted with DCM. The organic layer is washed with brine, dried over Na$_2$SO$_4$ and evaporated in vacuo. The residue is purified by silica gel chromatography (PE:EA=100:1) to give the desired product as colorless oil (30 g).

To a solution of 2,2,6,6-tetramethylpiperidine (HTMP, 6 g, 42.5 mmol) in THF (200 mL) is added n-BuLi (2.5 N, 17 mL, 42.6 mmol) at −78° C. It is then slowly warmed to 0° C. and stirred at this temperature for 0.5 h. The mixture is re-cooled to −78° C., and a solution of (3-bromo-5-fluorophenoxy)(tert-butyl)dimethylsilane (10 g, 32.8 mmol) in THF (80 mL) is slowly added over a period of 0.5 h. It is stirred at the same temperature for 1.5. DMF (4.8 g, 66 mmol) is added, stirred at −78° C. for 1 hr, and then slowly warmed to −10° C. 2N HCl is added until pH=3. The organics is separated, dried and concentrated to a residue, which is washed with hexane to give the desired product as a yellow solid (2.6 g, 36% yield).

To a solution of 2-bromo-6-fluoro-4-hydroxybenzaldehyde (2.6 g, 11.9 mmol) in MeOH (100 mL) at 0° C. is added NaBH$_4$ (1.4 g, 35.7 mmol) in portions. The mixture is stirred at rt for 1 h. Aq. NH$_4$Cl is added and extracted with EtOAc. The separated organics is dried and concentrated to give the desired product (2.2 g, yield 85%).

At 0° C., TFA (26 mg, 0.23 mmol) is slowly added to a mixture of ethoxyethene (980 mg, 13.6 mmol) and 3-bromo-5-fluoro-4-(hydroxymethyl)phenol (1 g, 4.5 mmol) in DCM (30 mL). It is slowly warmed to rt and stirred overnight. It is added with more DCM, washed H$_2$O, dried, concentrated and purified by column to give the desired product (900 mg, yield 55%).

To a solution of 1-bromo-5-(1-ethoxyethoxy)-2-((1-ethoxyethoxy)methyl)-3-fluorobenzene (2.5 g, 6.85 mmol) and B(O-iPr)$_3$ (1.55 g, 8.2 mmol) in THF (30 mL) is added n-BuLi (2.5 N, 3.6 mL, 8.9 mmol) at −78° C., stirred for 1 h, and then slowly warmed to 0° C. 2N HCl is added until pH=6. EtOAc is added and the organic layer is separated, dried and concentrated to give a residue 5-(1-ethoxyethoxy)-2-((1-ethoxyethoxy)methyl)-3-fluoro phenyl boronic acid (2 g, crude).

A solution of 4N HCl (8 mL), 5-(1-ethoxyethoxy)-2-((1-ethoxyethoxy)methyl)-3-fluoro phenylboronic acid (2 g, crude, 6 mmol) in acetone (20 mL) is stirred at rt overnight and concentrated to give a solid residue. EtOAc is added to dissolve the solid and hexane is slowly added while stirring. A precipitate is formed. Filtration gave the desired product as grey solid (800 mg, 79%).

To a solution of 4-fluorobenzo[c][1,2]oxaborole-1,6(3H)-diol (800 mg, 4.8 mmol) in DCM (50 mL) and DMF (7 mL) is added NCS (636 mg, 4.87 mmol). The reaction mixture is stirred at rt overnight, concentrated under reduced pressure, and purified by column chromatography to give the desired product (500 mg).

To a stirring solution of 7-chloro-4-fluorobenzo[c][1,2]oxaborole-1,6(3H)-diol (500 mg, 2.5 mmol) in DMF (10 mL) is slowly added NaH (200 mg, 5 mmol) at 0° C. It is stirred for 10 min before bromo-acetone (685 mg, 5 mmol) is added slowly at the same temperature. The resulting mixture is stirred at 0° C. for 3 h, poured into water, acidified with diluted HCl to pH=5.0 and extracted with EtOAc. The organic layer is dried and concentrated to give a residue, which is purified by silica gel chromatography (DCM:MeOH=100:1 to 10:1) to provide the desired product (300 mg).

To a stirring solution of 1-(7-chloro-4-fluoro-1-hydroxy-1,3-dihydrobenzo[c][1,2]oxaborole-6-yloxy)propan-2-one (100 mg, crude, 0.35 mmol) and NH$_4$Cl (40 mg, 0.7 mmol) in 7N NH$_3$ of MeOH (10 mL) is added TMSCN (70 mg, 0.7 mmol) in one portion. It is stirred at rt overnight, concentrated to give a residue. It is dissolved in EtOAc, washed with H$_2$O, dried and concentrated to give the desired product (crude, 100 mg), which is used for next step without purification.

To a stirring mixture of 2-amino-3-(7-chloro-4-fluoro-1-hydroxy-1,3-dihydrobenzo[c][1,2]oxaborol-6-yloxy)-2-methylpropanenitrile (100 mg, crude, 0.35 mmol) and DIPEA (90 mg, 0.7 mmol) in dry THF (20 mL) is added a solution of 4-(trifluoromethoxy)benzoyl chloride (0.1 N, 5 mL, 0.52 mmol) in THF (5 mL) dropwise at 0° C. After addition, the resulting mixture is slowly warmed to rt and stirred overnight. Diluted HCl is added until pH=5. It is added with EtOAc, washed with water, dried and concentrated to give a residue. It is purified by silica gel chromatography (DCM:MeOH=50:1 to 10:1) to give a crude product. The crude product is further purified by prep-HPLC (Column: Agilent XDB-C18, 150 mm*20 mm 5um, mobile phase A: H$_2$O+0.1% TFA; mobile phase B: ACN, B % 40~100, flow rate: 30 mL/min) to give N-(1-(7-chloro-4-fluoro-1-hydroxy-1,3-dihydrobenzo[c][1,2]oxaborol-6-yloxy)-2-cyanopropan-2-yl)-4-(trifluoromethoxy)benzamide as a white solid (4 mg, yield 2%). $^1$H NMR (Acetone-d$_6$, 400 MHz): δ 8.39 (s, 1H), 8.30 (br s, 1H), 8.03 (d, 2H, J=8.4 Hz), 7.43 (d, 2H, J=8.4 Hz), 7.22 (d, 1H, J=10 Hz), 5.00 (d, 2H, J=1.6 Hz), 4.69 (d, 1H, J=9.6 Hz), 4.60 (d, 1H, J=9.6 Hz), 2.01 (s, 3H) ppm; HPLC purity: 97.7% at 220 nm and 99.6% at 254 nm; MS: m/z=473.1 (M+1, ESI+).

EXAMPLE 27

N-(2-cyano-1-(1-hydroxy-7-(2,2,2-trifluoroethyl)-1,3-dihydrobenzo[c][1,2]oxaborol-6-yl oxy)propan-2-yl)-4-(trifluoromethoxy)benzamide

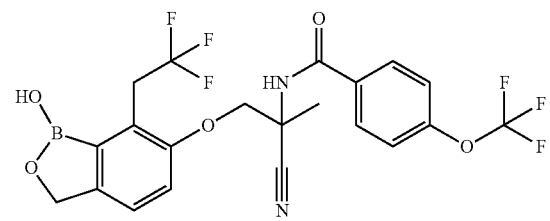 [SMILES: CC(C#N)(COc1ccc2c(c1CC(F)(F)F)B(O)OC2)NC(=O)c1ccc(OC(F)(F)F)cc1]

A solution of 2,6-dimethoxybenzaldehyde (4.98 g, 30 mmol) in THF (60 mL) is cooled to 0° C. and trimethyl (trifluoromethyl)silane (5.11 g, 36 mmol) is added followed by Bu$_4$NF (0.2 mL, 1N in THF). The solution is stirred at rt for 1.5 h. The solution is then treated with 30 mL of 1N HCl and stirred for 2 h. The solution is extracted with EA. The EA layer washed with brine, dried over Na$_2$SO$_4$, filtered and evaporated to give 1 the desired product (6.73 g, yield 95%) as a pale yellow solid.

To a solution of 1-(2,6-dimethoxyphenyl)-2,2,2-trifluoroethanol (2.89 g, 12.2 mmol) in toluene (60 mL) is added SOCl$_2$ (2.9 g, 24.4 mmol) and pyridine (0.2 mL). The reaction mixture is heated to 70° C. and allowed to stir at this temperature for 3 h, then is cooled to rt and concentrated in vacuo. The residue is purified by column chromatography on silica gel eluted with PE:EA=8:1 to give the desired product (2.85 g, yield 92%) as a yellow solid.

To a solution of 2-(1-chloro-2,2,2-trifluoroethyl)-1,3-dimethoxybenzene (2.63 g, 10.4 mmol) in MeOH (30 mL) and EA (30 mL) is hydrogenated using 10% Pd/C (263 mg) as catalyst under atmospheric pressure. The reaction mixture is stirred at 45° C. overnight. The catalyst is removed by filtration on Celite and the solvent is evaporated under the reduced pressure to give the desired product (2.19 g, yield 96%) as a white solid.

To a solution of 1,3-dimethoxy-2-(2,2,2-trifluoroethyl) benzene (3.3 g, 15.0 mmol) in DCM (50 mL) at −10° C. is added BBr$_3$ (9.38 mL, 37.5 mmol) dropwised. The mixture is stirred at −10° C. for 0.5 h and then at rt overnight. Water (50 mL) is added and the mixture is extracted with EA (100 mL*3). The combined organic extracts are washed with brine, dried over Na$_2$SO$_4$, filtered and concentrated under the reduced pressure. The residue is purified by column chromatography on silica gel eluted with PE:EA=6:1 to give the desired product (2.15 g, yield: 75%) as a solid.

POCl$_3$ (3.83 g, 25 mmol) is added to DMF (15 mL) at 0° C. After stirred for 20 min, 2-(2,2,2-trifluoroethyl)benzene- 1,3-diol (1.92 g, 10 mmol) in DMF (5 mL) is added slowly. The reaction mixture is stirred at rt for 4 h. The mixture is poured into ice water and the precipitate is filtered to give the desired product (1.6 g, yield 65%) as a yellow solid.

A mixture of 2,4-dihydroxy-3-(2,2,2-trifluoroethyl)benzaldehyde (1.6 g, 7.3 mmol), NaHCO$_3$ (0.74 g, 8.8 mmol) and KI (0.24 g, 1.5 mmol) in MeCN (50 mL) is slowly warmed to 60° C. Then benzyl bromide (1.44 g, 8.4 mmol) is added and the mixture is heated to 80° C. and stirred overnight. The mixture is then cooled to rt, filtered and the solvent is rotary evaporated. The residue is purified by column chromatography on silica gel eluted with PE:EA=8:1 to give the desired product (1.83 g, yield 81%) as a white solid.

To a solution of 4-(benzyloxy)-2-hydroxy-3-(2,2,2-trifluoroethyl)benzaldehyde (1.24 g, 4.0 mmol) and pyridine (1.58 g, 20.0 mmol) in DCM (40 mL) is added Tf$_2$O (2.48 mL, 8.8 mmol) slowly at 0° C. The reaction mixture is stirred for 3 h at rt. The mixture is poured into water and extracted with EA (150 mL*3). The combined organic layers are washed with brine, dried over Na$_2$SO$_4$, filtered and concentrated under the reduced pressure. The residue is purified by column chromatography on silica gel eluted with PE:EA=6:1 to give the desired product (636 mg, yield 36%) as a yellow oil.

A mixture of 3-(benzyloxy)-6-formyl-2-(2,2,2-trifluoroethyl)phenyl trifluoromethane sulfonate (3.14 g, 7.1 mmol), KOAc (5.57 g, 56.8 mmol), 5,5,5',5'-tetramethyl-2,2'-bi(1,3,2-dioxaborinane) (7.27 g, 28.4 mmol) and PdCl$_2$(dppf)$_2$ (0.624 g, 0.852 mmol) in 1.4-dioxane (100 mL) is heated to 100° C. and stirred for 16 h under N$_2$. The mixture is then cooled to rt, filtered and the filtrate is concentrated by rotary evaporation. The residue is purified by column chromatography on silica gel by elution with PE:EA=6:1 to give the desired product as a white solid (1.81 g, yield 63%).

To a solution of 4-(benzyloxy)-2-(5,5-dimethyl-1,3,2-dioxaborinan-2-yl)-3-(2,2,2-trifluoro ethyl)benzaldehyde (1.09 g, 2.68 mmol) in THF (25 mL) is added NaBH$_4$ (0.2 g, 5.36 mmol). The reaction mixture is stirred at rt for 3 h, then it is slowly added HCl (5 mL, 6N) at ice bath. The mixture is continued to stir for 16 h at rt. The reaction mixture is poured into water and extracted with EA (100 mL*3). The combined organic layers are washed with brine, dried over Na$_2$SO$_4$, filtered and concentrated under the reduced pressure. The residue is purified by silica gel column chromatography using PE:EA=5:1 as eluent to give the desired product (390 mg, yield 45%) as a light yellow solid.

The mixture of 6-(benzyloxy)-7-(2,2,2-trifluoroethyl)benzo[c][1,2]oxaborol-1(3H)-ol (390 mg, 1.21 mmol) in MeOH (20 mL) and EA (20 mL) is hydrogenated using 10% Pd/C (39 mg) as catalyst under atmospheric pressure overnight. The catalyst is removed by filtration on Celite and the solvent is evaporated under the reduced pressure to give the desired product (278 mg, yield 99%) as light yellow solid.

To a solution of 7-(2,2,2-trifluoroethyl)benzo[c][1,2]oxaborole-1,6(3H)-diol (278 mg, 1.2 mmol) and K$_2$CO$_3$ (331 mg, 2.4 mmol) in acetone (15 mL) is added bromoacetone (214 mg, 1.56 mmol). The reaction mixture is refluxed for 3 h. The reaction mixture is filtered and the residue is washed with acetone (5 mL). The filtrate is concentrated and the residue is purified by prep-TLC using PE:EA=4:1 as eluent to give the desired product (208 mg, yield 60%) as a white solid.

A mixture of 1-(1-hydroxy-7-(2,2,2-trifluoroethyl)-1,3-dihydrobenzo[c][1,2]-oxaborol-6-yloxy)-propan-2-one (208 mg, 0.72 mmol), NH$_4$Cl (77 mg, 1.44 mmol) and ammonia (7N in methanol, 3 mL) in MeOH (8 mL) is stirred at rt for 20 min before addition of NaCN (88 mg, 1.8 mmol). The reaction mixture is stirred at rt for 5 h. DCM (50 mL) is added and the solvent is evaporated under the reduced pressure. The residue is washed with THF, and the THF solution is evaporated to give the desired product (crude) as a white solid (226 mg). It is used in next step without further purification.

A solution of 4-(trifluoromethoxy)benzoic acid (178 mg, 0.86 mmol), HATU (547 mg, 1.44 mmol) and DIPEA (279 mg, 2.16 mmol) in DMF (12 mL) is stirred at rt for 30 min, then 2-amino-3-(1-hydroxy-7-(2,2,2-trifluoroethyl)-1,3-dihydrobenzo[c][1,2]oxaborol-6-yloxy)-2-methylpropanenitrile (226 mg, 0.72 mmol, crude) is added. The reaction mixture is stirred at rt overnight. It is purified by prep-HPLC to give N-(2-cyano-1-(1-hydroxy-7-(2,2,2-trifluoroethyl)-1,3-dihydro-benzo[c][1,2]oxaborol-6-yl oxy)propan-2-yl)-4-(trifluoromethoxy)benzamide (200 mg, yield 56% over 2 steps) as a white solid. $^1$H NMR (500 MHz, DMSO-d$_6$): δ 9.13 (s, 1H), 9.06 (s, 1H), 8.00 (d, J=8.5 Hz, 2H), 7.51 (d, J=8.5 Hz, 2H), 7.38 (d, J=8.5 Hz, 1H), 7.25 (d, J=8.5 Hz, 1H), 4.95 (s, 2H), 4.51 (d, J=9.0 Hz, 1H), 4.33 (d, J=9.0 Hz, 1H), 3.78 (q, J=11.0 Hz, 2H), 1.85 (s, 3H) ppm; HPLC purity: 100% at 220 nm and 100% at 254 nm; MS: m/z=503.0 (M+1, ESI+).

EXAMPLE 28

N-(2-cyano-1-(1-hydroxy-7-(2-methoxyethoxy)-1,3-dihydrobenzo[c][1,2]oxaborol-6-yloxy)propan-2-yl)-4-(trifluoromethoxy)benzamide

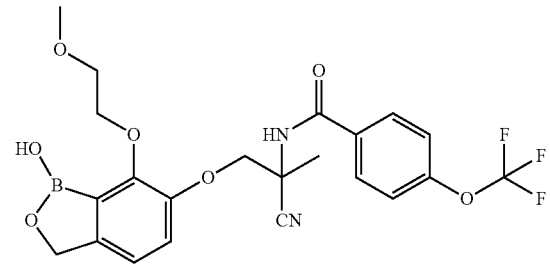 [SMILES: COCCOc1c(OCC(C)(C#N)NC(=O)c2ccc(OC(F)(F)F)cc2)ccc2c1B(O)OC2]

Into a round-bottom flask equipped with a stir bar is placed 3,4-dihydroxybenzaldehyde (10.0 g, 72.5 mmol), sodium bicarbonate (7.91 g, 94.2 mmol), KI (2.07 g, 14.5 mmol) and MeCN (200 mL). The flask is fitted with a reflux condenser and slowly warmed to 60° C. At this time, benzyl bromide (8.5 mL, 72.5 mmol) is added and the mixture warmed to 80° C. After refluxing overnight, the mixture is cooled to rt and concentrated by rotary evaporation. The residue is quenched with 10% aq. HCl (50 mL) and extracted with EtOAc (3×100 mL). The combined organic extracts are washed with brine (100 mL), dried over Na$_2$SO$_4$, filtered, and concentrated. The resulting oil is purified by column chromatography on silica gel eluted with PE:EA=6:1 to give the desired product (13.3 g, yield 80.6%) as an amorphous yellow solid.

To a solution of 4-(benzyloxy)-3-hydroxybenzaldehyde (13.3 g, 58.3 mmol) in 1,4-dioxane/H$_2$O (150 mL, 2:1) is added a solution of NBS (11.4 g, 64.2 mmol) in 1,4-dioxane/H$_2$O (50 mL, 2:1) dropwise at 0° C. The reaction mixture is warmed to rt and stirred for 3 h. Then EA (300 mL) is added and the organic layer is washed with water and brine, dried over Na$_2$SO$_4$, filtered, and concentrated under the reduced pressure. The residue is purified by column chromatography on silica gel eluted with PE:EA=15:1 to give the desired product (14.0 g, yield 77.8%) as a yellow solid.

A mixture of 4-(benzyloxy)-2-bromo-3-hydroxybenzaldehyde (5.0 g, 16.3 mmol), K$_2$CO$_3$ (6.75 g, 48.9 mmol), KI (541 mg, 3.26 mmol) and 1-bromo-2-methoxyethane (4.53 g, 32.6 mmol) in DMF (25 mL) is stirred at 70° C. for 16 h. The reaction mixture is filtered and the filtrate is poured to water (50 mL). The mixture is extracted with EA (100 ml*3). The combined organic layers are washed with water and brine, dried over Na$_2$SO$_4$, filtered and concentrated under the reduced pressure. The residue is purified by column chromatography on silica gel eluted with PE:EA=4:1 to give the desired product (4.16 g, yield 70.0%) as a light yellow solid.

A mixture of compound 4-(benzyloxy)-2-bromo-3-(2-methoxyethoxyl)benzaldehyde (3.5 g, 9.59 mmol), 5,5,5',5'-tetramethyl-2,2'-bi(1,3,2-dioxaborinane) (6.47 g, 28.77 mmol), Pd(dppf)$_2$Cl$_2$ (701 mg, 0.96 mmol) and KOAc (4.7 g, 47.95 mmol) in 1,4-dioxane (150 mL) is stirred at 100° C. overnight under argon. Water (100 mL) is added and the mixture is extracted with EA (200 mL*3). The combined organic layers are washed with brine, dried over Na$_2$SO$_4$, filtered and concentrated under the reduced pressure. The residue is purified by column chromatography on silica gel eluted with PE:EA=5:1 to give 4 the desired product (2.95 g, yield 75.0%) as a light yellow oil.

To a solution of 4-(benzyloxy)-2-(5,5-dimethyl-1,3,2-dioxaborinan-2-yl)-3-(2-methoxy ethoxy)benzaldehyde (3.55 g, 8.92 mmol) in THF (30 mL) is added NaBH$_4$ (678 mg, 17.84 mmol). The reaction mixture is stirred at rt for 3 h, then to it is slowly added 3N HCl to pH=2. The reaction mixture is stirred at rt overnight. The solvent is evaporated and the residue is purified by column chromatography on silica gel eluted with PE:EA=3:1 to give the desired product (1.9 g, yield 68.0%) as a white solid.

The mixture of 6-(benzyloxy)-7-(2-methoxyethoxyl)benzo[c][1,2]oxaborol-1(3H)-ol (1.0 g, 3.18 mmol) in MeOH (20 mL) and EA (20 mL) is hydrogenated using 10% Pd/C (318 mg, 0.318 mmol) as catalyst under atmospheric pressure overnight. The catalyst is removed by filtration on Celite and the solvent is evaporated under the reduced pressure. The residue is purified by column chromatography on silica gel eluted with PE:EA=2:1 to give the desired product (440 mg, yield 61.7%) as a white solid.

To a solution of 7-(2-methoxyethoxyl)benzo[c][1,2]oxaborole-1,6(3H)-diol (240 mg, 1.07 mmol) and K$_2$CO$_3$ (443 mg, 3.21 mmol) in acetone (20 mL) is added bromoacetone (293 mg, 2.14 mmol). The reaction mixture is refluxed for 3 h and evaporated under the reduced pressure. The residue is purified by column chromatography on silica gel eluted with PE:EA=3:1 to give the desired product (120 mg, yield 40.0%) as a white solid.

A mixture of 1-(1-hydroxy-7-isopropoxy-1,3-dihydrobenzo[c][1,2]oxaborol-6-yloxy) propan-2-one (120 mg, 0.43 mmol), NH$_4$Cl (46 mg, 0.86 mmol) and ammonia (7N in methanol, 1 mL) in MeOH (2 mL) is stirred at rt for 20 min before addition of NaCN (42 mg, 0.86 mmol). The reaction mixture is stirred at rt overnight. DCM (50 mL) is added and the solvent is removed under the reduced pressure at rt. The residue is mixed with THF and filtered. The filtrate is concentrated to give the desired product (crude) (200 mg) as a colorless oil. It is used in next step without further purification.

A solution of 4-(trifluoromethoxy)benzoic acid (133 mg, 0.645 mmol), DIPEA (0.25 mL, 1.29 mmol) and HATU (245 mg, 0.645 mmol) in DMF (3 mL) is stirred at rt for 10 min, and then the crude 2-amino-3-(1-hydroxy-7-isopropoxy-1,3-dihydrobenzo[c][1,2]-oxaborol-6-yloxy)-2-methylpropanenitrile (200 mg, 0.65 mmol) in DMF (2 mL) is added. The reaction mixture is stirred at 50° C. overnight and evaporated. It is purified by prep-HPLC to give N-(2-cyano-1-(1-hydroxy-7-(2-methoxyethoxy)-1,3-dihydrobenzo[c][1,2]oxaborol-6-yloxy)propan-2-yl)-4-(trifluoromethoxy)benzamide (40 mg, yield: 20% over two steps) as a white solid. $^1$H NMR (400 MHz, DMSO-d$_6$): δ 8.95 (s, 1H), 8.90 (s, 1H), 7.98 (d, J=8.0 Hz, 2H), 7.49 (d, J=8.0 Hz, 2H), 7.22 (d, J=8.0 Hz, 1H), 6.99 (d, J=8.0 Hz, 1H), 4.90 (s, 2H), 4.67 (d, J=9.2 Hz, 1H), 4.27-4.32 (m, 3H), 3.60-3.62 (m, 2H), 3.25 (s, 3H), 1.84 (s, 3H) ppm; HPLC purity: 94.15% at 214 nm and 100% at 254 nm; MS: m/z=495.1 (M+1, ESI+).

EXAMPLE 29 tert-butyl 2-(6-(2-cyano-2-(4-(trifluoromethoxy)benzamido)propoxy)-1-hydroxy-1,3-dihydro benzo[c][1,2]oxaborol-7-yloxy)ethylcarbamate

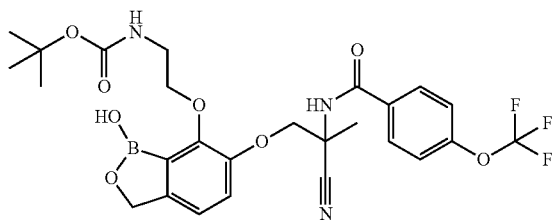 [SMILES: CC(C#N)(COc1ccc2c(c1OCCNC(=O)OC(C)(C)C)B(O)OC2)NC(=O)c1ccc(OC(F)(F)F)cc1]

A mixture of 3,4-dihydroxybenzaldehyde (10.0 g, 72.5 mmol), sodium bicarbonate (8.0 g, 94.3 mmol) and KI (2.4 g, 14.5 mmol) in MeCN (150 mL) is slowly warmed to 60° C. At this time, benzyl bromide (8.6 mL, 72.5 mmol) is added and the mixture warmed to 80° C. After refluxing overnight, the mixture is then cooled to rt and concentrated by rotary evaporation. The residue is quenched with 10% aq. HCl (50 mL) and extracted with EtOAc (3×100 mL). The combined organic extracts are washed with brine, dried over Na$_2$SO$_4$, filtered, and concentrated under the reduced pressure. The resulting oil is purified by column chromatography on silica gel by elution with PE:EA=6:1 to give the desired product (11.0 g, yield: 66.7%) as an amorphous yellow solid.

To a solution of 4-(benzyloxy)-3-hydroxybenzaldehyde (11.0 g, 48.2 mmol) in 1,4-dioxane and H$_2$O (100 mL, 5:2) is added a solution of NBS (9.44 g, 53.0 mmol) in 1,4-dioxane/H$_2$O (30 mL, 5:2) dropwise at 0° C. The reaction mixture is warmed to rt and stirred for 3 h. Then EA (300 mL) is added and the organic layer is washed with water and brine, dried over Na$_2$SO$_4$, filtered, and concentrated under the reduced pressure. The residue is purified by column chromatography on silica gel by elution with PE:EA=15:1 to give the desired product (11.85 g, yield 80%) as a yellow solid.

A mixture of 4-(benzyloxy)-2-bromo-3-hydroxybenzaldehyde (3.07 g, 10 mmol), K$_2$CO$_3$ (3.4 g, 2.5 mmol) and KI (330 mg, 0.2 mmol) in DMF (60 mL) is stirred at rt for 0.5 h, and then tert-butyl 2-bromoethylcarbamate (2.9 g, 1.3 mmol) is added and the mixture warmed to 70° C. overnight. After cooled to rt, the reaction mixture is filtered and the filtrate is poured into water (120 mL), extracted with EA (150 ml*3). The combined organic layers are washed with water and brine, dried over Na$_2$SO$_4$, filtered and concentrated under the reduced pressure. The residue is purified by column chromatography on silica gel by elution with PE:EA=5:1 to give the desired product (3.6 g, yield: 80%) as a white solid.

A mixture of tert-butyl 2-(6-(benzyloxy)-2-bromo-3-formylphenoxy)ethylcarbamate (3.0 g, 6.7 mmol), 5,5,5',5'-tetramethyl-2,2'-bi(1,3,2-dioxaborinane) (4.54 g, 20 mmol), Pd(dppf)$_2$Cl$_2$ (440 mg, 0.6 mmol) and KOAc (3.28 g, 33.5 mmol) in 1,4-dioxane (100 mL) is stirred at 100° C. overnight under argon. Water (100 mL) is added and the mixture is extracted with DCM (200 mL*2). The combined organic layers are washed with brine, dried over Na$_2$SO$_4$, filtered and concentrated under the reduced pressure. The residue is purified by column chromatography on silica gel by elution with PE:EA=5:1 to give tert-butyl the desired product (1.3 g, yield: 40.1%) as a white solid.

To a solution of tert-butyl 2-(6-(benzyloxy)-2-(5,5-dimethyl-1,3,2-dioxaborinan-2-yl)-3-formylphenoxy)ethylcarbamate (1.3 g, 2.7 mmol) in THF (30 mL) is added NaBH$_4$ (130 mg, 3.42 mmol). The reaction mixture is stirred at rt for 2 h, and then acetic acid (0.2 mL) is slowly added at 0° C. The solvent is removed and the residue is purified by column chromatography on silica gel by elution with PE:EA=3:1 to give the desired product (583 mg, yield 80%) as a white solid.

The solution of tert-butyl 2-(6-(benzyloxy)-2-(5,5-dimethyl-1,3,2-dioxaborinan-2-yl)-3-formylphenoxy)ethylcarbamate (580 mg, 1.45 mmol) in MeOH (20 mL) is hydrogenated using 10% Pd/C (80 mg, 0.145 mmol) as catalyst under atmospheric pressure overnight. The catalyst is removed by filtration on Celite and the solvent is evaporated under the reduced pressure. The residue is purified by column chromatography on silica gel by elution with PE:EA=2:1 to give the desired product.

To a solution of 2-(1,6-dihydroxy-1,3-dihydrobenzo[c][1,2]oxaborol-7-yloxy)ethylcarbamate (360 mg, 1.16 mmol) and K$_2$CO$_3$ (320 mg, 2.32 mmol) in acetone (20 mL) is added bromo-acetone (234 mg, 1.74 mmol). The reaction mixture is refluxed for 3 h. The solvent is evaporated under the reduced pressure. The residue is purified by column chromatography on silica gel by elution with PE:EA=3:1 to give the desired product (280 mg, yield 66%) as a white solid.

A mixture of tert-butyl 2-(1-hydroxy-6-(2-oxopropoxy)-1,3-dihydrobenzo[c][1,2]-oxaborol-7-yloxy)ethylcarbamate (280 mg, 0.77 mmol), NH$_4$Cl (84 mg, 1.54 mmol) and ammonia (7N in methanol, 5 mL) in MeOH (5 mL) is stirred at rt for 20 min before addition of NaCN (75 mg, 1.54 mmol). The reaction mixture is stirred at rt overnight. DCM (50 mL) is added and the solvent is removed under the reduced pressure at rt. The residue is washed with THF and filtered. The filtrate is concentrated to give the desired product (crude) (320 mg) as a colorless oil. It is used to next step without further purified.

A solution of 4-(trifluoromethoxy)benzoic acid (238 mg, 1.16 mmol), DIPEA (0.41 mL, 2.31 mmol) and HATU (585 mg, 1.54 mmol) in DMF (3 mL) is stirred at rt for 20 min, and then crude tert-butyl 2-(6-(2-amino-2-cyanopropoxy)-1-hydroxy-1,3-dihydrobenzo[c][1,2]oxaborol-7-yloxy)ethylcarbamate (320 mg, 0.77 mmol) in DMF (2 mL) is added. The reaction mixture is stirred at rt overnight and evaporated. It is purified by prep-HPLC to give tert-butyl 2-(6-(2-cyano-2-(4-(trifluoromethyl)benzamido) propoxy)-1-hydroxy-1,3-dihydrobenzo[c][1,2]oxaborol-7-yloxy) ethylcarbamate (107 mg, yield: 24% over two steps) as a white solid. $^1$H NMR (500 MHz, DMSO-d$_6$) δ 9.11 (s, 1H), 8.99 (s, 1H), 7.98 (d, J=8.0 Hz, 2H), 7.49 (d, J=8.0 Hz, 2H), 7.22 (d, J=8.0 Hz, 1H), 7.01 (d, J=8.0 Hz, 1H), 6.78 (b, 1H), 4.90 (s, 2H), 4.47 (d, J=9.0 Hz, 1H), 4.29 (d, J=9.0 Hz, 1H), 4.16 (t, J=6.0 Hz, 2H), 3.24 (q, J=6.0 Hz, 2H), 1.85 (s, 3H), 1.34 (s, 9H) ppm; HPLC purity: 98.15% at 214 nm and 100% at 254 nm; MS: m/z=602.1 (M+23, ESI+).

EXAMPLES 30 AND 31

N-(1-(7-(2-aminoethoxy)-1-hydroxy-1,3-dihydrobenzo[c][1,2]oxaborol-6-yloxy)-2-cyano propan-2-yl)-4-(trifluoromethoxy)benzamide

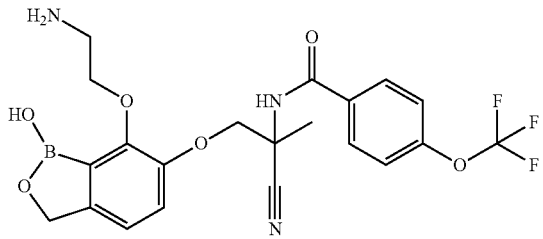 [SMILES: CC(C#N)(COc1ccc2c(c1OCCN)B(O)OC2)NC(=O)c1ccc(OC(F)(F)F)cc1]

N-(1-amino-3-(7-(2-aminoethoxy)-1-hydroxy-1,3-dihydrobenzo[c][1,2]oxaborol-6-yloxy)-2-methyl-1-oxopropan-2-yl)-4-(trifluoromethoxy)benzamide

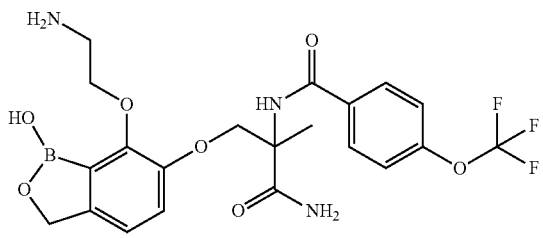 [SMILES: CC(COc1ccc2c(c1OCCN)B(O)OC2)(NC(=O)c1ccc(OC(F)(F)F)cc1)C(N)=O]

To a solution of tert-butyl 2-(6-(2-cyano-2-(4-(trifluoromethoxy)benzamido) propoxy)-1-hydroxy-1,3-dihydrobenzo[c][1,2]oxaborol-7-yloxy)ethylcarbamate (80 mg, 0.14 mmol) in DCM (10 mL) is added TFA (3 mL) in DCM (2 mL) dropwise. The reaction mixture is stirred at rt for 30 min. The solvent is removed under the reduced pressure and the residue is purified by prep-HPLC immediately to give N-(1-(7-(2-aminoethoxy)-1-hydroxy-1,3-dihydrobenzo[c][1,2]oxaborol-6-yloxy)-2-cyanopropan-2-yl)-4-(trifluoromethoxy)benzamide (11 mg, yield 33.3%) and N-(1-amino-3-(7-(2-aminoethoxy)-1-hydroxy-1,3-dihydrobenzo[c][1,2]oxaborol-6-yloxy)-2-methyl-1-oxopropan-2-yl)-4-(trifluoromethoxy)benzamide (12 mg, yield 35.0%) respectively as a white solid. Analytical data for Example 30: $^1$H NMR (400 MHz, DMSO-d$_6$) δ 8.97 (s, 1H), 7.98 (d, J=8.0 Hz, 2H), 7.50 (d, J=8.0 Hz, 2H), 7.11 (d, J=8.0 Hz, 1H), 6.87 (d, J=8.0 Hz, 1H), 5.33 (s, 1H), 4.99 (s, 2H), 4.75~3.80 (m, 4H), 3.02 (s, 1H), 1.81 (s, 3H) ppm; HPLC purity: 98.76% at 214 nm and 100% at 254 nm; MS: m/z=480.1 (M+1, ESI+). Analytical data for Example 31: $^1$H NMR (400 MHz, DMSO-d$_6$) δ 8.33 (s, 1H), 7.93 (d, J=8.0 Hz, 2H), 7.42-7.46 (m, 3H), 7.13 (s, 1H), 6.99 (d, J=8.0 Hz, 1H), 6.80 (d, J=8.0 Hz, 1H), 5.28 (s, 1H), 4.95 (s, 2H), 4.75-4.20 (m, 4H), 3.82 (s, 1H), 3.25 (s, 2H), 1.58 (s, 3H) ppm; HPLC purity: 100% at 214 nm and 100% at 254 nm; MS: m/z=498.2 (M+1, ESI+).

EXAMPLE 32

N-(2-cyano-1-(7-cyano-1-hydroxy-1,3-dihydrobenzo[c][1,2]oxaborol-6-yloxy)propan-2-yl)-4-(trifluoromethoxy)benzamide

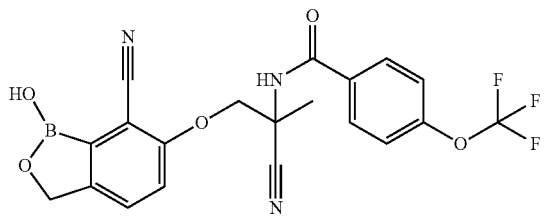 [SMILES: CC(C#N)(COc1ccc2c(c1C#N)B(O)OC2)NC(=O)c1ccc(OC(F)(F)F)cc1]

To a solution of 2-bromo-4-fluoro-1-methylbenzene (6.6 g, 35.1 mmol) in THF (150 mL) is added LDA (17 ml, 42.1 mmol) at −78° C. and the mixture is stirred at −78° C. for 2 h. Then DMF (3.1 g, 42.1 mmol) is added. After stirring at rt for 0.5 h, the reaction is quenched with water and extracted with EA (2×200 mL). The combined organic layers are washed with brine, dried over $Na_2SO_4$, filtered and concentrated under reduced pressure. The residue is purified by column chromatography to give the desired product as yellow oil (7.0 g, yield 92%).

To a solution of NaOMe (40 mL, 3 mol/l in MeOH), 2-bromo-6-fluoro-3-methylbenzaldehyde (7.0 g, 32.4 mmol) is added. After refluxing for 16 h, the reaction is quenched with 2N HCl to pH=2. The resulting mixture is concentrated in vacuum, washed with water and extracted with EA (2×30 mL). The combined organic layers are washed with brine, dried over $Na_2SO_4$, filtered and concentrated vacuo to give the desired product as a light yellow powder (5.0 g, yield 68%).

To a solution of 2-bromo-6-methoxy-3-methylbenzaldehyde (5.0 g, 22 mmol) in HOAc (100 mL) under $N_2$ atmosphere are added NaOAc (43.6 g, 44 mmol) and $NH_2OH·HCl$ (3.1 g, 44 mmol). The mixture is stirred at 125° C. overnight. Then the resulting mixture is concentrated in vacuum and extracted with EA (2×30 mL). The combined organic layers are washed with brine, dried over $Na_2SO_4$, filtered and concentrated under reduced pressure to give the desired product as a white powder (4.4 g, yield 89%).

A mixture of 2-bromo-6-methoxy-3-methylbenzonitrile (4.4 g, 19.6 mmol), NBS (10.5 g, 58.9 mmol) and BPO (474 mg, 1.96 mmol) in $CCl_4$ (100 mL) is stirred at 80° C. for 11 h under $N_2$. Then the resulting mixture is filtered and concentrated under reduced pressure. The residue is purified by column chromatography to give the desired product as a light yellow solid (7.2 g, yield 95%).

A mixture of 2-bromo-3-(dibromomethyl)-6-methoxy benzonitrile (7.2 g, 19 mmol), $NaHCO_3$ (4.8 g, 57 mmol) in $H_2O$ (100 mL) is stirred at 100° C. overnight under $N_2$. Then the resulting mixture is extracted with EA (2×50 mL). The combined organic layers are washed with brine, dried over $Na_2SO_4$, filtered and concentrated under reduced pressure to give the desired product as a white powder (4.1 g, yield 90%).

To a solution of 2-bromo-3-formyl-6-methoxybenzonitrile (4.1 g, 17.1 mmol) in MeOH (85 mL) is added $NaBH_4$ (1.9 g, 51.4 mmol). After stirring at rt for 2 h, the mixture is concentrated under reduced pressure and extracted with EA (2×50 mL). It is dried over $Na_2SO_4$, filtered and evaporated under reduced pressure to give the desired product (3.3 g, yield 80%).

A solution of 2-bromo-3-(hydroxymethyl)-6-methoxybenzonitrile (3.3 g, 13.7 mmol), DHP (1.4 g, 16.4 mmol) and PPTS (330 mg) in DCM (100 mL) is refluxed for 2 h under $N_2$ atmosphere. Then the resulting mixture is washed with water, dried over $Na_2SO_4$, evaporated under reduced pressure to afford the desired product as colorless oil (4.2 g, yield 90%).

A mixture of 2-bromo-3-formyl-6-methoxybenzonitrile (4.2 g, 12.9 mmol), $Pin_2B_2$ (9.0 g, 35.4 mmol), $Pd(dppf)_2Cl_2$ (433 mg, 0.53 mmol), KOAc (5.1 g, 53.1 mmol) in 1,4-dixoane (100 mL) is stirred at 80° C. overnight under $N_2$. Then the resulting mixture is filtered and concentrated under reduced pressure. The residue is purified by column chromatography to give a crude product (6.4 g).

To a solution of 6-methoxy-3-(((tetrahydro-2H-pyran-2-yl)oxy)methyl)-2-(4,4,5,5-tetra methyl-1,3,2-dioxaborolan-2-yl)benzonitrile (6.4 g, 12.9 mmol, crude) in THF (120 mL) is added 3N HCl (20 mL) at rt, and the mixture is stirred at rt for 14 h. Then the resulting mixture is extracted with EA (2×50 mL). The EA layer is dried over $Na_2SO_4$, filtered and evaporated under reduced pressure to give the desired product as a white solid (1.3 g).

To a solution of 1-hydroxy-6-methoxy-1,3-dihydrobenzo[c][1,2]oxaborole-7-carbonitrile (500 mg, 2.6 mmol) in DCM (20 mL) is added $BBr_3$ (2.0 g, 13.2 mmol) at −78° C., and the mixture is stirred at rt overnight. Then the reaction is quenched with water, extracted with EA (2×10 mL), dried over $Na_2SO_4$, and evaporated under reduced pressure. The residue is purified by prep-HPLC to give the desired product (31 mg).

To a solution of 1,6-dihydroxy-1,3-dihydrobenzo[c][1,2]oxaborole-7-carbonitrile (31 mg, 0.18 mmol) in DMF (2 mL) is added NaH (70.8 mg, 1.77 mmol) at 0° C. and the mixture is stirred at 0° C. for 20 min. Then chloroacetone (149 mg, 1.77 mmol) is added dropwise at 0° C. After stirring at rt overnight, the reaction is quenched with water, extracted with EA (2×10 mL), dried over $Na_2SO_4$, filtered and evaporated under reduced pressure to give the desired product (13 mg) as a oil. It is used in the next step directly without further purification.

To a solution of $NH_4Cl$ (5.5 mg, 0.10 mmol) and NaCN (4.1 mg, 0.08 mmol) in $NH_3·H_2O$ (0.5 mL), a solution of 1-hydroxy-6-(2-oxopropoxy)-1,3-dihydrobenzo[c][1,2]oxaborole-7-carbo-nitrile (13 mg, 0.06 mmol) in MeOH (0.5 mL) is added and the mixture is stirred at rt for 1 h before MeCN (100 mL) is added. It is stirred overnight and evaporated. It is dissolved in THF and filtered. The filtrate is evaporated under reduced pressure to afford the desired product (crude) as yellow oil, which is used in the next step directly without further purification (10 mg).

To a solution of 4-(trifluoromethoxy)benzoic acid (8 mg, 0.04 mmol) and HATU (17.7 mg, 0.05 mmol) in DMF (1 mL), DIPEA (0.02 mL, 0.12 mmol) is added. After stirring for 0.5 h, 6-(2-amino-2-cyanopropoxy)-1-hydroxy-1,3-dihydrobenzo[c][1,2]oxaborole-7-carbonitrile (10 mg, 0.04 mmol) is added and the mixture is stirred overnight. Then the reaction is quenched with water, extracted with EA, dried over $Na_2SO_4$, and concentrated in vacuum. The residue is purified by prep-HPLC to afford N-(2-cyano-1-((7-cyano-1-hydroxy-1,3-dihydrobenzo[c][1,2]oxaborol-6-yl)oxy)propan-2-yl)-4-(trifluoromethoxy)benzamide as a white solid. (3.8 mg, yield 22%). $^1$H NMR (400 MHz, DMSO-$d_6$): δ 9.45 (s, 1H), 9.14 (s, 1H), 7.99 (d, J=8.8 Hz, 2H), 7.69 (d, J=8.8 Hz, 1H), 7.50 (d, J=8.8 Hz, 2H), 7.45 (d, J=8.8 Hz, 1H), 4.97 (s, 2H), 4.67 (d, J=9.2 Hz, 1H), 4.53 (d, J=9.2 Hz, 1H), 1.87 (s, 3H) ppm. HPLC purity: 97.5% at 220 nm and 95.7% at 254 nm; MS: m/z=446.0 (M+1, ESI+).

EXAMPLE 33

N-(2-cyano-1-(1-hydroxy-7-phenoxy-1,3-dihydrobenzo[c][1,2]oxaborol-6-yloxy)propan-2-yl)-4-(trifluoromethoxy)benzamide

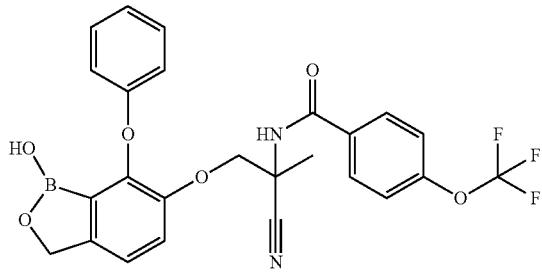 [SMILES: CC(C#N)(COc1ccc2c(c1Oc1ccccc1)B(O)OC2)NC(=O)c1ccc(OC(F)(F)F)cc1]

3-Hydroxy-4-methoxybenzaldehyde (30.4 g, 0.2 mol), 1,4-dioxane (250 ml) and water (100 ml) are mixed, and N-bromosuccinimide (37.38 g, 0.21 mol) is added over 30 minutes at 0° C. After 2 h, water (400 ml) is added, and the precipitated crystals are collected by filtration. The crystals are washed with water (1000 ml) to give the desired product (38.5 g, yield 83%) as a white solid.

2-Bromo-3-hydroxy-4-methoxybenzaldehyde (4.62 g, 20 mmol) is dissolved in DMSO (50 mL). Potassium hydroxide (1.23 g, 22 mmol) and 1-fluoro-4-nitrobenzene (4.23 g, 30 mmol) are added to the solution. The reaction mixture is stirred at 130° C. for 3 h. As the crude is poured into water (100 mL), precipitation is occurred. The solid is filtered, washed with water and dried under vacuum overnight to give the desired product (5.96 g, yield 84.9%) as a pale-brown solid.

To a mixed solvent of 80% ethanol (200 mL) and THF (200 mL), 2-bromo-4-methoxy-3-(4-nitrophenoxy)benzaldehyde (7 g, 19.95 mmol) and concentrated hydrochloric acid (20 ml) are added with stirring for 30 min at 20° C. Then iron powder (8.93 g, 160 mmol) is added to the mixture. It is stirred overnight at 20° C. Insoluble matters are filtered off and the filtrate is concentrated. The residue is mixed with 0.5N NaOH and precipitation occurred. The solid is filtered and dissolved with THF. It is filtered to further remove insoluble matters. The organic solution is dried over with anhydrous sodium sulfate, filtered and concentrated to give the desired product (crude) which is used for the next reaction without further purification.

To a solution of 3-(4-aminophenoxy)-2-bromo-4-methoxybenzaldehyde (6.42 g, 19.95 mmol, the crude product) in $H_3PO_2$ (50%, 100 mL) is added a solution of $NaNO_2$ (1.65 g, 23.9 mmol) in water (10 mL) at 0° C. The mixture is stirred at 0° C. for 2 h and then ammonia is added to adjust the pH value to 9 at 0° C. The obtained mixture is filtered and the filter cake is dissolved with THF. The organic solution is dried over with anhydrous sodium sulfate, filtered, concentrated and purified by silica gel column using PE:EA=5:1 as eluent to give the desired product (1.24 g, yield: 20.4% over 2 steps) as a yellow solid.

To a solution of 2-bromo-4-methoxy-3-phenoxybenzaldehyde (650 mg, 3.13 mmol) in DCM (10 mL) is added $BBr_3$ (2.35 mL, 9.39 mmol, 4N in DCM) at −15° C. The reaction mixture is stirred for 16 h at rt. The solution is poured into ice water, and extracted with EA (100 mL*2). The combined organic extracts are washed with water, dried over $Na_2SO_4$, filtered and concentrated under the reduced pressure. The residue is purified by prep-HPLC to give the desired product (650 mg, yield 71.1%) as a white solid.

To a solution of 2-bromo-4-hydroxy-3-phenoxybenzaldehyde (650 mg, 2.23 mmol) in DCM (50 mL) is added (chloromethoxy) ethane (631 mg, 6.68 mmol) followed by DIPEA (1.44 g, 11.13 mmol). The reaction mixture is stirred at rt for 14 h. Water (100 mL) is added and the mixture is extracted three times with ethyl acetate. The combined extracts are washed with water and brine, dried over $Na_2SO_4$, filtered and concentrated under the reduced pressure. The residue is purified by column chromatography on silica gel eluted with PE:EA=5:1 to give 2 the desired product (597 mg, yield 76.3%) as a yellow oil.

To a solution of 2-bromo-4-(ethoxymethoxy)-3-phenoxybenzaldehyde (454 mg, 1.29 mmol), 5,5,5',5'-tetramethyl-2,2'-bi(1,3,2-dioxaborinane) (1.17 g, 5.17 mmol) and KOAc (1.27 g, 12.9 mmol) in 1,4-dioxane (50 mL) is added $PdCl_2(dppf)_2$ (142 mg, 0.19 mmol). The reaction mixture is stirred at 60° C. under argon atmosphere overnight. The solvent is removed and the residue is purified by column chromatography on silica gel eluted with PE:EA=5:1 to give the desired product (crude) (495 mg) as a light yellow solid. It is used in the next step without further purification.

To a solution of 2-(5,5-dimethyl-1,3,2-dioxaborinan-2-yl)-4-(ethoxymethoxy)-3-phenoxy-benzaldehyde (495 mg, 1.29 mmol, crude) in THF (30 mL) is added $NaBH_4$ (133 mg, 3.49 mmol). The reaction mixture is stirred at rt for 2 h, and then to it is slowly added 3N HCl to pH=1. The reaction mixture is stirred at rt overnight. The solvent is evaporated and the residue is purified by column chromatography on silica gel eluted with PE:EA=5:1 to give the desired product (184 mg, yield: 58.9% over 2 steps) as a white solid.

To a solution of 7-phenoxybenzo[c][1,2]oxaborole-1,6 (3H)-diol (100 mg, 0.413 mmol) and $K_2CO_3$ (171 mg, 1.24 mmol) in acetone (30 mL) is added bromoacetone (113 mg, 0.826 mmol). The reaction mixture is refluxed for 3 h. It is filtered and the filtrate is evaporated to give the desired product (crude) (35 mg, yield 28.4%) as a white solid. It is used in next step without further purification.

A mixture of 1-(1-hydroxy-7-phenoxy-1,3-dihydrobenzo[c][1,2]oxaborol-6-yloxy)-propan-2-one (58 mg, 0.19 mmol), $NH_4Cl$ (21 mg, 0.39 mmol) and ammonia (7N in methanol, 1 mL) in MeOH (2 mL) is stirred at rt for 20 min before addition of NaCN (24 mg, 0.49 mmol). The reaction mixture is stirred at .t for 5 h. DCM (50 mL) is added and the solvent is removed under the reduced pressure. The residue is mixed with THF and filtered. The THF filtrate is evaporated to give the desired product (crude) (63 mg). It is used in next step without further purification.

A solution of 4-(trifluoromethoxy)benzoic acid (40 mg, 0.19 mmol), HATU (145 mg, 0.39 mmol) and DIPEA (50 mg, 0.39 mmol) in DMF (2 mL) is stirred at rt for 30 min, then 2-amino-3-(1-hydroxy-7-phenoxy-1,3-dihydrobenzo[c][1,2]oxaborol-6-yloxy)-2-methylpropanenitrile (63 mg, crude, 0.19 mmol) is added. The reaction mixture is stirred at rt overnight. It is purified by prep-HPLC to give N-(2-cyano-1-(7-ethyl-1-hydroxy-1,3-dihydrobenzo[c][1,2]oxaborol-6-yloxy)propan-2-yl)-4-(trifluoromethoxy)benzamide (4.6 mg, yield 4.6% over two steps) as a white solid. $^1$H NMR (500 MHz, DMSO-$d_6$): δ 8.86 (s, 1H), 8.77 (s, 1H), 7.87 (d, J=9.0 Hz, 2H), 7.47 (d, J=8.5 Hz, 2H), 7.36 (d, J=8.5 Hz, 1H), 7.25 (d, J=8.0 Hz, 1H), 7.20 (t, J=8.0 Hz, 2H), 6.89 (t, J=7.5 Hz, 1H), 6.79 (d, J=8.0 Hz, 2H), 4.95 (s, 2H), 4.45

(d, J=9.5 Hz, 1H), 4.19 (d, J=9.5 Hz, 1H), 1.45 (s, 3H) ppm; HPLC purity: 100% at 214 nm and 100% at 254 nm; MS: m/z=513.1 (M+1, ESI+).

EXAMPLES 34 AND 35

N-(1-(4-(aminomethyl)-1-hydroxy-1,3-dihydrobenzo[c][1,2]oxaborol-6-yloxy)-2-cyanopropan-2-yl)-4-(trifluoromethoxy)benzamide

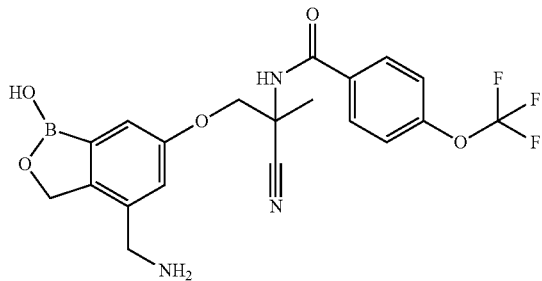 [SMILES: CC(C#N)(COc1cc(CN)c2c(c1)B(O)OC2)NC(=O)c1ccc(OC(F)(F)F)cc1]

N-(1-amino-3-(4-(aminomethyl)-1-hydroxy-1,3-dihydrobenzo[c][1,2]oxaborol-6-yloxy)-2-methyl-1-oxopropan-2-yl)-4-(trifluoromethoxy)benzamide

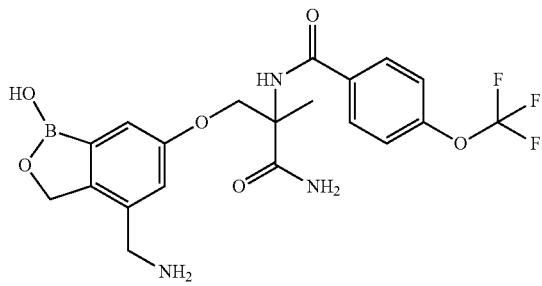 [SMILES: CC(COc1cc(CN)c2c(c1)B(O)OC2)(NC(=O)c1ccc(OC(F)(F)F)cc1)C(N)=O]

To a solution of tert-butyl (6-(2-cyano-2-(4-(trifluoromethoxy)benzamido)propoxy)-1-hydroxy-1,3-dihydrobenzo[c][1,2]oxaborol-4-yl)methylcarbamate (50 mg, 0.091 mmol) in DCM (2.5 mL) is added TFA (0.5 mL) in DCM (0.5 mL) dropwise. The reaction mixture is stirred at rt for 30 min. The solvent is removed under the reduced pressure and the residue is purified by prep-HPLC immediately to give N-(1-(4-(aminomethyl)-1-hydroxy-1,3-dihydrobenzo[c][1,2]oxaborol-6-yloxy)-2-cyanopropan-2-yl)-4-(trifluoromethoxy)benzamide (12.5 mg) and N-(1-amino-3-(4-(aminomethyl)-1-hydroxy-1,3-dihydrobenzo[c][1,2]oxaborol-6-yloxy)-2-methyl-1-oxopropan-2-yl)-4-(trifluoromethoxy)benzamide (6.3 mg) respectively as a white solid. Analytical data for the 1$^{st}$ product: $^1$H NMR (400 MHz, DMSO-d$_6$) δ 9.07 (s, 1H), 9.06 (s, 1H), 8.00 (d, J=8.8 Hz, 2H), 7.51 (d, J=8.4 Hz, 2H), 7.17-7.16 (m, 2H), 4.96 (s, 2H), 4.53 (d, J=9.2 Hz, 1H), 4.26 (d, J=9.2 Hz, 1H), 3.65 (s, 2H), 1.83 (s, 3H) ppm; HPLC purity: 100% at 214 nm and 100% at 254 nm; MS: m/z=450.0 (M+1, ESI+). Analytical data for the 2$^{nd}$ product: $^1$H NMR (400 MHz, CD$_3$OD-d$_6$) 6.7.92 (d, J=8.8 Hz, 2H), 7.35 (d, J=8.4 Hz, 2H), 7.06 (d, J=2 Hz, 1H), 6.80 (s, 1H), 4.84 (s, 2H), 4.60 (d, J=9.2 Hz, 1H), 4.43 (d, J=9.6 Hz, 1H), 3.86 (s, 2H), 1.74 (s, 3H) ppm; HPLC purity: 100% at 214 nm and 100% at 254 nm; MS: m/z=468.1 (M+1, ESI+).

EXAMPLE 36

(S)—N-(2-cyano-1-(1-hydroxy-7-phenyl-1,3-dihydrobenzo[c][1,2]oxaborol-6-yloxy)propan-2-yl)-4-(trifluoromethoxy)benzamide

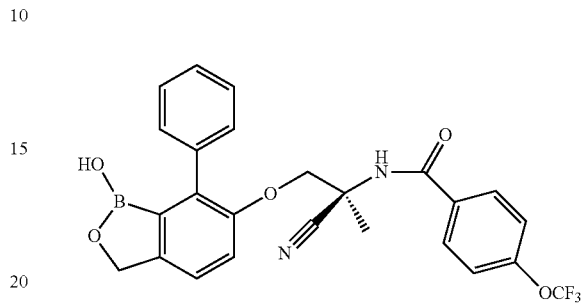

To a solution of resorcinol (11.0 g, 0.10 mol) and I$_2$ (25.4 g, 0.01 mmol) in H$_2$O (100 mL) is slowly added NaHCO$_3$ (9.24 g, 0.11 mol) in portions at 0° C. with vigorous stirring (strong evolution of CO$_2$). After warming to rt, the mixture is stirred for 10 min. The mixture is extracted with EA (3×500 mL), and the organic layer is dried and concentrated to give the crude product, which is purified by silica gel chromatography (PE:EA=20:1, v:v) to give the desired product (20 g, 85% yield) as a white solid.

POCl$_3$ (166 mL) is added dropwise to DMF (330 mL) at 0° C. The mixture is stirred at rt for 1.5 h. A solution of 2-iodo-benzene-1,3-diol (43.0 g, 182 mmol) in DMF (170 mL) is added dropwise keeping the temperature below 30° C. The reaction mixture is stirred at rt overnight, poured into ice-water (200 mL), adjusted to pH 2~3 with NaHCO$_3$, and extracted with EA (3×1 L). The organics are dried and concentrated to give a residue, which is used for next step without purification (51.0 g).

To a solution of 2,4-dihydroxy-3-iodo-benzaldehyde (67.0 g) in DCM (500 mL) is added DIPEA (167 g, 1.29 mol) at 0° C. MOMCl (61.0 g, 745 mmol) is added dropwise at 0° C. The mixture is stirred at rt for 16 h, added with H$_2$O (800 mL), neutralized with 6N HCl until pH=7, and extracted with DCM (3×800 mL). The organics are dried and concentrated to give a residue, which is purified by silica gel chromatography (PE:EA=10:1, v:v) to give the desired product (19.6 g, 30% yield over two steps) as a white solid.

To a stirring solution of 3-iodo-2,4-bis-methoxymethoxy-benzaldehyde (10.0 g, 28.4 mmol), phenylboronic acid (11.9 g, 113.6 mmol) and K$_3$PO$_4$ (36.1 g, 170.4 mmol) in toluene (500 mL) is added Pd(dppf)Cl$_2$ (11.6 g, 14.2 mmol) under N$_2$. The resulting mixture is refluxed overnight, poured into ice-water (200 mL) and extracted with EtOAc (2×100 mL). The organic layer is dried over sodium sulfate and concentrated to give a residue, which is purified by silica gel chromatography (PE:EA=50:1, v:v) to give the desired product (7.50 g, 88% yield) as a red oil.

To a stirring solution of 2,6-bis(methoxymethoxy)biphenyl-3-carbaldehyde (7.00 g, 23.2 mmol) in MeOH (150 mL) is added 6N HCl (20 mL) dropwise at 0° C. The mixture is stirred at rt overnight and evaporated. The residue is dissolved in EA (300 mL), washed with water, dried over sodium sulfate and concentrated to give a residue, which is purified by silica gel chromatography (PE:EA=1:1) to give the desired product (5.00 g, yield 100%) as a yellow solid.

To a stirring solution of 2,6-dihydroxy-biphenyl-3-carbaldehyde (2.50 g, 11.6 mmol) in dry acetone (100 mL) are added benzyl bromide (2.18 g, 12.8 mmol) and potassium carbonate (2.08 g, 15.1 mmol). The mixture is stirred at rt overnight, filtered. Acetone is removed and the crude product is purified by chromatography over silica gel (EA: PE=50:1, v:v) to afford 6 the desired product (1.70 g, 50% yield) as a white solid.

To a stirring solution of 6-benzyloxy-2-hydroxy-biphenyl-3-carbaldehyde (1.50 g, 4.93 mmol) in DCM (10 mL) and pyridine (10 mL) is added $Tf_2O$ (2 mL) dropwise at 0° C. And the reaction is stirred at 0° C. for 1 h. Another portion of $Tf_2O$ (2 mL) is added and the reaction is stirred at 0° C. for 2 h. It is evaporated and the residue is purified directly by silica gel chromatography (PE:EA=40:1 to 5:1, v:v) to give the desired product (900 mg) as a yellow oil.

The mixture of 6-(benzyloxy)-3-formylbiphenyl-2-yl trifluoromethanesulfonate (900 mg, 2.06 mmol), $pin_2B_2$ (1.08 mg, 4.13 mmol) and KOAc (550 mg, 5.52 mmol) in THF (30 mL) is degassed with $N_2$ for 30 min, and then $Pd(dppf)_2Cl_2$ (375 mg, 0.46 mmol) is added. The mixture is heated to 60° C. overnight. The reaction is cooled and the solid is filtered off. The solvent is removed to give a residue which is purified by flash column providing the desired product (230 mg, 27% yield).

To a solution of 6-benzyloxy-2-(4,4,5,5-tetramethyl-[1,3,2]dioxaborolan-2-yl)biphenyl-3-carb-aldehyde (23 mg, 0.55 mmol) in MeOH (7 mL) at 0° C. is added $NaBH_4$ (42.0 g, 1.11 mol). The mixture is stirred at rt for 1 h. And then, the solvent is removed, and 3N HCl (3 mL) and THF (1 mL) are added dropwise at 0° C. The reaction is warmed to rt and stirred for 3 h. The mixture is diluted with EA (30 mL), washed with water to pH=6, dried over sodium sulfate and concentrated to give a residue, which is purified by prep-TLC (PE:EA=3:1, v:v) to give the desired product (150 mg, 86% yield) as a white solid.

To a solution of 6-(benzyloxy)-7-phenylbenzo[c][1,2]oxaborol-1(3H)-ol (150 mg, 0.47 mmol) in MeOH (25 mL) is added Pd/C (100 mg, 10 mol %) and the reaction mixture is degassed with $H_2$. It is stirred at rt overnight. LCMS indicated that the starting material had been consumed. It is filtrated and concentrated to give the desired product (95 mg, 89% yield).

To a stirring solution of 7-phenylbenzo[c][1,2]oxaborole-1,6(3H)-diol (95.0 mg, 0.42 mmol) and $K_2CO_3$ (87.0 mg, 0.63 mmol) in acetone (20 mL) is slowly added 1-bromo-2-propaone (98.0 mg, 0.71 mmol), and then it is stirred at rt overnight. The solid is filtered off and the filtrate is concentrated to give a yellow solid (100 mg, 85% yield), which is used for next step without further purification.

To the solution of 1-(1-hydroxy-7-phenyl-1,3-dihydrobenzo[c][1,2]oxaborol-6-yloxy)-propan-2-one (100 mg, 0.35 mmol) in MeOH (13.0 mL) is bubbled $NH_3$ for 1 h at −30° C. The solution is added to a mixture of KCN (46 mg, 0.71 mmol), $NH_4Cl$ (79.0 mg, 1.51 mmol) and $NH_3*H_2O$ (13 mL) at 0° C. Then the mixture is stirred overnight at rt. The solution is concentrated under reduce pressure. The residue is diluted with EA (150 mL). The organic layer is dried with $Na_2SO_4$ and the solvent is removed to give the desired product (109 mg, quant. yield). It is used for next step without further purification.

To the solution of 4-trifluoromethoxy-benzoic acid (120 mg, 0.58 mmol) in DMF (5.0 mL) is added HATU (294 mg, 0.78 mmol) and DIEA (151 mg, 1.17 mmol), and the mixture is stirred for 1 h at rt. Then 2-Amino-3-(1-hydroxy-7-phenyl-1,3-dihydro-benzo[c][1,2]oxaborol-6-yloxy)-2-methyl-propionitrile (120 mg, 0.39 mmol) is added. The mixture is stirred overnight at rt. The solvent is removed and the residue is purified by Prep-HPLC to give N-(2-cyano-1-(1-hydroxy-7-phenyl-1,3-dihydrobenzo[c][1,2]oxaborol-6-yloxy)-propan-2-yl)-4-(trifluoromethoxy)benzamide (70 mg, 36% yield). $^1$H NMR (400 MHz, DMSO-$d_6$): δ 8.83 (s, 1H), 8.58 (s, 1H), 7.85 (d, J=8.8 Hz, 2H), 7.48 (d, J=8 Hz, 2H), 7.42 (d, J=8 Hz, 2H), 7.37 (d, J=8.4 Hz, 1H), 7.30-7.24 (m, 4H), 4.97 (s, 2H), 4.46 (d, J=9.2 Hz, 1H), 4.22 (d, J=9.6 Hz, 1H), 1.59 (s, 3H) ppm. HPLC purity: 99% at 220 nm and 98% at 254 nm; MS: m/z=497.2 (M+1, ESI$^+$).

The chromatography mobile phase condition described in Example 1 is changed to $CO_2$/MeOH/$Et_2NH$=70/30/0.2 to separate the racemic mixture giving peak 2 as the chiral enantiomer (S)—N-(2-cyano-1-(1-hydroxy-7-phenyl-1,3-dihydro benzo[c][1,2]oxaborol-6-yloxy)propan-2-yl)-4-(trifluoromethoxy)benzamide. $^1$H NMR (400 MHz, DMSO-$d_6$): δ 8.84 (s, 1H), 8.58 (s, 1H), 7.85 (d, J=8.8 Hz, 2H), 7.48 (d, J=8 Hz, 2H), 7.43 (d, J=8 Hz, 2H), 7.37 (d, J=8.4 Hz, 1H), 7.30-7.25 (m, 4H), 4.97 (s, 2H), 4.46 (d, J=9.2 Hz, 1H), 4.22 (d, J=9.6 Hz, 1H), 1.59 (s, 3H) ppm. HPLC purity: 98.4% at 220 nm and 98.6% at 254 nm; Chiral HPLC purity 99.6%; MS: m/z=497.2 (M+1, ESI$^+$).

EXAMPLE 37

N-(2-cyano-1-(1-hydroxy-7-propyl-1,3-dihydrobenzo[c][1,2]oxaborol-6-yloxy)propan-2-yl)-4-(trifluoromethoxy)benzamide

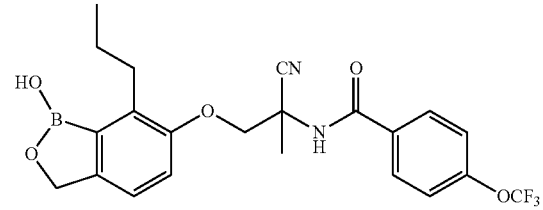 [SMILES: CCCc1c(OCC(C)(C#N)NC(=O)c2ccc(OC(F)(F)F)cc2)ccc2c1B(O)OC2]

To a solution of 2-bromobenzene-1,3-diol (114 g, 0.6 mol) and PPTS (7.53 g, 30 mmol) in DCM (300 mL) is added DHP (48 g, 0.57 mol) at rt under $N_2$. The mixture is stirred at rt overnight. Then water is added and the mixture is extracted twice with DCM. The combined organic layers are concentrated to give the crude product. The residue is purified by column chromatography on silica gel by elution with PE:EtOAc=10:1 to give the desired product (64 g, yield 38.7%) as a white solid.

To a solution of 2-bromo-3-(tetrahydro-2H-pyran-2-yloxy)phenol (50 g, 183 mmol) and $K_2CO_3$ (51 g, 367 mmol) in acetone (400 mL) is added chloroacetone (33.8 g, 367 mmol) at rt under $N_2$. The reaction mixture is refluxed for 3 h. The mixture is filter and concentrated to give the crude product. The residue is purified by column chromatography on silica gel by elution with PE:EtOAc=10:1 to give the desired product (52 g, yield 86%) as colorless oil.

To a solution of 1-(2-bromo-3-(tetrahydro-2H-pyran-2-yloxy)phenoxy)propan-2-one (40 g, 122 mmol) and $NH_4Cl$ (9.6 g, 179 mmol) in $NH_3$/MeOH is added NaCN (9 g, 184 mmol) at −78° C. The mixture is stirred at rt overnight. Then water is added and the mixture is extracted twice with EtOAc. The combined organic layers are washed with brine and water, dried over $Na_2SO_4$ and then concentrated to give the crude product. The residue is purified by column chromatography on silica gel eluted with PE:EtOAc=1:1 to give the desired product (40 g, yield 87%) as colorless oil.

To a solution of 4-(trifluoromethoxy)benzoic acid (23.2 g, 113 mmol), HATU (42.8 g, 113 mmol) and DIEA (43.6 g, 339 mmol) in DMF (500 mL) is added 2-amino-3-(2-bromo-3-(tetrahydro-2H-pyran-2-yloxy)phenoxy)-2-methylpropanenitrile (40 g, 113 mmol) at rt. The mixture is stirred at rt overnight. Then water is added and the mixture is extracted three times with EtOAc. The combined organic layers are washed with brine and water, dried over $Na_2SO_4$ and then concentrated to give the crude product. The residue is purified by column chromatography on silica gel eluted with PE:EtOAc=3:1 to give the desired product (38 g, yield 64%) as light yellow solid.

Allyltributyltin (1.18 g, 3.86 mmol) and $Pd(PPh_3)_2Cl_2$ (5 mol %) are added to a solution of N-(1-(2-bromo-3-(tetrahydro-2H-pyran-2-yloxy)phenoxy)-2-cyanopropan-2-yl)-4-(trifluoromethoxy)benzamide (0.3 g, 0.55 mmol) in DMF (2 mL). The mixture is stirred at 100° C. overnight and then cooled rt. Water is added to the mixture and the mixture is extracted twice with EtOAc. The combined organic layers are concentrated and the residue is purified by silica chromatography to give the desired product as yellow oil (0.15 g, yield 55%).

PPTS (10 mg) is added to a solution of N-(1-(2-allyl-3-(tetrahydro-2H-pyran-2-yloxy)phenoxy)-2-cyanopropan-2-yl)-4-(trifluoromethoxy)benzamide (0.15 g, 0.29 mmol) in 95% EtOH (20 mL). The mixture is refluxed for 2 h. The solvent is evaporated to give the desired product (crude) (0.12 g, yield 96%), which is used directly in next step.

N-(2-cyano-1-(3-hydroxy-2-propylphenoxy)propan-2-yl)-4-(trifluoromethoxy)benzamide (0.12 g, 0.29 mmol) and Pd/C (20 mg, 10% pure) in MeOH (15 mL) is stirred under hydrogen atmosphere at rt for 40 min. The mixture is filtered and the filtrate is evaporated to give the desired product (crude) (0.1 g, yield 83%), which is used directly in next step.

A mixture of N-(2-cyano-1-(3-hydroxy-2-propylphenoxy)propan-2-yl)-4-(tri fluoro methoxy)benzamide (1.3 g, 3 mmol), $MgCl_2$ (1.17 g, 12 mmol), paraformaldehyde (1.62 g, 18 mmol) and TEA (2.42 g, 24 mmol) in acetonitrile (50 mL) is refluxed for 2 h. The solvent is evaporated. Water is added to the residue and the mixture is extracted twice with EtOAc. The combined organic layers are concentrated and the residue is purified by silica chromatography to give the desired product (1 g, yield 72%).

$Tf_2O$ (2.16 g, 7.56 mmol) is added to a mixture of N-(2-cyano-1-(4-formyl-3-hydroxy-2-propylphenoxy)propan-2-yl)-4-(trifluoromethoxy)benzamide (1.7 g, 7.78 mmol) and TEA (1.52 g, 15.1 mmol) in DCM (50 mL) at 0° C. The mixture is stirred at rt for 3 h. Water is added and the mixture is extracted twice with DCM. The combined organic layers are concentrated and the residue is purified by prep-HPLC to give the desired product (450 mg, yield 20%).

To a stirring solution of 3-(2-cyano-2-(4-(trifluoromethoxy)benzamido)propoxy)-6-formyl-2-propylphenyl trifluoromethanesulfonate (50 mg) in THF (0.5 mL) are added $pin_2B_2$ (17.1 mg, 0.17 mmol), $Pd(dppf)_2Cl_2$ (2.5 mg) and AcOK (14 mg, 0.36 mmol) at rt. The mixture is stirred at 80° C. for 18 h under $N_2$. The reaction mixture is filtered and evaporated to give the desired product (crude) (50 mg, yield 100%). Nine parallel reactions are operated and combined, used directly in next step.

N-(2-Cyano-1-(4-formyl-2-propyl-3-(4,4,5,5-tetramethyl-1,3,2-dioxaborolan-2-yl) phenoxy)propan-2-yl)-4-(trifluoromethoxy)benzamide (400 mg, 0.71 mmol) in MeOH (20 mL) is cooled to 0° C., and $NaBH_4$ (81 mg, 2.1 mmol) is added to the mixture. The mixture is stirred at rt for 40 min LCMS showed the SM is consumed and main peak is the desired product. Water is added, and the solution is adjusted to pH=4 with 1N HCl. The aqueous layer is extracted with DCM and the crude product is purified by prep-TLC to give N-(2-cyano-1-(1-hydroxy-7-propyl-1,3-dihydrobenzo[c][1,2]oxaborole-6-yloxy) propan-2-yl)-4-(trifluoromethoxy) benzamide (designated as Example 37a) (109 mg, yield 33%). $^1$H NMR (400 MHz, DMSO-$d_6$): δ 0.83 (t, J=7.3 Hz, 3H), 1.47-1.60 (m, 2H), 1.85 (s, 3H), 2.80 (t, J=6.8 Hz, 2H), 4.25 (d, J=8.8 Hz, 1H), 4.47 (d, J=9.0 Hz, 1H), 4.90 (s, 2H), 7.09 (d, J=8.0 Hz, 1H), 7.17 (d, J=8.0 Hz, 1H), 7.52 (d, J=8.3 Hz, 2H), 8.01 (d, J=8.5 Hz, 2H), 8.90 (s, 1H), 9.06 (s, 1H) ppm; HPLC purity: 98.4% at 220 nm and 95.7% at 254 nm MS: m/z=463 (M+1, ESI+).

EXAMPLE 38

(S)—N-(2-cyano-1-(1-hydroxy-7-(trifluoromethoxy)-1,3-dihydrobenzo[c][1,2]oxaborol-6-yloxy)propan-2-yl)-4-(trifluoromethoxy)benzamide

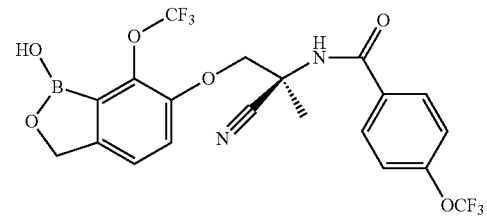 [SMILES: C[C@](C#N)(COc1ccc2c(c1OC(F)(F)F)B(O)OC2)NC(=O)c1ccc(OC(F)(F)F)cc1]

To a solution of 2-(trifluoromethoxy)phenol (9.0 g, 50.56 mmol) in TFA (150 mL) at 0° C. is added HMTA (14.2 g, 101.1 mmol). The reaction mixture is stirred at 70° C. overnight. EA (350 mL) is added and the mixture is washed with water (100 mL*3). The organic layer is dried over $Na_2SO_4$, filtered and concentrated under the reduced pressure. The residue is purified by silica gel column chromatography using PE:EA=5:1 as eluent to give the desired product (4.56 g, yield 43%) as a yellow solid.

To a solution of 4-hydroxy-3-(trifluoromethoxy)benzaldehyde (3.64 g, 17.7 mmol) and DIPEA (9.8 mL, 53 mmol) in DCM (150 mL) is added (chloromethoxy)ethane (2.5 mL, 26.5 mmol). The reaction mixture is stirred at rt overnight. Water (150 mL) is added and the mixture is extracted with DCM (150 mL*2). The combined organic layers are washed with brine, dried over $Na_2SO_4$, filtered and concentrated under the reduced pressure. The residue is purified by silica gel column chromatography using PE:EA=10:1 as eluent to give the desired product (3.8 g, yield 82%) as a colorless oil.

In a dry, $N_2$-flushed flask, $N^1,N^1,N^2$-trimethylethane-1,2-diamine (1.7 mL, 13.3 mmol) is dissolved in anhydrous THF (150 mL), and a solution of n-BuLi (2.5M, 5.3 mL) in hexane is added dropwise at 0° C. After being stirred for 15 min at rt, the mixture is cooled to −20° C., and a solution of 4-(ethoxymethoxy)-3-(trifluoromethoxy)benzaldehyde (3.2 g, 12.1 mmol) in anhydrous THF (30 mL) is added slowly. The mixture is stirred at −20° C. for 3 h, and then cooled to −40° C. A solution of $B(OMe)_3$ (6 mL, 54.5 mmol) is added. After 5 min, the cooling bath is removed and the mixture is allowed to warm to rt and stirred at rt for 16 h. After the addition of saturated aq. $NH_4Cl$ (30 mL) followed by saturated aq. $Na_2S_2O_3$ (10 mL), the solution is extracted with EtOAc (100 mL*2). The water is removed by lyophilization and the residue is washed with THF (120 mL). THF is evaporated to give the desired product (crude) (1.5 g) as colorless oil. It is used in next step without further purification.

To a solution of 3-(ethoxymethoxy)-6-formyl-2-(trifluoromethoxy)phenylboronic acid (1.5 g, crude) in THF (100 mL) is added $NaBH_4$ (300 mg). The reaction mixture is stirred at rt for 2 h, and then 6N HCl is added to pH=3. The mixture is stirred at rt overnight. HCl (4N in dioxane, 30 mL) is added and the mixture is continued to be stirred at rt for 2 h. The solvent is removed and the residue is purified by Combiflash to give the desired product (350 mg, yield: 12.4% over 2 steps) as a white solid.

To a solution of 7-(trifluoromethoxy)benzo[c][1,2]oxaborole-1,6(3H)-diol (200 mg, 0.85 mmol) and $K_2CO_3$ (354 mg, 2.56 mmol) in acetone (30 mL) is added bromoacetone (108 µL, 1.28 mmol). The reaction mixture is refluxed for 3 h. The solid is removed by filtration and the solvent is evaporated under the reduced pressure. The residue is purified by prep-HPLC to give the desired product (134 mg, yield 54%) as a white solid.

A mixture of 1-(1-hydroxy-7-(trifluoromethoxy)-1,3-dihydrobenzo[c][1,2]oxaborol-6-yloxy)propan-2-one (134 mg, 0.46 mmol), $NH_4Cl$ (74 mg, 1.39 mmol) and ammonia (7N in methanol, 2 mL) in MeOH (5 mL) is stirred at rt for 20 min before addition of NaCN (45 mg, 0.92 mmol). The reaction mixture is stirred at rt for 2 h. DCM (50 mL) is added and the solvent is removed under the reduced pressure at rt. The residue is mixed with THF and filtered. The filtrate is concentrated to give the crude the desired product (150 mg) as a yellow solid. It is used in next step without further purification.

A solution of 4-(trifluoromethoxy)benzoic acid (143 mg, 0.69 mmol), DIPEA (254 µL, 1.38 mmol) and HATU (350 mg, 0.92 mmol) in DMF (2 mL) is stirred at rt for 20 min before a solution of 2-amino-3-(1-hydroxy-7-(trifluoromethoxy)-1,3-dihydrobenzo[c][1,2]oxaborol-6-yloxy)-2-methylpropanenitrile (150 mg, crude) in DMF (1 mL) is added. The reaction mixture is stirred at rt overnight. It is purified by prep-HPLC to give N-(2-cyano-1-(1-hydroxy-7-(trifluoromethoxy)-1,3-dihydrobenzo[c][1,2]oxaborol-6-yloxy)-propan-2-yl)-4-(trifluoromethoxy)benzamide (designated as Example 38a) (160 mg, yield 69% over 2 steps) as a white solid. $^1$H NMR (400 MHz, DMSO-$d_6$): δ 9.22 (s, 1H), 9.06 (s, 1H), 7.99 (dd, J=7.2 Hz, 2H), 7.51 (d, J=8.0 Hz, 2H), 7.45 (d, J=8.4 Hz, 1H), 7.40 (d, J=8.4 Hz, 1H), 4.96 (s, 2H), 4.59 (d, J=9.2 Hz, 1H), 4.37 (d, J=9.2 Hz, 1H), 1.83 (s, 3H) ppm; HPLC purity: 100% at 214 nm and 100% at 254 nm; MS: m/z=505.1 (M+1, ESI+).

By following the procedure described in Example 1, the racemic mixture is separated to collect peak 1 giving the chiral enantiomer as white solid. $^1$H NMR (400 MHz, DMSO-$d_6$): δ 9.23 (s, 1H), 9.06 (s, 1H), 7.99 (d, J=7.2 Hz, 2H), 7.51 (d, J=8.0 Hz, 2H), 7.45 (d, J=8.4 Hz, 1H), 7.40 (d, J=8.4 Hz, 1H), 4.96 (s, 2H), 4.59 (d, J=9.2 Hz, 1H), 4.37 (d, J=9.2 Hz, 1H), 1.84 (s, 3H) ppm; HPLC purity: 100% at 214 nm and 100% at 254 nm; Chiral HPLC purity: 98.7% at 230 nm; MS: m/z=505 (M+1, ESI+).

EXAMPLE 39

N-(2-cyano-1-(1-hydroxy-4-methyl-1,3-dihydrobenzo[c][1,2]oxaborol-6-yloxy)propan-2-yl)-4-(trifluoromethoxy)benzamide

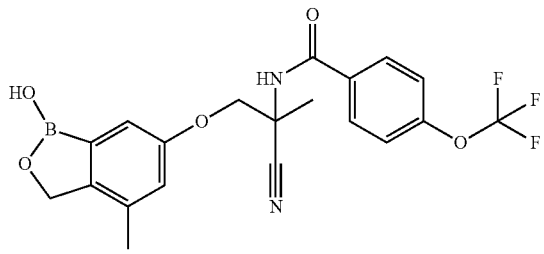 [SMILES: Cc1cc(OCC(C)(C#N)NC(=O)c2ccc(OC(F)(F)F)cc2)cc2c1COB2O]

To DMF (233 mL) is added slowly $POCl_3$ (115 mL, 1.23 mol) at 0-10° C. To the resulting mixture is added 5-methyl resorcinol (50.0 g, 0.40 mol) in DMF (116 mL) over 1 h. The resulting mixture is slowly warmed to rt and stirred overnight. It is cooled to −10° C. and ice/water (166 mL) is slowly added at −10 to 0° C. The pH is adjusted to 10 with 30% NaOH solution (116 g, 0.87 mol). The mixture is heated to 100° C. and stirred for 45 min. Then the mixture is cooled to 0° C. and acidified by conc. HCl to pH=1-2. The mixture is stirred at rt for 1 h, filtered, washed with water and dried to afford the desired product (46.1 g, 75% yield) as a brown solid.

To a mixture of 2,4-dihydroxy-6-methylbenzaldehyde (6.37 g, 37.9 mmol) in DCM (150 mL) is added 3,4-dihydro-2H-pyran (DHP, 4.78 g, 56.8 mmol) and pyridium p-toluenesulfonic acid (PPTS, 1.90 g, 7.58 mmol) at rt. The resulting mixture is stirred at rt for 18 h, and then quenched by adding saturated $NaHCO_3$ at 0° C. The organic layer is washed with brine, dried over $Na_2SO_4$ and concentrated in vacuo. The residue is purified by column chromatography using silica gel (EtOAc/hexane=1/3, v/v) to give pure product (8.78 g, 98% yield).

To a solution of 2-hydroxy-6-methyl-4-(tetrahydro-pyran-2-yloxy)benzaldehyde (8.70 g, 36.8 mmol) and pyridine (14.6 g, 184 mmol) in DCM (40 mL) is slowly added $Tf_2O$ (15.6 g, 55.2 mol) at −10 to 0° C. The mixture is stirred at 0° C. for 3 h. It is diluted with cold brine and extracted with 50% EtOAc in hexane. The organic extracts are washed with brine, dried and concentrated in vacuo. The residue is purified by column chromatography using silica gel (EtOAc/hexane=1/4, v/v) to give pure product (9.48 g, 69% yield).

To a solution of $Pin_2B_2$ (9.72 g, 38.3 mmol) in 1,4-dioxane (95 mL) is added KOAc (7.52 g, 76.6 mmol). After degassing for 10 min with $N_2$, $Pd(dppf)Cl_2$ (1.87 g, 2.55 mmol) and 2-formyl-3-methyl-5-(tetrahydro-2H-pyran-2-yloxy)phenyl trifluoromethanesulfonate (9.40 g, 25.5 mmol) are added to the reaction mixture. The mixture is stirred at 80° C. for 1 h, quenched with ice-water and extracted with 50% EtOAc in hexane. The organic extracts are washed with brine, dried and concentrated in vacuo. The residue is purified by column chromatography using silica gel (EtOAc/hexane=1/4, v/v) to give pure product (4.50 g, 51% yield).

To a stirring solution of 2-methyl-4-(tetrahydro-2H-pyran-2-yloxy)-6-(4,4,5,5-tetramethyl-1,3,2-dioxaborolan-2-yl)benzaldehyde (5.00 g, 14.4 mmol) in MeOH (50 mL) at 0° C. are added $NaBH_4$ (1.36 g, 36.0 mmol) in portions. The mixture is stirred at 0° C. for 3 h. To the reaction solution is added 6 N HCl (50 mL) and it is stirred at rt overnight. The mixture is extracted with EtOAc (50 mL×3). The combined organic layers are washed with brine (50 mL), dried over $Na_2SO_4$, filtered, and concentrated under vacuum. The residue is purified by prep-TLC to give pure product (1.25 g, 53% yield) as a white solid.

To a stirring solution of 4-methylbenzo[c][1,2]oxaborole-1,6(3H)-diol (110 mg, 0.55 mmol) in acetone (10 mL) at rt are added $K_2CO_3$ (383 mg, 2.77 mmol) and bromoacetone (228 mg, 1.66 mmol). The mixture is stirred at rt overnight. To the reaction solution is added 6 N HCl (10 mL), and stirred at rt for 10 min. The mixture is extracted with EtOAc (10 mL×3). The combined organic layers are washed with brine (50 mL), dried over $Na_2SO_4$, filtered and concentrated under vacuum. The residue is purified by prep-TLC to give the desired product (75 mg, 51% yield) as a yellow solid.

To a solution of 1-(1-hydroxy-4-methyl-1,3-dihydrobenzo[c][1,2]oxaborol-6-yloxy)-propan-2-one (75.0 mg, 0.34 mmol) in MeOH (10 mL) is bubbled with $NH_3$ at −30° C. to 0° C. for 1 h. The solution is then added to a mixed solution of KCN (58.0 mg, 0.89 mmol) and $NH_4Cl$ (85.0 mg, 1.59 mmol) in 28% $NH_3.H_2O$ (10 mL). The mixture is sealed and stirred at rt for 18 h. The reaction solution is partitioned between EtOAc (25 mL) and brine (25 mL). The aqueous layer is extracted with EtOAc (25 mL×2). The combined organic layers are washed with brine and dried over Na$_2$SO$_4$. The solvent is removed under reduced pressure to afford crude product (84.0 mg, quant. yield) as yellow solid.

To a solution of 2-amino-3-(1-hydroxy-4-methyl-1,3-dihydrobenzo[c][1,2]-oxaborol-6-yloxy)-2-methylpropanenitrile (84.0 mg, 0.34 mmol) and 4-trifluoromethoxybenzoic acid (105 mg, 0.51 mmol) in DMF (5 mL) at rt under N$_2$ are added HATU (259 mg, 0.68 mmol) and DIPEA (132 mg, 1.02 mmol). The reaction mixture is stirred at 30-35° C. overnight. The reaction mixture is purified by prep-HPLC to give N-(2-cyano-1-(1-hydroxy-4-methyl-1,3-dihydrobenzo[c][1,2]-oxaborol-6-yloxy)propan-2-yl)-4-(trifluoromethoxy)benzamide (60.0 mg, 40% yield) as white solid. $^1$H NMR (400 MHz, DMSO-d$_6$): δ 9.09 (s, 1H), 9.04 (s, 1H), 8.00 (d, J=8.8 Hz, 2H), 7.51 (d, J=8.4 Hz, 2H), 7.13 (d, J=2.0 Hz, 1H), 6.96 (d, J=2.0 Hz, 1H), 4.89 (s, 2H), 4.51 (d, J=8.8 Hz, 1H), 4.26 (d, J=9.2 Hz, 1H), 2.19 (s, 3H), 1.82 (s, 3H) ppm; HPLC purity: 92.6% at 220 nm and 94.9% at 254 nm; MS: m/z=435.1 (M+1, ESI+).

EXAMPLES 40 AND 41

N-(1-(4-(aminomethyl)-7-chloro-1-hydroxy-1,3-dihydrobenzo[c][1,2]oxaborol-6-yloxy)-2-cyanopropan-2-yl)-4-(trifluoromethoxy)benzamide

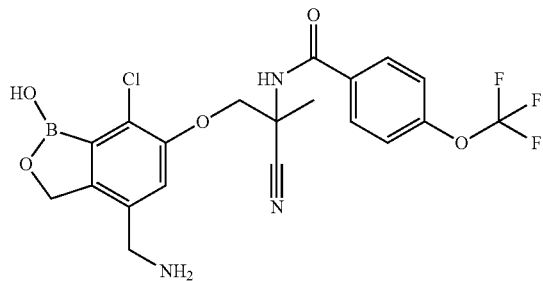 [SMILES: CC(C#N)(COc1cc(CN)c2c(c1Cl)B(O)OC2)NC(=O)c1ccc(OC(F)(F)F)cc1]

N-(1-amino-3-(4-(aminomethyl)-7-chloro-1-hydroxy-1,3-dihydrobenzo[c][1,2]oxaborol-6-yloxy)-2-methyl-1-oxopropan-2-yl)-4-(trifluoromethoxy)benzamide

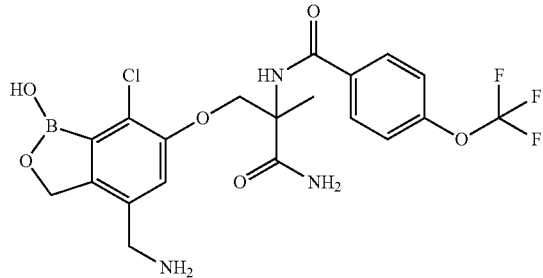 [SMILES: CC(COc1cc(CN)c2c(c1Cl)B(O)OC2)(NC(=O)c1ccc(OC(F)(F)F)cc1)C(N)=O]

To the solution of tert-butyl (7-chloro-6-(2-cyano-2-(4-(trifluoromethoxy)benzamido)-propoxy)-1-hydroxy-1,3-dihydrobenzo[c][1,2]oxaborol-4-yl)methylcarbamate (80 mg, 0.137 mmol) in DCM (2.5 mL) is added a solution of TFA (0.5 mL) in DCM (0.5 mL) dropwise. The reaction mixture is stirred at rt for 30 min. The solvent is removed under the reduced pressure and the residue is immediately purified by prep-HPLC to give N-(1-(4-(amino-methyl)-7-chloro-1-hydroxy-1,3-dihydrobenzo[c][1,2]oxaborol-6-yloxy)-2-cyanopropan-2-yl)-4-(trifluoromethoxy)benzamide (28.4 mg) and N-(1-amino-3-(4-(aminomethyl)-7-chloro-1-hydroxy-1,3-dihydrobenzo[c][1,2]oxaborol-6-yloxy)-2-methyl-1-oxopropan-2-yl)-4-(trifluoromethoxy)benzamide (12.3 mg) respectively as a white solid. Analytical data for 1$^{st}$ product: $^1$H NMR (400 MHz, DMSO-d$_6$) δ 9.09 (s, 1H), 9.07 (s, 1H), 8.00 (d, J=8.8 Hz, 2H), 7.51 (d, J=8.4 Hz, 2H), 7.36 (s, 1H), 4.95 (s, 2H), 4.59 (d, J=8.8 Hz, 1H), 4.38 (d, J=9.2 Hz, 1H), 3.63 (s, 2H), 1.87 (s, 3H) ppm; HPLC purity: 100% at 214 nm and 100% at 254 nm; MS: m/z=484.0 (M+1, ESI+). Analytical data for 2$^{nd}$ product: $^1$H NMR (400 MHz, DMSO-d$_6$) δ 8.98 (s, 1H), 8.46 (s, 1H), 7.96 (d, J=8.8 Hz, 2H), 7.45 (d, J=8.4 Hz, 2H), 7.44 (s, 1H), 7.28 (s, 1H), 7.16 (s, 1H), 4.91 (s, 2H), 4.69 (d, J=9.6 Hz, 1H), 4.39 (d, J=9.6 Hz, 1H), 3.60 (s, 2H), 1.62 (s, 3H) ppm; HPLC purity: 100% at 214 nm and 100% at 254 nm; MS: m/z=502.1 (M+1, ESI+).

EXAMPLE 42

N-(1-(7-chloro-1-hydroxy-4-methyl-1,3-dihydrobenzo[c][1,2]oxaborol-6-yloxy)-2-cyano propan-2-yl)-4-(trifluoromethoxy)benzamide

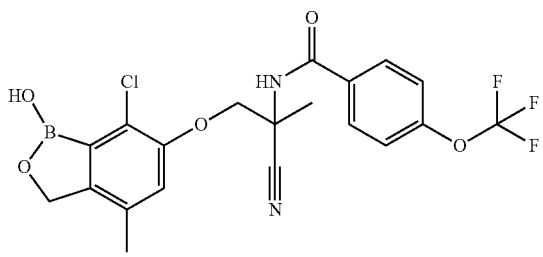 [SMILES: Cc1cc(OCC(C)(C#N)NC(=O)c2ccc(OC(F)(F)F)cc2)c(Cl)c2c1COB2O]

To a solution of 4-methylbenzo[c][1,2]oxaborole-1,6(3H)-diol (140 mg, 0.85 mmol) in DMF (5 mL) at rt under N$_2$ is added NCS (143 mg, 1.07 mmol). The reaction mixture is stirred at rt overnight and concentrated under reduced pressure. The residue is purified by prep-TLC (EtOAc/Petroleum ether=1/5, v/v) to give the desired product (100 mg, 60% yield) as yellow solid.

To a solution of 1-(7-chloro-1-hydroxy-4-methyl-1,3-dihydrobenzo[c][1,2]oxaborol-6-yloxy)propan-2-one (100 mg, 0.51 mmol) and K$_2$CO$_3$ (112 mg, 0.82 mmol) in acetone (50 mL) is added dropwise bromoacetone (117 mg, 0.87 mmol) at 15° C. under N$_2$. The mixture is stirred at 15° C. overnight and then partitioned between EtOAc (30 mL) and water (30 mL). The aqueous layer is extracted with EtOAc (30 mL×2). The combined organic layers are washed with brine and dried over Na$_2$SO$_4$. The solvent is removed under reduced pressure to afford 1 the desired product (126 mg, 49% yield) as white solid.

To a solution of 1-(7-chloro-1-hydroxy-4-methyl-1,3-dihydrobenzo[c][1,2]oxaborol-6-yloxy)propan-2-one (60.0 mg, 0.24 mmol) in MeOH (5 mL) is bubbled with NH$_3$ at −30° C. to 0° C. for 1 h. Afterwards, the solution is added to a mixture of KCN (46.0 mg, 0.72 mmol) and NH$_4$Cl (64.0 mg, 1.20 mmol) in 28% NH$_3$.H$_2$O (3.5 mL). The mixture is sealed and stirred at rt for 18 h. The reaction solution is partitioned between EtOAc (30 mL) and brine (25 mL). The aqueous layer is extracted with EtOAc (30 mL×2). The combined organic layers are washed with brine and dried over Na$_2$SO$_4$. The solvent is removed under reduced pressure to afford 2 the desired product (66.0 mg, quant. yield) as white solid.

To a solution of 2-amino-3-(7-chloro-1-hydroxy-4-methyl-1,3-dihydrobenzo-[c][1,2]oxaborol-6-yloxy)-2-methylpropanenitrile (60.0 mg, 0.21 mmol) and 4-trifluoromethoxybenzoic acid (57 mg, 0.28 mmol) in DMF (5 mL) at rt under N$_2$ are added HATU (105 mg, 0.28 mmol) and DIPEA (83.0 mg, 0.64 mmol). The reaction mixture is stirred at 30-35° C. overnight. The reaction mixture is purified by prep-HPLC to give N-(1-(7-chloro-1-hydroxyl-4-methyl-1,3-dihydrobenzo[c][1,2]oxaborol-6-yloxy)-2-cyanopropan-2-yl)-4-(trifluoromethoxy)benzamide as a white solid (30 mg, 30% yield).

EXAMPLE 43

N-(2-cyano-1-(7-(furan-2-yl)-1-hydroxy-L3-dihydrobenzo[c][1,2]oxaborol-6-yloxy)propan-2-yl)-4-(trifluoromethoxy)benzamide

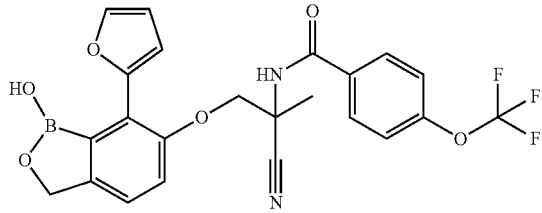 [SMILES: CC(C#N)(COc1ccc2c(c1-c1ccco1)B(O)OC2)NC(=O)c1ccc(OC(F)(F)F)cc1]

To a stirring solution of 3-iodo-2,4-bis(methoxymethoxy)benzaldehyde (2.00 g, 5.68 mmol), furan-2-ylboronic acid (2.50 g, 22.7 mmol) and K$_3$PO$_4$ (7.00 g, 34.0 mmol) in toluene (40 mL) and H$_2$O (9.5 mL) is added Pd(dppf)Cl$_2$ (500 mg) under N$_2$. The resulting mixture is refluxed overnight. The mixture is poured into ice-water (200 mL), and extracted with EtOAc (2×100 mL). The extracts are dried over sodium sulfate and concentrated to give a residue, which is purified by column chromatography over silica gel (PE/EA=10/1, v/v) to give the desired product (900 mg, 54% yield) as a yellow oil.

To a stirring solution of 3-furan-2-yl-2,4-bis(methoxymethoxy)benzaldehyde (6.50 g, 22.3 mmol) in THF (50 mL) is added 3N HCl (45 mL) dropwise at 0° C. The mixture is stirred at rt for 3 h. The mixture is diluted with EA (300 mL). The extracts are washed with water to pH=6, dried over sodium sulfate and concentrated to give a residue, which is purified by column chromatography using silica gel (PE/EA=100/1, v/v) to give the desired product (2.00 g, 36% yield) as a yellow oil.

To a stirring solution of 3-furan-2-yl-2-hydroxy-4-(methoxymethoxy)benzaldehyde (600 mg, 2.42 mmol) and pyridine (0.60 g, 7.26 mmol) in DCM (10 mL) is added Tf$_2$O (1.02 g, 3.63 mmol) dropwise at 0° C. It is stirred at 0° C. for 1 h, evaporated and purified by column chromatography using silica gel (PE/EA=40/1 to 5/1, v/v) to give the desired product (700 mg) as a yellow oil.

The mixture of 6-formyl-2-(furan-2-yl)-3-(methoxymethoxy)phenyl trifluoromethane-sulfonate (700 mg, 1.84 mmol), Pin$_2$B$_2$ (940 mg, 3.68 mmol) and KOAc (550 mg, 5.52 mmol) in THF (30 mL) is degassed by N$_2$ for 30 min, and then Pd(dppf)Cl$_2$ (50 mg) is added. The mixture is stirred at 70° C. for 36 h. The reaction is cooled and the solid is filtered off. The solvent is removed to give a residue which is purified by column chromatography using silica gel (PE/EA=20/1, v/v) to give the desired product (400 mg, 45% yield).

To a solution of 3-furan-2-yl-4-(methoxymethoxy)-2-(4,4,5,5-tetramethyl-[1,3,2]dioxaborolan-2-yl)benzaldehyde (200 mg, 0.56 mmol) in EtOH (7 mL) at 0° C. is added NaBH$_4$ (55.0 mg, 1.45 mmol). The mixture is stirred at rt for 50 min and evaporated. 3N HCl (3 mL) and THF (1 mL) are added dropwise at 0° C. The reaction is warmed to rt and stirred at rt for 3 h. The mixture is diluted with EA (30 mL) and washed wither water to pH=6. The organic layer is dried over sodium sulfate, filtered and concentrated to give a residue, which is purified by prep-TLC (PE/EA=3/1, v/v) to give 7 the desired product 30 mg, 24% yield) as a white solid.

To a stirring solution of 7-(furan-2-yl)benzo[c][1,2]-oxaborole-1,6(3H)-diol (58.0 mg, 0.28 mmol) and K$_2$CO$_3$ (77.0 mg, 0.55 mmol) in acetone (10 mL) is slowly added 1-bromopropan-2-one (65.0 mg, 0.47 mmol), and it is stirred at rt for 16 h. The solid is filtered off and the filtrate is concentrated to give the desired product as a yellow solid (70.0 mg, 96% yield), which is used for next step without further purification.

To the solution of 1-(7-furan-2-yl-1-hydroxy-1,3-dihydro-benzo[c][1,2]oxaborol-6-yloxy)-propan-2-one (70.0 mg, 0.26 mmol) in MeOH (13 mL) is bubbled NH$_3$ for 1 h at 0° C. The above solution is added to a mixture of KCN (105 mg, 1.54 mmol), NH$_4$Cl (125 mg, 2.30 mmol) and NH$_3$H$_2$O (5 mL) at 0° C. It is stirred overnight at 25° C. and evaporated. The residue is diluted with EA (150 mL). The organic layer is dried with Na$_2$SO$_4$ and the solvent is removed. The residue is purified by prep-TLC to give the desired product (73.0 mg, 94% yield).

To the solution of 4-trifluoromethoxybenzoic acid (66.0 mg, 0.32 mmol) in DMF (5.0 mL) are added HATU (122 mg, 0.32 mmol) and DIPEA (70.0 mg, 0.49 mmol), and the mixture is stirred for 1 h at 35° C. before 2-amino-3-(7-(furan-2-yl)-1-hydroxy-1,3-dihydrobenzo-[c][1,2]oxaborol-6-yloxy)-2-methylpropanenitrile (73.0 mg, 0.25 mmol) is added. The mixture is stirred at 35° C. overnight. The solvent is removed and the residue is purified by prep-HPLC to give N-(2-cyano-1-(7-(furan-2-yl)-1-hydroxy-1,3-dihydrobenzo[c][1,2]-oxaborol-6-yloxy)propan-2-yl)-4-(trifluoromethoxy)benzamide as a white solid (25.5 mg, 21% yield). $^1$H NMR (300 MHz, DMSO-d$_6$): δ 9.08 (s, 1H), 8.37 (s, 1H), 7.95 (d, J=8.0 Hz, 2H), 7.75 (m, 1H), 7.50 (d, J=8.0 Hz, 1H), 7.34 (m, 2H), 6.95 (d, J=3.3 Hz, 1H), 6.54 (m, 1H), 4.96 (s, 2H), 4.58 (d, J=9.3 Hz, 1H), 4.39 (d, J=9.3 Hz, 1H), 1.81 (s, 3H) ppm; HPLC purity: 98.5% at 220 nm and 99.2% at 254 nm; MS: m/z=487.1 (M+1, ESI+).

EXAMPLE 44

N-(1-(7-acetamido-1-hydroxy-1,3-dihydrobenzo[c][1,2]oxaborol-6-yloxy)-2-cyanopropan-2-yl)-4-(trifluoromethoxy)benzamide

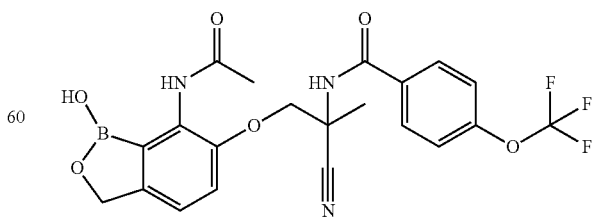

To a solution of benzo[c][1,2]oxaborole-1,6(3H)-diol (6 g, 0.03 mol) in DMF (20 mL) and DCM (600 mL), HNO$_3$ (9 mL, 2.3 M in DCM) is added at −30° C. After stirring at 0° C. for 2 h, the mixture is cooled to −30° C., and HNO₃ (9 mL, 2.3 M in DCM) is added. Then the resulting mixture is stirred at rt overnight and evaporated under reduced pressure. The residue is purified by prep-HPLC to afford the desired product (2.1 g) and 5-nitrobenzo[c][1,2]oxaborole-1,6(3H)-diol as yellow solid (1.1 g).

To a solution of 7-nitrobenzo[c][1,2]oxaborole-1,6(3H)-diol (4.0 g, 20.5 mmol) in EtOAc (400 mL) is added Pd/C (400 mg) under nitrogen. The mixture is stirred under H₂ atmosphere overnight and filtered. The filtrate is evaporated under reduced pressure to afford the desired product (3.0 g, yield 88.7%).

Acetic anhydride (2.0 g, 12.1 mmol) in THF is added to the solution of 7-aminobenzo[c][1,2]oxaborole-1,6(3H)-diol (2.4 g, 24.2 mmol) in THF and the mixture is stirred overnight. Water (100 mL) is added. The mixture is extracted with EA, died over Na₂SO₄, and concentrated to give the desired product as solid (2.0 g, yield 80%).

To a suspension of N-(1,6-dihydroxy-1,3-dihydrobenzo[c][1,2]oxaborol-7-yl)acetamide (1.8 g, 8.7 mmol) and Cs₂CO₃ (8.4 g, 26.0 mmol) in MeCN (200 mL) is added 1-chloropropan-2-one (1.22 g, 13.0 mmol). The mixture is heated at 60° C. overnight, cooled to rt and filtered. The filtrate is concentrated and mixed with EA/PE. The solid after filtration is used in next step directly (1.6 g, yield 70.0%).

To a stirring solution of NaCN (223.5 mg, 4.56 mmol) and 25% aq NH₃ (4.0 mL) in H₂O (2.0 mL) is added NH₄Cl (244 mg, 4.56 mmol), followed by addition of crude N-(1-hydroxy-6-(2-oxopropoxy)-1,3-dihydrobenzo[c][1,2]oxaborol-7-yl)acetamide (800 mg, 3.04 mmol). The mixture is stirred overnight. The resulting mixture is diluted with MeCN, dried over Na₂SO₄, and evaporated under reduced pressure to the crude product. It is used in the next step without further purification. (600 mg, yield 45.0%).

The solution of 4-(trifluoromethoxy)benzoic acid (356.4 mg, 1.73 mmol), HATU (988 mg, 2.6 mmol) and DIPEA (670.8 mg, 5.2 mmol) in DMF (4 mL) is stirred at rt for 30 min, and then N-(6-(2-amino-2-cyanopropoxy)-1-hydroxy-1,3-dihydrobenzo[c][1,2]oxaborol-7-yl)-acetamide (500 mg, 1.73 mmol) is added. The reaction is stirred overnight, added with water, extracted with EA, dried over Na₂SO₄, and evaporated under reduced pressure. The residue is purified twice by prep-HPLC to give the desired product N-(1-((7-acetamido-1-hydroxy-1,3-dihydrobenzo[c][1,2]oxaborol-6-yl)oxy)-2-cyanopropan-2-yl)-4-(trifluoromethoxy)benzamide as a white solid (8 mg, yield 1.2%). ¹H NMR (400 MHz, DMSO d₆): δ ppm 9.28 (s, 1H), 8.83 (s, 1H), 8.55 (s, 1H), 8.01 (d, J=8.8 Hz, 2H), 7.49 (d, J=8.0 Hz, 2H), 7.28 (d, J=8.0 Hz, 1H), 7.23 (d, J=8.8 Hz, 1H), 4.90 (s, 2H), 4.40 (d, J=9.2 Hz, 1H), 4.34 (d, J=9.2 Hz, 1H), 1.91 (s, 3H), 1.81 (s, 3H) ppm; HPLC purity: 90.3% at 220 nm and 96.2% at 254 nm; MS: m/z=478.0 (M+1, ESI+).

EXAMPLE 45

N-(2-cyano-1-(7-(dimethylamino)-1-hydroxy-1,3-dihydrobenzo[c][1,2]oxaborol-6-yloxy) propan-2-yl)-4-(trifluoromethoxy)benzamide

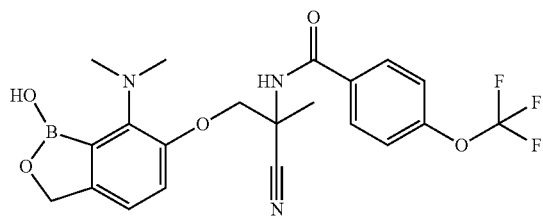 [SMILES: CN(C)c1c(OCC(C)(C#N)NC(=O)c2ccc(OC(F)(F)F)cc2)ccc2c1B(O)OC2]

To a solution of 7-aminobenzo[c][1,2]oxaborole-1,6(3H)-diol (500 mg, 3 mmol) in THF (10 mL) is added K₂CO₃ (1.66 g, 12 mmol) and MeI (1.70 mg, 12 mmol). The mixture is stirred overnight under Ar atmosphere, filtered and evaporated under reduced pressure to afford the desired product as a light yellow solid (450 mg, 74%).

To a solution of 7-(dimethylamino)benzo[c][1,2]oxaborole-1,6(3H)-diol (300 mg, 1.55 mmol) and chloroacetone (392.7 mg, 4.66 mmol) in acetone (10 mL) is added K₂CO₃ (643 mg, 4.66 mmol). The mixture is heated at 50° C. overnight under Ar atmosphere, cooled to rt, extracted with EA, dried and evaporated. The residue is purified by prep-HPLC to give the desired product as yellow solid (35 mg, yield 9.1%).

To a stirring solution of NaCN (10 mg, 0.21 mmol) and 25% aq NH₃ (0.5 mL) in MeOH (0.5 mL) are added NH₄Cl (13 mg, 0.25 mmol) and 1-((7-(dimethylamino)-1-hydroxy-1,3-dihydrobenzo[c][1,2]oxaborol-6-yl)oxy)propan-2-one (35 mg, 0.14 mmol, pure). The mixture is stirred overnight and evaporated under reduced pressure at rt. The residue is diluted with MeCN, dried over Na₂SO₄, and evaporated under reduced pressure to provide the crude product. It is used in the next step directly (37 mg).

The solution of 4-(trifluoromethoxy)benzoic acid (32 mg, 0.15 mmol), HATU (73 mg, 0.19 mmol), DIPEA (50 mg, 0.38 mmol) in DMF (1 mL) is stirred at rt for 30 min before 2-amino-3-((7-(dimethylamino)-1-hydroxy-1,3-dihydrobenzo[c][1,2]oxaborol-6-yl)oxy)-2-methylpropanenitrile (37 mg, 0.13 mmol) is added. After stirring at rt overnight, the reaction is quenched with water, extracted with EA, dried over Na₂SO₄ and concentrated. The residue is purified by prep-HPLC to afford N-(2-cyano-1-((7-(dimethylamino)-1-hydroxy-1,3-dihydrobenzo[c][1,2]oxaborol-6-yl)oxy)propan-2-yl)-44 trifluoromethoxy)benzamide as a white solid (9 mg, 13.8% yield over two steps). ¹H NMR (400 MHz, DMSO-d₆): δ 9.04 (s, 1H), 8.83 (s, 1H), 7.99 (d, J=8.4 Hz, 2H), 7.52 (d, J=8.0 Hz, 2H), 7.11 (d, J=8.4 Hz, 1H), 6.90 (d, J=8.0 Hz, 1H), 4.86 (s, 2H), 4.44 (d, J=9.2 Hz, 1H), 4.24 (d, J=9.2 Hz, 1H), 2.88 (s, 6H), 1.85 (s, 3H) ppm; HPLC purity: 96.2% at 220 nm and 95% at 254 nm; MS: m/z=464.1 (M+1, ESI+).

EXAMPLE 46 tert-butyl (6-(2-cyano-2-(4-(trifluoromethoxy)benzamido)propoxy)-1-hydroxy-1,3-dihydro-benzo[c][1,2]oxaborol-7-yl)methylcarbamate

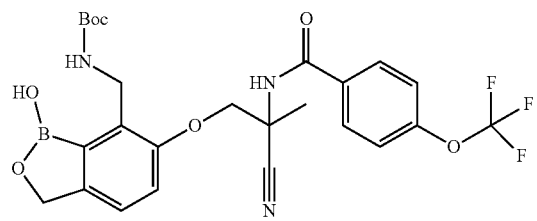 [SMILES: CC(C#N)(COc1ccc2c(c1CNC(=O)OC(C)(C)C)B(O)OC2)NC(=O)c1ccc(OC(F)(F)F)cc1]

6-(Benzyloxy)-1-hydroxy-1,3-dihydrobenzo[c][1,2]oxaborole-7-carbonitrile can be synthesized by following the procedures described previously for the preparation of 1-hydroxy-6-methoxy-1,3-dihydrobenzo[c][1,2]oxaborole-7-carbonitrile in Example 32. The solution of 6-(benzyloxy)-1-hydroxy-1,3-dihydrobenzo[c][1,2]oxaborole-7-carbonitrile (100 mg, 0.38 mmol) in MeOH (15 mL) is hydrogenated using Rany Ni (200 mg) as catalyst at 65° C.

for 3 h. The catalyst is removed by filtration on Celite and the solvent is evaporated under the reduced pressure to give the desired product (crude) (100 mg) as a white solid. It is used in next step without further purification.

To a solution of 7-(aminomethyl)benzo[c][1,2]oxaborole-1,6(3H)-diol (100 mg, crude) and Et₃N (164 μL, 1.14 mmol) in MeOH (15 mL) is added (Boc)₂O (174 μL, 0.76 mmol). The reaction mixture is stirred at rt for 1 h. After removal of the solvent, the residue is purified by prep-HPLC to give the desired product (50 mg, yield 48% over two steps) as a white solid.

To a solution of tert-butyl (1,6-dihydroxy-1,3-dihydrobenzo[c][1,2]oxaborol-7-yl)methyl-carbamate (80 mg, 0.29 mmol) and K₂CO₃ (118 mg, 0.86 mmol) in acetone (20 mL) is added bromoacetone (48 μL, 0.57 mmol). The reaction mixture is refluxed for 3 h. The solid is removed by filtration and the solvent is evaporated under the reduced pressure. The residue is purified by prep-HPLC to give the desired product (53 mg, yield 55%) as a white solid.

A mixture of tert-butyl (1-hydroxy-6-(2-oxopropoxy)-1,3-dihydrobenzo[c][1,2]oxaborol-7-yl)methylcarbamate (53 mg, 0.16 mmol), NH₄Cl (25 mg, 0.47 mmol) and ammonia (7N in methanol, 2 mL) in MeOH (3 mL) is stirred at rt for 20 min before addition of NaCN (15 mg, 0.32 mmol). The reaction mixture is stirred at rt for 2 h. DCM (50 mL) is added and the solvent is removed under the reduced pressure at rt. The residue is washed with THF and filtered. The filtrate is concentrated to give the desired product (crude) (70 mg) as a colorless oil. It is used in next step without further purification.

A solution of 4-(trifluoromethoxy)benzoic acid (49 mg, 0.24 mmol), DIPEA (87 μL, 0.47 mmol) and HATU (120 mg, 0.32 mmol) in DMF (3 mL) is stirred at rt for 20 min before tert-butyl (6-(2-amino-2-cyanopropoxy)-1-hydroxy-1,3-dihydrobenzo[c][1,2]oxaborol-7-yl)methylcarbamate (70 mg, crude) in DMF (2 mL) is added. The reaction mixture is stirred at rt overnight and evaporated. It is purified by prep-HPLC to give tert-butyl (6-(2-cyano-2-(4-(trifluoromethoxy)benzamido)-propoxy)-1-hydroxy-1,3-dihydrobenzo[c]-[1,2]oxaborol-7-yl)methylcarbamate (35 mg, yield 40% over two steps) as a white solid. ¹H NMR (400 MHz, DMSO-d₆): δ 9.23 (s, 1H), 9.06 (s, 1H), 8.03 (d, J=8.4 Hz, 2H), 7.50 (d, J=8.4 Hz, 2H), 7.30 (d, J=8.4 Hz, 1H), 7.19 (d, J=8.4 Hz, 1H), 6.78 (br s, 1H), 4.93 (s, 2H), 4.32-4.49 (m, 4H), 1.86 (s, 3H), 1.31 (s, 9H) ppm; HPLC purity: 100% at 214 nm and 100% at 254 nm; MS: m/z=572.1 (M+23, ESI+).

EXAMPLES 47 AND 48

N-(1-(7-(aminomethyl)-1-hydroxy-1,3-dihydrobenzo[c][1,2]oxaborol-6-yloxy)-2-cyanopropan-2-yl)-4-(trifluoromethoxy)benzamide

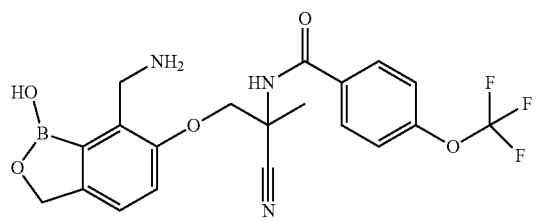 [SMILES: CC(C#N)(COc1ccc2c(c1CN)B(O)OC2)NC(=O)c1ccc(OC(F)(F)F)cc1]

N-(1-amino-3-(7-(aminomethyl)-1-hydroxy-1,3-dihydrobenzo[c][1,2]oxaborol-6-yloxy)-2-methyl-1-oxopropan-2-yl)-4-(trifluoromethoxy)benzamide

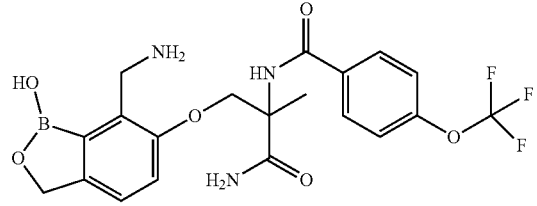 [SMILES: CC(COc1ccc2c(c1CN)B(O)OC2)(NC(=O)c1ccc(OC(F)(F)F)cc1)C(N)=O]

To a solution of tert-butyl (6-(2-cyano-2-(4-(trifluoromethoxy)benzamido)propoxy)-1-hydroxy-1,3-dihydrobenzo[c][1,2]oxaborol-7-yl)methylcarbamate (25 mg, 0.046 mmol) in DCM (2.5 mL) is added a solution of TFA (0.5 mL) in DCM (0.5 mL) dropwise. The reaction mixture is stirred at rt for 30 min. The solvent is removed under the reduced pressure and the residue is immediately purified by prep-HPLC to give N-(1-(7-(aminomethyl)-1-hydroxy-1,3-dihydrobenzo[c][1,2]oxaborol-6-yloxy)-2-cyanopropan-2-yl)-4-trifluoromethoxy)benzamide (7.3 mg) and N-(1-amino-3-(7-(aminomethyl)-1-hydroxy-1,3-dihydrobenzo[c][1,2]oxaborol-6-yloxy)-2-methyl-1-oxopropan-2-yl)-4-(trifluoromethoxy)benzamide (3.4 mg) respectively as a white solid.

Analytical data for the 1ˢᵗ product: ¹H NMR (500 MHz, CD₃OD) δ 7.96-7.99 (m, 2H), 7.41 (d, J=8.0 Hz, 2H), 7.24-6.84 (m, 2H), 4.87 (s, 2H), 4.63-4.12 (m, 4H), 1.95-1.92 (m, 3H) ppm; HPLC purity: 100% at 214 nm and 100% at 254 nm; MS: m/z=450.1 (M+1, ESI+). Analytical data for the 2ⁿᵈ product: ¹H NMR (500 MHz, CD₃OD) δ 7.92-7.95 (m, 2H), 7.39-7.36 (m, 2H), 7.04-6.85 (m, 2H), 4.83-3.99 (m, 6H), 1.77-1.74 (m, 3H) ppm; HPLC purity: 97.0% at 214 nm and 100% at 254 nm; MS: m/z=468.1 (M+1, ESI+).

EXAMPLE 49

N-(1-(7-amino-1-hydroxy-1,3-dihydrobenzo[c][1,2]oxaborol-6-yloxy)-2-cyanopropan-2-yl)-4-(trifluoromethoxy)benzamide

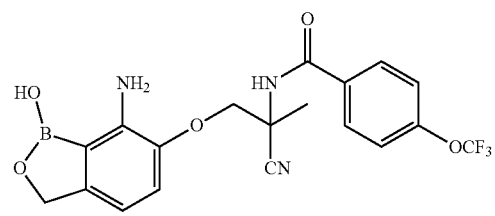 [SMILES: CC(C#N)(COc1ccc2c(c1N)B(O)OC2)NC(=O)c1ccc(OC(F)(F)F)cc1]

To a solution of 7-nitrobenzo[c][1,2]oxaborole-1,6(3H)-diol (250 mg, 1.28 mmol) and K₂CO₃ (531 mg, 3.84 mmol) in acetone (15 mL) is added bromoacetone (351 mg, 2.56 mmol). The reaction mixture is refluxed for 3 h. The reaction mixture is filtered and the residue is washed with acetone (5 mL). The filtrate is concentrated and the residue is purified by prep-TLC using PE:EA=4:1 as eluent to give the desired product (193 mg, yield 60%) as a white solid.

A mixture of 1-(1-hydroxy-7-nitro-1,3-dihydrobenzo[c][1,2]oxaborol-6-yloxy) propan-2-one (193 mg, 0.77 mmol), NH$_4$Cl (82 mg, 1.54 mmol) and ammonia (7N in methanol, 1 mL) in MeOH (5 mL) is stirred at rt for 20 min before addition of NaCN (76 mg, 1.54 mmol). The reaction mixture is stirred at rt for 5 h. DCM (50 mL) is added and the solvent is removed under the reduced pressure. The residue is washed with THF, and THF is evaporated to give the desired product (crude) (220 mg). It is used in next step without further purification.

A solution of 4-(trifluoromethoxy)benzoic acid (317 mg, 1.54 mmol), HATU (585 mg, 1.54 mmol) and DIPEA (298 mg, 2.31 mmol) in DMF (5 mL) is stirred at rt for 30 min before 2-amino-3-(1-hydroxy-7-nitro-1,3-dihydrobenzo[c][1,2]oxaborol-6-yloxy)-2-methylpropanenitrile (220 mg, 0.77 mmol, crude) is added. The reaction mixture is stirred at rt overnight. It is purified by prep-HPLC to give the desired product (47 mg, yield 13% over 2 steps) as a white solid.

A mixture of N-(2-cyano-1-(1-hydroxy-7-nitro-1,3-dihydrobenzo[c][1,2]oxaborol-6-yloxy)propan-2-yl)-4-(trifluoromethoxy)benzamide (80 mg, 0.172 mmol) and Fe (96 mg, 1.72 mmol) in AcOH (10 mL) is stirred at rt for 4 h. It is filtered, evaporated and purified by prep-HPLC to give N-(1-(7-amino-1-hydroxy-1,3-dihydrobenzo[c][1,2]-oxaborol-6-yloxy)-2-cyanopropan-2-yl)-4-(trifluoromethoxy)benzamide (25 mg, yield 33.4%) as a light yellow solid. $^1$H NMR (400 MHz, DMSO-d$_6$): δ 9.00 (s, 1H), 8.00 (d, J=8.4 Hz, 2H), 7.50 (d, J=8.4 Hz, 2H), 6.98 (d, J=8.4 Hz, 1H), 6.52 (d, J=8.4 Hz, 1H), 4.81 (s, 2H), 4.39 (d, J=9.2 Hz, 1H), 4.33 (br s, 2H), 4.26 (d, J=9.2 Hz, 1H), 1.86 (s, 3H) ppm; HPLC purity: 93.8% at 220 nm and 100.0% at 254 nm; MS: m/z=436.1 (M+1, ESI+).

MeOH (30 mL) is added TMSCN (448 mg, 4.9 mmol) in one portion. It is stirred at rt overnight. TLC monitoring showed STM is consumed. The mixture is concentrated to give a residue, which is extracted with THF (5×10 mL). The combined organics are concentrated to give the desired product (crude, 700 mg), which is used for next step without purification.

To a stirring mixture of 2-amino-3-(1-hydroxy-7-iodo-1,3-dihydrobenzo[c][1,2]oxaborol-6-yloxy)-2-methylpropanenitrile (584 mg, 1.6 mmol) and DIPEA (439 mg, 4.1 mmol) in dry THF (20 mL) is added a solution of 4-(trifluoromethoxy)benzoic acid (511 mg, 2.28 mmol) in THF (3 mL). After addition, the resulting mixture is stirred at rt for 2 h. Diluted HCl is added until pH=5. The separated organics are dried and concentrated to give a residue, which is purified by silica gel chromatography (DCM:MeOH=150:1) to give a crude product. The crude product is further purified by prep-HPLC (Column: Agilent XDB-C18, 150 mm*20 mm Sum, mobile phase A: H$_2$O+0.1% TFA: mobile phase B: ACN, B % 40~100, flow rate: 30 mL/min) to give N-(2-cyano-1-(1-hydroxy-7-iodo-1,3-dihydrobenzo[c][1,2]-oxaborol-6-yloxy)propan-2-yl)-4-(trifluoromethoxy)benzamide as a white solid (123 mg). $^1$H NMR: (500 MHz, DMSO-d$_6$): δ 9.10 (s, 1H), 9.03 (s, 1H), 8.02 (d, J=8.7 Hz, 2H), 7.52 (d, J=8.3 Hz, 2H), 7.37 (d, J=8.4 Hz, 1H), 7.14 (d, J=8.3 Hz, 1H), 4.91 (d, J=16.4 Hz, 2H), 4.58 (d, J=9.2 Hz, 1H), 4.35 (d, J=9.2 Hz, 1H), 1.91 (s, 3H) ppm; HPLC purity: 99.2% at 220 nm and 99.3% at 254 nm; MS: m/z=547 (M+1, ESI+).

EXAMPLE 50

N-(2-cyano-1-(1-hydroxy-7-iodo-1,3-dihydrobenzo[c][1,2]oxaborol-6-yloxy)propan-2-yl)-4-(trifluoromethoxy)benzamide

EXAMPLE 51

Methyl 6-(2-cyano-2-(4-(trifluoromethoxy)benzamido)propoxy)-1-hydroxy-1,3-dihydro-benzo[c][1,2]oxaborole-7-carboxylate

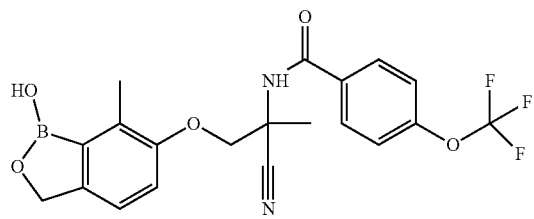 [SMILES: Cc1c(OCC(C)(C#N)NC(=O)c2ccc(OC(F)(F)F)cc2)ccc2c1B(O)OC2]

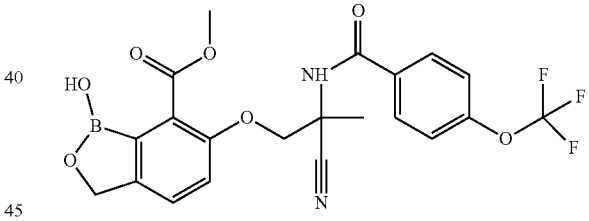

To a stirring solution of benzo[c][1,2]oxaborole-1,6(3H)-diol (5.5 g, 37 mmol) in EtOAc (110 mL) is slowly added NIS (6.6 g, 29 mmol) at 0° C. It is stirred at rt for 4 h. The mixture is poured into water and extracted with EtOAc. The EtOAc layer is dried and concentrated to give a residue, which is purified by prep-HPLC (Column: Agilent XDB-C18, 150 mm*20 mm Sum, mobile phase A: H$_2$O+0.1% TFA; mobile phase B: ACN, B % 40~100, flow rate: 30 mL/min) to give the desired product (150 mg).

To a stirring solution of 7-iodobenzo[c][1,2]oxaborole-1,6(3H)-diol (900 mg, 3.3 mmol) and K$_2$CO$_3$ (1.13 g, 8.1 mmol) in acetone (30 mL) is slowly added bromoacetone (581 mg, 4.2 mmol). The mixture is refluxed for 2 h, cooled to rt, added with 1N HCl until pH=2 and extracted with EtOAc. The organic layer is dried over Na$_2$SO$_4$ and concentrated. The residue is purified by column chromatography to give the desired product as a white solid (700 mg).

To a stirring solution of 1-(1-hydroxy-7-iodo-1,3-dihydrobenzo[c][1,2]oxaborol-6-yloxy)propan-2-one (600 mg, 1.8 mmol) and NH$_4$Cl (242 mg, 4.9 mmol) in 7N NH$_3$/

To a solution of diisopropylamine (39.4 g, 385 mmol) in THF (600 mL) is added n-BuLi (2.5 M, 154 mL) at −10° C. during 20 min. The mixture is stirred at −20° C. for 1 h and cooled to −78° C. Then 2-bromo-4-fluoro-1-methylbenzene (60 g, 308 mmol) is added to the solution for 30 min. After being stirred for 3 h, DMF (32.0 g, 431 mmol) is added to the mixture during 30 min at −78° C. and stirred for additional 30 min. The mixture is quenched with water (500 mL), extracted with EA (3×300 mL), dried over anhydrous Na$_2$SO$_4$, filtered and concentrated under reduced pressure. The residue is purified by column chromatography using silica gel (PE-EA, 50/1 to 20/1, v/v) to provide the desired product (56.0 g, yield 84%) as a yellow solid.

To a solution of 2-bromo-6-fluoro-3-methylbenzaldehyde (56.0 g, 0.25 mol) in t-BuOH (1000 mL) are added 2-methyl-2-butene (138 g, 1.77 mol), a solution of NaClO$_2$ (53.8 g, 0.506 mol) and NaH$_2$PO$_4$ (92.0 g, 0.759 mol) in water (700 mL). The mixture is stirred at rt for 30 min and then is quenched with 1 N HCl (75 mL) and extracted with EA (3×500 mL). The organic phase is washed with brine, dried over anhydrous Na$_2$SO$_4$, filtered and concentrated under reduced pressure. The residue is purified by column chromatography using silica gel (PE/EA, 5/1 to 2/1, v/v) to provide the desired product (52.7 g, yield 90%) as yellow oil.

To a solution of 2-bromo-6-fluoro-3-methylbenzoic acid (52.7 g, 0.226 mol) in DMF (1000 mL) is added $K_2CO_3$ (78.9 g, 0.57 mol), and the mixture is stirred at rt for 10 min before MeI (54.8 g, 0.45 mol) is added. The reaction is stirred for 1 h, quenched with 1 N HCl (50 mL), diluted with water (500 mL) and extracted with EA (3×500 mL). The organic phase is washed with brine, dried over anhydrous $Na_2SO_4$, filtered and concentrated under reduced pressure. The residue is purified by column chromatography using silica gel (30/1 to 10/1, v/v) to provide the desired product (52.3 g, yield 94%) as colorless oil.

MeONa (14.0 g, 253 mmol) in MeOH (50 mL) is dissolved in DMF (500 mL), and then $K_2CO_3$ (38.3 g, 274 mmol) is added. It is stirred for 15 min and 2-bromo-6-fluoro-3-methylbenzoic acid methyl ester (52.3 g, 211 mmol) is added to the solution at 0° C. Then the reaction mixture is heated to 100° C. and stirred overnight. After cooling to rt, EA (200 mL) is added, washed with saturated $NaHCO_3$ solution, dried over anhydrous $Na_2SO_4$, filtered and concentrated under reduced pressure. The residue is purified by column chromatography using silica gel (PE-EA, 10/1 to 4/1, v/v) to provide the desired product (33.6 g, yield 62%) as colorless oil.

To a solution of 2-bromo-6-methoxy-3-methylbenzoic acid methyl ester (33.6 g, 130 mmol) in $CCl_4$ (500 L) are added NBS (24.5 g, 136 mmol) and BPO (1.61 g, 6.50 mmol). The reaction is stirred under $N_2$ at 85° C. overnight, cooled to rt, filtered and evaporated. The residue is purified by column chromatography using silica gel (PE/EA, 15/1 to 4/1, v/v) to give 2 the desired product (34.4 g, 78.2%) as a white solid.

The mixture of 2-bromo-3-bromomethyl-6-methoxybenzoic acid methyl ester (34.4 g, 101 mmol) and KOAc (15.0 g, 152 mmol) in DMF (600 mL) is stirred for 2 h at 80° C., cooled to rt, diluted with water (1000 mL), and extracted with EA (3×500 mL). The organic phase is washed with brine, dried over anhydrous $Na_2SO_4$, filtered and concentrated under reduced pressure. The residue is purified by column chromatography using silica gel (PE/EA, 10/1 to 5/1, v/v) to provide the desired product (28.7 g, 90%) as colorless oil.

To a solution of 3-acetoxymethyl-2-bromo-6-methoxybenzoic acid methyl ester (28.7 g, 90.5 mmol) in 1,4-dioxane (600 mL) at rt are added bis(pinacolato)diboron (46.9 g, 181 mmol) and KOAc (38.6 g, 389 mmol). After being degassed with $N_2$, $Pd(dppf)Cl_2$ (7.54 g, 9.05 mmol) is added. The reaction mixture is stirred overnight at 110° C. under $N_2$, cooled to rt, and filtered through a celite pad. The filter cake is washed with EA (1000 mL). The filtrate is dried over $Na_2SO_4$, filtered and concentrated under reduced pressure. The residue is purified by column chromatography using silica gel eluted with PE/EA (10/1 to 3/1, v/v) to give the desired product (10.1 g, 31%) as colorless oil.

$K_2CO_3$ (7.71 g, 55.2 mmol) is added to a solution of methyl 3-(acetoxymethyl)-6-methoxy-2-(4,4,5,5-tetramethyl-1,3,2-dioxaborolan-2-yl)benzoate (10.1 g, 27.6 mmol) in MeOH (200 mL). The mixture is stirred at rt overnight and quenched with the addition of 1N HCl. MeOH is removed from the mixture in vacuo. The mixture is extracted EA (3×100 mL), washed with brine, dried over anhydrous $Na_2SO_4$, filtered and concentrated under reduced pressure. The residue is purified by column chromatography using silica gel (PE/EA, 5/1 to 1/1, v/v) to provide the desired product (6.58 g, yield 54%) as white solid.

To a stirring mixture of $AlCl_3$ (78.2 g, 580 mmol) in DCM (1000 mL) at −20° C. is added dropwise a solution of methyl 1-hydroxy-6-methoxy-1,3-dihydrobenzo[c][1,2]oxaborole-7-carboxylate (6.58 g, 29.0 mmol) in DCM (50 mL) dropwise. The reaction mixture is allowed to warm to rt and stirred for 16 h. After removal of DCM in vacuo, the residue is cooled to 0° C., and water (18 mL) is added very slowly. To this reaction mixture is added EA (300 mL), and the separated organic layer is washed with water and brine, and dried over anhydrous $Na_2SO_4$, filtered and concentrated under reduced pressure. The residue is purified by column chromatography using silica gel (DCM-MeOH, 300/1 to 100/1, v/v) to provide the desired product (1.81 g, yield 30.0%) as white solid.

To a mixture of methyl 1,6-dihydroxy-1,3-dihydrobenzo[c][1,2]oxaborole-7-carboxylate (130 mg, 0.62 mmol) and $K_2CO_3$ (174 mg, 1.25 mmol) in acetonitrile (15 mL) is added dropwise 1-bromo-propan-2-one (141 mg, 0.998 mmol) at 0° C. The reaction mixture is stirred overnight at 30° C. under $N_2$, and filtered through a celite pad. The filter cake is washed with EA (200 mL). The filtrate is dried over $Na_2SO_4$, filtered, and concentrated under reduced pressure. The residue is purified by prep-TLC (DCM/MeOH, 300/1, v/v) to afford the desired product (107 mg, yield 65.0%) as a white solid.

To a solution of methyl 1-hydroxy-6-(2-oxopropoxy)-1,3-dihydrobenzo[c][1,2]oxaborole-7-carboxylate (100 mg, 0.371 mmol) in MeOH (8 mL) is bubbled $NH_3$ for 20 min at −30° C. Then KCN (61.6 mg, 0.928 mmol), $NH_4Cl$ (80.2 mg, 1.48 mmol) and $NH_3 \cdot H_2O$ (1.50 mL) are added. The reaction mixture is stirred overnight at 25° C. and evaporated. The residue is purified by prep-HPLC to give the desired product (45.0 mg, 42.1%) as a light yellow solid.

To a solution of 4-trifluoromethoxybenzoic acid (64.5 mg, 0.30 mmol) and DIPEA (79.2 mg, 0.61 mmol) in DMF (3 mL) is added HATU (118 mg, 0.30 mmol). The mixture is stirred for 2 h at 35° C. Then the solution of methyl 6-(2-amino-2-cyanopropoxy)-1-hydroxy-1,3-dihydrobenzo[c][1,2]oxaborole-7-carboxylate (45.0 mg, 0.152 mmol) in DMF (2 mL) is added dropwise at 0° C. The reaction mixture is stirred overnight at 35° C., cooled to rt, diluted with water (20 mL) and extracted with EA (3×15 mL). The organic layer is washed with brine, dried over $Na_2SO_4$, filtered and concentrated under reduced pressure. The residue is purified by prep-HPLC to give the title compound methyl 6-(2-cyano-2-(4-(trifluoromethoxy)benzamido)propoxy)-1-hydroxy-1,3-dihydrobenzo[c][1,2]oxaborole-7-carboxylate (14.0 mg, 19%) as a white solid. $^1H$ NMR (400 MHz, MeOD-$d_4$): δ 7.93 (d, J=9.2 Hz, 2H), 7.44 (d, J=8.4 Hz, 1H), 7.36 (d, J=8.0 Hz, 2H), 7.25 (d, J=8.0 Hz, 1H), 4.98 (d, J=1.6 Hz, 2H), 4.52 (d, J=9.2 Hz, 1H), 4.49 (d, J=9.2 Hz, 1H), 3.85 (s, 3H), 1.89 (s, 3H) ppm; HPLC purity: 95.1% at 220 nm and 95.1% at 254 nm; MS: m/z=479.2 (M+1, ESI+).

EXAMPLE 52

N-(2-cyano-1-(1-hydroxy-7-(thiophen-2-yl)-1,3-dihydrobenzo[c][1,2]oxaborol-6-yloxy)propan-2-yl)-4-(trifluoromethoxy)benzamide

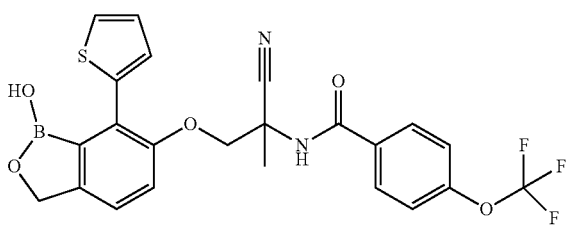 [SMILES: CC(C#N)(COc1ccc2c(c1-c1cccs1)B(O)OC2)NC(=O)c1ccc(OC(F)(F)F)cc1]

A mixture of 3-iodo-2,4-bis(methoxymethoxy)benzaldehyde (1.00 g, 2.84 mmol), tributyl(thiophen-2-yl)stannane (1.16 g, 3.12 mmol) and Pd(PPh₃)₄ (164 mg, 0.14 mmol) is refluxed under nitrogen overnight in 1,4-dioxane (25 mL). The mixture is cooled to rt. Saturated KF solution (20 mL) is added. And the mixture is stirred for another 30 min. The solid is removed by filtration and the organic layer is washed with water (3×50 mL), dried over sodium sulfate and concentrated to give a residue, which is purified by column chromatography using silica gel (PE/EA=5/1, v/v) to give the desired product (869 mg, 99% yield) as a yellow oil.

To a stirring solution of 2,4-bis(methoxymethoxy)-3-(thiophen-2-yl)benzaldehyde (4.50 g, 14.6 mmol) in THF (30 mL), 6 N HCl (30 mL) are added dropwise at 0° C. The mixture is stirred at rt for 1.5 h and the product is participated as white solid. The solid is collected by filtration, washed with water (5×30 mL), and dried to give the desired product (2.30 g, 59% yield) as a white solid.

To a stirring solution of 2-hydroxy-4-(methoxymethoxy)-3-(thiophen-2-yl)benzaldehyde (500 mg, 1.89 mmol) and pyridine (450 mg, 5.66 mmol) in DCM (10 mL) is added Tf₂O (800 mg, 2.83 mmol) dropwise at 0° C. The reaction is stirred at rt for 1.5 h and evaporated. The residue is purified by column chromatography using silica gel (PE/EA=40/1 to 5/1, v/v) to give the desired product (400 mg) as a yellow oil.

The mixture of 6-formyl-3-(methoxymethoxy)-2-(thiophen-2-yl)phenyl trifluoromethanesulfonate (160 mg, 0.40 mmol), Pin₂B₂ (205 mg, 0.81 mmol) and KOAc (170 mg, 1.70 mmol) in THF (10 mL) is degassed by N₂ for 30 min, and then Pd(dppf)Cl₂ (37 mg) is added. The mixture is reacted under microwave at 100° C. for 2 h. The reaction is cooled and the solid is filtered off. The solvent is removed to give a residue which is purified by prep-TLC (PE/EA=3/1, v/v) to give the desired product (45 mg, 30% yield).

To a solution of 4-(methoxymethoxy)-2-(4,4,5,5-tetramethyl-1,3,2-dioxaborolan-2-yl)-3-(thiophen-2-yl)benzaldehyde (65 mg, 0.17 mmol) in MeOH (5 mL) at 0° C. is added NaBH₄ (13 mg, 0.34 mmol). The mixture is stirred at rt for 30 min and evaporated. Aqueous HCl (6N, 2 mL) and THF (1 mL) are added dropwise to the residue at 0° C. The reaction is warmed to rt and stirred for 30 min. The mixture is diluted with EA (10 mL), washed with water to pH=6, then dried over sodium sulfate and concentrated to give a residue. It is purified by prep-TLC (PE/EA=3/1, v/v) to give the desired product (14 mg, 35% yield) as a white solid.

To a stirring solution of 7-(thiophen-2-yl)benzo[c][1,2]oxaborole-1,6(3H)-diol (50.0 mg, 0.22 mmol) and K₂CO₃ (60 mg, 0.44 mmol) in acetone (20 mL) is slowly added 1-bromo-2-propaone (50 mg, 0.37 mmol), and then stirred at rt for 12 hrs. The solid is filtered off and the filtrate is concentrated to give a yellow solid, which is purified by prep-TLC (PE/EA=3/1, v/v) to give the desired product (53 mg, 85% yield) as a white solid.

The solution of 1-(1-hydroxy-7-(thiophen-2-yl)-1,3-dihydrobenzo[c][1,2]oxaborole-6-yloxy)-propan-2-one (53.0 mg, 0.18 mmol) in MeOH (10 mL) is cooled to −30° C. and NH₃ is bubbled for 0.5 h. The above solution is added to a mixture of KCN (36.0 mg, 0.54 mmol), NH₄Cl (49.0 mg, 0.90 mmol) and NH₃.H₂O (3 mL) at 0° C. It is stirred overnight at 25° C., concentrated under reduce pressure and diluted with EA (50 mL). The organic layer is dried over Na₂SO₄, filtered and evaporated. The residue is purified by prep-TLC to give the desired product (30 mg, 52% yield).

To the solution of 4-trifluoromethoxybenzoic acid (23.0 mg, 0.11 mmol) in DMF (5.0 mL) are added HATU (43.0 mg, 0.11 mmol) and DIPEA (33.0 mg, 0.26 mmol). It is stirred at 35° C. for 1 h. Then 2-amino-3-(1-hydroxy-7-(thiophen-2-yl)-1,3-dihydrobenzo[c][1,2]oxaborol-6-yloxy)-2-methylpropanenitrile (27.0 mg, 0.08 mmol) is added. The mixture is stirred at 35° C. overnight. The solvent is removed and the residue is purified by prep-HPLC to give N-(2-cyano-1-(1-hydroxy-7-(thiophen-2-yl)-1,3-dihydrobenzo[c][1,2]oxaborol-6-yloxy)-propan-2-yl)-4-(trifluoromethoxy)benzamide (28.0 mg, 65% yield) as a white solid. ¹H NMR (400 MHz, DMSO-d₆): δ 8.99 (s, 1H), 8.90 (s, 1H), 7.89 (d, J=8.8 Hz, 2H), 7.54-7.48 (m, 4H), 7.36 (d, 1H), 7.31 (d, 1H), 7.07-7.05 (m, 1H), 4.95 (s, 2H), 4.54 (d, J=9.6 Hz, 1H), 4.37 (d, J=9.6 Hz, 1H), 1.79 (s, 3H) ppm. MS: m/z=503 (M+1, ESI+).

EXAMPLE 53

N-(2-cyano-1-(7-cyclopropoxy-1-hydroxy-1,3-dihydrobenzo[c][1,2]oxaborol-6-yloxy)propan-2-yl)-4-(trifluoromethoxy)benzamide

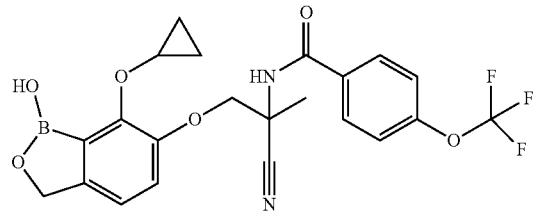 [SMILES: CC(C#N)(COc1ccc2c(c1OC1CC1)B(O)OC2)NC(=O)c1ccc(OC(F)(F)F)cc1]

To the mixture of 3-hydroxy-4-methoxybenzaldehyde (30.4 g, 0.2 mol), 1,4-dioxane (250 mL) and water (100 mL) is added N-bromosuccinimide (37.38 g, 0.21 mol) at 0° C. over 30 min and it is stirred for 2 h. Water (400 mL) is added, and the precipitated crystals are collected by filtration. The crystals are washed with water (1000 mL) to give the desired product (38.5 g, yield 83%) as a white solid.

To the mixture of chloro(1,5-cyclooctadiene)iridium(I) dimer (201 mg, 0.3 mmol) and sodium carbonate (3.18 g, 30 mmol) in 1,4-dioxane (8 mL) are added 2-bromo-3-hydroxy-4-methoxybenzaldehyde (3.45 g, 15 mmol) and vinyl acetate (5 mL). It is stirred at 100° C. in a sealed tube under argon atmosphere for 16 h. After cooled to rt, the mixture is filtered and the solvent is removed. The residue is purified by silica gel column chromatography using PE:EA=5:1 as eluent to give the desired product (1.62 g, yield 42.2%) as a straw yellow solid.

A solution of trichloroacetic acid (4.09 g, 25 mmol) in 1,2-dichloroethane (20 mL) is added to a cooled solution of 1.0 M Et₂Zn (25 mL, 25 mmol) in 1,2-dichloroethane (20 mL) at −45° C. The solution is warmed to 0° C. and stirred for 20 min. Methylene iodide (6.7 g, 25 mmol) is added to the reaction mixture and it is stirred at 0° C. for another 10 min To the reaction mixture is added a solution of 2-bromo-4-methoxy-3-(vinyloxy)benzaldehyde (2.57 g, 10 mmol) in 1,2-dichloroethane (20 mL) and toluene (5 mL). It is stirred at rt for 16 h, diluted with 1N HCl and the aqueous phase is extracted with EtOAc. The combined organic layers are washed with saturated aqueous NaHCO₃, water, brine, dried over Na₂SO₄ and concentrated. The crude product is purified by silica gel column chromatography using PE:EA=5:1 as eluent to give the desired product (1.68 g, yield 62.2%) as a brown oil.

To a solution of 2-bromo-3-cyclopropoxy-4-methoxybenzaldehyde (3.58 g, 13.26 mmol), 5,5,5',5'-tetramethyl-2,2'-bi(1,3,2-dioxaborinane) (11.99 g, 53 mmol) and KOAc (12.99 g, 0.133 mol) in 1,4-dioxane (100 mL) is added PdCl₂(dppf)₂ (970 mg, 1.33 mmol). The reaction mixture is stirred at 60° C. under argon atmosphere overnight. The solvent is removed and the residue is purified by silica gel column chromatography using PE:EA=5:1 as eluent to give the desired product (crude) (3.4 g) as a yellow solid. It is used in the next step without further purification.

To a solution of 3-cyclopropoxy-2-(5,5-dimethyl-1,3,2-dioxaborinan-2-yl)-4-methoxy benzaldehyde (3.4 g, 11.18 mmol, crude) in THF (50 mL) is added NaBH$_4$ (850 mg, 22.37 mmol). The reaction mixture is stirred at rt for 2 h, and then to it is slowly added 3N HCl until pH=1. The reaction mixture is stirred at rt overnight. The solvent is evaporated and the residue is purified by prep-HPLC to give the desired product (813 mg, yield 28% over two steps) as a white solid.

To a solution of 7-cyclopropoxy-6-methoxybenzo[c][1,2]oxaborol-1(3H)-ol (110 mg, 0.5 mmol) in dry dichloromethane (10 ml) is added boron tribromide (3M in dichloromethane, 200 μL, 0.6 mmol) under argon atmosphere at −70° C. After completion of the addition, the mixture is gradually warmed to 0° C., and stirred for 30 min. It is poured into ice-water, and extracted with ethyl acetate. The combined organic extracts are washed with water, dried over Na$_2$SO$_4$, filtered and concentrated under the reduced pressure. The residue is purified by prep-HPLC to give the desired product (24 mg, yield 23.3%) as a brown solid.

To a solution of 7-cyclopropoxybenzo[c][1,2]oxaborole-1,6(3H)-diol (60 mg, 0.29 mmol) and K$_2$CO$_3$ (121 mg, 0.87 mmol) in acetone (30 mL) is added bromoacetone (80 mg, 0.58 mmol). The reaction mixture is refluxed for 5 h. The solid is removed by filtration and the filtrate is evaporated. The residue is purified by prep-HPLC to give the desired product (18 mg, yield 23.7%) as a white solid.

A mixture of 1-(7-cyclopropoxy-1-hydroxy-1,3-dihydrobenzo[c][1,2]oxaborol-6-yloxy)propan-2-one (38 mg, 0.145 mmol), NH$_4$Cl (15 mg, 0.29 mmol) and ammonia (7N in methanol, 1 mL) in MeOH (2 mL) is stirred at rt for 20 min before addition of NaCN (18 mg, 0.37 mmol). The reaction mixture is stirred at rt for 5 h. DCM (30 mL) is added and the solvent is removed under the reduced pressure. The residue is washed with THF, and the THF solution is evaporated to give the desired product (crude) as a white solid (40 mg). It is used in the next step without further purification.

A solution of 4-(trifluoromethoxy)benzoic acid (30 mg, 0.145 mmol), HATU (110 mg, 0.29 mmol) and DIPEA (37 mg, 0.29 mmol) in DMF (4 mL) is stirred at rt for 30 min before 2-amino-3-(7-cyclopropoxy-1-hydroxy-1,3-dihydrobenzo[c][1,2]oxaborol-6-yloxy)-2-methyl propanenitrile (40 mg, crude, 0.145 mmol) is added. The reaction mixture is stirred at rt overnight and evaporated. It is purified by prep-HPLC to give N-(2-cyano-1-(7-cyclo-propoxy-1-hydroxy-1,3-dihydrobenzo[c][1,2]oxaborol-6-yloxy)propan-2-yl)-4-(trifluoromethoxy)benzamide (10.6 mg, yield 15.3% over two steps) as a white solid. $^1$H NMR (400 MHz, DMSO-d$_6$): δ 9.08 (s, 1H), 9.01 (s, 1H), 7.99 (d, J=8.8 Hz, 2H), 7.51 (d, J=8.4 Hz, 2H), 7.22 (d, J=8.4 Hz, 1H), 7.03 (d, J=8.4 Hz, 1H), 4.91 (s, 2H), 4.54-4.55 (m, 1H), 4.45 (d, J=9.6 Hz, 1H), 4.23 (d, J=9.6 Hz, 1H), 1.83 (s, 3H), 0.72-0.70 (m, 2H), 0.45-0.42 (m, 2H) ppm; HPLC purity: 100% at 214 nm and 100% at 254 nm; MS: m/z=477.2 (M+1, ESI+).

EXAMPLE 54

N-(1-(7-chloro-1-hydroxy-5-methyl-1,3-dihydrobenzo[c][1,2]oxaborol-6-yloxy)-2-cyano propan-2-yl)-4-(trifluoromethoxy)benzamide

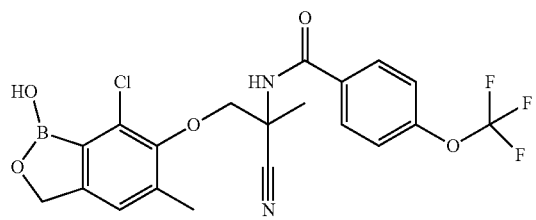 [SMILES: Cc1cc2c(c(Cl)c1OCC(C)(C#N)NC(=O)c1ccc(OC(F)(F)F)cc1)B(O)OC2]

To a solution of 2,4-dihydroxybenzaldehyde (4.14 g, 30 mmol) and sodium cyanoborohydride (5.67 g, 90 mmol) in 80 mL of THF is added methyl orange as an indicator giving the solution a yellow color. Aqueous 1N HCl solution (90 mL) is slowly added to the reaction system keeping the solution orange. The mixture is stirred for 3 h at rt. Water is added, and the mixture is extracted with Et$_2$O three times. After removal of solvent, the product (3.7 g, yield 99%) is obtained as a white solid.

Phosphorous oxychloride (11.4 mL, 125 mmol) is added dropwise to DMF (50 mL) stirring at 0° C. in a round-bottom flask under N$_2$ atmosphere for 30 min. The mixture is then transferred via cannula to a solution of 4-methylbenzene-1,3-diol (6.2 g, 50 mmol) in DMF (20 mL) stirring at 0° C. in a round-bottom flask under N$_2$ atmosphere. The mixture is slowly warmed to rt and stirred overnight. The mixture is poured into ice water and extracted with ethyl acetate (150 mL*3). The organic layers are dried over Na$_2$SO$_4$, filtered and concentrated under the reduced pressure. The residue is purified by column chromatography on silica gel by elution with PE:EA=3:1 to give the desired product (2.37 g, yield 31%) as a white solid.

A solution of 2,4-dihydroxy-5-methylbenzaldehyde (2.28 g, 15 mmol), NaHCO$_3$ (2.52 g, 30 mmol) and KI (498 mg, 3 mmol) in MeCN (40 mL) is slowly warmed to 60° C. At this time, BnBr (2.82 g, 16.5 mmol) is added. The mixture is warmed to 80° C. and stirred overnight. The mixture is then cooled to rt and evaporated. The residue is quenched with 10% aq HCl to pH=6 and extracted with EA (150 mL*2). The combined organic extracts are washed with brine, dried over Na$_2$SO$_4$, filtered and concentrated under the reduced pressure. The residue is purified by column chromatography on silica gel by elution with PE:EA=8:1 to give the desired product (2.3 g, yield 63%) as a white solid.

To a solution of 4-(benzyloxy)-2-hydroxy-5-methylbenzaldehyde (1.94 g, 80 mmol) and Et$_3$N (4.04 g, 40 mmol) in DCM (40 mL) at 0° C. is added a solution of Tf$_2$O (4.96 g, 17.6 mmol) in DCM (5 mL) dropwise. The reaction mixture is stirred at rt for 3 h. Water (50 mL) is added and the mixture is extracted with DCM (50 mL*2). The combined organic extracts are washed with brine, dried over Na$_2$SO$_4$, filtered and concentrated under the reduced pressure. The residue is purified by column chromatography on silica gel by elution with PE:EA=10:1 to give the desired product (2.83 g, yield 76%) as a white solid.

To a solution of 5-(benzyloxy)-2-formyl-4-methylphenyl trifluoromethanesulfonate (1.2 g, 3.2 mmol), 5,5,5',5'-tetramethyl-2,2'-bi(1,3,2-dioxaborinane) (2.46 g, 9.6 mmol) and KOAc (1.57 g, 16 mmol) in 1,4-dioxane (60 mL) is added PdCl$_2$(dppf)$_2$ (234 mg, 0.32 mmol). The reaction mixture is stirred at 90° C. under argon atmosphere overnight. The solvent is removed and the residue is purified by column chromatography on silica gel by elution with PE:EA=4:1 to give the desired product (1.05 g, crude) as a yellow solid. It is used in next step without further purification.

To a solution of crude 4-(benzyloxy)-2-(5,5-dimethyl-1,3,2-dioxaborinan-2-yl)-5-methylbenzaldehyde (1.05 g, 3.1 mmol) in THF (20 mL) is added NaBH$_4$ (236 mg, 6.2 mmol). The reaction mixture is stirred at rt for 3 h, and then to it is slowly added 3N HCl to pH=2. The reaction mixture is stirred at rt overnight and evaporated. The residue is purified by prep-HPLC to give the desired product (500 mg, yield 61% over 2 steps) as a white solid.

The solution of 6-(benzyloxy)-5-methylbenzo[c][1,2]oxaborol-1(3H)-ol (500 mg, 1.48 mmol) in MeOH (30 mL) is hydrogenated using 10% Pd/C (50 mg) as catalyst under atmospheric pressure at 40° C. overnight. The catalyst is removed by filtration on Celite and the solvent is evaporated under the reduced pressure. The residue is purified by column chromatography on silica gel by elution with PE:EA=2:1 to give the desired product (295 mg, yield 91%) as a white solid.

To a solution of 5-methylbenzo[c][1,2]oxaborole-1,6 (3H)-diol (295 mg, 1.8 mmol) in DMF (10 mL) is added NCS (360 mg, 2.7 mmol). The mixture is stirred at 30° C. overnight. The crude is purified by prep-HPLC to give the desired product (208 mg, yield 58%) as a white solid.

To a solution of 7-chloro-5-methylbenzo[c][1,2]oxaborole-1,6(3H)-diol (208 mg, 1.05 mmol) and $K_2CO_3$ (290 mg, 2.1 mmol) in acetone (20 mL) is added bromoacetone (173 mg, 1.26 mmol). The reaction mixture is refluxed for 3 h. The solid is removed by filtration and the filtrate is concentrated. The residue is purified by prep-HPLC to give the desired product (200 mg, yield 75%) as a white solid.

A mixture of 1-(7-chloro-1-hydroxy-5-methyl-1,3-dihydrobenzo[c][1,2]oxaborol-6-yloxy)propan-2-one (100 mg, 0.39 mmol), $NH_4Cl$ (42 mg, 0.78 mmol) and ammonia (7N in methanol, 2 mL) in MeOH (2 mL) is stirred at rt for 20 min before addition of NaCN (48 mg, 0.97 mmol). The reaction mixture is stirred at rt for 5 h. DCM (50 mL) is added and the solvent is removed under the reduced pressure. The residue is extracted with THF, and the THF solution is concentrated to give crude the desired product as a white solid (110 mg). It is used in the next step without further purification. MS: m/z=281.1 (M+1, ESI+).

A solution of 4-(trifluoromethoxy)benzoic acid (120 mg, 0.58 mmol), HATU (296 mg, 0.78 mmol) and DIPEA (151 mg, 1.17 mmol) in DMF (5 mL) is stirred at rt for 30 min before 2-amino-3-(7-chloro-1-hydroxy-5-methyl-1,3-dihydrobenzo[c][1,2]oxaborol-6-yloxy)-2-methylpropanenitrile (110 mg, crude, 0.39 mmol) is added. The reaction mixture is stirred at rt overnight. It is purified by prep-HPLC to give N-(1-(7-chloro-1-hydroxy-5-methyl-1,3-dihydrobenzo[c][1,2]oxaborol-6-yloxy)-2-cyano propan-2-yl)-4-(trifluoromethoxy)benzamide (35 mg, yield 19% over 2 steps) as a white solid. $^1$H NMR (400 MHz, DMSO-$d_6$): δ 9.12 (s, 1H), 9.02 (s, 1H), 8.00 (d, J=8.0 Hz, 2H), 7.51 (d, J=8.0 Hz, 2H), 7.23 (s, 1H), 4.91 (s, 2H), 4.35 (d, J=8.4 Hz, 1H), 4.19 (d, J=8.4 Hz, 1H), 2.34 (s, 3H), 1.94 (s, 3H) ppm; HPLC purity: 99.1% at 214 nm and 100% at 254 nm; MS: m/z=469.1 (M+1, ESI+).

EXAMPLE 55

N-(2-Cyano-1-(1-hydroxy-4,7-dimethyl-1,3-dihydrobenzo[c][1,2]oxaborol-6-yloxy)propan-2-yl)-4-(trifluoromethoxy)benzamide

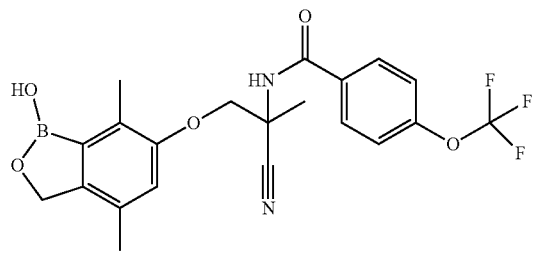 [SMILES: Cc1cc(OCC(C)(C#N)NC(=O)c2ccc(OC(F)(F)F)cc2)c(C)c2c1COB2O]

To a solution of 5-methylbenzene-1,3-diol (8.0 g, 65 mmol) and DIPEA (48 mL, 325 mmol) in DCM (250 mL) is added chloromethyl ethyl ether (15 mL, 163 mmol) dropwise at rt and stirred overnight. Water (100 mL) is added and the mixture is extracted with DCM (3×100 mL). The organic layers are washed with brine, dried over $Na_2SO_4$, filtered and concentrated to give the desired product (13.0 g, yield 83%) as a colorless oil.

To a solution of 1,3-bis(ethoxymethoxy)-5-methylbenzene (13.0 g, 54 mmol) in THF (200 mL) at 0° C. under nitrogen is added dropwise n-BuLi (23.8 mL of a 2.5M solution in hexane, 60 mmol). The resulting suspension is warmed to 18° C. and stirred slowly at this temperature for 1.5 h, and then treated with dry DMF (5 mL, 65 mmol). The resulting mixture is poured into water (100 mL) and extracted with diethyl ether (3×100 mL). The combined organic phases are then washed with water (40 mL) and brine (40 mL), dried over $Na_2SO_4$, filtered, and concentrated under reduced pressure. The residue is purified by column chromatography on silica gel by elution with PE:EA=5:1 to give the desired product (10.5 g, yield 72%) as a pale-yellow solid.

To a solution of 2,6-bis(ethoxymethoxy)-4-methylbenzaldehyde (10.5 g, 39 mmol) in THF (120 mL) is added 4 N HCl in 1,4-dioxane (40 mL). Then the mixture is stirred overnight at rt. After removal of solvent, the residue is purified by Combiflash to give the desired product (2.9 g, yield 50%) as a yellow solid.

To a solution of 2,6-dihydroxy-4-methylbenzaldehyde (2.9 g, 19 mmol) and sodium cyanoborohydride (3.6 g, 57 mmol) in 80 mL of THF is added methyl orange as an indicator giving the solution a yellow color. Aqueous 1N HCl solution (57 mL) is slowly added to the reaction system maintaining the color of orange. The mixture is stirred for 3 h at rt. Water is added, and the mixture is extracted with $Et_2O$ three times. After removal of solvent, the residue is purified by Combiflash to give the desired product (1.0 g, yield 40%) as a white solid.

Phosphorous oxychloride (1.6 mL, 18 mmol) is added dropwise to DMF (7 mL) stirring at 0° C. in a round-bottom flask under $N_2$ atmosphere for 30 min. The mixture is then transferred via cannula to a solution of 2,5-dimethylbenzene-1,3-diol (1.0 g, 7 mmol) in DMF (10 mL) stirring at 0° C. in a round-bottom flask under $N_2$ atmosphere. The mixture is slowly warmed to rt and stirred overnight. The mixture is poured into ice water. Solid is precipitated out after 10 h. The mixture is filtered to give the desired product (1.2 g, yield 60%) as a white solid.

A solution of 2,4-dihydroxy-3,6-dimethylbenzaldehyde (1.2 g, 7 mmol), $NaHCO_3$ (1.82 g, 21 mmol) and KI (240 mg, 1.4 mmol) in MeCN (40 mL) is slowly warmed to 60° C. At this time, BnBr (1.36 g, 8 mmol) is added. The mixture is warmed to 80° C. and stirred overnight. The mixture is then cooled to rt, filtered and evaporated. The residue is mixed with water (20 mL) and extracted with EA (50 mL*2). The combined organic extracts are washed with brine, dried over $Na_2SO_4$, filtered and concentrated under the reduced pressure. The residue is purified by column chromatography on silica gel by elution with PE:EA=10:1 to give the desired product (1.48 g, yield 80%) as a white solid.

To a solution of 4-(benzyloxy)-2-hydroxy-3,6-dimethylbenzaldehyde (1.48 g, 5.7 mmol) and $Et_3N$ (2.92 g, 29 mmol) in DCM (40 mL) at 0° C. is added a solution of $Tf_2O$ (3.59 g, 12.7 mmol) in DCM (5 mL) dropwise. The reaction mixture is stirred at rt for 3 h. Water (50 mL) is added and the mixture is extracted with DCM (50 mL*2). The combined organic extracts are washed with brine, dried over $Na_2SO_4$, filtered and concentrated under the reduced pressure. The residue is purified by prep-HPLC to give the desired product (515 mg, yield 23%) as a white solid.

To a solution of 3-(benzyloxy)-6-formyl-2,5-dimethylphenyl trifluoromethane sulfonate (515 mg, 1.33 mmol), 5,5,5',5'-tetramethyl-2,2'-bi(1,3,2-dioxaborinane) (896 mg, 3.98 mmol) and KOAc (650 mg, 6.63 mmol) in 1,4-dioxane (30 mL) is added $PdCl_2(dppf)_2$ (108 mg, 0.13 mmol). The reaction mixture is stirred at 90° C. under argon atmosphere overnight. The solvent is removed and the residue is purified by column chromatography on silica gel by elution with PE:EA=6:1 to give the desired product (320 mg, crude) as a yellow solid. It is used in next step without further purification.

To a solution of crude 4-(benzyloxy)-2-(5,5-dimethyl-1,3,2-dioxaborinan-2-yl)-3,6-dimethylbenzaldehyde (320 mg, 0.9 mmol) in THF (15 mL) is added $NaBH_4$ (68 mg, 1.8 mmol). The reaction mixture is stirred at rt for 3 h, and then to it is slowly added 3N HCl to pH=2. The reaction mixture is stirred at rt overnight. The solvent is evaporated and the residue is purified by Combiflash to give the desired product (190 mg, yield 53% over 2 steps) as a white solid.

The solution of 6-(benzyloxy)-4,7-dimethylbenzo[c][1,2]oxaborol-1(3H)-ol (190 mg, 0.71 mmol) in MeOH (30 mL) is hydrogenated using 10% Pd/C (20 mg) as catalyst under atmospheric pressure at 40° C. overnight. The catalyst is removed by filtration on Celite and the solvent is evaporated under the reduced pressure. The residue is purified by prep-HPLC to give the desired product (115 mg, yield 91%) as a white solid.

To a solution of 4,7-dimethylbenzo[c][1,2]oxaborole-1,6(3H)-diol (115 mg, 0.65 mmol) and $K_2CO_3$ (178 mg, 1.29 mmol) in acetone (20 mL) is added bromoacetone (106 mg, 0.78 mmol). The reaction mixture is refluxed for 3 h. The solid is removed by filtration and the filtrate is concentrated. The residue is purified by prep-HPLC to give the desired product (75 mg, yield 50%) as a white solid.

A mixture of 1-(1-hydroxy-4,7-dimethyl-1,3-dihydrobenzo[c][1,2]oxaborol-6-yloxy)propan-2-one (75 mg, 0.32 mmol), $NH_4Cl$ (34 mg, 0.64 mmol) and ammonia (7N in methanol, 2 mL) in MeOH (2 mL) is stirred at rt for 20 min before addition of NaCN (31 mg, 0.64 mmol). The reaction mixture is stirred at rt for 5 h. DCM (50 mL) is added and the solvent is removed under the reduced pressure. The residue is washed with THF and the THF solution is concentrated to give the desired product (crude) as a white solid (120 mg). It is used in next step without further purification.

A solution of 4-(trifluoromethoxy)benzoic acid (99 mg, 0.48 mmol), HATU (182 mg, 0.48 mmol) and DIPEA (1124 mg, 0.96 mmol) in DMF (2 mL) is stirred at rt for 30 min before 2-amino-3-(1-hydroxy-4,7-dimethyl-1,3-dihydrobenzo[c][1,2]oxaborol-6-yloxy)-2-methylpropanenitrile (120 mg, crude, 0.32 mmol) is added. The reaction mixture is stirred at rt overnight. It is purified by prep-HPLC to give N-(2-cyano-1-(1-hydroxy-4,7-dimethyl-1,3-dihydrobenzo[c][1,2]oxaborol-6-yloxy)propan-2-yl)-4-(trifluoromethoxy)benzamide (20 mg, yield 14% over 2 steps) as a white solid. $^1$H NMR (400 MHz, DMSO-$d_6$): δ 9.05 (s, 1H), 8.90 (s, 1H), 8.00 (d, J=8.4 Hz, 2H), 7.51 (d, J=8.4 Hz, 2H), 6.92 (s, 1H), 4.85 (s, 2H), 4.46 (d, J=9.2 Hz, 1H), 4.24 (d, J=9.2 Hz, 1H), 2.31 (s, 3H), 2.16 (s, 3H), 1.84 (s, 3H) ppm; HPLC purity: 100% at 214 nm and 100% at 254 nm; MS: m/z=449.1 (M+1, ESI+).

EXAMPLE 56

N-(1-(7-chloro-1-hydroxy-4-methoxy-1,3-dihydrobenzo[c][1,2]oxaborol-6-yloxy)-2-cyanopropan-2-yl)-4-(trifluoromethoxy)benzamide

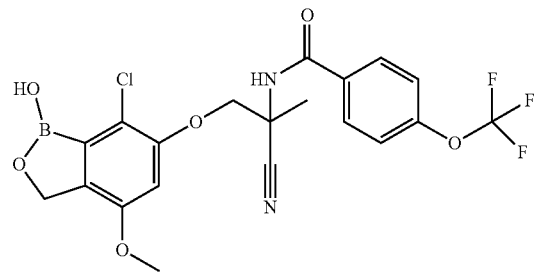 [SMILES: COc1cc(OCC(C)(C#N)NC(=O)c2ccc(OC(F)(F)F)cc2)c(Cl)c2c1COB2O]

To a solution of benzene-1,3,5-triol (12.0 g, 95.24 mmol) and $K_2CO_3$ (26.3 g, 190.48 mmol) in DMF (150 mL) at 0° C. is added $CH_3I$ (13.6 g, 95.24 mmol) slowly. The reaction mixture is stirred at 0° C. for 3 h. EA (500 mL) is added and the mixture is washed with water (100 mL*3). The organic layer is dried over $Na_2SO_4$, filtered and concentrated under the reduced pressure. The residue is purified by prep-HPLC to give the desired product (5.33 g, yield 40%) as a white solid.

Phosphorous oxychloride (9.1 mL, 95.18 mmol) is added dropwise to DMF (20 mL) stirring at 0° C. in a round-bottom flask under $N_2$ atmosphere for 30 min, and then the solution of 5-methoxybenzene-1,3-diol (5.33 g, 38.07 mmol) in DMF (15 mL) is added slowly at 0° C. The mixture is stirred for 3 h at rt. The solution is poured into ice water (500 mL) and stirred for 1 h, and the solution is standing overnight. The precipitate is filtered, washed with water and dried to give the desired product (3.84 g, yield 60%) as a yellow solid.

A mixture of 2,4-dihydroxy-6-methoxybenzaldehyde (3.84 g, 22.86 mmol), $NaHCO_3$ (5.76 g, 68.57 mmol) and KI (759 mg, 4.57 mmol) in MeCN (60 mL) is slowly warmed to 60° C. At this time, benzyl bromide (3.0 mL, 25.15 mmol) is added and the mixture is heated to 80° C. and stirred overnight. The mixture is then cooled to rt, filtered and the solvent is concentrated by rotary evaporation. The residue is purified by column chromatography on silica gel by elution with PE:EA=10:1 to give the desired product (4.78 g, yield 81%) as a yellow solid.

To a solution of 4-(benzyloxy)-2-hydroxy-6-methoxybenzaldehyde (4.78 g, 18.53 mmol) and $Et_3N$ (7.45 mL, 55.59 mmol) in DCM (100 mL) is added $Tf_2O$ (7.8 mL, 46.33 mmol) slowly at 0° C. The reaction mixture is stirred for 3 h at rt. The mixture is poured into water and extracted with EA (150 mL*3). The combined organic layers are washed with brine, dried over $Na_2SO_4$, filtered and concentrated under the reduced pressure. The residue is purified by column chromatography on silica gel by elution with PE:EA=10:1 to give the desired product (4.5 g, yield 62%) as a light yellow solid.

A mixture of 5-(benzyloxy)-2-formyl-3-methoxyphenyl trifluoromethanesulfonate (4.5 g, 11.54 mmol), KOAc (5.65 g, 57.7 mmol), 5,5,5',5'-tetramethyl-2,2'-bi(1,3,2-dioxaborinane) (5.2 g, 23.08 mmol) and $PdCl_2(dppf)_2$ (844 mg, 1.154 mmol) in 1.4-dioxane (150 mL) is stirred at 100° C. for 16 h under nitrogen atmosphere. The mixture is then cooled to rt, filtered and the solvent is concentrated by rotary evaporation. The residue is purified by column chromatography on silica gel by elution with PE:EA=10:1 to give the desired product (2.4 g, yield 58%) as a yellow oil. It is used in next step without further purification.

To a solution of 4-(benzyloxy)-2-(5,5-dimethyl-1,3,2-dioxaborinan-2-yl)-6-methoxybenzaldehyde (2.4 g, 6.78 mmol) in THF (100 mL) is added NaBH$_4$ (515 mg, 13.56 mmol). The reaction mixture is stirred at rt for 3 h, and then to it is slowly added HCl (10.0 mL, 6N) at ice bath. The mixture is stirred for 16 h at rt and evaporated. The residue is purified by prep-HPLC to give the desired product (1.23 g, yield 67%) as a white solid.

A solution of 6-(benzyloxy)-4-methoxybenzo[c][1,2]oxaborol-1(3H)-ol (1.23 g, 4.56 mmol) in MeOH (25 mL) and EA (25 mL) is hydrogenated using 10% Pd/C (123 mg) as catalyst under atmospheric pressure overnight. The catalyst is removed by filtration on Celite and the solvent is evaporated under the reduced pressure. The residue is purified by prep-HPLC to give the desired product (492 mg, yield 60%) as a light yellow oil.

A mixture of 4-methoxybenzo[c][1,2]oxaborole-1,6(3H)-diol (200 mg, 1.11 mmol) and NCS (163 mg, 1.22 mmol) in DMF (3 mL) is stirred for 5 h at 60° C. The mixture is purified by prep-HPLC to give the desired product (130 mg, yield 55%) as a white solid.

A mixture of 7-chloro-4-methoxybenzo[c][1,2]oxaborole-1,6(3H)-diol (130 mg, 0.607 mmol), 1-bromopropan-2-one (166 mg, 1.214 mmol) and K$_2$CO$_3$ (251 mg, 1.821 mmol) in acetone (20 mL) is stirred for 2 h at 60° C. The solvent is removed and the residue is purified by prep-HPLC to give the desired product (80 mg, yield 53%) as a white solid.

A mixture of 1-(7-chloro-1-hydroxy-4-methoxy-1,3-dihydrobenzo[c][1,2]oxaborol-6-yloxy)propan-2-one (80 mg, 0.296 mmol), NH$_4$Cl (32 mg, 0.593 mmol) and ammonia (7N in methanol, 1 mL) in MeOH (5 mL) is stirred at rt for 20 min before addition of NaCN (30 mg, 0.593 mmol). The reaction mixture is stirred at rt overnight. DCM (50 mL) is added and the solvent is removed under the reduced pressure at rt. The residue is mixed with THF and filtered. The filtrate is removed to give the desired product (crude) (120 mg) as a yellow oil. It is used in the next step without further purification.

A solution of 4-(trifluoromethoxy)benzoic acid (122.0 mg, 0.592 mmol), DIPEA (0.2 mL, 0.888 mmol) and HATU (225 mg, 0.592 mmol) in DMF (3 mL) is stirred at rt for 10 min, then crude 2-amino-3-(7-chloro-1-hydroxy-4-methoxy-1,3-dihydrobenzo[c][1,2]oxaborol-6-yloxy)-2-methylpropanenitrile (120 mg, 0.296 mmol) in DMF (2 mL) is added. The reaction mixture is stirred at rt overnight. It is purified by Prep-HPLC to give N-(1-(7-chloro-1-hydroxy-4-methoxy-1,3-dihydrobenzo[c][1,2]oxaborol-6-yloxy)-2-cyanopropan-2-yl)-4-(trifluoromethoxy)benzamide (8 mg, yield 6% over 2 steps) as a white solid. $^1$H NMR (400 MHz, DMSO-d$_6$) δ 9.17 (s, 1H), 9.08 (s, 1H), 7.98 (d, J=8.0 Hz, 2H), 7.50 (d, J=8.0 Hz, 2H), 6.97 (s, 1H), 4.83 (d, 2H), 4.60 (d, J=8.8 Hz, 1H), 4.46 (d, J=8.8 Hz, 1H), 3.82 (s, 3H), 1.87 (s, 3H) ppm; HPLC purity: 100.0% at 214 nm and 100.0% at 254 nm; MS: m/z=485.1 (M+1, ESI+).

EXAMPLE 57

(S)— N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide

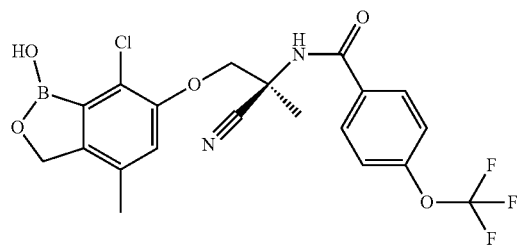 [SMILES: Cc1cc(OC[C@](C)(C#N)NC(=O)c2ccc(OC(F)(F)F)cc2)c(Cl)c2c1COB2O]

The above-titled chiral enantiomer is obtained from its racemic mixture in Example 42 (1.9 g) by using chiral supercritical fluid chromatography (SFC, column: Chiralpak AD-H, 250×30 mm i.d; 35% methanol/CO$_2$; flow rate: 62 g/min; injection amount: 50 mg/injection). The solvent of the desired chiral chromatography peak 1 fractions is removed and then freeze-dried to give the desired enantiomer (740 mg, yield 78%) as white solid. $^1$H NMR (DMSO-d$_6$, 400 MHz): δ 9.10 (s, 1H), 9.07 (s, 1H), 7.98 (d, J=8.4 Hz, 2H), 7.51 (d, J=8.4 Hz, 2H), 7.17 (s, 1H), 4.88 (s, 2H), 4.56 (d, J=9.6 Hz, 1H), 4.37 (d, J=9.6 Hz, 1H), 2.17 (s, 3H), 1.86 (s, 3H) ppm. MS: m/z=469 (M+1). HPLC purity: 98.9% at 214 nm and 96.3% at 254 nm Chiral HPLC purity: 99.4% at 230 nm In Vitro Larval Migration Assay Using *Haemonchus contortus*

The larval migration assay (LMA), a drug screening assay conducted in 96-well micro titer plates that discriminates between motile and non-motile parasitic nematodes of the Trichostrongylidae family, has been described previously (Gonzalez et al., 2004, Bioorg. Med. Chem. Lett. 14, 4037-4043, White et al., 2007, Vet. Parasitol. 146, 58-65). Briefly, third stage (L3) infective larvae of the barber pole worm (*Haemonchus contortus*), obtained from mono-specific propagation in sheep or goats, are diluted in M9 buffer (per liter, 6 g of Na$_2$HPO$_4$, 3 g of KH$_2$PO$_4$, 5 g of NaCl, 250 mg of MgSO$_4$-7H$_2$O, pH adjusted to 7.0) and aliquoted into wells of a micro titer plate so as to obtain approximately 25 larvae per well. For single concentration tests, experimental compounds are formulated in dimethylsulfoxide at a concentration of 10 millimolar (mM) and added to micro titer plate wells so as to achieve a compound concentration of 100 micromolar (μM). For determining EC$_{50}$ (50% effective concentration) values, doubling dilutions are performed in M9 buffer and added to micro titer plates so as to yield a concentration range from 100-1.563 μM. Plates are covered and incubated at 27-28° C. and >75% relative humidity for 24 hours. The contents are then transferred to respective top wells of a 96-well MultiScreen™ Nylon Mesh plate (Millipore) containing 2% low melting point agarose overlaying the 60 micro nylon mesh screen. The top barrier plates are inserted into accompanying 96-well bottom trays containing 150 micro liters (μl) of attractant solution per well (per liter, 62.5 ml high salt rumen buffer concentrate, 3 ml glacial acetic acid, 0.75 ml propionic acid, 0.25 ml butyric acid, adjusted to pH 6.5). Plates are incubated at 27-28° C. and >75% relative humidity for 24 hours, at which time motile (viable) larvae are able to migrate downward through the agarose-nylon mesh barrier into the attractant solution while non-motile (dead or paralyzed) larvae remain in the upper wells. Contents of both top and bottom wells are stained with 10-20 μl of a 0.1 N iodine solution and visualized under a stereoscopic microscope. Percent inhibition of migration is calculated as a fraction of larvae remaining in upper wells to the total number larvae in respective upper and lower wells, and adjusted to negative control migration using the method of Schneider-Orelli (Schneider-Orelli, O., 1947. Entomoligisches Praktikum. H. R. Sauerlander, Aarau, Switzerland).

The compounds from the following Examples exhibit ≥50% activity (inhibition of migration) when evaluated in this assay at a concentration of no greater than 100 μM: 1, 1a, 2, 2a, 3, 3a, 4, 4a, 5, 5a, 6, 6a, 7, 8, 9 10, 13, 15, 16, 17, 17a, 18, 21, 21a, 22, 22a, 23, 24, 25 26, 27, 28, 33, 36, 37, 37a, 38, 38a, 39, 42, 43, 44, 45, 47, 48, 49, 50, 51, 52, 53, 55, 56, and 57.

In Vivo Gerbil Antihelminthic Test

In vivo experiments are conducted using slight modifications of methods previously described for co-infection of gerbils with 3$^{rd}$ stage larvae of the ruminant parasitic nematodes *H. contortus* and *Trichostrongylus colubriformis* (Conder et al., 1991, J. Parasitol. 77, 621-623 and White et al., 2007, Vet. Parasitol. 146, 58-65.). Briefly, immunosuppressed Mongolian gerbils (*Meriones unguiculatus*) are infected via oral gavage with approximately 1,500 larvae of a triple drug-resistant strain of *H. contortus* (resistant to macrocyclic lactones, benzimidazoles, levamisole) and a benzimidazole-resistant field isolated strain of *T. colubriformis*. A minimum of five (n=5) gerbils are used for each compound and/or at each concentration. One week later, experimental test compounds are formulated in a solution of polyethylene glycol 300, propylene glycol and water and administered to nematode infected gerbils via oral gavage and/or subcutaneous injection at a maximum dose of 100 mg/kg body weight. Approximately 72 hours after treatment, gerbils are euthanized and sections of the gastrointestinal tract (stomach and small intestine) are removed and processed separately. Tissue samples are macerated and soaked in 10 ml of physiological saline at 37° C. for approximately 2 h, followed by addition of 3 ml of a 1 N iodine solution to kill and stain nematodes. A 25% volumetric sub-sample of each solution is transferred to a Petri dish and nematodes are enumerated under a stereoscopic microscope. The total nematode burden in each organ, per animal, is determined by multiplying the mean number of nematodes counted from each sub-sample by a factor of four. The efficacy (% reduction in nematode burden) against each nematode species is calculated using the following formula:

$$\% \text{ Efficacy} = \frac{(GM \text{ \# nematodes untreated control} - GM \text{ \# nematodes treated})}{GM \text{ \# nematodes untreated control}} \times 100$$

where GM denotes geometric mean.

The compounds in the following Examples exhibit ≥80% efficacy against *H. contortus* when tested in this assay at a dose of not more than 25 mg/kg: 1, 1a, 2, 3, 3a, 4, 4a, 5a, 6, 7, 8, 9, 13, 16, 17, 18, 21, 23, 28, 38a, 42, 43, 45, 52, 53, 55, and 57.

The compounds in the following Examples exhibit ≥80% efficacy against *T. colubriformis* when tested in this assay at a dose of not more than 25 mg/kg: 1, 1a, 2, 2a, 3, 3a, 4, 4a, 5a, 6, 6a, 7, 8, 9, 16, 17, 17a, 18, 21, 23, 25, 27, 38, 42, 43, 44, 45, and 57.

Activity of Compounds Against Gastrointestinal Nematode Infections in Sheep

Studies are conducted to evaluate the antihelminthic activity of compounds, when administered via oral drench or subcutaneous injection, against ruminant gastrointestinal nematode infections in sheep. Young adult animals (approximately 20-45 kg) free from endogenous nematode infection are inoculated with 3$^{rd}$-stage infective larvae of *Haemonchus contortus* and/or *Trichostrongylus colubriformis* and/or *Teladorsagia circumcincta* and/or *Cooperia curticeu*, per W.A.A.V.P. Guidelines (Wood, I. B., N. K. Amaral, K. Bairden, et al., 1995. Vet. Parasitol. 58: 181-213). Based on pre-treatment egg counts, sheep are allocated to negative control and treated groups, generally at least three (n=3) animals per group. Compounds are dissolved in a suitable vehicle (for example, a polyethylene glycol-300 plus propylene glycol based solution or a Cremphor based solution), filter-sterilized as applicable (for subcutaneous injection) and administered to infected animals on Day 0 so as to achieve a point dose of no greater than 6 mg/kg body weight (≤6 mg/kg b.w.). Between Day 5 and Day 18 post-treatment, animals are euthanized and selected sections of the gastrointestinal tract (abomasum and small intestine) are processed using routine techniques (ligature of abomasum and small intestine followed by removal, water rinse with concurrent manual stripping of organ linings, followed by sieving to separate and isolate nematodes). Organ contents from each animal are adjusted to an equivalent volume with water. Samples are stirred and a 400 ml sub-sample is removed. Three separate 40 ml aliquots are removed from the sub-sample (3.3% sampling rate), stained with 0.1 N iodine, and nematodes are visualized and enumerated under a stereoscopic microscope. Untreated, infected control groups are used for comparison to the sheep receiving treatments for the purposes of calculating efficacy (geometric mean % reduction in nematode burden for each species).

TABLE 1

The following compounds exhibit ≥50% reduction (geometric mean) in nematode burden at a point dose of ≤6 mg/kg b.w.

| Route | Abomasum Species | | Small Intestinal Species | |
|---|---|---|---|---|
| | *H. contortus* | *T. circumcincta* | *T. colubriformis* | *C. curticei* |
| Oral Drench | 1, 17, 18, 57 | 1, 17 | 1, 17, 18 | 1, 57 |
| Subcutaneous Injection | 1, 2, 3, 4, 5, 6, 36, 38, 57 | 1, 2, 3, 4, 5, 6, 36, 38 | 1, 2, 3, 4, 5, 6, 36, 38 | 1, 2, 3, 4, 5, 6, 36, 38, 57 |

Activity of Example 1 Compound Against Experimental Hookworm Infections in Dogs

The antihelminthic activity of the Example 1 compound, when administered orally at a point dose of no greater than 25 mg/kg bodyweight, is evaluated against experimental infections of the hookworms *Ancylostoma caninum* and *Uncinaria stenocephala* in dogs. Four (4) beagle dogs in good health are inoculated with 3$^{rd}$-stage infective larvae of each hookworm species, per W.A.A.V.P. Guidelines (Jacobs, D. E., A. Arakawa, C. H. Courtney, et al., 1994. Vet. Parasitol. 52: 179-202) so as to provide sufficient time for development of full patency. Fecal egg counts are conducted twice before treatment (Day-2 and Day-1). On Day 0, test article (technical active dissolved in 55-65% polyethylene glycol-300, 25-35% propylene glycol and 10-20% water) is administered to all four dogs via esophageal feeding tube. Fecal egg counts are conducted post-treatment on Days 3, 5 and 7. The average of two pre-treatment fecal egg counts is used for comparison to post-treatment egg counts for the purposes of calculating efficacy (geometric mean % reduction in fecal egg count) against each hookworm species.

Example 1 compound treatment yields >50% reduction in *A. caninum* fecal egg counts by Day 3 and >50% reduction in *U. stenocephala* fecal egg count by Day 5. Treatment with the compound is well tolerated by all dogs.

Activity in the above assays demonstrates the compounds of the invention are useful for controlling endoparasite infestations.

Activity of Compounds Against Gastrointestinal Nematode Infections in Cattle

The compounds of Examples 1, 2, 3, 4, and 6 are used. Studies are conducted to evaluate the antihelminthic activity of the compounds, when administered via subcutaneous injection, against natural gastrointestinal nematode infections in cattle. Young adult beef cattle (approximately 65-230 kg, n=6 per group) naturally infected with various gastrointestinal nematode species are obtained from commercial vendors. Based on pre-treatment fecal egg counts and speciation, animals are allocated to negative control and experimental compound treated groups, using six (n=6) animals per group. Compounds are dissolved in a suitable vehicle (for example, a polyethylene glycol-300 plus propylene glycol based solution), filter-sterilized and administered to infected animals on Day 0 so as to achieve a point dose of ≤10 mg/kg b.w.

Between Day 14 and Day 18 post-treatment, animals are euthanized and the digestive system is separated into different anatomical segments: abomasum, small intestine and large intestine (cecum and colon). Contents from these three organs are collected in totum and the mucosa of each portion of the system was washed and the washings added to the associated contents. Aliquots are obtained and fixed in 10% formalin for subsequent inspection, enumeration and speciation of parasitic nematodes. The abomasum is soaked overnight in water according to the methodology described by Wood, I. B.; Amaral, N. K.; Bairden, K.; World Association for the Advancement of Veterinary Parasitology (W.A.A.V.P.), second edition of guidelines for evaluating the efficacy of antihelminthics in ruminants (cattle, ovine, caprine), Veterinary Parasitology, 1995. v. 58, p. 181-213, and Vercruysse et al. (2001), and the soak fluids collected in total, from which aliquots are fixed in formalin for inspection, enumeration, and speciation of parasitic nematodes. Large and small intestines are soaked for 4 hours, with aliquots being fixed in formalin as required for inspection, enumeration, and parasitic nematode speciation. The collection, counting, and speciation of the parasites present is conducted per methodologies of Levine, N.D., Nematode parasites of domestic animals and of man, Burgess, Minneapolis, 1968, p. 600; Costa, A. J., Diagnostico laboratorial em Parasitologia, I. Helmintologia. FCAV-UNESP, Jaboticabal-SP, 1982, p. 89; Ueno, H.; Gongalves, P. C., Manual para diagnostico das helmintoses de Ruminantes, Japio. JICA, 4 ed., 1998, p. 166.

Treatment with the compounds yielded ≥50% efficacy (reduction) of one or more of the following adult nematode species present in cattle at the time of treatment: *Haemonchus placei, Ostertagia ostergi, Cooperia punctata, Oesphagostomum radiatum, Nematodirus helvetianus*, and *Bunostonum phlebotomum*.

We claim:

1. A compound of the formula I:

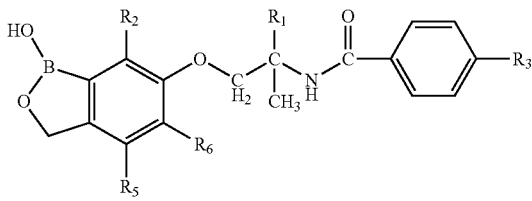

wherein $R_1$ is cyano or carbamoyl;

$R_2$ is hydrogen; halo; $C_1$-$C_3$ alkyl; $C_1$-$C_3$ alkyl substituted 1-3 times with halo; $C_1$-$C_3$ alkoxy; $C_1$-$C_3$ alkoxy substituted 1-3 times with halo; cyclopropyl; cyclopropoxy; phenoxy; phenyl; thienyl; furyl; amino; aminomethyl; dimethylamino; cyano; acetylamino; methoxycarbonyl; —CH$_2$—NH—C(O)—O—C(CH$_3$)$_3$; or —O(CH$_2$)$_2$—R$_4$; wherein R$_4$ is methoxy, amino, or —NH—C(O)—O—C(CH$_3$)$_3$;

$R_3$ is cyano, trifluoromethoxy, trifluoromethylthio, trifluoromethylsulfonyl, trifluoromethylsulfonyl, or pentafluorosulfanyl;

$R_5$ is hydrogen, halo, $C_1$-$C_3$ alkyl, $C_1$-$C_3$ alkoxy, or aminomethyl; and $R_6$ is hydrogen, halo, $C_1$-$C_3$ alkyl, or trifluoromethyl;

or a salt thereof.

2. The compound of claim 1, or a salt thereof, of the formula Ib:

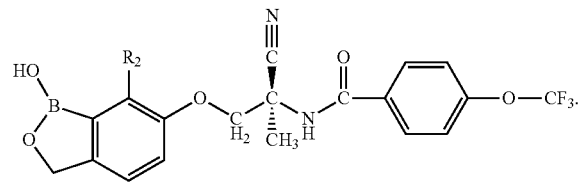

3. The compound of claim 2, or a salt thereof, wherein $R_2$ is selected from the group of bromo, chloro, methyl, ethyl, propyl, isopropyl, cyclopropyl, phenyl, trifluoromethoxy, methoxy, ethoxy, propoxy, and isopropoxy.

4. The compound of claim 1, or a salt thereof, which is
N-(2-cyano-1-(1-hydroxy-1,3-dihydrobenzo[c][1,2]oxaborol-6-yloxy)propan-2-yl)-4-(trifluoromethoxy)benzamide;
N-(2-cyano-1-(1-hydroxy-5-(trifluoromethyl)-1,3-dihydrobenzo[c][1,2]oxaborol-6-yloxy)propan-2-yl)-4-(trifluoromethoxy)benzamide;
N-(2-cyano-1-(5-fluoro-1-hydroxy-1,3-dihydrobenzo[c][1,2]oxaborol-6-yloxy)propan-2-yl)-4-(trifluoromethoxy)benzamide;
N-(1-(7-chloro-5-fluoro-1-hydroxy-1,3-dihydrobenzo[c][1,2]oxaborol-6-yloxy)-2-cyanopropan-2-yl)-4-(trifluoromethoxy)benzamide;
N-(2-cyano-1-(5,7-dichloro-1-hydroxy-1,3-dihydrobenzo[c][1,2]oxaborol-6-yloxy)propan-2-yl)-4-(trifluoromethoxy)benzamide;
N-(1-(5-chloro-1-hydroxy-1,3-dihydrobenzo[c][1,2]oxaborol-6-yloxy)-2-cyanopropan-2-yl)-4-(trifluoromethoxy)benzamide;
N-(1-(4-chloro-1-hydroxy-1,3-dihydrobenzo[c][1,2]oxaborol-6-yloxy)-2-cyanopropan-2-yl)-4-(trifluoromethoxy)benzamide;
N-(1-(7-chloro-4,5-difluoro-1-hydroxy-1,3-dihydrobenzo[c][1,2]oxaborol-6-yloxy)-2-cyanopropan-2-yl)-4-(trifluoromethoxy)benzamide;
N-(2-cyano-1-(1-hydroxy-7-(trifluoromethyl)-1,3-dihydrobenzo[c][1,2]oxaborol-6-yloxy)propan-2-yl)-4-(trifluoromethoxy)benzamide;
N-(2-cyano-1-(4,7-dichloro-1-hydroxy-1,3-dihydrobenzo[c][1,2]oxaborol-6-yloxy)propan-2-yl)-4-(trifluoromethoxy)benzamide;
N-(2-cyano-1-(7-fluoro-1-hydroxy-1,3-dihydrobenzo[c][1,2]oxaborol-6-yloxy)propan-2-yl)-4-(trifluoromethoxy)benzamide;
N-(1-(7-chloro-4-fluoro-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-(2,2,2-trifluoroethyl)-1,3-dihydrobenzo[c][1,2]oxaborol-6-yloxy)propan-2-yl)-4-(trifluoromethoxy)benzamide;

N-(2-cyano-1-(1-hydroxy-7-(2-methoxyethoxy)-1,3-dihydrobenzo[c][1,2]oxaborol-6-yloxy)propan-2-yl)-4-(trifluoromethoxy)benzamide;

tert-butyl 2-(6-(2-cyano-2-(4-(trifluoromethoxy)benzamido)propoxy)-1-hydroxy-1,3-dihydro benzo[c][1,2]oxaborol-7-yloxy)ethylcarbamate;

N-(1-(7-(2-aminoethoxy)-1-hydroxy-1,3-dihydrobenzo[c][1,2]oxaborol-6-yloxy)-2-cyanopropan-2-yl)-4-(trifluoromethoxy)benzamide;

N-(1-amino-3-(7-(2-aminoethoxy)-1-hydroxy-1,3-dihydrobenzo[c][1,2]oxaborol-6-yloxy)-2-methyl-1-oxopropan-2-yl)-4-(trifluoromethoxy)benzamide;

N-(2-cyano-1-(7-cyano-1-hydroxy-1,3-dihydrobenzo[c][1,2]oxaborol-6-yloxy)propan-2-yl)-4-(trifluoromethoxy)benzamide;

N-(2-cyano-1-(1-hydroxy-7-phenoxy-1,3-dihydrobenzo[c][1,2]oxaborol-6-yloxy)propan-2-yl)-4-(trifluoromethoxy)benzamide;

N-(1-(4-(aminomethyl)-1-hydroxy-1,3-dihydrobenzo[c][1,2]oxaborol-6-yloxy)-2-cyanopropan-2-yl)-4-(trifluoromethoxy)benzamide;

N-(1-amino-3-(4-(aminomethyl)-1-hydroxy-1,3-dihydrobenzo[c][1,2]oxaborol-6-yloxy)-2-methyl-1-oxopropan-2-yl)-4-(trifluoromethoxy)benzamide;

N-(2-cyano-1-(1-hydroxy-7-propyl-1,3-dihydrobenzo[c][1,2]oxaborol-6-yloxy)propan-2-yl)-4-(trifluoromethoxy)benzamide;

N-(2-cyano-1-(1-hydroxy-4-methyl-1,3-dihydrobenzo[c][1,2]oxaborol-6-yloxy)propan-2-yl)-4-(trifluoromethoxy)benzamide;

N-(1-(4-(aminomethyl)-7-chloro-1-hydroxy-1,3-dihydrobenzo[c][1,2]oxaborol-6-yloxy)-2-cyanopropan-2-yl)-4-(trifluoromethoxy)benzamide;

N-(1-amino-3-(4-(aminomethyl)-7-chloro-1-hydroxy-1,3-dihydrobenzo[c][1,2]oxaborol-6-yloxy)-2-methyl-1-oxopropan-2-yl)-4-(trifluoromethoxy)benzamide;

N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide;

N-(2-cyano-1-(7-(furan-2-yl)-1-hydroxy-1,3-dihydrobenzo[c][1,2]oxaborol-6-yloxy)propan-2-yl)-4-(trifluoromethoxy)benzamide;

N-(1-(7-acetamido-1-hydroxy-1,3-dihydrobenzo[c][1,2]oxaborol-6-yloxy)-2-cyanopropan-2-yl)-4-(trifluoromethoxy)benzamide;

N-(2-cyano-1-(7-(dimethylamino)-1-hydroxy-1,3-dihydrobenzo[c][1,2]oxaborol-6-yloxy)propan-2-yl)-4-(trifluoromethoxy)benzamide;

tert-butyl (6-(2-cyano-2-(4-(trifluoromethoxy)benzamido)propoxy)-1-hydroxy-1,3-dihydro-benzo[c][1,2]oxaborol-7-yl)methylcarbamate;

N-(1-(7-(aminomethyl)-1-hydroxy-1,3-dihydrobenzo[c][1,2]oxaborol-6-yloxy)-2-cyanopropan-2-yl)-4-(trifluoromethoxy)benzamide;

N-(1-amino-3-(7-(aminomethyl)-1-hydroxy-1,3-dihydrobenzo[c][1,2]oxaborol-6-yloxy)-2-methyl-1-oxopropan-2-yl)-4-(trifluoromethoxy)benzamide;

N-(1-(7-amino-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-iodo-1,3-dihydrobenzo[c][1,2]oxaborol-6-yloxy)propan-2-yl)-4-(trifluoromethoxy)benzamide;

Methyl 6-(2-cyano-2-(4-(trifluoromethoxy)benzamido)propoxy)-1-hydroxy-1,3-dihydro-benzo[c][1,2]oxaborole-7-carboxylate;

N-(2-cyano-1-(1-hydroxy-7-(thiophen-2-yl)-1,3-dihydrobenzo[c][1,2]oxaborol-6-yloxy)propan-2-yl)-4-(trifluoromethoxy)benzamide;

N-(2-cyano-1-(7-cyclopropoxy-1-hydroxy-1,3-dihydrobenzo[c][1,2]oxaborol-6-yloxy)propan-2-yl)-4-(trifluoromethoxy)benzamide;

N-(1-(7-chloro-1-hydroxy-5-methyl-1,3-dihydrobenzo[c][1,2]oxaborol-6-yloxy)-2-cyanopropan-2-yl)-4-(trifluoromethoxy)benzamide;

N-(2-Cyano-1-(1-hydroxy-4,7-dimethyl-1,3-dihydrobenzo[c][1,2]oxaborol-6-yloxy)propan-2-yl)-4-(trifluoromethoxy)benzamide;

N-(1-(7-chloro-1-hydroxy-4-methoxy-1,3-dihydrobenzo[c][1,2]oxaborol-6-yloxy)-2-cyanopropan-2-yl)-4-(trifluoromethoxy)benzamide;

N-(1-(7-chloro-1-hydroxy-1,3-dihydrobenzo[c][1,2]oxaborol-6-yloxy)-2-cyanopropan-2-yl)-4-(trifluoromethoxy)benzamide;

N-(1-(7-bromo-1-hydroxy-1,3-dihydrobenzo[c][1,2]oxaborol-6-yloxy)-2-cyanopropan-2-yl)-4-(trifluoromethoxy)benzamide;

N-(2-cyano-1-(1-hydroxy-7-methyl-1,3-dihydrobenzo[c][1,2]-oxaborol-6-yloxy)propan-2-yl)-4-(trifluoromethoxy)benzamide;

N-(2-cyano-1-(7-ethyl-1-hydroxy-1,3-dihydrobenzo[c][1,2]-oxaborole-6-yloxy)propan-2-yl)-4-(trifluoromethoxy)benzamide;

N-(2-cyano-1-(1-hydroxy-7-methoxy-1,3-dihydrobenzo[c][1,2]oxaborol-6-yloxy)propan-2-yl)-4-(trifluoromethoxy)benzamide;

N-(2-cyano-1-(1-hydroxy-7-isopropyl-1,3-dihydrobenzo[c][1,2]oxaborol-6-yloxy)propan-2-yl)-4-(trifluoromethoxy)benzamide;

N-(1-((7-chloro-1-hydroxy-1,3-dihydrobenzo[c][1,2]oxaborol-6-yl)oxy)-2-cyanopropan-2-yl)-4-((trifluoromethyl)sulfonyl)benzamide;

N-(1-(7-chloro-1-hydroxy-1,3-dihydrobenzo[c][1,2]oxaborol-6-yloxy)-2-cyanopropan-2-yl)-4-(pentafluorothio)benzamide;

N-(1-(7-chloro-1-hydroxy-1,3-dihydrobenzo[c][1,2]oxaborol-6-yloxy)-2-cyanopropan-2-yl)-4-cyanobenzamide;

N-(2-cyano-1-(1-hydroxy-7-phenyl-1,3-dihydrobenzo[c][1,2]oxaborol-6-yloxy)propan-2-yl)-4-(trifluoromethoxy)benzamide;

N-(2-cyano-1-(1-hydroxy-7-propyl-1,3-dihydrobenzo[c][1,2]oxaborol-6-yloxy)propan-2-yl)-4-(trifluoromethoxy)benzamide;

N-(2-cyano-1-(7-cyclopropyl-1-hydroxy-1,3-dihydrobenzo[c][1,2]oxaborol-6-yloxy)propan-2-yl)-4-(trifluoromethoxy)benzamide;

N-[1-Cyano-2-(7-ethoxy-1-hydroxy-1,3-dihydro-benzo[c][1,2]oxaborol-6-yloxy)-1-methyl-ethyl]-4-trifluoromethoxy-benzamide;

N-(2-cyano-1-(1-hydroxy-7-isopropoxy-1,3-dihydrobenzo[c][1,2]oxaborol-6-yloxy)propan-2-yl)-4-(trifluoromethoxy)benzamide; or N-(2-cyano-1-(1-hydroxy-7-(trifluoromethoxy)-1,3-dihydrobenzo[c][1,2]oxaborol-6-yloxy)propan-2-yl)-4-(trifluoromethoxy)benzamide.

5. The compound of claim 3, or a salt thereof, which is (S)—N-(1-(7-chloro-1-hydroxy-1,3-dihydrobenzo[c][1,2]oxaborol-6-yloxy)-2-cyanopropan-2-yl)-4-(trifluoromethylsulfonyl)benzamide;

(S)—N-(1-((7-chloro-1-hydroxy-1,3-dihydrobenzo[c][1,2]oxaborol-6-yl)oxy)-2-cyanopropan-2-yl)-4-((trifluoromethyl)thio)benzamide;

(S)—N-(1-(7-chloro-1-hydroxy-1,3-dihydrobenzo[c][1,2]oxaborol-6-yloxy)-2-cyanopropan-2-yl)-4-(pentafluorothio)benzamide;

(S)—N-(1-(7-chloro-1-hydroxy-1,3-dihydrobenzo[c][1,2]oxaborol-6-yloxy)-2-cyanopropan-2-yl)-4-cyanobenzamide;

(S)—N-(2-cyano-1-(1-hydroxy-7-phenyl-1,3-dihydrobenzo[c][1,2]oxaborol-6-yloxy)propan-2-yl)-4-(trifluoromethoxy)benzamide;

(S)—N-(2-cyano-1-(1-hydroxy-7-(trifluoromethoxy)-1,3-dihydrobenzo[c][1,2]oxaborol-6-yloxy)propan-2-yl)-4-(trifluoromethoxy)benzamide;

(S)—N-(2-cyano-1-(1-hydroxy-7-methoxy-1,3-dihydrobenzo[c][1,2]oxaborol-6-yloxy)propan-2-yl)-4-(trifluoromethoxy)benzamide; or (S)—N-(2-cyano-1-(1-hydroxy-7-isopropyl-1,3-dihydrobenzo[c][1,2]oxaborol-6-yloxy)propan-2-yl)-4-(trifluoromethoxy)benzamide.

6. The compound of claim 3, which is (S)—N-(1-(7-chloro-1-hydroxy-1,3-dihydrobenzo[c][1,2]oxaborol-6-yloxy)-2-cyanopropan-2-yl)-4-(trifluoromethoxy)benzamide, or a salt thereof.

7. The compound of claim 3, which is (S)—N-(1-(7-bromo-1-hydroxy-1,3-dihydrobenzo[c][1,2]oxaborol-6-yloxy)-2-cyanopropan-2-yl)-4-(trifluoromethoxy)benzamide, or a salt thereof.

8. The compound of claim 3, which is (S)—N-(2-cyano-1-(1-hydroxy-7-methoxy-1,3-dihydrobenzo[c][1,2]oxaborol-6-yloxy)propan-2-yl)-4-(trifluoromethoxy)benzamide, or a salt thereof.

9. The compound of claim 3, which is (S)—N-(2-cyano-1-(7-ethyl-1-hydroxy-1,3-dihydrobenzo[c][1,2]oxaborol-6-yloxy)propan-2-yl)-4-(trifluoromethoxy)benzamide, or a salt thereof.

10. The compound of claim 3, which is (S)—N-(2-cyano-1-(1-hydroxy-7-isopropyl-1,3-dihydrobenzo[c][1,2]oxaborol-6-yloxy)propan-2-yl)-4-(trifluoromethoxy)benzamide, or a salt thereof.

11. The compound of claim 1, which is (S)—N-(1-(7-chloro-1-hydroxy-4-methyl-1,3-dihydrobenzo[c][1,2]oxaborol-6-yloxy)-2-cyanopropan-2-yl)-4-(trifluoromethoxy)benzamide, or a salt thereof.

12. A formulation comprising a compound of claim 1, or salt thereof, and at least one acceptable carrier.

13. The formulation of claim 12, wherein said formulation is adapted for oral administration.

14. A method of controlling an endoparasite infestation in or on an animal in need thereof comprising administering an effective amount of a compound of claim 1, or salt thereof, to said animal.

15. The method of claim 14, wherein said animal is a companion animal.

16. The method of claim 15, wherein said companion animal is a dog.

17. The method of claim 14, wherein said administration is oral administration.

* * * * *